United States Patent
Arslan et al.

(10) Patent No.: US 12,421,545 B2
(45) Date of Patent: Sep. 23, 2025

(54) COMPOSITIONS AND METHODS FOR PREPARING NUCLEIC ACID NANOSTRUCTURES USING COMPACTION OLIGONUCLEOTIDES

(71) Applicant: Element Biosciences, Inc., San Diego, CA (US)

(72) Inventors: Sinan Arslan, San Diego, CA (US); Michael Kim, El Cajon, CA (US); Ramreddy Tippana, San Diego, CA (US); Chunhong Zhou, San Diego, CA (US); William Light, Poway, CA (US); Hua Yu, La Jolla, CA (US); Junhua Zhao, San Diego, CA (US); Tsung-Li Liu, San Diego, CA (US)

(73) Assignee: Element Biosciences, Inc., San Diego, CA (US)

( * ) Notice: Subject to any disclaimer, the term of this patent is extended or adjusted under 35 U.S.C. 154(b) by 0 days.

(21) Appl. No.: 18/450,302

(22) Filed: Aug. 15, 2023

(65) Prior Publication Data

US 2024/0084380 A1   Mar. 14, 2024

Related U.S. Application Data

(60) Provisional application No. 63/398,178, filed on Aug. 15, 2022.

(51) Int. Cl.
    *C12Q 1/6874* (2018.01)
    *C12Q 1/6806* (2018.01)
    *C12Q 1/6844* (2018.01)

(52) U.S. Cl.
    CPC ......... *C12Q 1/6874* (2013.01); *C12Q 1/6844* (2013.01); *C12Q 1/6806* (2013.01)

(58) Field of Classification Search
    CPC ................ C12Q 1/6806; C12Q 1/6844; C12Q 1/6874; C12Q 2525/307; C12Q 2531/125
    See application file for complete search history.

(56) References Cited

U.S. PATENT DOCUMENTS

| 5,558,991 A | 9/1996 | Trainor |
| 6,323,009 B1 | 11/2001 | Lasken et al. |

(Continued)

FOREIGN PATENT DOCUMENTS

| CN | 112111560 A | 12/2020 |
| WO | WO-2005111240 A2 | 11/2005 |

(Continued)

OTHER PUBLICATIONS

Wang, F. et al., "Tequila-seq: a versatile and low-cost method for targeted long-read RNA sequencing," Nat Commun., (2023); 14(1):4760, pp. 1-15.

(Continued)

*Primary Examiner* — Young J Kim
(74) *Attorney, Agent, or Firm* — Fenwick & West LLP; Heidi A. Erlacher; Jessica D. Cande

(57) ABSTRACT

The present disclosure provides compositions and related methods, e.g., for preparing immobilized nucleic acid nanostructures using compaction oligonucleotides. In some embodiments, rolling circle amplification reaction can be conducted with compaction oligonucleotides on-support or in-solution to generate concatemer molecules having multiple copies of a polynucleotide unit arranged in tandem. Each polynucleotide unit comprises a sequence-of-interest and at least one universal adaptor sequence that binds one end of a compaction oligonucleotide. The 5' and 3' regions of the compaction oligonucleotide can hybridize to the concatemer to pull together distal portions of the concatemer causing compaction of the concatemer to form a nanostructure. Nanostructures having tighter size and shape compared (Continued)

to concatemers generated in the absence of the compaction oligonucleotides. The compact and stable characteristics of the nucleic acid nanostructures improves sequencing accuracy by increasing signal intensity and they retain their shape and size during multiple sequencing cycles.

20 Claims, 77 Drawing Sheets
(10 of 77 Drawing Sheet(s) Filed in Color)

Specification includes a Sequence Listing.

(56) References Cited

U.S. PATENT DOCUMENTS

| | | | |
|---|---|---|---|
| 6,329,150 B1 | 12/2001 | Lizardi et al. | |
| 7,910,354 B2 | 3/2011 | Drmanac et al. | |
| 7,968,702 B2 | 6/2011 | Wegener et al. | |
| 8,252,910 B2 | 8/2012 | Korlach et al. | |
| 8,445,194 B2 | 5/2013 | Drmanac et al. | |
| 8,445,196 B2 | 5/2013 | Drmanac et al. | |
| 8,476,022 B2 | 7/2013 | Ronaghi et al. | |
| 8,637,650 B2 | 1/2014 | Cherkasov et al. | |
| 8,906,612 B2 | 12/2014 | Shen et al. | |
| 8,927,212 B2 | 1/2015 | Kong et al. | |
| 9,217,167 B2 | 12/2015 | Heller et al. | |
| 9,228,228 B2 | 1/2016 | Drmanac et al. | |
| 9,416,415 B2 | 8/2016 | Ronaghi et al. | |
| 9,453,258 B2 | 9/2016 | Kain et al. | |
| 9,624,538 B2 | 4/2017 | Church et al. | |
| 9,650,673 B2 | 5/2017 | Drmanac et al. | |
| 9,777,326 B2 | 10/2017 | Ronaghi et al. | |
| 9,822,408 B2 | 11/2017 | Amorese et al. | |
| 9,862,994 B2 | 1/2018 | Schmidt et al. | |
| 9,938,568 B2 | 4/2018 | Heller et al. | |
| 9,944,984 B2 | 4/2018 | Drmanac et al. | |
| 9,957,291 B2 | 5/2018 | Sebo et al. | |
| 9,982,293 B2 | 5/2018 | Fu et al. | |
| 10,246,744 B2 | 4/2019 | Vijayan et al. | |
| 10,351,909 B2 | 7/2019 | Drmanac et al. | |
| 10,669,299 B2 | 6/2020 | Sebo et al. | |
| 10,704,094 B1* | 7/2020 | Arslan | G01N 21/6428 |
| 10,731,141 B2 | 8/2020 | Iyidogan | |
| 10,781,483 B2 | 9/2020 | Sebo et al. | |
| 10,837,879 B2 | 11/2020 | Burns et al. | |
| 11,220,707 B1 | 1/2022 | Arslan et al. | |
| 11,230,731 B2 | 1/2022 | Sekedat et al. | |
| 11,236,388 B1 | 2/2022 | Arslan et al. | |
| 11,427,855 B1 | 8/2022 | Arslan et al. | |
| 11,535,892 B1* | 12/2022 | Arslan | C12Q 1/6853 |
| 11,578,320 B2 | 2/2023 | Glezer et al. | |
| 11,608,528 B2 | 3/2023 | Patterson et al. | |
| 11,649,452 B2 | 5/2023 | Glezer et al. | |
| 11,781,185 B2* | 10/2023 | Arslan | C12Q 1/6806 435/6.12 |
| 11,859,241 B2 | 1/2024 | Arslan et al. | |
| 11,891,651 B2 | 2/2024 | Arslan et al. | |
| 2008/0242560 A1 | 10/2008 | Gunderson et al. | |
| 2009/0186343 A1 | 7/2009 | Wang et al. | |
| 2014/0378317 A1* | 12/2014 | Fu | C12Q 1/6876 506/9 |
| 2020/0216899 A1* | 7/2020 | Arslan | C12Y 306/04012 |
| 2020/0263230 A1 | 8/2020 | Zhou et al. | |
| 2022/0403445 A1 | 12/2022 | Arslan et al. | |
| 2022/0403463 A1 | 12/2022 | Arslan et al. | |
| 2023/0193354 A1 | 6/2023 | Arslan et al. | |
| 2023/0203564 A1 | 6/2023 | Arslan et al. | |
| 2023/0279382 A1 | 9/2023 | Light et al. | |
| 2023/0279483 A1 | 9/2023 | Light et al. | |
| 2024/0011022 A1 | 1/2024 | Zhao et al. | |
| 2024/0191225 A1 | 6/2024 | Zhao et al. | |
| 2024/0191278 A1 | 6/2024 | Arslan et al. | |
| 2024/0240249 A1 | 7/2024 | Zheng et al. | |
| 2025/0019760 A1 | 1/2025 | Light et al. | |

FOREIGN PATENT DOCUMENTS

| | | | | |
|---|---|---|---|---|
| WO | WO-2020102594 A1 | 5/2020 | | |
| WO | WO-2021061841 A1 * | 4/2021 | | C12Q 1/6834 |
| WO | WO-2022266470 A1 | 12/2022 | | |
| WO | WO-2024040058 A1 | 2/2024 | | |
| WO | WO-2025024465 A1 | 1/2025 | | |

OTHER PUBLICATIONS

Clausson, C-M., et al., "Compaction of rolling circle amplification products increases signal integrity and signal-to-noise ratio," Sci Rep., (2015); 5:12317, pp. 1-10.
Eschenmoser, A., "Chemical Etiology of Nucleic Acid Structure," Science, Jun. 25, 1999, 284:2118-2124.
Ferraro, M. & Gotor, V., "Biocatalytic Selective Modifications of Conventional Nucleosides, Carbocyclic Nucleosides, and C-Nucleosides," Chem. Rev., 2000, 100:4319-4347.
Jeong, L.S. et al., "Structure-Activity Relationships of B-D-(2S,5R)- and a-D-(2S,5S)-1,3-Oxathiolanyl Nucleosides as Potential Anti-HIV Agents," J. Med. Chem., 1993, 36:2627-2638.
Kim, H. O. et al., "1,3-Dioxolanylpurine Nucleosides (2R,4R) and (2R,4S) with Selective Anti-HIV-1 Activity in Human Lymphocytes," J. Med. Chem., 1993, 36:30-37.
Martinez, C. I. et al., "Acyclic Nucleoside Triphosphate Analogs as Terminators in Biocatalytic DNA Replication" Bioorganic & Medicinal Chemistry Letters, 1997, 7(23):3013-3016.
Martinez, C. I. et al., "An allylic/acyclic adenosine nucleoside triphosphate for termination of DNA synthesis by DNA template-dependent polymerases," Nucleic Acids Research, 1999, 27(5):1271-1274.
Anderson, J.P. et al.; Fluorescent Structural DNA Nanoballs Functionalized with Phosphate-Linked Nucleotide Triphosphates. Nano Letters 10(3):788-792 (2010).
Chen, X., et al.; "Efficient in situ barcode sequencing using padlock probe-based BaristaSeq," Nucleic Acids Research; 46(4):e22 pp. 1-10 (2018).
Mignardi, M., et al.; "Fourth-generation sequencing in the cell and the clinic," Genome Med.; 6(4):31; pp. 1-4 (2014).
Szemes, M., et al.; "Diagnostic application of padlock probes—multiplex detection of plant pathogens using universal microarrays," Nucleic Acids Research; 33(8): e70; pp. 1-13 (Apr. 2005).
U.S. Appl. No. 18/824,527 as filed Sep. 4, 2024, by Sinan Arslan, et al.; and preliminary amendment filed Apr. 11, 2025, 530 pages.

* cited by examiner

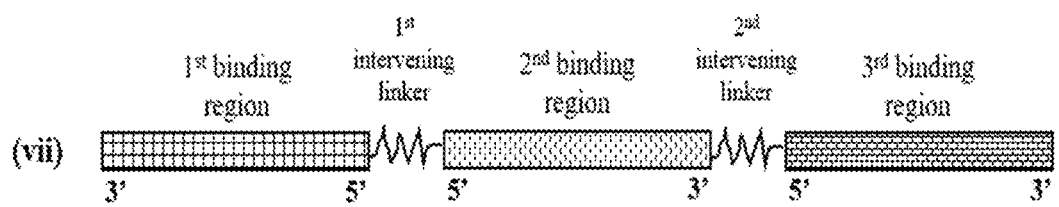
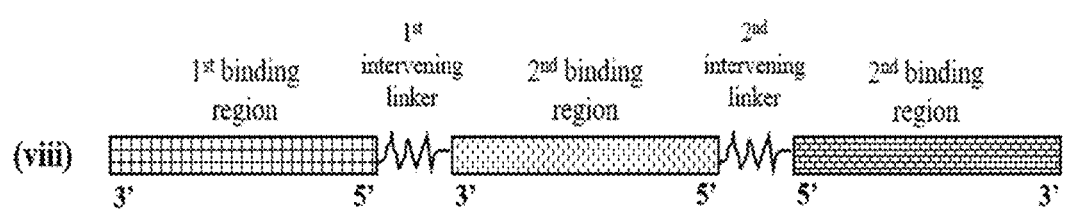
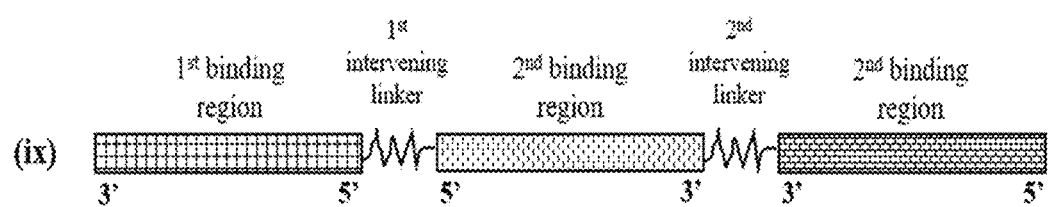
FIG. 2C (i)
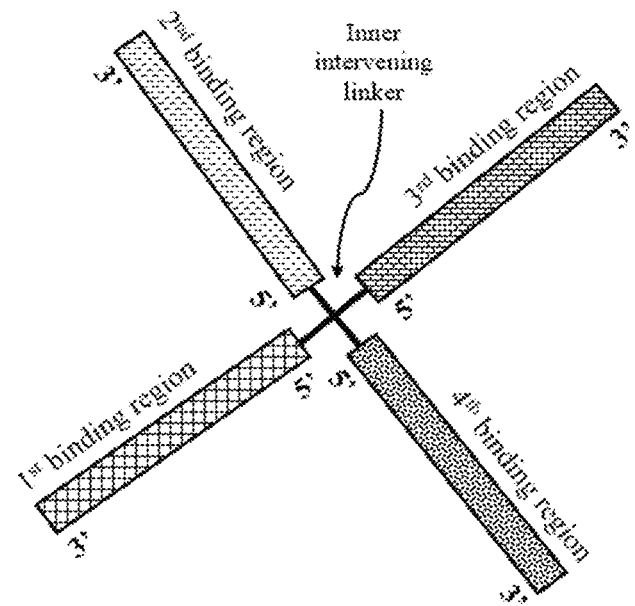
(ii)
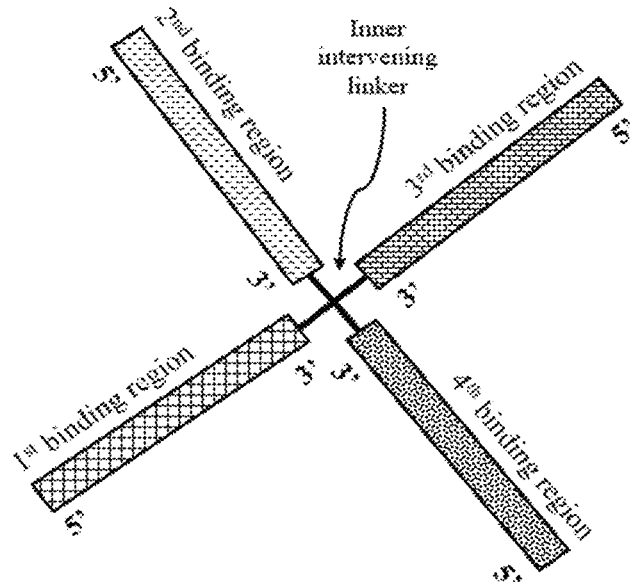
FIG. 5

Table 1: Compaction Oligonucleotides

| SEQ ID NO: | Sequence (5' to 3' orientation) |
|---|---|
| 1 | ACACGTCTGAACTCCAGTCAC |
| 2 | CACTGACCTCAAGTCTGCACA |
| 3 | ACACGTCTGAACTCCAGTCACAAAACACGTCTGAACTCCAGTCAC |
| 4 | GAGCACACGTCTGAACTCCAGTCAC |
| 5 | CACTGACCTCAAGTCTGCACACGAG |
| 6 | GAGCACACGTCTGAACTCCAGTCACAAAGAGCACACGTCTGAACTCCAGTCAC |
| 7 | CTGAACTCCAGTCACAAAAAAACCCTGAAAG |
| 8 | GAAAGTCCCAAAAAAACACTGACCTCAAGTC |
| 9 | CTGAACTCCAGTCACAAAAAAACCCTGAAAGAAACTGAACTCCAGTCACAAAAAAACCCTGAAAGTAC |
| 10 | CTGAACTCCAGTCACAAAAAAACCCTGAAAG |
| 11 | GAAAGTCCCAAAAAAACACTGACCTCAAGTC |
| 12 | CTGAACTCCAGTCACAAAAAAACCCTGAAAGAAACTGAACTCCAGTCACAAAAAAACCCTGAAAGTAC |
| 13 | CTGAACTCCAGTCACAAAAAAATCTCGTATGC |
| 14 | CGTATGCTCTAAAAAAACACTGACCTCAAGTC |
| 15 | CTGAACTCCAGTCACAAAAAAATCTCGTATGCAAACTGAACTCCAGTCACAAAAAAATCTCGTATGCCGT |
| 16 | CTTCTGCTTGAATGATACGGCGACC |
| 17 | CCAGCGGCATAGTAAGTTCGTCTTC |
| 18 | CTTCTGCTTGAATGATACGGCGACCAAACTTCTGCTTGAATGATACGGCGACC |
| 19 | GCATTACATGCATAATAGTGTGACG |
| 20 | GCAGTGTGATAATACGTACATTACG |
| 21 | GCATTACATGCATAATAGTGTGACGAAAGCATTACATGCATAATAGTGTGACG |

FIG. 14A

Table 1 (continued): Compaction Oligonucleotides

| SEQ ID NO: | Sequence (5' to 3' orientation) |
|---|---|
| 22 | CATAATAGTGTGACGTAATAG |
| 23 | GATAATGCAGTGTGATAATAC |
| 24 | CATAATAGTGTGACGTAATAG<u>AAA</u>CATAATAGTGTGACGTAATAG |
| 25 | CGTAATAGACATACACTCTTTCCC |
| 26 | CCCTTTCTCACATACAGATAATGC |
| 27 | CGTAATAGACATACACTCTTTCCC<u>AAA</u>CGTAATAGACATACACTCTTTCCC |
| 28 | AATGATACGGCGACCACCGA |
| 29 | AGCCACCAGCGGCATAGTAA |
| 30 | AATGATACGGCGACCACCGA<u>AAA</u>AATGATACGGCGACCACCGA |
| 31 | TGTAGGGAAAGAGTGTAGTCGTCGCAGCCTCACCT |
| 32 | TCCACTCCGACGCTGCTGATGTGAGAAAGGGATGT |
| 33 | TGTAGGGAAAGAGTGTAGTCGTCGCAGCCTCACCT<u>AAA</u>TGTAGGGAAAGAGTGTAGTCGTCGCAGCCTCACCT |
| 34 | AGGTGAGGCTGCGACGACTACACTCTTTCCCTACA |
| 35 | ACATCCCTTTCTCACATCAGCAGCGTCGGAGTGGA |
| 36 | AGGTGAGGCTGCGACGACTACACTCTTTCCCTACA<u>AAA</u>AGGTGAGGCTGCGACGACTACACTCTTTCCCTACA |
| 37 | GATGAGGTGAGGCTGCGACGACT |
| 38 | TCAGCAGCGTCGGAGTGGAGTAG |
| 39 | GATGAGGTGAGGCTGCGACGACT<u>AAA</u>GATGAGGTGAGGCTGCGACGACT |
| 40 | TGACGTAATAGACATCTTTCCCTAC |
| 41 | CATCCCTTTCTACAGATAATGCAGT |
| 42 | TGACGTAATAGACATCTTTCCCTAC<u>AAA</u>TGACGTAATAGACATCTTTCCCTAC |

FIG. 14B

Table 1 (continued): Compaction Oligonucleotides

| SEQ ID NO: | Sequence (5' to 3' orientation) |
|---|---|
| 43 | GTAGGGAAAGATGTCTATTACGTCA |
| 44 | ACTGCATTATCTGTAGAAAGGGATG |
| 45 | GTAGGGAAAGATGTCTATTACGTCAAAAGTAGGGAAAGATGTCTATTACGTCA |
| 46 | AGGGAAAGATGTCTATTA |
| 47 | ATTATCTGTAGAAAGGGA |
| 48 | AGGGAAAGATGTCTATTAAAAAGGGAAAGATGTCTATTA |
| 49 | TTACATGGATGAGGTGAGGCTGCGACGACT |
| 50 | TCAGCAGCGTCGGAGTGGAGTAGGTACATT |
| 51 | TTACATGGATGAGGTGAGGCTGCGACGACTAAATTACATGGATGAGGTGAGGCTGCGACGACT |
| 52 | CACACTATTATGCGAGCT |
| 53 | TCGAGCGTATTATCACAC |
| 54 | CACACTATTATGCGAGCTAAACACACTATTATGCGAGCT |
| 55 | CATGTAATGCACGTACTTTCAGGGT |
| 56 | TGGGACTTTCATGCACGTAATGTAC |
| 57 | CATGTAATGCACGTACTTTCAGGGTAAACATGTAATGCACGTACTTTCAGGGT |
| 58 | TCATCCATGTAATGCACGTACTTTCAGGGT |
| 59 | TGGGACTTTCATGCACGTAATGTACCTACT |
| 60 | TCATCCATGTAATGCACGTACTTTCAGGGTAAATCATCCATGTAATGCACGTACTTTCAGGGT |
| 61 | TGTAGGGAAAGAGTGTAGTCGT |
| 62 | TGCTGATGTGAGAAAGGGATGT |
| 63 | TGTAGGGAAAGAGTGTAGTCGTAAATGTAGGGAAAGAGTGTAGTCGT |

FIG. 14C

Table 1 (continued): Compaction Oligonucleotides

| SEQ ID NO: | Sequence (5' to 3' orientation) |
|---|---|
| 64 | ACGACTACACTCTTTCCCTACA |
| 65 | ACATCCCTTTCTCACATCAGCA |
| 66 | ACGACTACACTCTTTCCCTACAAAAACGACTACACTCTTTCCCTACA |
| 67 | TCCAGTCACCGAGCT |
| 68 | TCGAGCCACTGACCT |
| 69 | TCCAGTCACCGAGCTAAATCCAGTCACCGAGCT |
| 70 | AATGATACGGCGACCACCGA |
| 71 | AGCCACCAGCGGCATAGTAA |
| 72 | AATGATACGGCGACCACCGAAAAAATGATACGGCGACCACCGA |
| 73 | GTAGGGAAAGAGTGTIIIIIIIIGTGTAGATC |
| 74 | CTAGATGTGIIIIIIIITGTGAGAAAGGGATG |
| 75 | GTAGGGAAAGAGTGTIIIIIIIIGTGTAGATCAAAGTAGGGAAAGAGTGTIIIIIIIIGTGTAGATC |
| 76 | AATGATACGGCGACCACCGAGATCTACAC |
| 77 | CACATCTAGAGCCACCAGCGGCATAGTAA |
| 78 | AATGATACGGCGACCACCGAGATCTACACAAAAATGATACGGCGACCACCGAGATCTACAC |
| 79 | GAGCGTCGTGTAGGGAAAGAGTGT |
| 80 | TGTGAGAAAGGGATGTGCTGCGAG |
| 81 | GAGCGTCGTGTAGGGAAAGAGTGTAAAGAGCGTCGTGTAGGGAAAGAGTGT |
| 82 | CTTCTGCTTGAATGATACGGCGACC |
| 83 | CCAGCGGCATAGTAAGTTCGTCTTC |
| 84 | CTTCTGCTTGAATGATACGGCGACCAAACTTCTGCTTGAATGATACGGCGACC |

FIG. 14D

Table 1 (continued): Compaction Oligonucleotides

| SEQ ID NO: | Sequence (5' to 3' orientation) |
|---|---|
| 85 | CAAGCAGAAGACGGCATACGAGAT |
| 86 | TAGAGCATACGGCAGAAGACGAAC |
| 87 | CAAGCAGAAGACGGCATACGAGATAAACAAGCAGAAGACGGCATACGAGAT |
| 88 | ACACTCTTTCCCTACACGACGCTC |
| 89 | CTCGCAGCACATCCCTTTCTCACA |
| 90 | ACACTCTTTCCCTACACGACGCTCAAAACACTCTTTCCCTACACGACGCTC |
| 91 | GTGACTGGAGTTCAGACGTGTGCTC |
| 92 | CTCGTGTGCAGACTTGAGGTCAGTG |
| 93 | GTGACTGGAGTTCAGACGTGTGCTCAAAGTGACTGGAGTTCAGACGTGTGCTC |
| 94 | GAGCACACGTCTGAACTCCAGTCAC |
| 95 | CACTGACCTCAAGTCTGCACACGAG |
| 96 | GAGCACACGTCTGAACTCCAGTCACAAAGAGCACACGTCTGAACTCCAGTCAC |
| 97 | CTGAACTCCAGTCACIIIIIIIIATCTCGTAT |
| 98 | TATGCTCTAIIIIIIIICACTGACCTCAAGTC |
| 99 | CTGAACTCCAGTCACIIIIIIIIATCTCGTATAAACTGAACTCCAGTCACIIIIIIIIATCTCGTAT |
| 100 | GAGCTCGACCCTGAAAG |
| 101 | GAAAGTCCCAGCTCGAG |
| 102 | GAGCTCGACCCTGAAAGAAAGAGCTCGACCCTGAAAG |
| 103 | CGTGCATTACATGCGAG |
| 104 | GAGCGTACATTACGTGC |
| 105 | CGTGCATTACATGCGAGAAACGTGCATTACATGCGAG |

FIG. 14E

Table 1 (continued): Compaction Oligonucleotides

| SEQ ID NO: | Sequence (5' to 3' orientation) |
|---|---|
| 106 | GCAGGCTACCGCTTGTCAACT |
| 107 | TCAACTGTTCGCCATCGGACG |
| 108 | GCAGGCTACCGCTTGTCAACTAAAGCAGGCTACCGCTTGTCAACT |
| 109 | AGTTGACAAGCGGTAGCCTGC |
| 110 | CGTCCGATGGCGAACAGTTGA |
| 111 | AGTTGACAAGCGGTAGCCTGCAAAAGTTGACAAGCGGTAGCCTGC |
| 112 | GGTGTGCAGGCTACCGCTTGTCAACT |
| 113 | TCAACTGTTCGCCATCGGACGTGTGG |
| 114 | GGTGTGCAGGCTACCGCTTGTCAACTAAAGGTGTGCAGGCTACCGCTTGTCAACT |
| 115 | AGTTGACAAGCGGTAGCCTGCACACC |
| 116 | CCACACGTCCGATGGCGAACAGTTGA |
| 117 | AGTTGACAAGCGGTAGCCTGCACACCAAAAGTTGACAAGCGGTAGCCTGCACACC |
| 118 | AGTCGTCGCAGCCTCACCTGATC |
| 119 | CTAGTCCACTCCGACGCTGCTGA |
| 120 | AGTCGTCGCAGCCTCACCTGATCAAAAGTCGTCGCAGCCTCACCTGATC |
| 121 | GATCAGGTGAGGCTGCGACGACT |
| 122 | TCAGCAGCGTCGGAGTGGACTAG |
| 123 | GATCAGGTGAGGCTGCGACGACTAAAGATCAGGTGAGGCTGCGACGACT |
| 124 | GGAAGGTGTGCAGGCTACCGCTT |
| 125 | TTCGCCATCGGACGTGTGGAAGG |
| 126 | GGAAGGTGTGCAGGCTACCGCTTAAAGGAAGGTGTGCAGGCTACCGCTT |

FIG. 14F

Table 1 (continued): Compaction Oligonucleotides

| SEQ ID NO: | Sequence (5' to 3' orientation) |
|---|---|
| 127 | TGGTGAGCCAATCCAGCACG |
| 128 | GCACGACCTAACCGAGTGGT |
| 129 | TGGTGAGCCAATCCAGCACGAAATGGTGAGCCAATCCAGCACG |
| 130 | ATGTCGGAAGGTGTGCAGGCTA |
| 131 | ATCGGACGTGTGGAAGGCTGTA |
| 132 | ATGTCGGAAGGTGTGCAGGCTAAAAATGTCGGAAGGTGTGCAGGCTA |
| 133 | TGTCTGGTGAGCCAATCCAGCACG |
| 134 | GCACGACCTAACCGAGTGGTCTGT |
| 135 | TGTCTGGTGAGCCAATCCAGCACGAAATGTCTGGTGAGCCAATCCAGCACG |
| 136 | TTGAGTCGTCGCAGCCTCACCTGAT |
| 137 | TAGTCCACTCCGACGCTGCTGAGTT |
| 138 | TTGAGTCGTCGCAGCCTCACCTGATAAATTGAGTCGTCGCAGCCTCACCTGAT |
| 139 | TCTTCTGCTTGAGTCGTCGCAGCC |
| 140 | CCGACGCTGCTGAGTTCGTCTTCT |
| 141 | TCTTCTGCTTGAGTCGTCGCAGCCAAATCTTCTGCTTGAGTCGTCGCAGCC |
| 142 | ATCTCGTATGCCGTCTTCTGCTTG |
| 143 | GTTCGTCTTCTGCCGTATGCTCTA |
| 144 | ATCTCGTATGCCGTCTTCTGCTTGAAAATCTCGTATGCCGTCTTCTGCTTG |
| 145 | CCTGATCCATGTAATGCACGTACTTT |
| 146 | TTTCATGCACGTAATGTACCTAGTCC |
| 147 | CCTGATCCATGTAATGCACGTACTTTAAACCTGATCCATGTAATGCACGTACTTT |

FIG. 14G

Table 1 (continued): Compaction Oligonucleotides

| SEQ ID NO: | Sequence (5' to 3' orientation) |
|---|---|
| 148 | CACGTACTTTCAGGGTAATGATACG |
| 149 | GCATAGTAATGGGACTTTCATGCAC |
| 150 | CACGTACTTTCAGGGTAATGATACGAAACACGTACTTTCAGGGTAATGATACG |
| 151 | AATGATACGCACGTACTTTCAGGGT |
| 152 | TGGGACTTTCATGCACGCATAGTAA |
| 153 | AATGATACGCACGTACTTTCAGGGTAAAAATGATACGCACGTACTTTCAGGGT |
| 154 | GTAGGGAAAGATGTCTATTACGTC |
| 155 | CTGCATTATCTGTAGAAAGGGATG |
| 156 | GTAGGGAAAGATGTCTATTACGTCAAAAGTAGGGAAAGATGTCTATTACGTC |

FIG. 14H

Table 2: Universal Adaptor Sequences

| SEQ ID NO: | Description: | Sequence (5' to 3' orientation) |
|---|---|---|
| 157 | Surface Primer 1 | AATGATACGGCGACCACCGAGATC |
| 158 | Surface Primer 1 | GATCTCGGTGGTCGCCGTATCATT |
| 159 | Surface Primer 2 | ATCTCGTATGCCGTCTTCTGCTTG |
| 160 | Surface Primer 2 | CAAGCAGAAGACGGCATACGAGAT |
| 161 | FWD Seq | ACACTCTTTCCCTACACGACGCTCTTCCGATCT |
| 162 | FWD Seq | AGATCGGAAGAGCGTCGTGTAGGGAAAGAGTGT |
| 163 | REV Seq | AGATCGGAAGAGCACACGTCTGAACTCCAGTCAC |
| 164 | REV Seq | GTGACTGGAGTTCAGACGTGTGCTCTTCCGATCT |
| 165 | FWD Seq | TCGTCGGCAGCGTCAGATGTGTATAAGAGACAG |
| 166 | FWD Seq | CTGTCTCTTATACACATCTGACGCTGCCGACGA |
| 167 | REV Seq | CTGTCTCTTATACACATCTCCGAGCCCACGAGAC |
| 168 | REV Seq | GTCTCGTGGGCTCGGAGATGTGTATAAGAGACAG |
| 169 | Surface Primer 1 | AGTCGTCGCAGCCTCACCTGATC |
| 170 | Surface Primer 1 | GATCAGGTGAGGCTGCGACGACT |
| 171 | Surface Primer 2 | CATGTAATGCACGTACTTTCAGGGT |
| 172 | Surface Primer 2 | ACCCTGAAAGTACGTGCATTACATG |
| 173 | FWD Seq | CGTGCTGGATTGGCTCACCAGACACCTTCCGACAT |
| 174 | FWD Seq | ATGTCGGAAGGTGTCTGGTGAGCCAATCCAGCACG |
| 175 | REV Seq | ATGTCGGAAGGTGTGCAGGCTACCGCTTGTCAACT |
| 176 | REV Seq | AGTTGACAAGCGGTAGCCTGCACACCTTCCGACAT |

FIG. 15

Class I
Valency = 0-4
Homogenous population with saturation

"starburst"    "Helter-Skelter"

PEG length = 1k-10k    PEG length = 1.25k-5k

Class II
Valency >4
Homogenous population with Saturation

Dendrimer core 12,24,48,96 arms
PEG length = 1K-10K

Other cores = dextrans, other polymers

Spacer:
Linkers:
11 atom Linker:
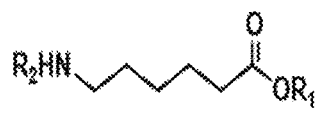
16 atom Linker:
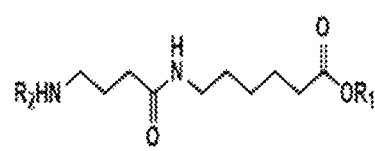
23 atom Linker:
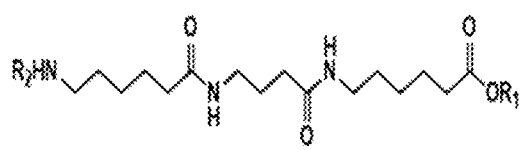
N3 Linker:
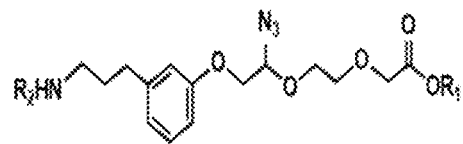
FIG. 60 dNTP-PA-NH₂:
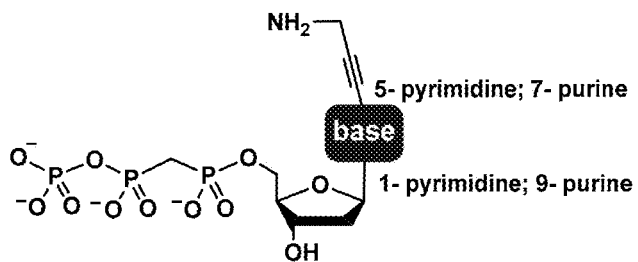
dNTP-PA-11 Atom Linker-NH₂:
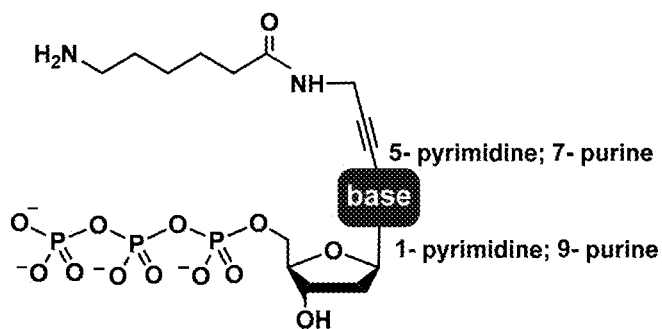
dNTP-PA-16 Atom Linker-NH₂:
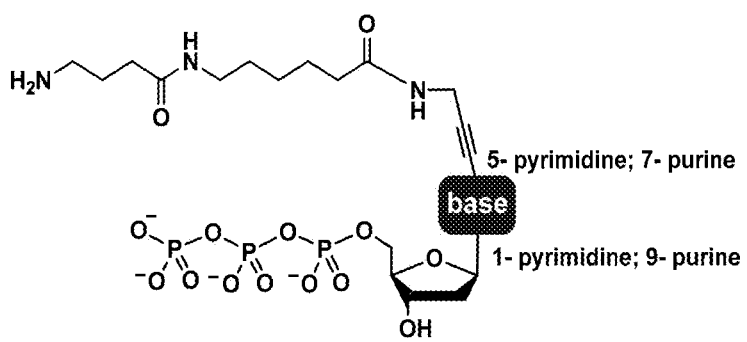
FIG. 62A dNTP-PA-23 Atom Linker-NH₂:
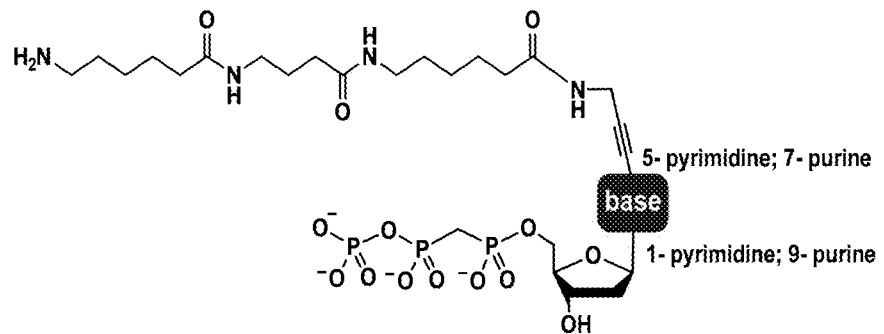
dNTP-PA-N3 Linker-NH₂:
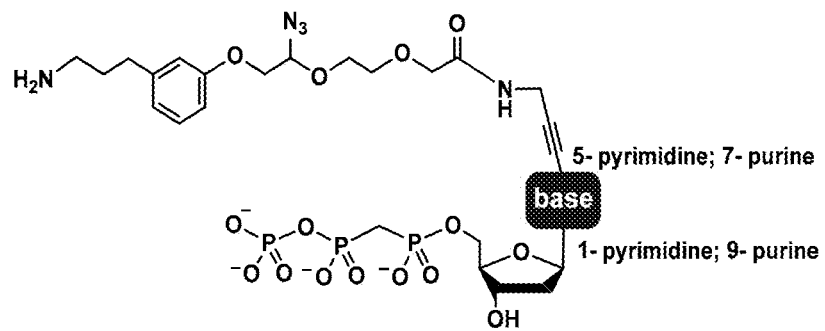
dNTP-PA-Linker 1-NH₂:
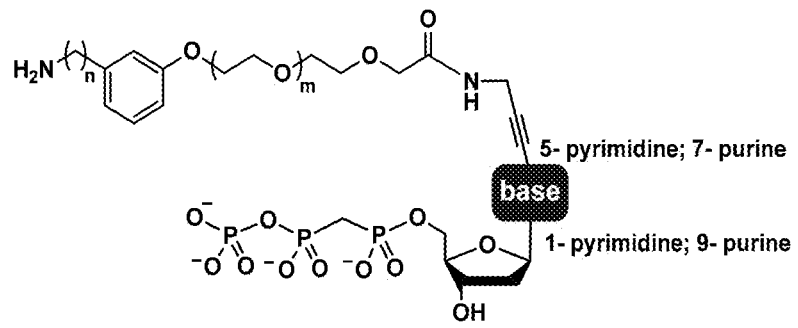
FIG. 62B dNTP-PA-Linker 2-NH₂:
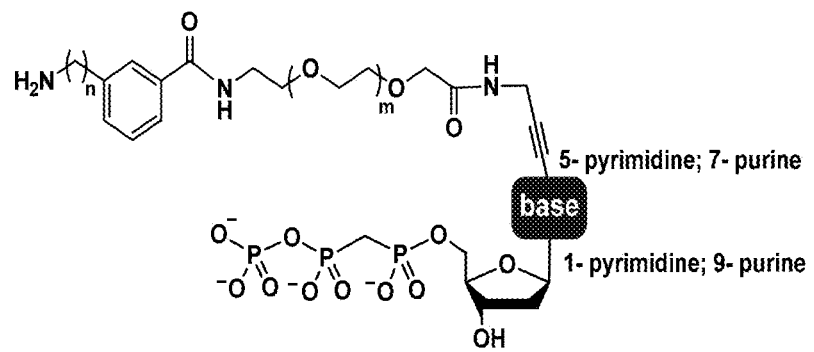
dNTP-PA-Linker 3-NH₂:
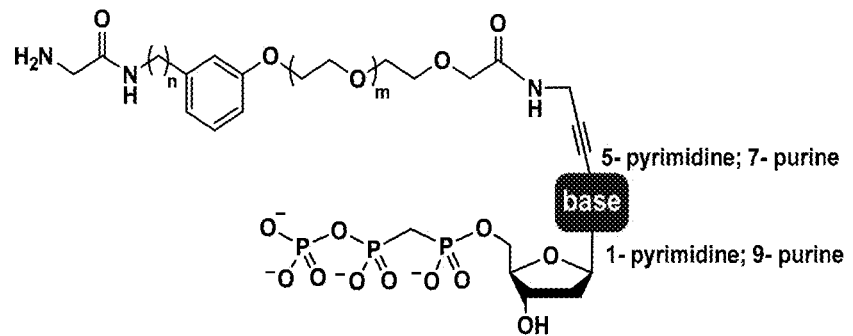
FIG. 62C dNTP-PA-Linker 4-NH₂:
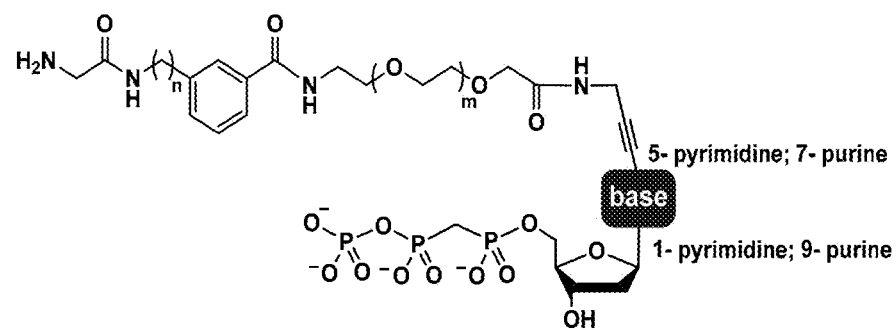
dNTP-PA-N3 Linker-NH₂:
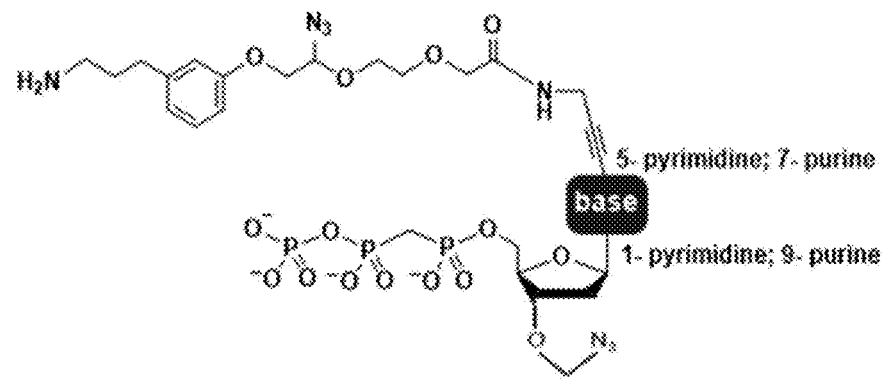
FIG. 62D

G-tetrad

COMPOSITIONS AND METHODS FOR PREPARING NUCLEIC ACID NANOSTRUCTURES USING COMPACTION OLIGONUCLEOTIDES

CROSS-REFERENCE TO RELATED APPLICATIONS

This application claims priority to, and the benefit of, U.S. Provisional Patent Application No. 63/398,178, filed Aug. 15, 2022, the contents of which are incorporated by reference herein in their entireties.

REFERENCE TO AN ELECTRONIC SEQUENCE LISTING

The contents of the electronic sequence listing (ELEM-005-001US-SeqList-ST26.xml; Size 161,077 bytes; and Date of Creation: Aug. 14, 2023) are herein incorporated by reference in their entireties.

TECHNICAL FIELD

The present disclosure provides compositions and methods that employ the compositions for preparing immobilized nucleic acid nanostructures, including nucleic acid nanoballs, using compaction oligonucleotides.

BACKGROUND

Polynucleotide sequencing technology has applications in biomedical research and healthcare settings. Improved methods of polynucleotide require enhanced surface chemistry, on-support polynucleotide amplification, and base calling. Currently, these elements produce barriers in existing sequencing technology that result in limits in throughput and poor signal-to-noise ratio, and ultimately to increased costs associated with polynucleotide sequencing. Thus, there exists a need for improved sequencing methods and associated assembly techniques.

SUMMARY

In one aspect, the present disclosure provides a method for generating high density nucleic acid nanostructures immobilized on a support, comprising:
a) providing a support having a plurality of first universal surface primers immobilized thereon, wherein the density of the first universal surface primers on the support is about $10^2$-$10^{15}$ per mm$^2$; and
b) generating a plurality of immobilized single stranded nucleic acid concatemer template molecules by:
1) hybridizing a plurality of single stranded circular nucleic acid library molecules to the plurality of immobilized first universal surface primers; and
2) conducting an on-support rolling circle amplification reaction with (i) a plurality of strand-displacing polymerases, (ii) a plurality of nucleotides, and (iii) a plurality of compaction oligonucleotides,
thereby generating the plurality of immobilized single stranded nucleic acid concatemer template molecules, wherein individual compaction oligonucleotides comprise a single-stranded linear oligonucleotide having a first binding region capable of hybridizing to a first portion of a concatemer molecule and a second binding region capable of hybridizing to a second portion of the concatemer molecule,
wherein the plurality of immobilized concatemer molecules forms a compact nucleic acid nanostructure, and
wherein the plurality of concatemers remains immobilized to the support upon forming the compact nucleic acid nanostructure, thereby generating a support having a density of about $10^2$-$10^{15}$ per mm$^2$ of nanostructures immobilized to the support.

In some embodiments, the support is passivated with at least one layer of a hydrophilic polymer coating including the plurality of first universal surface primers. In some embodiments, the plurality of immobilized first universal surface primers is located on the support or hydrophilic polymer coating at random positions. In some embodiments, the plurality of immobilized first universal surface primers is located on the support or hydrophilic polymer coating at pre-determined positions. In some embodiments, each of the first universal surface primers lacks a scissile moiety that can be converted into abasic sites. In some embodiments, the scissile moiety is a uridine, an 8-oxo-7,8-dihydroguanine, or a deoxyinosine. In some embodiments, the plurality of nucleotides for the rolling circle amplification reaction comprises dATP, dCTP, dGTP and dTTP, and wherein the nucleotides lack a scissile moiety that can be converted into an abasic site. In some embodiments, the plurality of nucleotides for the rolling circle amplification reaction comprises dATP, dCTP, dGTP, dTTP, and nucleotides having a scissile moiety that can be converted into abasic sites. In some embodiments, the nucleotide having the scissile moiety comprises uridine, 8-oxo-7,8-dihydroguanine, or deoxyinosine. In some embodiments, the rolling circle amplification reaction of step (b), generates a plurality of single stranded nucleic acid concatemer template molecules, wherein individual concatemer template molecules include at least two nucleotides each having a scissile moiety distributed at random positions along individual immobilized concatemer template molecules.

In some embodiments, the plurality of compaction oligonucleotides in step (b) comprises the same sequence. In some embodiments, the sequence is according to any one of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156.

In some embodiments, the plurality of compaction oligonucleotides in step (b) comprises a mixture of two or more different populations of compaction oligonucleotides, each population having different sequences, wherein the compaction oligonucleotides in the different populations have different sequences. In some embodiments, the mixture comprises 2, 3, 4, 5, 6, 7, 8, 9, or 10 different populations of compaction oligonucleotides. In some embodiments, each population of compaction oligonucleotides in the mixture comprises a sequence according to any of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, or 156.

In some embodiments, the compact nucleic acid nanostructures comprise one or more loops, or comprises a spherical shape, elongated shape, proto-toroid shape, or toroid shape. In some embodiments, the spherical shape is a nanoball. In some embodiments, the elongated shape is a nanorod. In some embodiments, the toroid shape is a nanotoroid.

In some embodiments, the nucleic acid nanostructure comprises a compact nucleic acid structure having a full width half maximum (FWHM) smaller than a concatemer that is not collapsed/folded into a nanostructure.

In some embodiments, the method further comprises imaging the high-density nucleic acid nanostructures immobilized on the support.

In some embodiments, the method further comprises:
a) contacting the plurality of immobilized nucleic acid nanostructures with an oligonucleotide labeled with a detectable reporter moiety under a condition suitable for hybridizing the labeled oligonucleotides to the immobilized nucleic acid nanostructures to generate a plurality of immobilized labeled nanostructures; and
b) imaging the plurality of immobilized labeled nanostructures.

In some embodiments, the method further comprises contacting individual immobilized nanostructures with (i) a plurality of soluble sequencing primers, (ii) a plurality of sequencing polymerases, and (iii) a plurality of nucleotide reagents, under a condition suitable for:
hybridizing the plurality of soluble sequencing primers to an individual immobilized nanostructure to generate a plurality of nucleic acid duplexes along the individual nanostructures, and
for binding at least one nucleic acid duplexes with a sequencing polymerase and a nucleotide reagent.

In some embodiments, the plurality of nucleotide reagents comprises a plurality of nucleotides, each nucleotide comprising an aromatic base, a five-carbon sugar, and at least one phosphate group. In some embodiments, at least one of the nucleotides in the plurality further comprises a detectable reporter moiety. In some embodiments, the detectable reporter moiety is a fluorophore.

In some embodiments, the method further comprises:
a) contacting the plurality of immobilized nucleic acid nanostructures with a labeled nucleotide; and
b) imaging the high-density nucleic acid nanostructures immobilized on the support.

In some embodiments, the plurality of nucleotide reagents comprises a plurality of nucleotide analogs each comprising an aromatic base, a five-carbon sugar having a 3' chain terminating moiety that inhibits polymerase-catalyzed nucleotide incorporation, and at least one phosphate group. In some embodiments, at least one of the nucleotide analogs in the plurality further comprises a detectable reporter moiety. In some embodiments, the detectable reporter moiety is a fluorophore.

In some embodiments, the method further comprises
a) contacting the plurality of immobilized nucleic acid nanostructures with a labeled a labeled nucleotide analog; and
b) imaging the high-density nucleic acid nanostructures immobilized on a support.

In some embodiments, the plurality of nucleotide reagents comprises a plurality of multivalent molecules, wherein individual multivalent molecules comprise: (1) a core; and (2) a plurality of nucleotide arms which comprise (i) a core attachment moiety, (ii) a spacer, (iii) a linker, and (iv) a nucleotide unit, wherein the core is attached to the plurality of nucleotide arms, the spacer is attached to the linker, the linker is attached to the nucleotide unit, and the nucleotide unit comprises an aromatic base, a five-carbon sugar, and at least one phosphate group.

In some embodiments, the method further comprises forming a plurality of binding complexes, comprising the steps:
a) binding a first sequencing primer, a first sequencing polymerase, and a first multivalent molecule to a first portion of an individual immobilized nanostructure thereby forming a first binding complex, wherein a first nucleotide unit of the first multivalent molecule binds to the first sequencing polymerase; and
b) binding a second sequencing primer, a second sequencing polymerase, and the first multivalent molecule to a second portion of the same individual immobilized nanostructure thereby forming a second binding complex, wherein a second nucleotide unit of the first multivalent molecule binds to the second sequencing polymerase, wherein the first and second binding complexes including the same multivalent molecule form an avidity complex.

In some embodiments, at least one of the multivalent molecules in the plurality further comprises at least one detectable reporter moiety. In some embodiments, the at least one detectable reporter moiety comprises at least one fluorophore.

In some embodiments, the method further comprises:
a) contacting the plurality of immobilized nucleic acid nanostructures with a labeled multivalent molecule; and
b) imaging the high-density nucleic acid nanostructures immobilized on the support.

In some embodiments, the method further comprises contacting the plurality of immobilized nanostructures with a cellular biological sample. In some embodiments, the cellular biological sample comprises a single cell, a section of a single cell, a plurality of cells, a section of a plurality of cells, a tissue, a section of a tissue, an organ, a section of an organ, an organism, or a section of an organism.

In some embodiments, the plurality of immobilized nucleic acid nanostructures is in fluid communication with each other to permit flowing a solution of reagents onto the support so that the plurality of immobilized nucleic acid nanostructures on the support react with the solution of reagents in a massively parallel manner.

DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

The features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2C shows schematics of several embodiments of linear compaction oligonucleotides each comprising a first binding region, a first intervening linker, a second binding region, a second intervening linker, and a third binding region. In some embodiments, a compaction oligonucleotide comprises a first binding region arranged in a 3' to 5' orientation, a second binding region arranged in a 5' to 3' orientation, and a third binding region arranged in a 5' to 3' orientation (FIG. 2C (vii)). In some embodiments, a compaction oligonucleotide comprises a first binding region arranged in a 3' to 5' orientation, a second binding region arranged in a 3' to 5' orientation, and a third binding region arranged in a 5' to 3' orientation (FIG. 2C (viii)). In some embodiments, a compaction oligonucleotide comprises a first binding region arranged in a 3' to 5' orientation, a second binding region arranged in a 5' to 3' orientation, and a third binding region arranged in a 3' to 5' orientation (FIG. 2C (ix)).

FIG. 5 shows schematics of several embodiments of compaction oligonucleotides each comprising four binding arms linked together by at least one inner intervening linker, wherein individual binding arms comprise a binding region. In some embodiments, a compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 5' to 3' orientation where the 3' end of the second binding region is directed away from the inner intervening linker; (3) an inner intervening linker and a third binding region arranged in a 5' to 3' orientation where the 3' end of the third binding region is directed away from the inner intervening linker; and (4) an inner intervening linker and a fourth binding region arranged in a 5' to 3' orientation where the 3' end of the fourth binding region is directed away from the inner intervening linker (FIG. 5 (i)). In some embodiments, a compaction oligonucleotide comprises: (1) an inner intervening linker and a first binding region arranged in a 3' to 5' orientation where the 5' end of the first binding region is directed away from the inner intervening linker; (2) an inner intervening linker and a second binding region arranged in a 3' to 5' orientation where the 5' end of the second binding region is directed away from the inner intervening linker; (3) an inner intervening linker and a third binding region arranged in a 3' to 5' orientation where the 5' end of the third binding region is directed away from the inner intervening linker; and (4) an inner intervening linker and a fourth binding region arranged in a 3' to 5' orientation where the 5' end of the fourth binding region is directed away from the inner intervening linker (FIG. 5 (ii)).

In FIG. 13B a portion of the first binding region (110) of the first nucleic acid strand (100) hybridizes to a first portion of the concatemer which dissociates a portion of the third binding region (210) from the first binding region (110) as indicated by the two arrows. Hybridization of a portion of the first binding region (110) and the first portion of the concatemer forms a toehold duplex region. The second binding region (120) of the first nucleic acid strand (100) can remain hybridized to the fourth binding region (220) and the fifth binding region (300).

In FIG. 13C a portion of the second binding region (120) of the first nucleic acid strand (100) hybridizes to a second portion of the concatemer which dissociates a portion of the fifth binding region (300) from the second binding region (120) as indicated by the two arrows. Hybridization of the portion of the second binding region (120) and the second portion of the concatemer forms another toehold duplex region. The second nucleic acid strand (200) is completely dissociated from the first binding region (110) of the first nucleic acid strand (100).

FIGS. 14A-14H show Table 1 (8 sheets) which contains the nucleotide sequences of compaction oligonucleotides or portions of compaction oligonucleotides. The sequences are listed in sets of three: (i) sequence of a first or second binding region of a compaction oligonucleotide; (ii) reverse sequence of the first or second binding region of a compaction oligonucleotide; and (iii) full length sequence of a compaction oligonucleotide with the intervening homopolymer region that is bolded and underlined.

FIG. 15 shows Table 2 (1 sheet) which contains the nucleotide sequences of various universal adaptor sequences. The universal adaptor sequence can be part of a concatemer molecule having multiple copies of a polynucleotide unit arranged in tandem, where each polynucleotide unit comprises a sequence-of-interest and at least one universal adaptor sequence. The first binding region of a compaction oligonucleotide can hybridize to at least a portion of any one of the universal adaptor sequences listed in Table 2. The second binding region of a compaction oligonucleotide sequence can hybridize to at least a portion of any one of the universal adaptor sequences listed in Table 2.

FIG. 21-28 show the workflow of pairwise sequencing the immobilized concatemer template molecule depicted in FIG. 21.

FIG. 22 is a schematic showing an exemplary immobilized nucleic acid nanostructure generated by conducting the on-support rolling circle amplification reaction depicted in FIG. 21. The first binding region of the compaction oligonucleotide hybridizes to a first portion of the immobilized concatemer molecule, and the second binding region of the compaction oligonucleotide hybridizes to a second portion of the concatemer molecule which causes the concatemer molecule to collapse or fold into a nucleic acid nanostructure.

FIG. 23 is a schematic showing an exemplary forward sequencing reaction conducted on the immobilized nucleic acid nanostructure shown in FIG. 22. The forward sequencing reaction can be conducted with a plurality of soluble forward sequencing primers and generates a plurality of extended forward sequencing primer strands. The immobilized nanostructure can have two or more extended forward sequencing primer strands hybridized thereon.

FIG. 24 is a schematic showing an exemplary method for replacing the extended forward sequencing primer strands by conducting a primer extension reaction with a strand displacing polymerase in the absence of a soluble primer thereby generating a forward extension strand. The primer extension reaction comprises a strand displacing polymerase, a plurality of nucleotides, and a plurality of compaction oligonucleotides.

FIG. 25 is a schematic showing a forward extension strand generated by conducting a primer extension reaction as shown in FIG. 24. For the sake of clarity, the compaction oligonucleotides hybridized to the forward extension strand are not shown.

FIG. 26 is a schematic showing an exemplary method for generating abasic sites in the immobilized nucleic acid nanostructure at the nucleotides having the scissile moiety and generating gaps at the abasic sites to generate a plurality of gap-containing nanostructures while retaining the plurality of forward extension strands and retaining the plurality of immobilized first surface primers. For the sake of clarity, the compaction oligonucleotides hybridized to the forward extension strand are not shown.

FIG. 27 is a schematic showing an exemplary retained forward extension strand after removal of the gap-containing nanostructure as shown in FIG. 26.

FIG. 28 is a schematic showing an exemplary reverse sequencing reaction conducted on the retained forward extension strand shown in FIG. 27. The reverse sequencing reaction can be conducted with a plurality of soluble reverse sequencing primers, a plurality of sequencing polymerases, and a plurality of nucleotide reagents. The retained forward extension strand can have two or more extended reverse sequencing primer strands hybridized thereon.

FIG. 30-37 show the workflow of pairwise sequencing the concatemer molecule depicted in FIG. 30.

FIG. 31 is a schematic showing an exemplary method comprising distributing the rolling circle amplification reaction depicted in FIG. 30 onto a support having a first surface primer immobilized thereon. The concatemer molecule can hybridize to the immobilized first surface primer.

FIG. 32 is a schematic showing an exemplary method which depicts the rolling circle amplification reaction (e.g., from FIG. 31) continuing on the support thereby generating an immobilized concatemer template molecule which includes at least one nucleotide with a scissile moiety which can be cleaved to generate an abasic site in the immobilized concatemer template molecule. The rolling circle amplification reaction includes a plurality of compaction oligonucleotides. The first binding region of the compaction oligonucleotide hybridizes to a first portion of the immobilized concatemer molecule, and the second binding region of the compaction oligonucleotide hybridizes to a second portion of the concatemer molecule which causes the concatemer molecule to collapse or fold into a nucleic acid nanostructure.

FIG. 33 is a schematic showing an exemplary forward sequencing reaction conducted on the immobilized nucleic acid nanostructure shown in FIG. 32. The forward sequencing reaction can be conducted with a plurality of soluble forward sequencing primers. The immobilized nucleic acid nanostructure can have two or more extended forward sequencing primer strands hybridized thereon.

FIG. 34 is a schematic showing an exemplary method for replacing the extended forward sequencing primer strands by conducting a primer extension reaction with a strand displacing polymerase in the absence of a soluble primer.

The primer extension reaction comprises a strand displacing polymerase, a plurality of nucleotides, and a plurality of compaction oligonucleotides.

Figure 34:
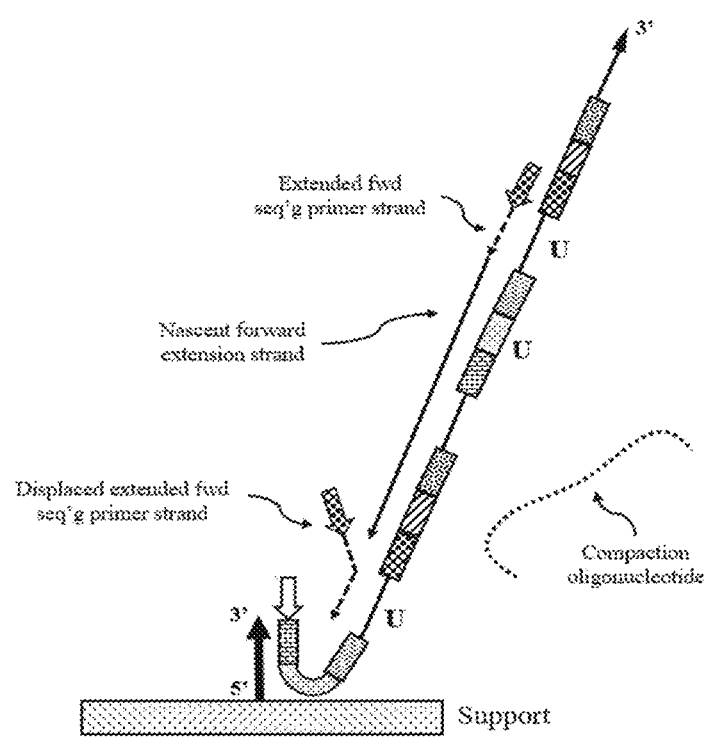
Figure 35:
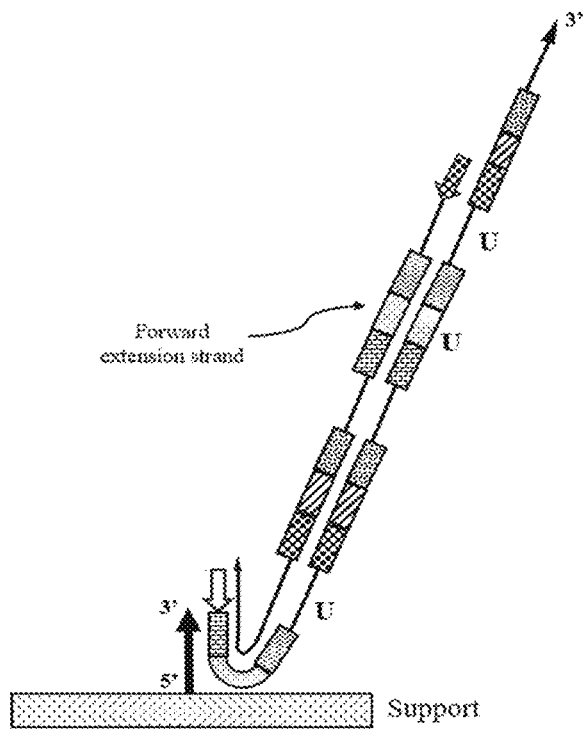

FIG. 35 is a schematic showing a forward extension strand generated by conducting a primer extension reaction as shown in FIG. 34. For the sake of clarity, the compaction oligonucleotides hybridized to the forward extension strand are not shown.

Figure 36:
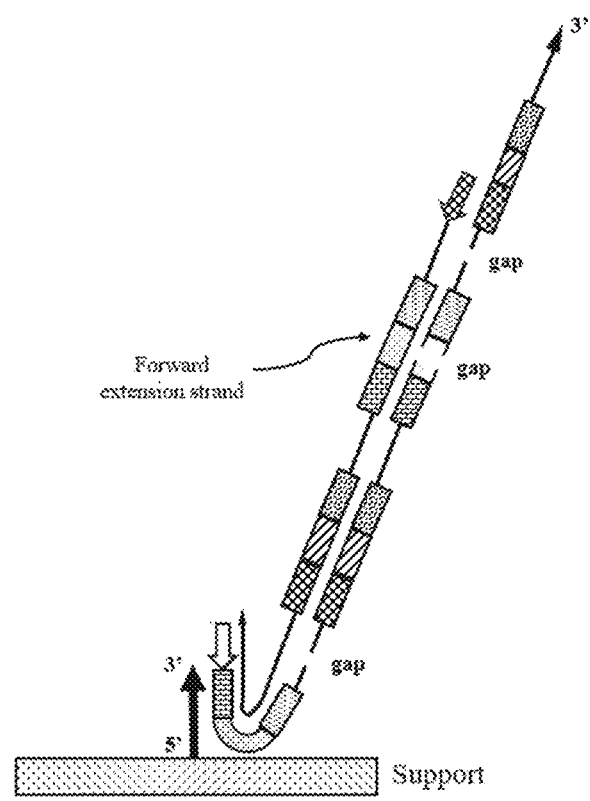

FIG. 36 is a schematic showing an exemplary method for generating abasic sites in the immobilized nucleic acid nanostructure at the nucleotides having the scissile moiety and generating gaps at the abasic sites to generate a plurality of gap-containing nanostructures while retaining the plurality of forward extension strands and retaining the plurality of immobilized first surface primers. For the sake of clarity, the compaction oligonucleotides hybridized to the forward extension strand are not shown.

Figure 37:
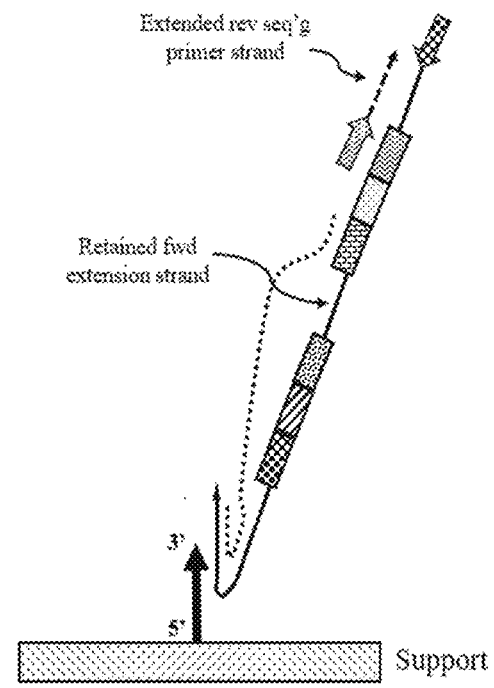

FIG. 37 is a schematic showing an exemplary reverse sequencing reaction conducted on the retained forward extension strand (e.g., from FIG. 36). The reverse sequencing reaction can be conducted with a plurality of soluble reverse sequencing primers, a plurality of sequencing polymerases, and a plurality of nucleotide reagents. The retained forward extension strand is a concatemer molecule that can include two or more tandem copies of the sequence of interest and various primer binding sites. Such a concatemer molecule can have two or more extended reverse sequencing primer strands hybridized thereon. For the sake of simplicity, FIG. 37 shows an exemplary immobilized retained forward extension strand hybridized with one reverse sequencing primer and undergoing a reverse sequencing reaction to generate an extended reverse sequencing primer strand. The skilled artisan will appreciate that the immobilized retained forward extension strand can be hybridized to two or more extended reverse sequencing primer strands.

Figure 30:
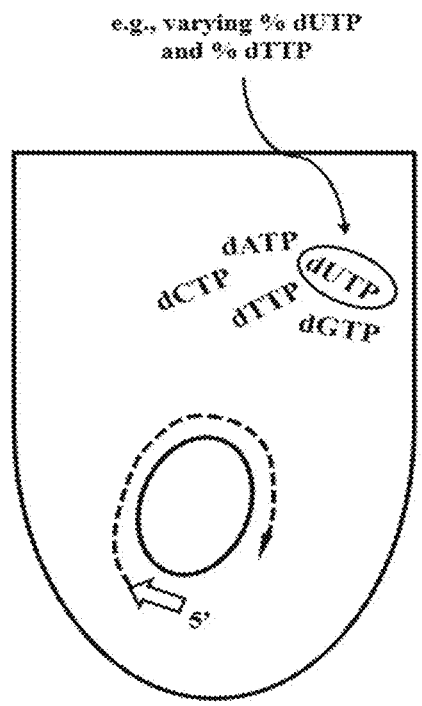
FIG. 30 is a schematic showing an exemplary in-solution rolling circle amplification reaction using (i) a nucleic acid circular library molecule, (ii) a soluble first amplification primer, (iii) a mixture of nucleotides including nucleotides having a scissile moiety that can be cleaved to generate an abasic site, and (iv) a strand displacing polymerase. The rolling circle amplification reaction generates in solution single stranded nucleic acid concatemer molecules having at least one nucleotide with a scissile moiety which can be cleaved to generate an abasic site in the concatemer molecule. The circular library molecule comprises a sequence-of-interest and at least one universal adaptor sequence including for example a binding sequence for a first surface primer.
Figure 31:
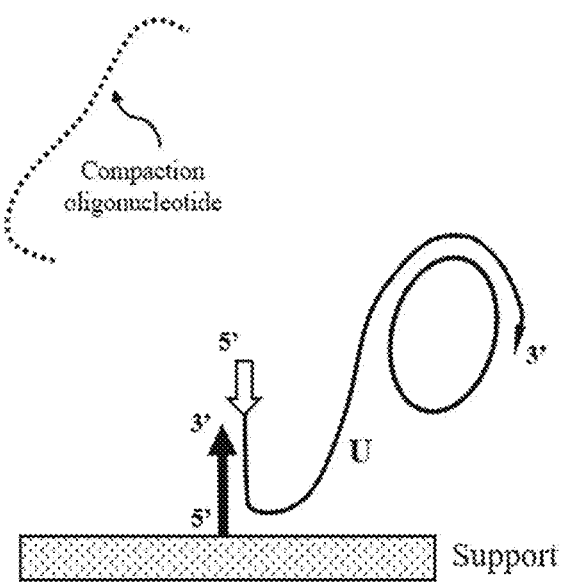
Figure 32:
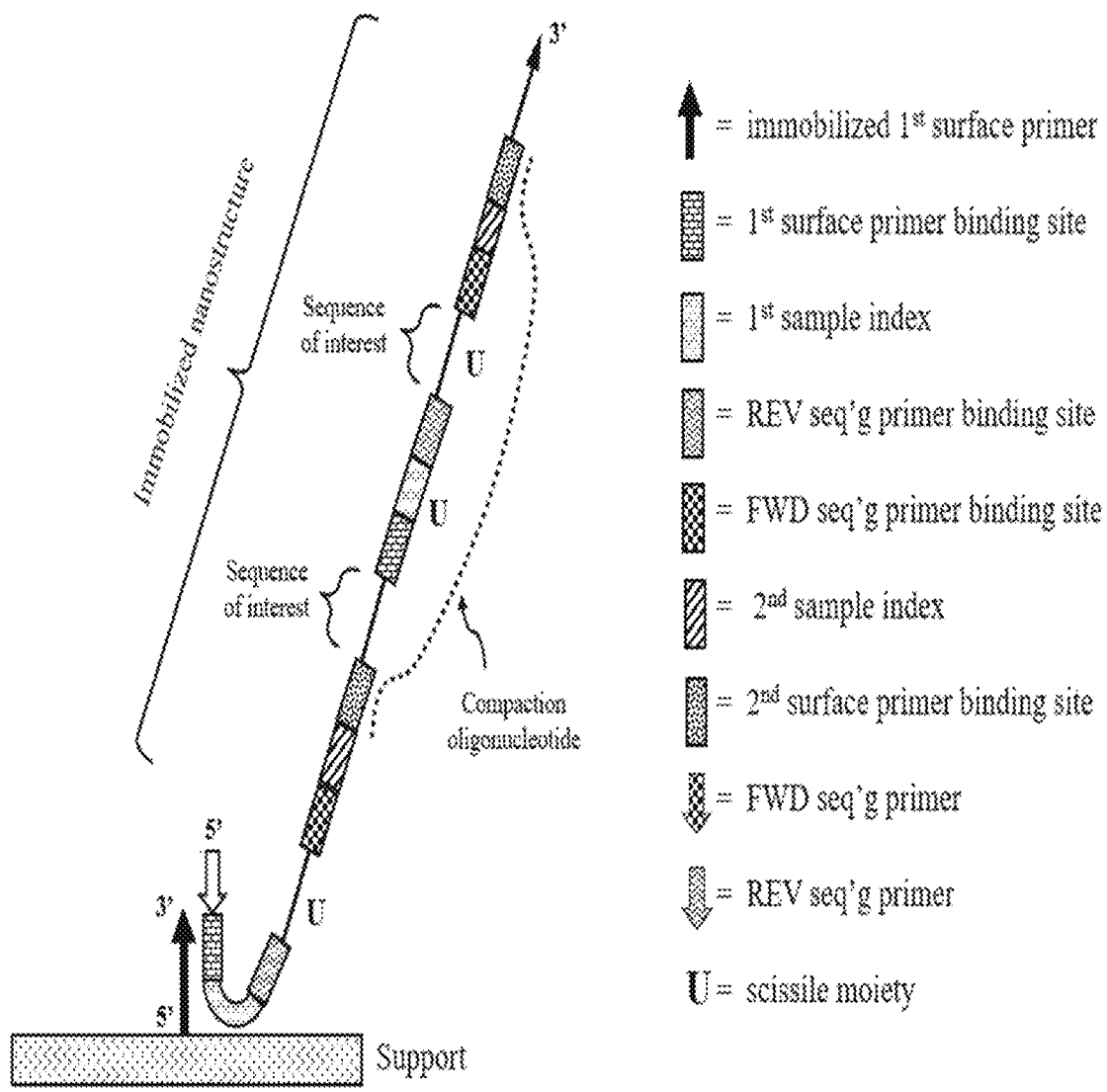
Figure 38:
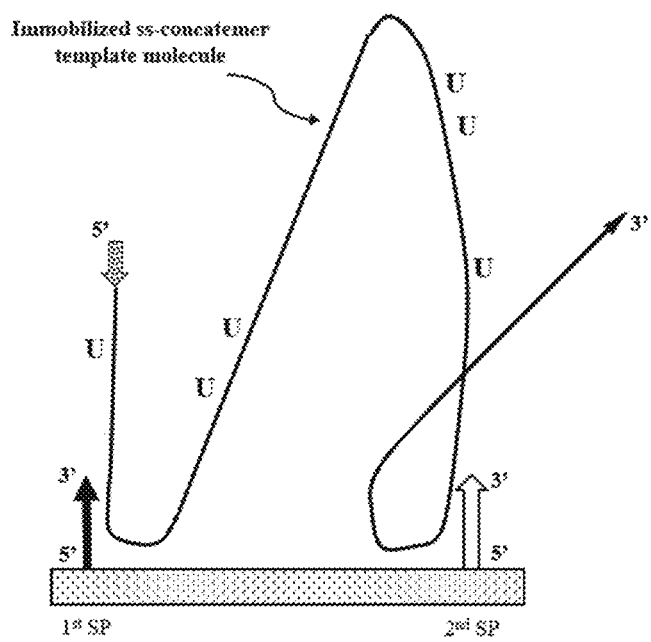

FIG. 38 is a schematic showing an exemplary support having a first and second surface primers immobilized thereon, and an immobilized concatemer which was generated by the in-solution RCA workflow depicted in FIGS. 30-32. A portion of the concatemer is hybridized to the immobilized second surface primer. The immobilized concatemer template molecule has two or more copies of a universal binding sequence for an immobilized second surface primer. The portion of the immobilized concatemer template molecule that includes the universal binding sequence for an immobilized second surface primer can hybridize to the immobilized second surface primer.

Figure 39:
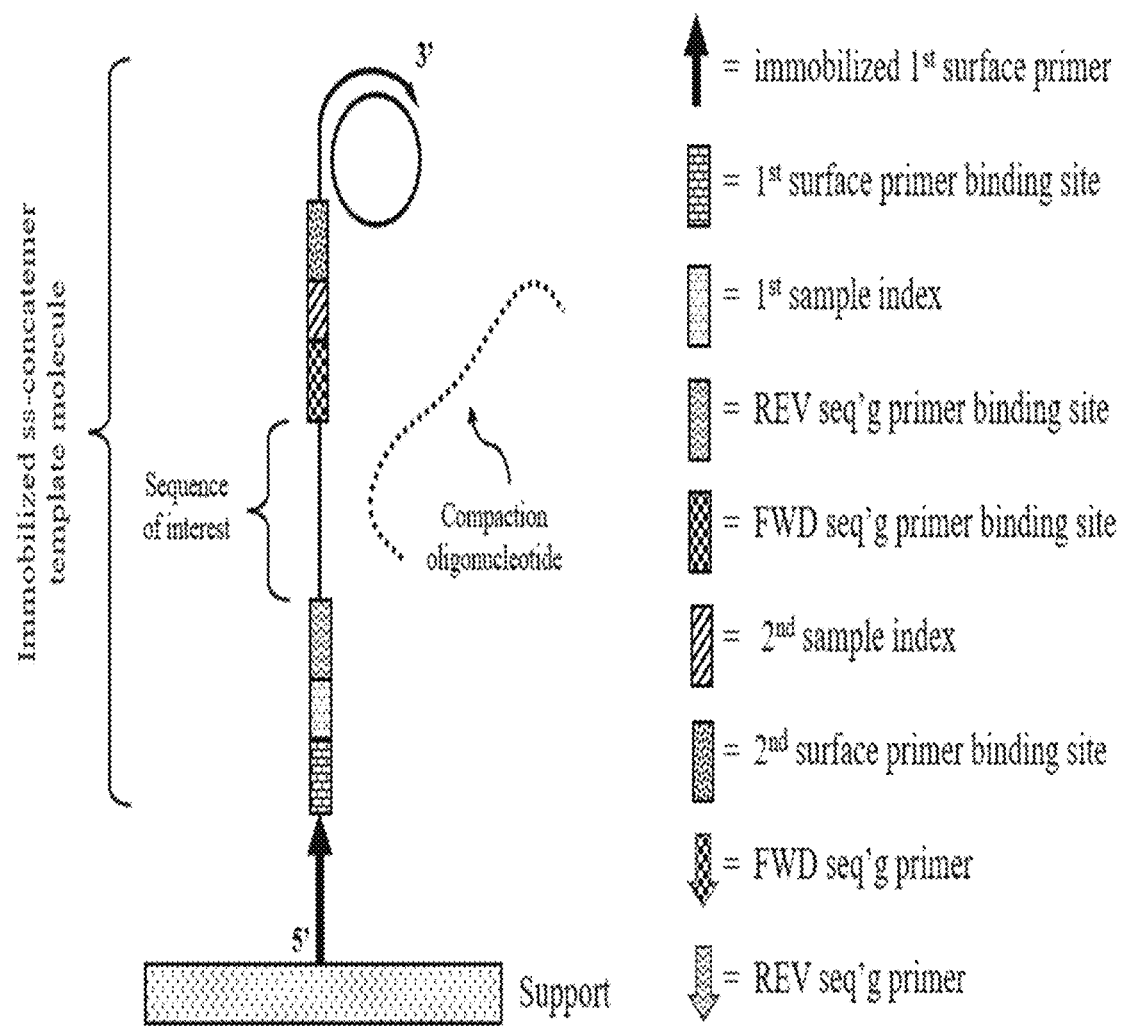

FIG. 39 is a schematic showing an exemplary on-support rolling circle amplification reaction using (i) an immobilized first surface primer, (ii) a nucleic acid circular library molecule, (iii) a mixture of nucleotides which lacks nucleotides having a scissile moiety that can be cleaved to generate an abasic site, (iv) a strand-displacing polymerase, and (iv) a compaction oligonucleotide. The rolling circle amplification reaction generates an immobilized single stranded nucleic acid concatemer template molecule. The arrangement of the various primer binding sequences in the nucleic acid circular library molecule is for illustration purposes. The skilled artisan will appreciate that many other arrangements are possible. FIGS. 39-45 show the workflow of pairwise sequencing the immobilized concatemer template molecule depicted in FIG. 39.

Figure 40:
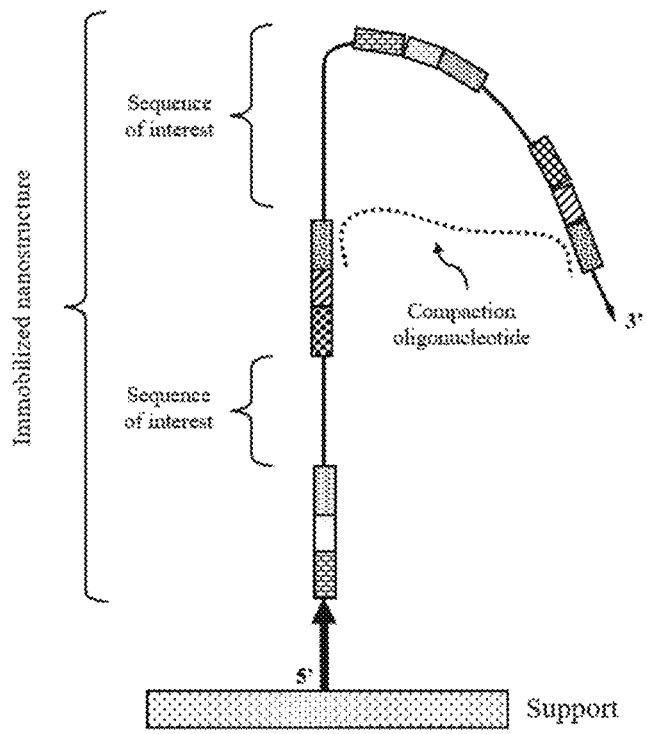

FIG. 40 is a schematic showing an exemplary immobilized nucleic acid nanostructure generated by conducting the on-support rolling circle amplification reaction depicted in FIG. 39. The first binding region of the compaction oligonucleotide hybridizes to a first portion of the immobilized concatemer molecule, and the second binding region of the compaction oligonucleotide hybridizes to a second portion of the concatemer molecule which causes the concatemer molecule to collapse or fold into a nucleic acid nanostructure.

Figure 41:
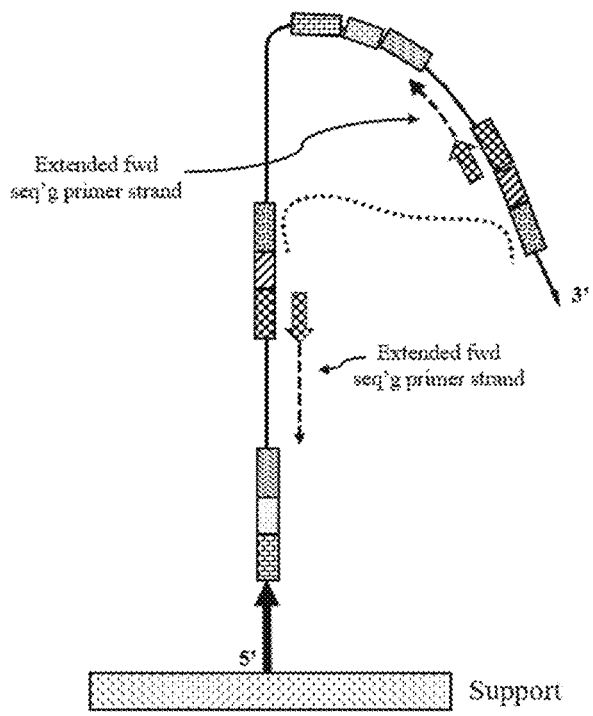

FIG. 41 is a schematic showing an exemplary forward sequencing reaction conducted on the immobilized nucleic acid nanostructure shown in FIG. 40. The forward sequencing reaction can be conducted with a plurality of soluble forward sequencing primers and generates a plurality of extended forward sequencing primer strands. The immobilized nanostructure can have two or more extended forward sequencing primer strands hybridized thereon.

Figure 42:
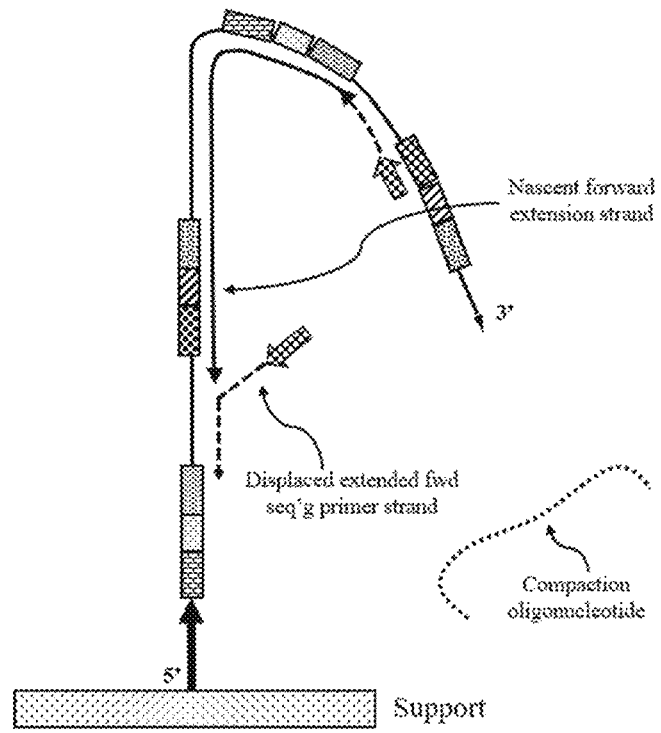

FIG. 42 is a schematic showing an exemplary method for replacing the extended forward sequencing primer strands by conducting a primer extension reaction with a strand displacing polymerase in the absence of a soluble primer thereby generating a forward extension strand. The primer extension reaction comprises a strand displacing polymerase, a plurality of nucleotides, and a plurality of compaction oligonucleotides.

Figure 43:
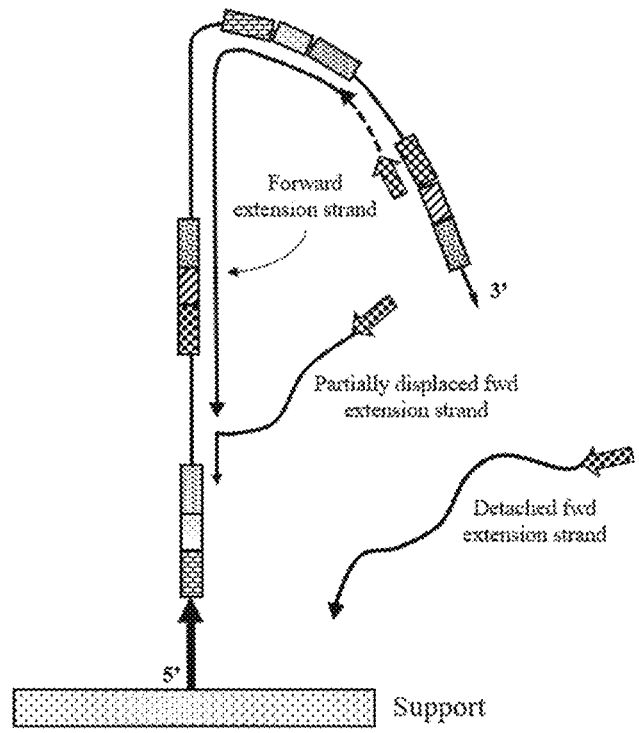

FIG. 43 is a schematic showing a continuation of the exemplary strand displacing method shown in FIG. 42, where the polymerase-catalyzed strand displacing reaction generates a forward extension strand and a partially displaced forward extension strand which are hybridized to the immobilized concatemer molecule, and a detached forward extension strand which is not hybridized to the immobilized concatemer molecule.

Figure 44:
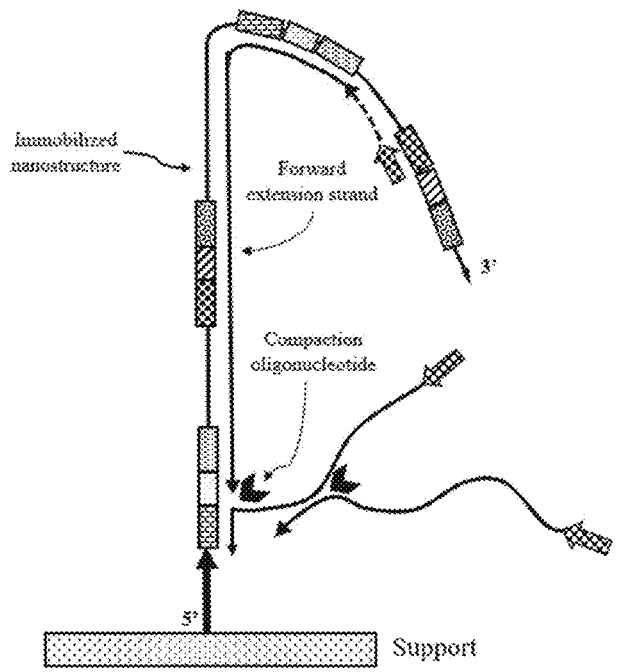

FIG. 44 is a schematic showing an exemplary hybridization complex comprising a forward extension strand and a partially displaced forward extension strand which are hybridized to the immobilized concatemer molecule, and an immobilized detached forward extension strand which is hybridized to the partially displaced forward extension strand via a compaction oligonucleotide.

Figure 45:
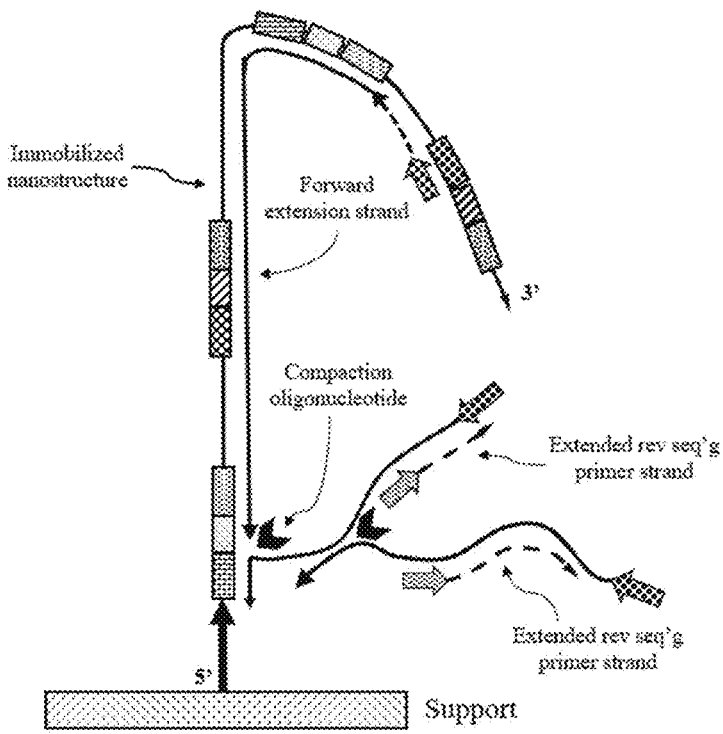

FIG. 45 is a schematic showing an exemplary reverse sequencing reaction conducted on the hybridization complex shown in FIG. 44. The reverse sequencing reaction can be conducted with a plurality of soluble reverse sequencing primers on the partially displaced forward extension strand and the immobilized detached forward extension strand. The reverse sequencing reaction generates extended reverse sequencing primer strands. For the sake of simplicity, FIG. 45 shows one copy of an extended reverse sequencing primer strand on the partially displaced forward extension strand, and one copy of an extended reverse sequencing primer strand on the immobilized detached forward extension strand. The skilled artisan will appreciate that the partially displaced forward extension strand and the immobilized detached forward extension strand can include two or more extended reverse sequencing primer strands hybridized thereon.

Figure 46:
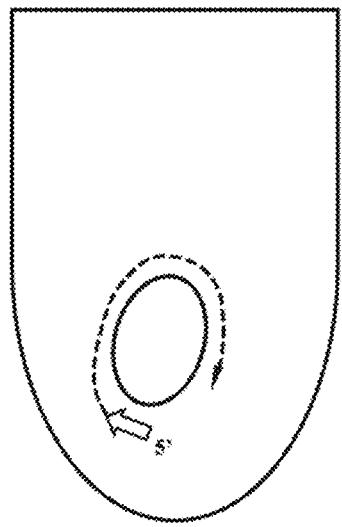

FIG. 46 is a schematic showing an exemplary in-solution rolling circle amplification reaction using (i) a nucleic acid circular library molecule, (ii) a soluble first amplification primer, (iii) a mixture of nucleotides which lacks nucleotides having a scissile moiety that can be cleaved to generate an abasic site, and (iv) a strand displacing polymerase. The rolling circle amplification reaction generates in solution single stranded nucleic acid concatemer molecules. The circular library molecule comprises a sequence-of-interest and at least one universal adaptor sequence including for example a binding sequence for a first surface primer. FIGS. 46-53 show the workflow of pairwise sequencing the concatemer molecule depicted in FIG. 46.

Figure 47:
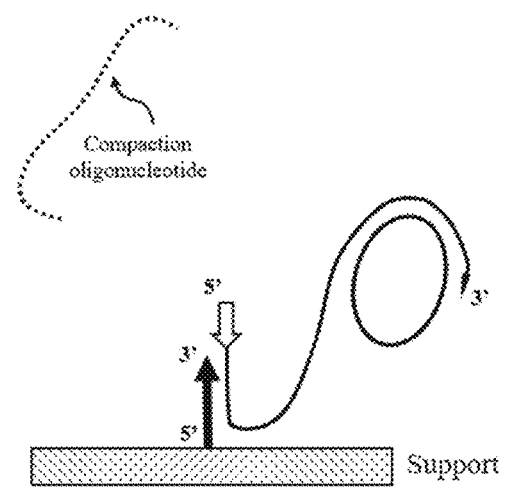

FIG. 47 is a schematic showing an exemplary method comprising distributing the rolling circle amplification reaction depicted in FIG. 46 onto a support having a first surface primer immobilized thereon. The concatemer molecule can hybridize to the immobilized first surface primer.

Figure 48:
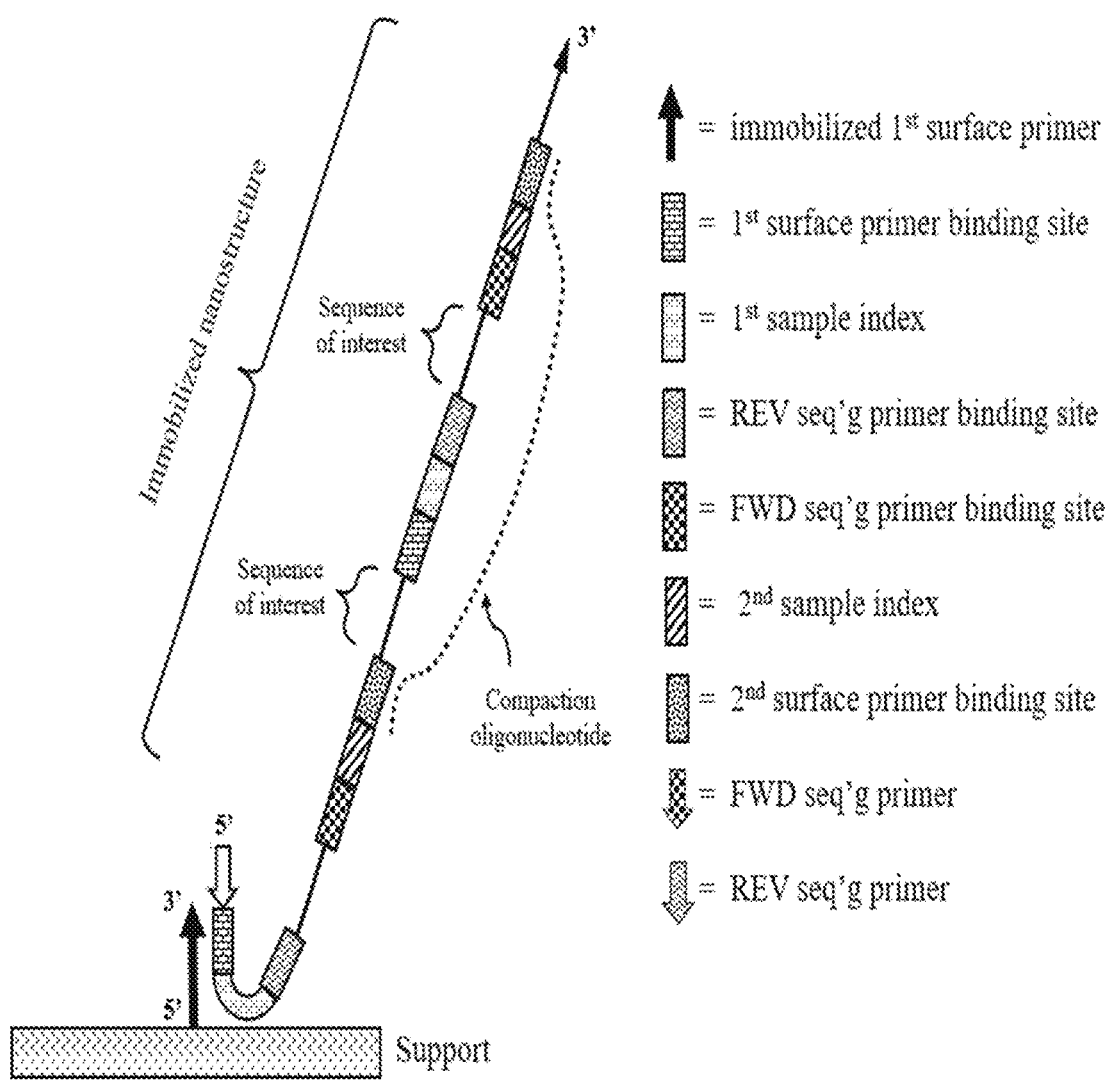

FIG. 48 is a schematic showing an exemplary method which depicts the rolling circle amplification reaction (e.g., from FIG. 47) continuing on the support thereby generating an immobilized concatemer template molecule. The rolling circle amplification reaction includes a plurality of compaction oligonucleotides. The first binding region of the compaction oligonucleotide hybridizes to a first portion of the immobilized concatemer molecule, and the second binding region of the compaction oligonucleotide hybridizes to a second portion of the concatemer molecule which causes the concatemer molecule to collapse or fold into a nucleic acid nanostructure.

Figure 49:
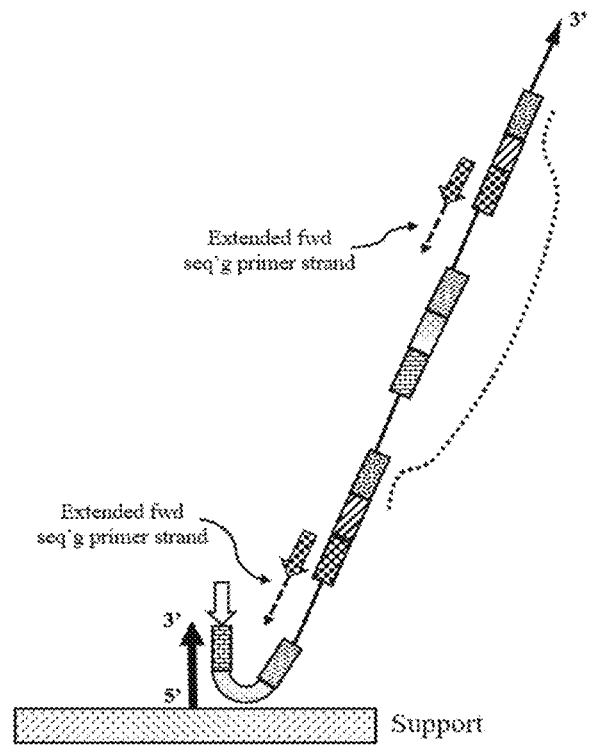

FIG. 49 is a schematic showing an exemplary forward sequencing reaction conducted on the immobilized nucleic acid nanostructure shown in FIG. 48. The forward sequencing reaction can be conducted with a plurality of soluble forward sequencing primers. The immobilized nucleic acid nanostructure can have two or more extended forward sequencing primer strands hybridized thereon.

Figure 50:
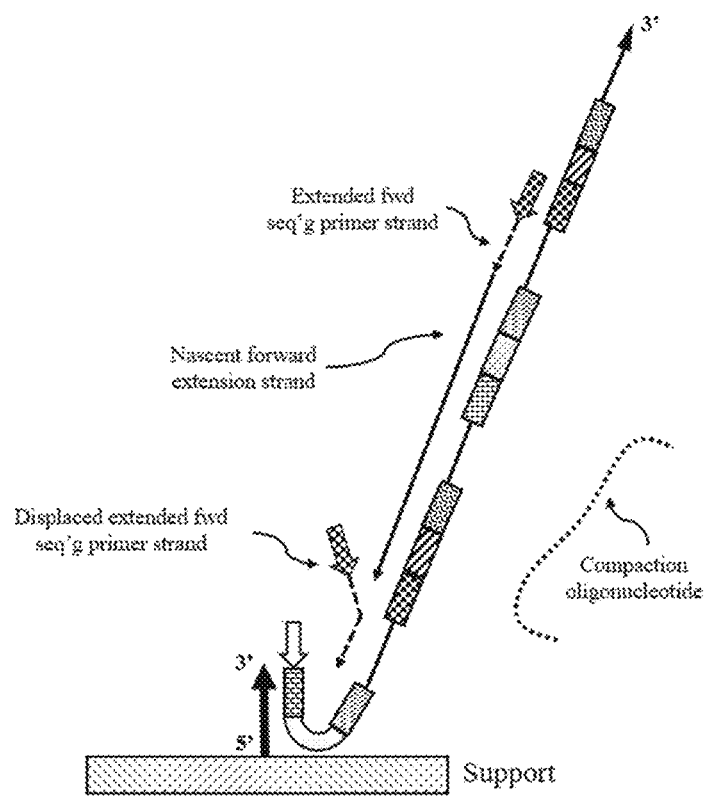

FIG. 50 is a schematic showing an exemplary method for replacing the extended forward sequencing primer strands by conducting a primer extension reaction with a strand displacing polymerase in the absence of a soluble primer. The primer extension reaction comprises a strand displacing polymerase, a plurality of nucleotides, and a plurality of compaction oligonucleotides.

Figure 51:
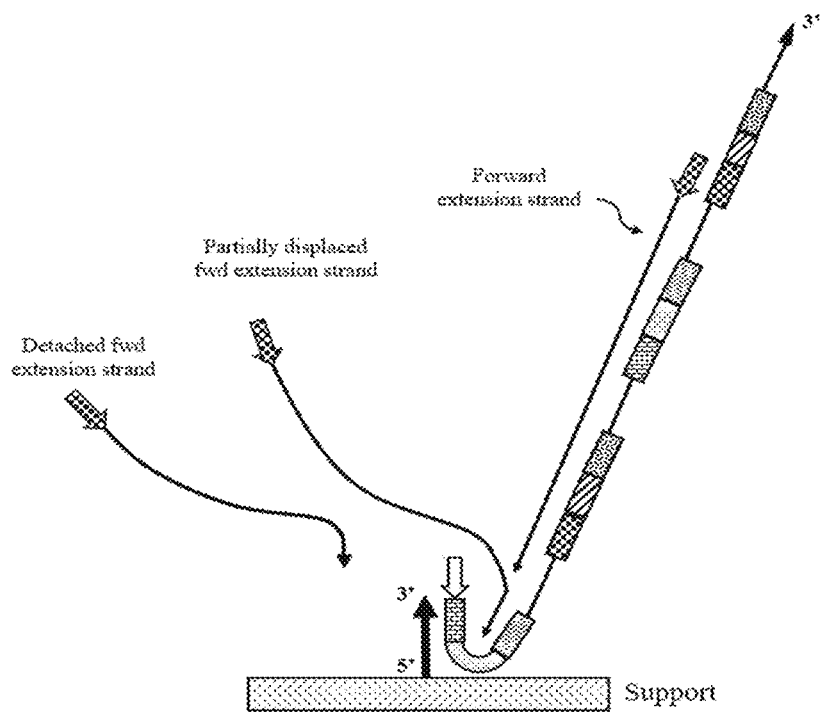

FIG. 51 is a schematic showing a continuation of the exemplary strand displacing method shown in FIG. 50, where the polymerase-catalyzed strand displacing reaction generates a forward extension strand and a partially displaced forward extension strand which are hybridized to the immobilized concatemer molecule, and a detached forward extension strand which is not hybridized to the immobilized concatemer molecule.

Figure 52:
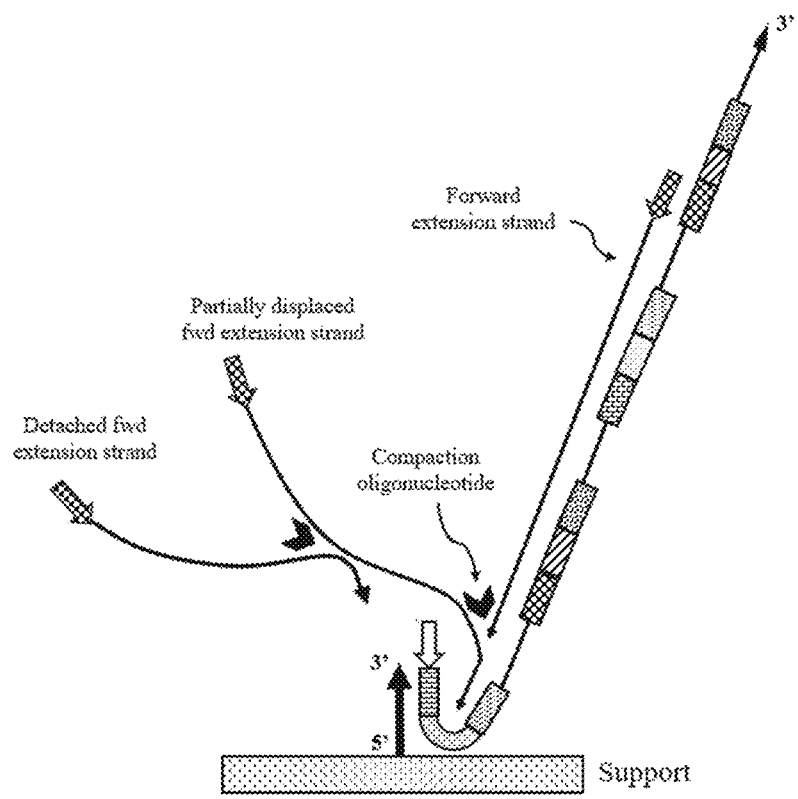

FIG. 52 is a schematic showing an exemplary hybridization complex comprising a forward extension strand and a partially displaced forward extension strand which are hybridized to the immobilized concatemer molecule, and an immobilized detached forward extension strand which is hybridized to the partially displaced forward extension strand via a compaction oligonucleotide.

Figure 53:
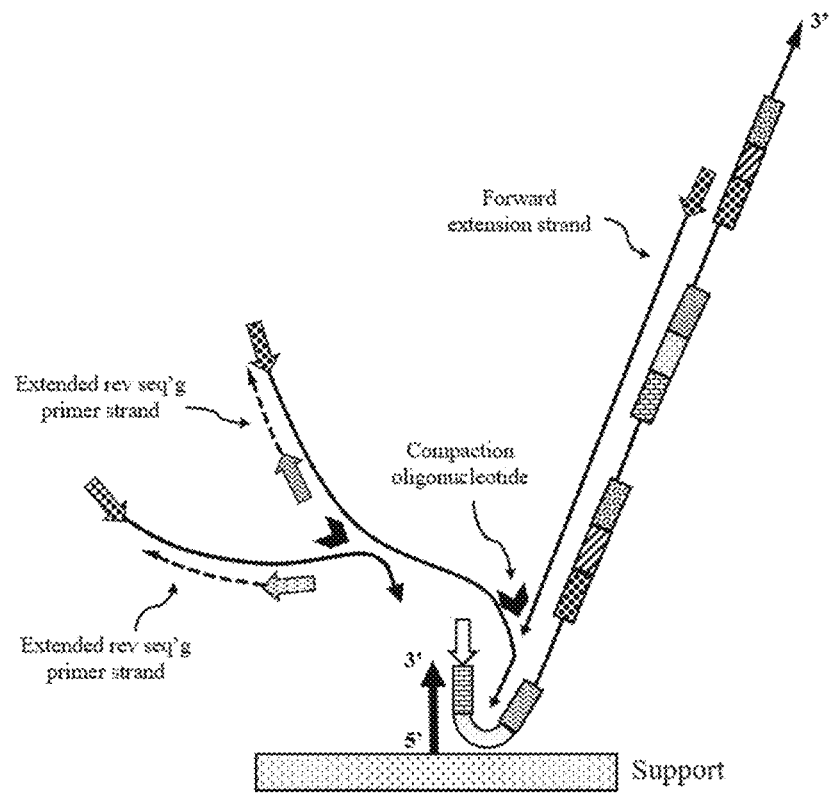

FIG. 53 is a schematic showing an exemplary reverse sequencing reaction conducted on the hybridization complex shown in FIG. 52. The reverse sequencing reaction can be conducted with a plurality of soluble reverse sequencing primers on the partially displaced forward extension strand and the immobilized detached forward extension strand. The reverse sequencing reaction generates extended reverse sequencing primer strands. For the sake of simplicity, FIG. 53 shows one copy of an extended reverse sequencing primer strand on the partially displaced forward extension strand, and one copy of an extended reverse sequencing primer strand on the immobilized detached forward extension strand. The skilled artisan will appreciate that the partially displaced forward extension strand and the immobilized detached forward extension strand can include two or more extended reverse sequencing primer strands hybridized thereon.

Figure 54:
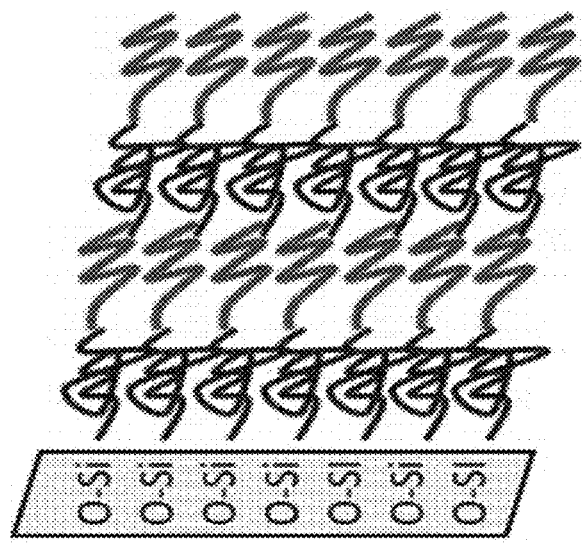

FIG. 54 is a schematic of one embodiment of the low binding support comprising a glass substrate and alternating layers of hydrophilic coatings which are covalently or non-covalently adhered to the glass, and which further comprises chemically-reactive functional groups that serve as attachment sites for oligonucleotide primers (e.g., capture oligonucleotides and circularization oligonucleotides). In an alternative embodiment, the support can be made of any material such as glass, plastic or a polymer material.

Figure 55A:
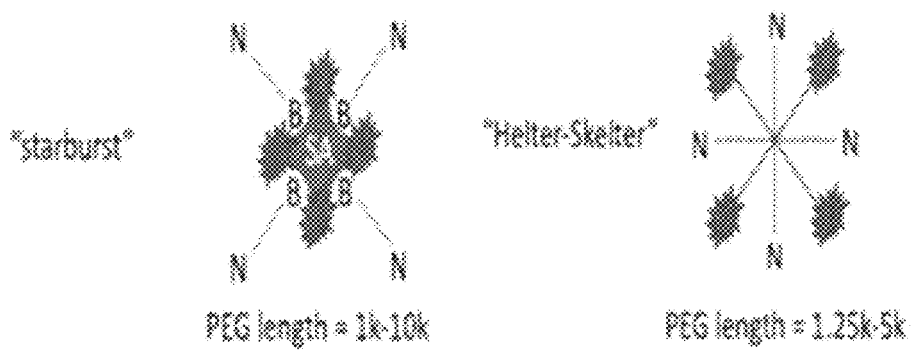

FIG. 55A is a schematic of various exemplary configurations of multivalent molecules having a starburst or helter-skelter configuration. Nucleotide units are designated 'N', biotin is designated 'B', and streptavidin is designated 'SA'.

Figure 55B:
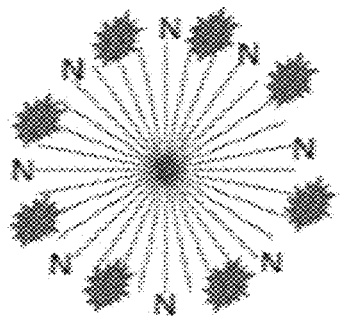

FIG. 55B a schematic of an exemplary multivalent molecule having a dendrimer configuration. Nucleotide units are designated 'N'.

Figure 55C:
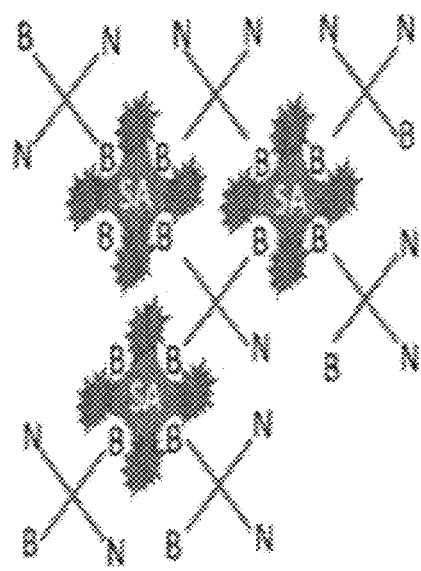

FIG. 55C a schematic of an embodiment of multiple multivalent molecules formed by reacting streptavidin with 4-arm or 8-arm PEG-NHS with biotin and dNTPs. Nucleotide units are designated 'N', biotin is designated 'B', and streptavidin is designated 'SA'.

Figure 56:
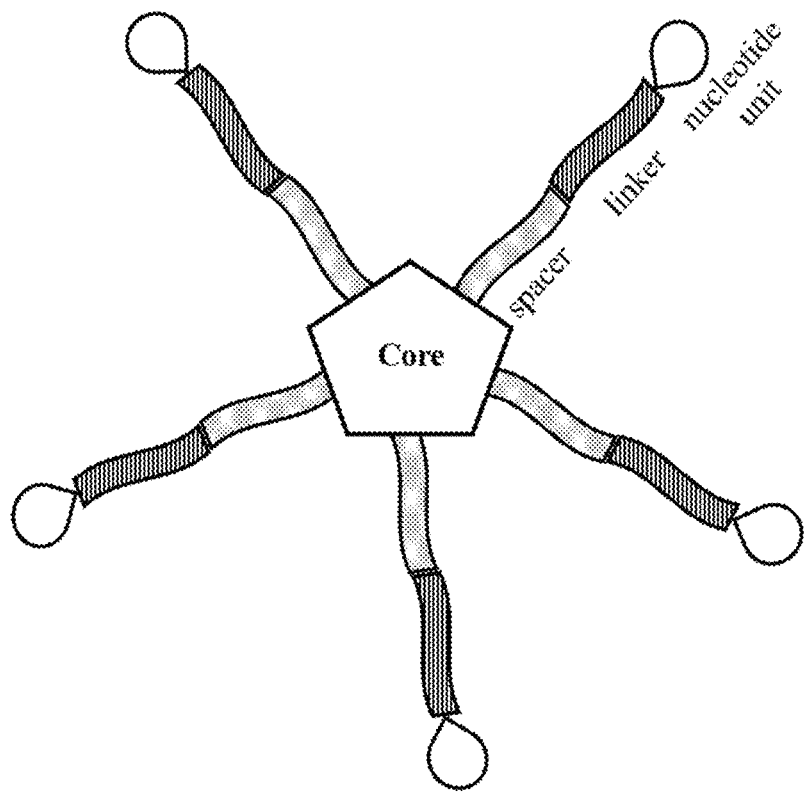

FIG. 56 is a schematic of an exemplary multivalent molecule comprising a generic core attached to a plurality of nucleotide-arms.

Figure 57:
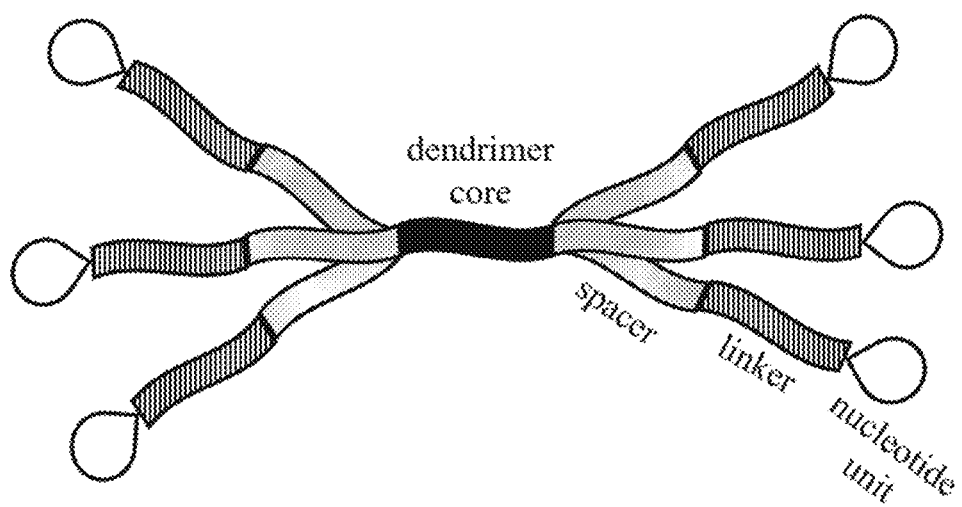

FIG. 57 is a schematic of an exemplary multivalent molecule comprising a dendrimer core attached to a plurality of nucleotide-arms.

Figure 58:
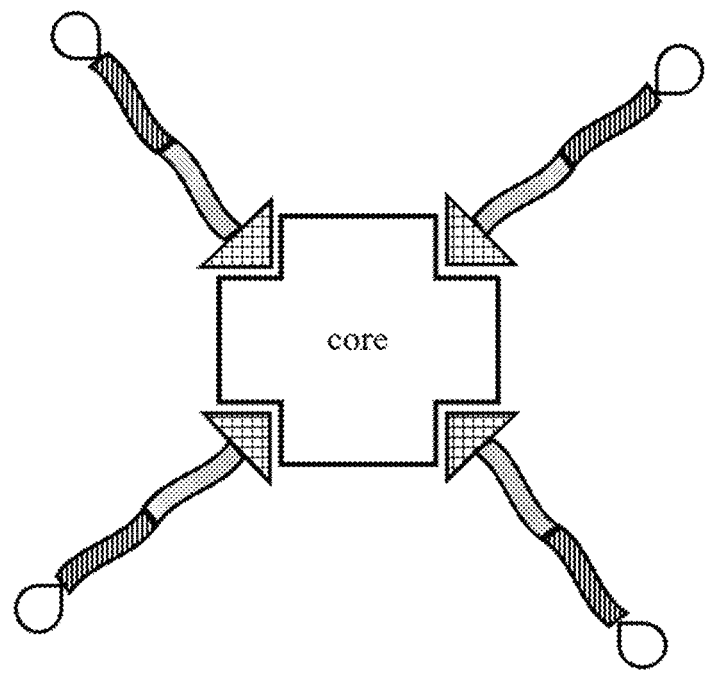

FIG. 58 shows a schematic of an exemplary multivalent molecule comprising a core attached to a plurality of nucleotide-arms, where the nucleotide arms comprise biotin, spacer, linker and a nucleotide unit.

Figure 59:
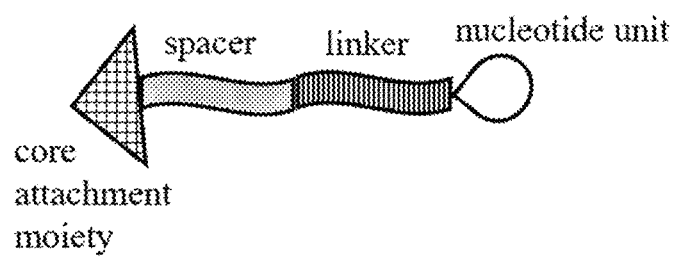

FIG. 59 is a schematic of an exemplary nucleotide-arm comprising a core attachment moiety, spacer, linker and nucleotide unit.

FIG. 60 shows the chemical structure of an exemplary spacer (top), and the chemical structures of various exemplary linkers including an 11-atom Linker, 16-atom Linker, 23-atom Linker and an N3 Linker (bottom).

Figure 61:
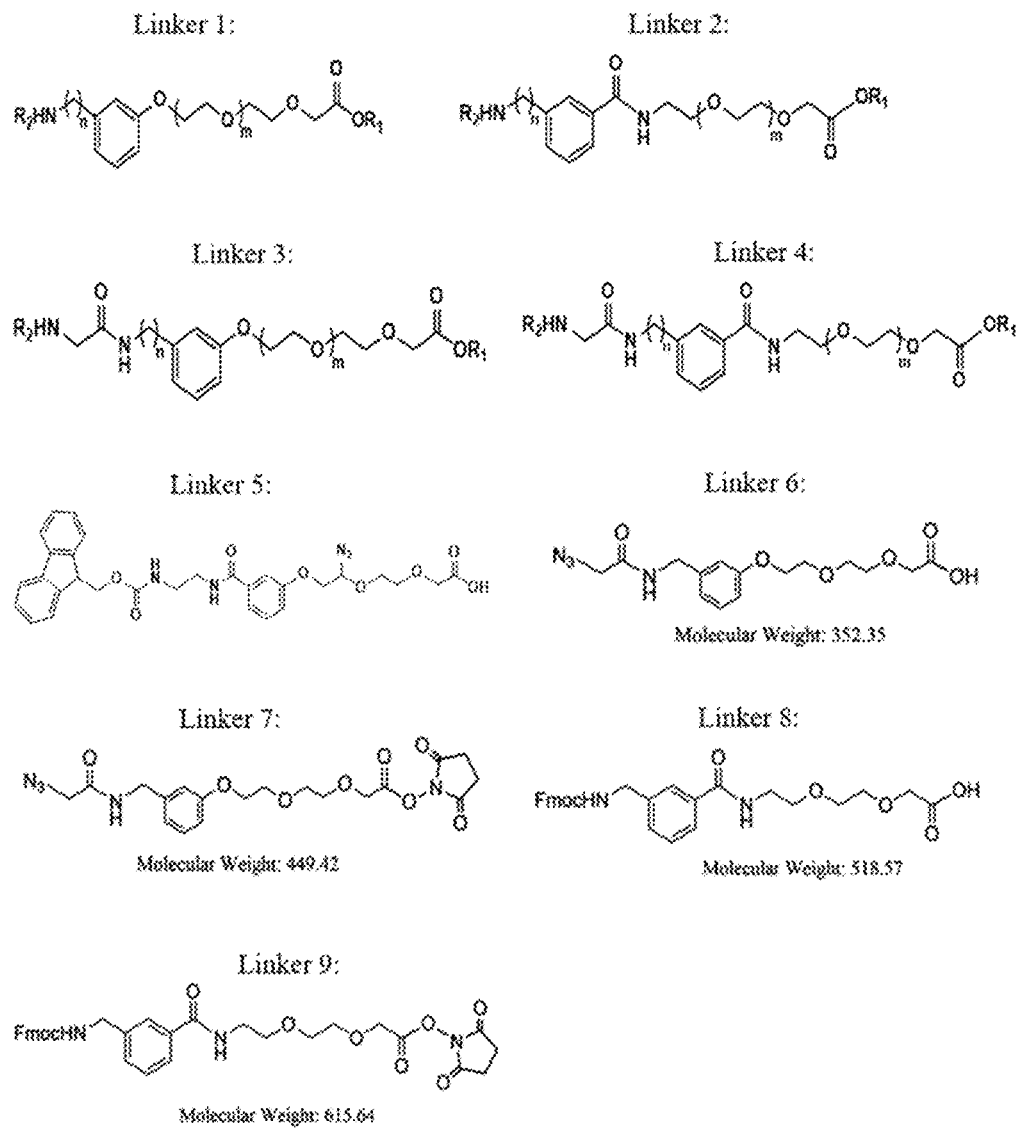

FIG. 61 shows the chemical structures of various exemplary linkers, including Linkers 1-9.

FIG. 62A shows the chemical structures of various exemplary linkers joined/attached to nucleotide units.

FIG. 62B shows the chemical structures of various exemplary linkers joined/attached to nucleotide units.

FIG. 62C shows the chemical structures of various exemplary linkers joined/attached to nucleotide units.

FIG. 62D shows the chemical structures of various exemplary linkers joined/attached to nucleotide units.

Figure 63:
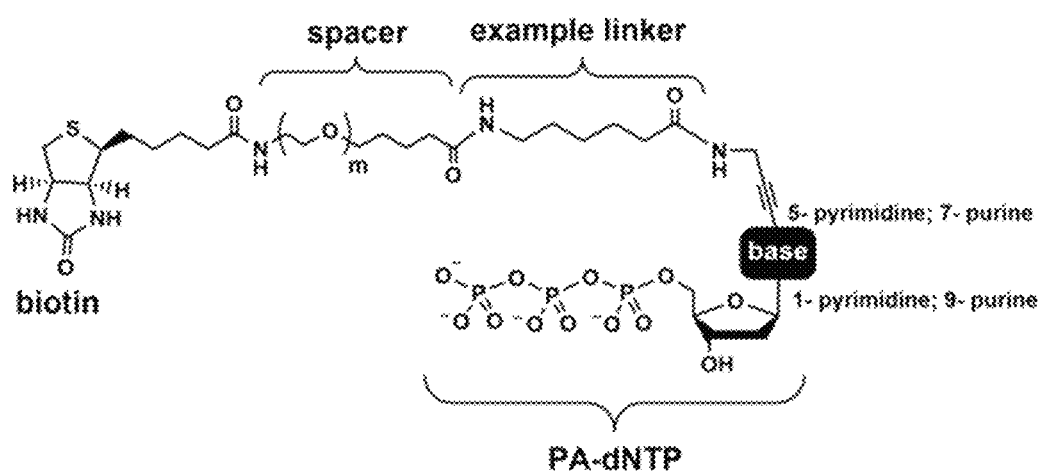

FIG. 63 shows the chemical structure of an exemplary nucleotide-arm. In this embodiment, the nucleotide unit is connected to the linker via a propargyl amine attachment at the 5 position of a pyrimidine base or the 7 position of a purine base. This nucleotide-arm shows an exemplary biotinylated nucleotide-arm.

Figure 64:
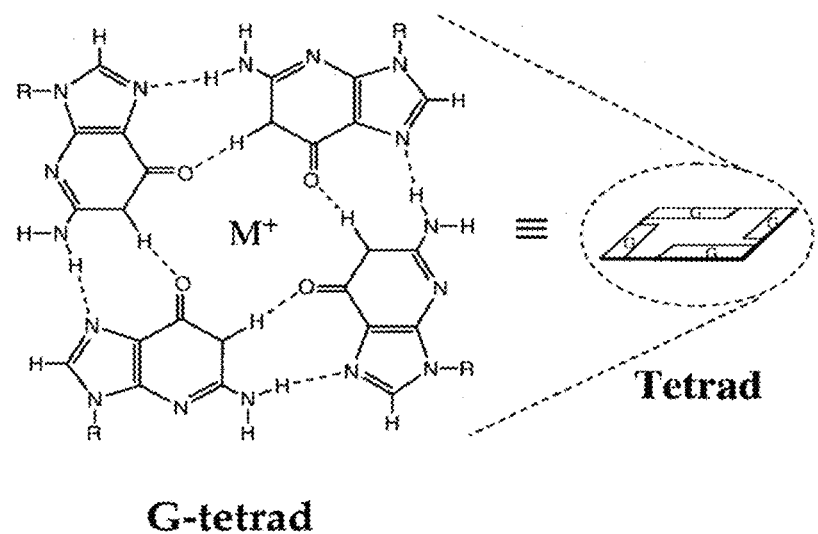

FIG. 64 is a schematic of a guanine tetrad (e.g., G-tetrad).

Figure 65:
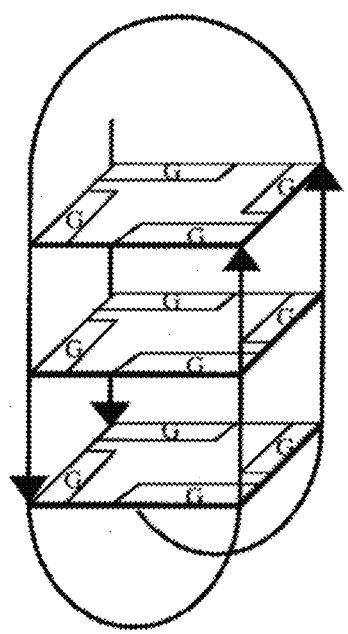

FIG. 65 is a schematic of an exemplary intramolecular G-quadruplex structure.

Figure 66:
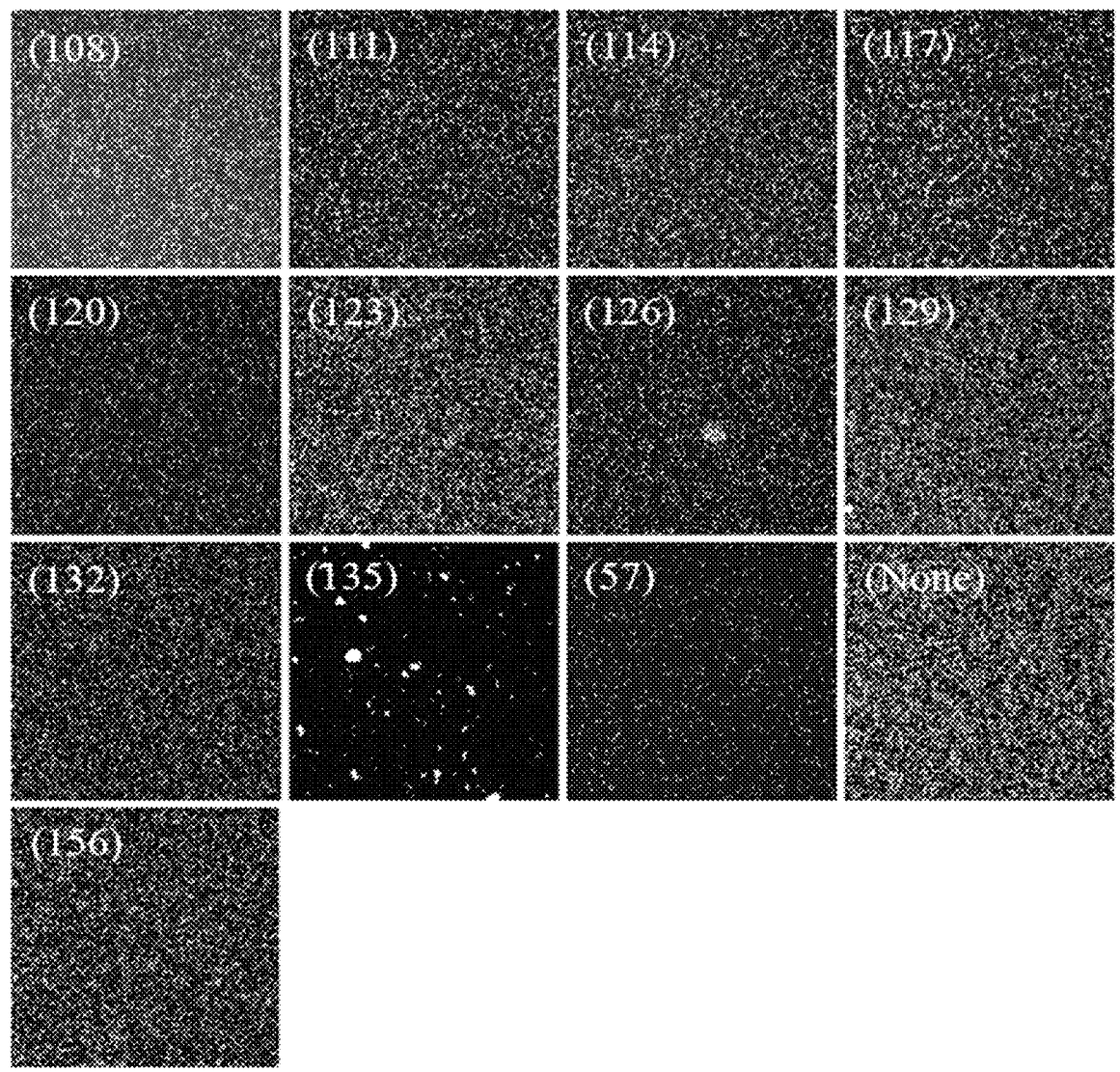

FIG. 66 shows a series of fluorescent images of nucleic acid nanostructures immobilized to a support. The nanostructures were generated by conducting on-support rolling circle amplification with various compaction oligonucleotides (100 nM) or no compaction oligonucleotides as a negative control (None). The immobilized nanostructures were hybridized with fluorescently-labeled probes, washed, and imaged. The SEQ ID NO of the compaction oligonucleotide is indicated in the upper left corner of each image. The images show that the shape and size of the resulting immobilized nanostructures are influenced by the type of compaction oligonucleotide tested.

Figure 67A:
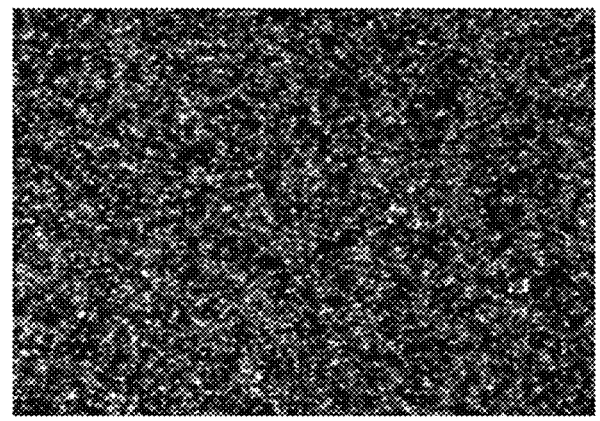
Figure 67B:
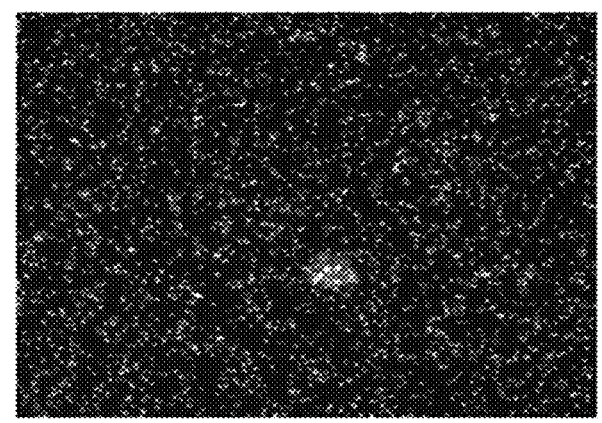
Figure 67C:
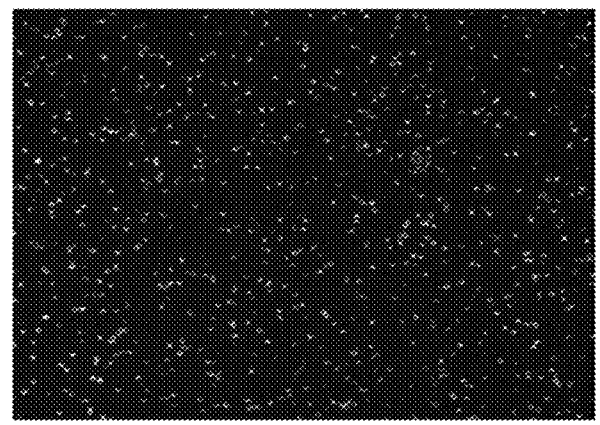

FIGS. 67A, 67B and 67C show an enlargement of certain images from FIG. 66. FIG. 67A shows a negative control:

the immobilized concatemers are less compact and have a "fuzzy" appearance. FIG. 67B shows a compaction oligonucleotide (SEQ ID NO: 126): the immobilized nucleic acid nanostructures are more compact compared to the negative control. FIG. 67C shows a compaction oligonucleotide (SEQ ID NO:57): the immobilized nucleic acid nanostructures are more compact and discrete compared to the negative control and the image shown in panel (FIG. 67B).

Figure 68:
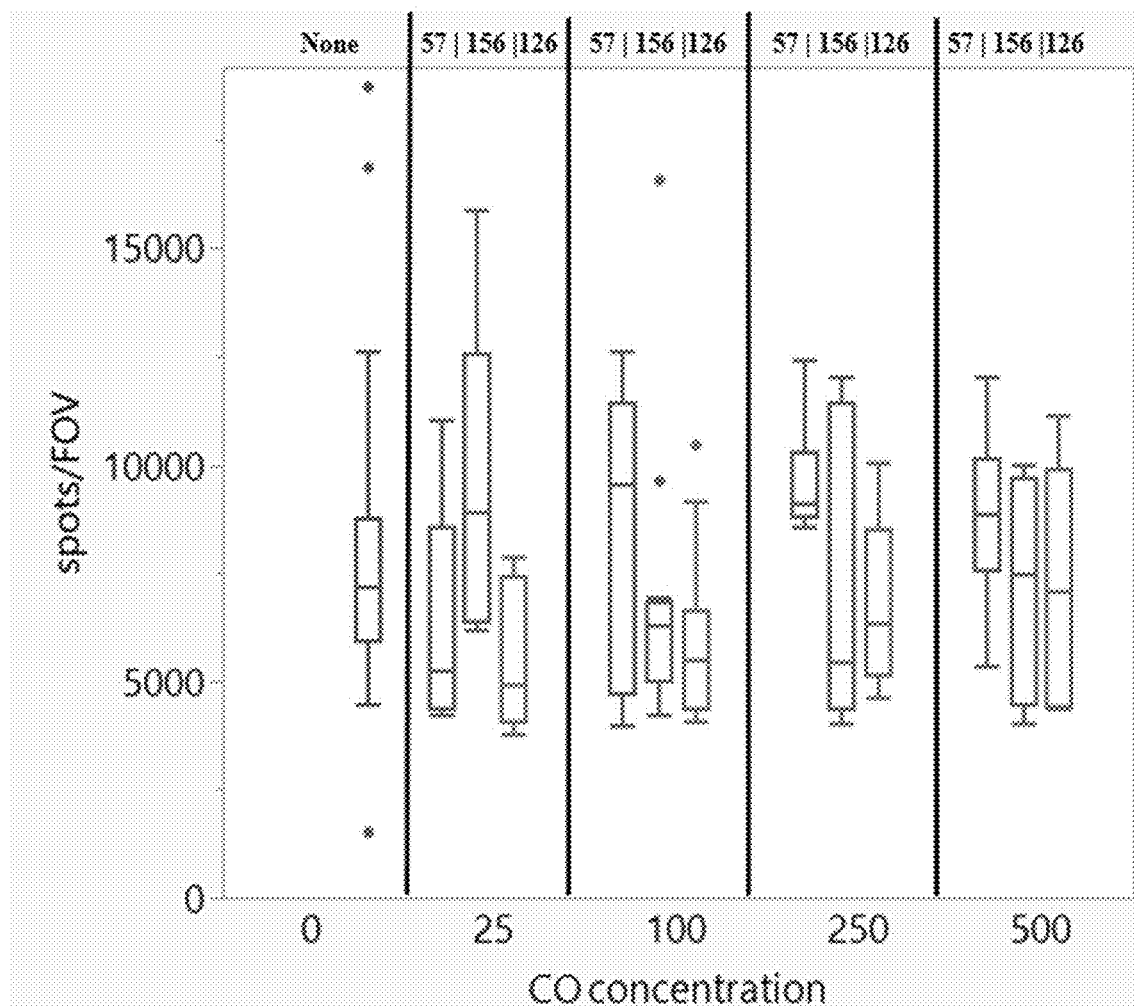

FIG. 68 is a box plot showing the number of immobilized nanostructures per field of view. The nanostructures were generated by conducting on-support rolling circle amplification with titration concentrations of various compaction oligonucleotides or no compaction oligonucleotides as a negative control. The compaction oligonucleotides were tested at 25 nM, 100 nM, 250 nM and 500 nM. Compaction oligonucleotides that were tested included SEQ ID NOS: 57, 126 and 156 (see the sequences in Table 1). The data shows that the compaction oligonucleotides did not inhibit the rolling circle amplification reaction. The number of immobilized nanostructures (spots) was similar for the negative control and the three different compaction oligonucleotides tested in this experiment.

Figure 69:
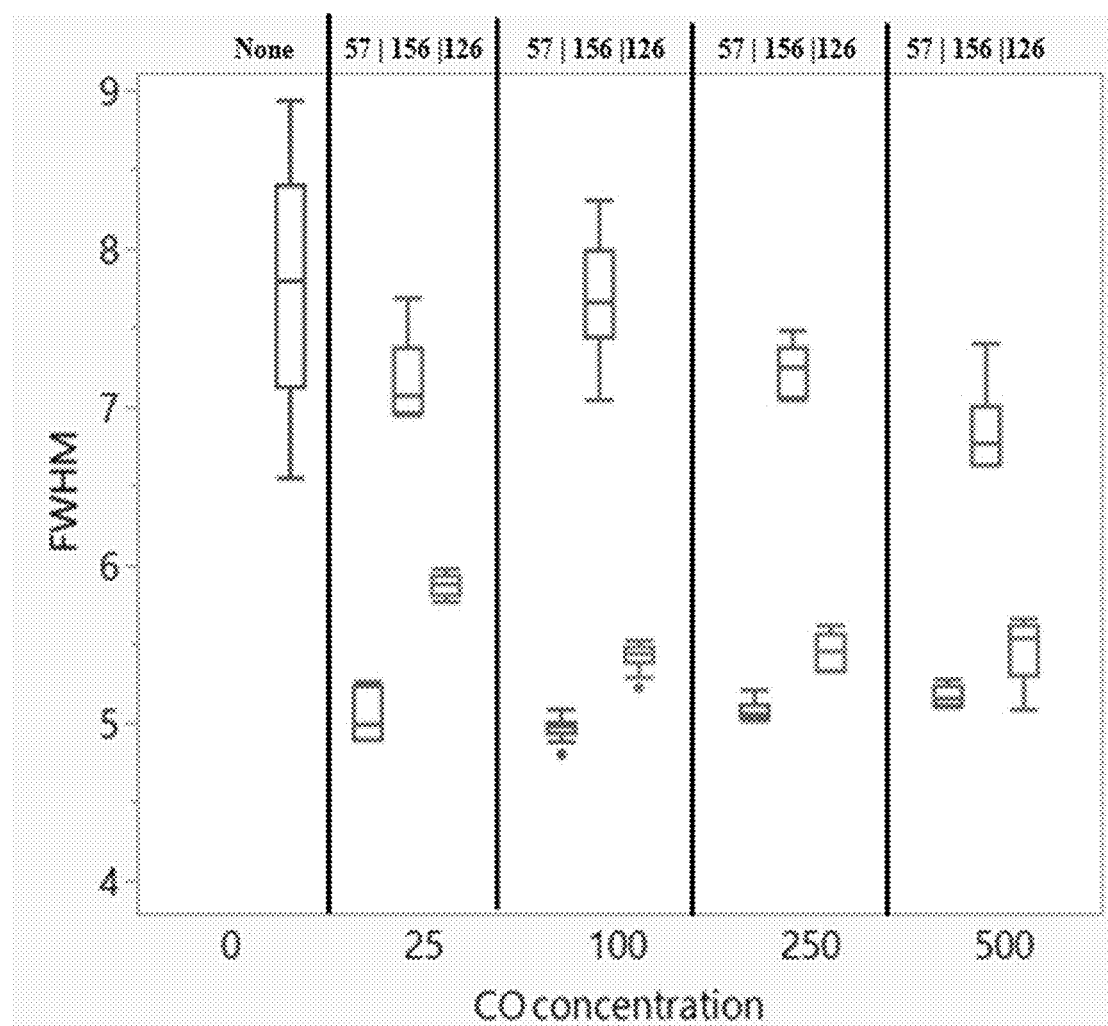

FIG. 69 is a box plot showing the full width half maximum (FWHM) of the immobilized nanostructures described in FIG. 68. The data shows that the FWHM of the nanostructures generated with compaction oligonucleotides is smaller compared to the negative control. The data also shows that the immobilized nanostructures generated with compaction oligonucleotides comprising SEQ ID NO:57 have a smaller FWHM compared to the immobilized nanostructures generated with compaction oligonucleotides comprising SEQ ID NO: 126 or 156.

Figure 70:
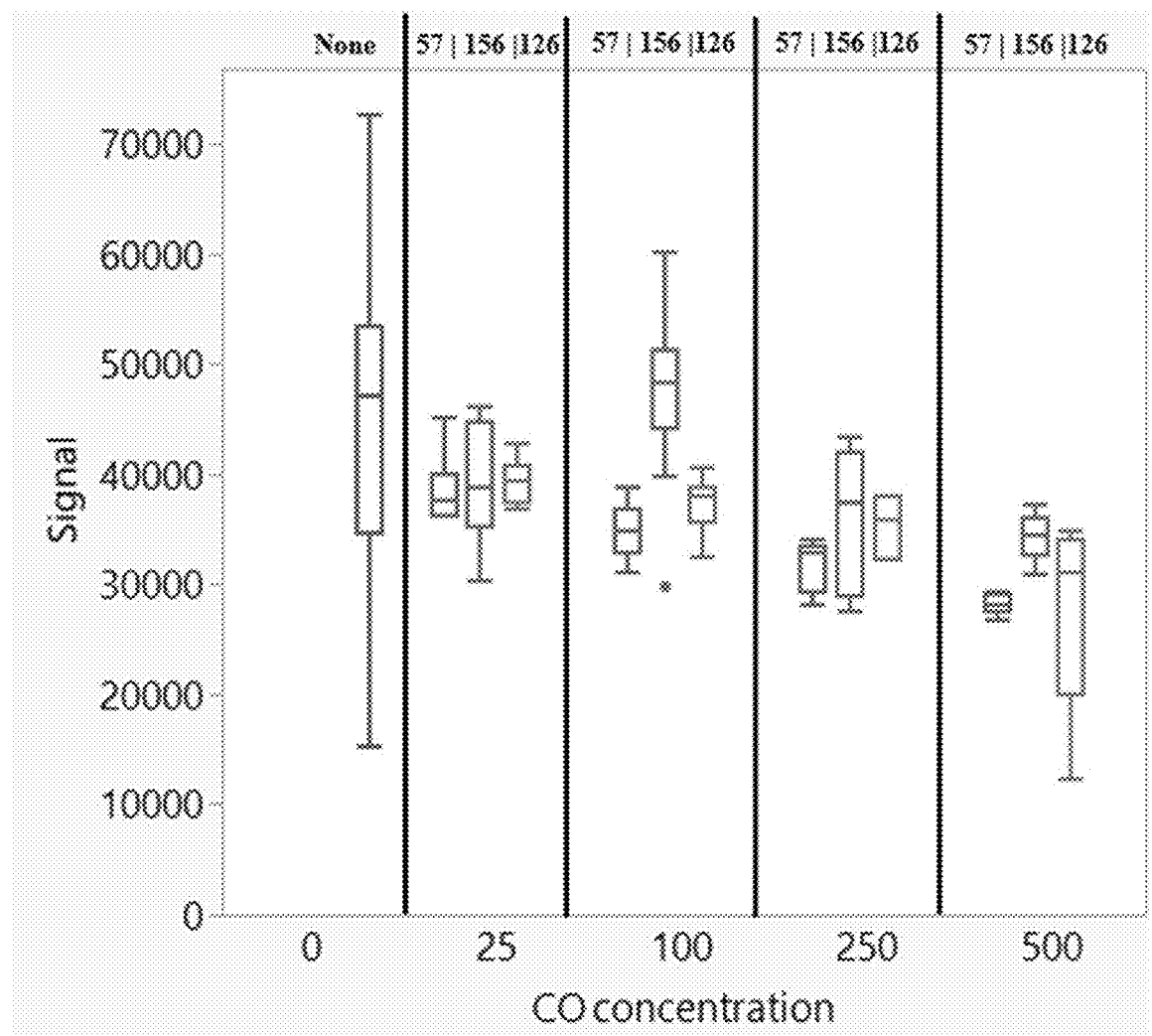

FIG. 70 is a box plot showing the signal intensity of the immobilized nanostructures described in FIG. 68. The data shows a smaller (more discrete) distribution range of the signals detected from the nanostructures generated with compaction oligonucleotides compared to the negative control.

Figure 71:
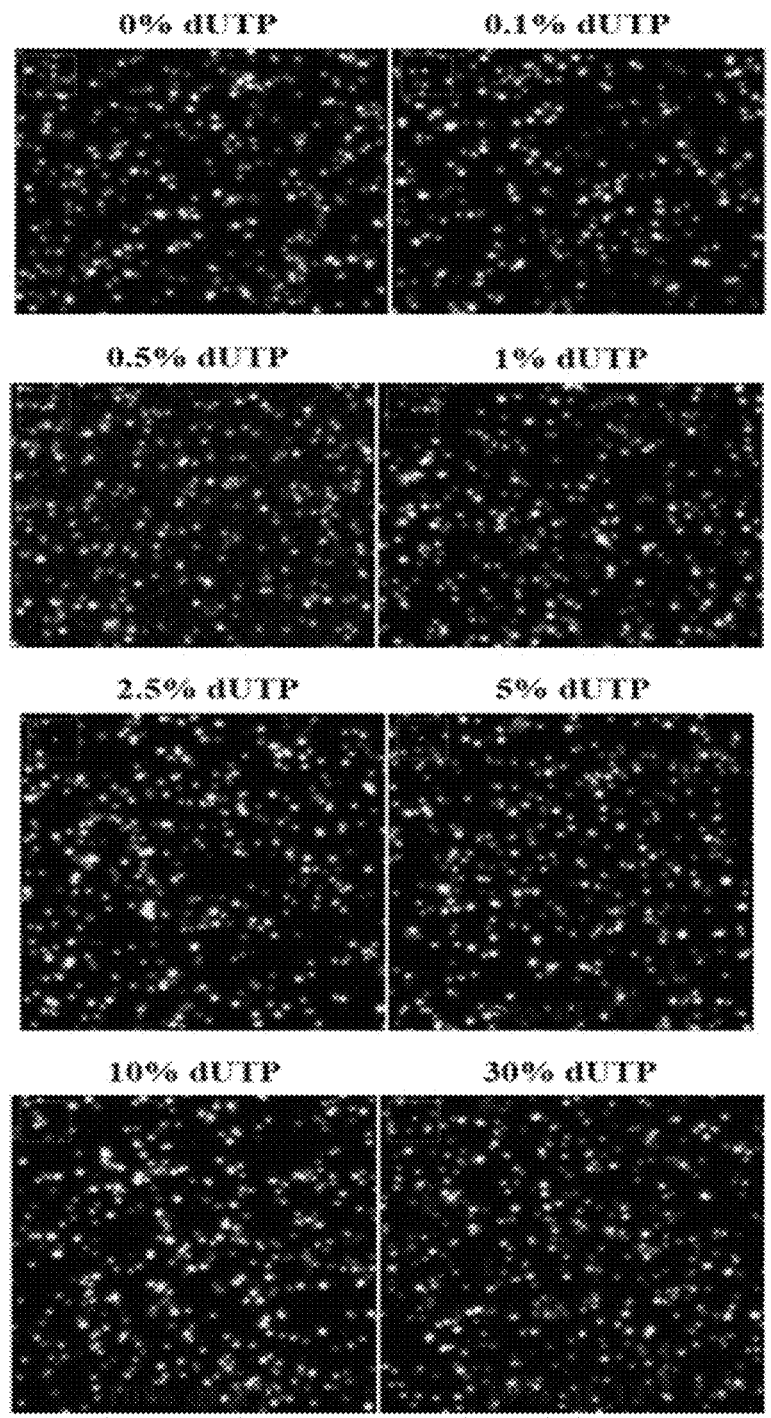

FIG. 71 shows a series of four-color fluorescent images of first strand nanostructures immobilized to a support. The first strand nanostructures were generated by conducting on-support rolling circle amplification with compaction oligonucleotides, and a mixture of nucleotides with titrating concentrations of dUTP or no dUTP as a negative control. Sequencing reagents were flowed onto the immobilized nanostructures to form fluorescent binding complexes on the first strand nanostructures. Images of the resulting binding complexes were obtained. The procedure for obtaining the fluorescent images is described in Example 3.

Figure 72:
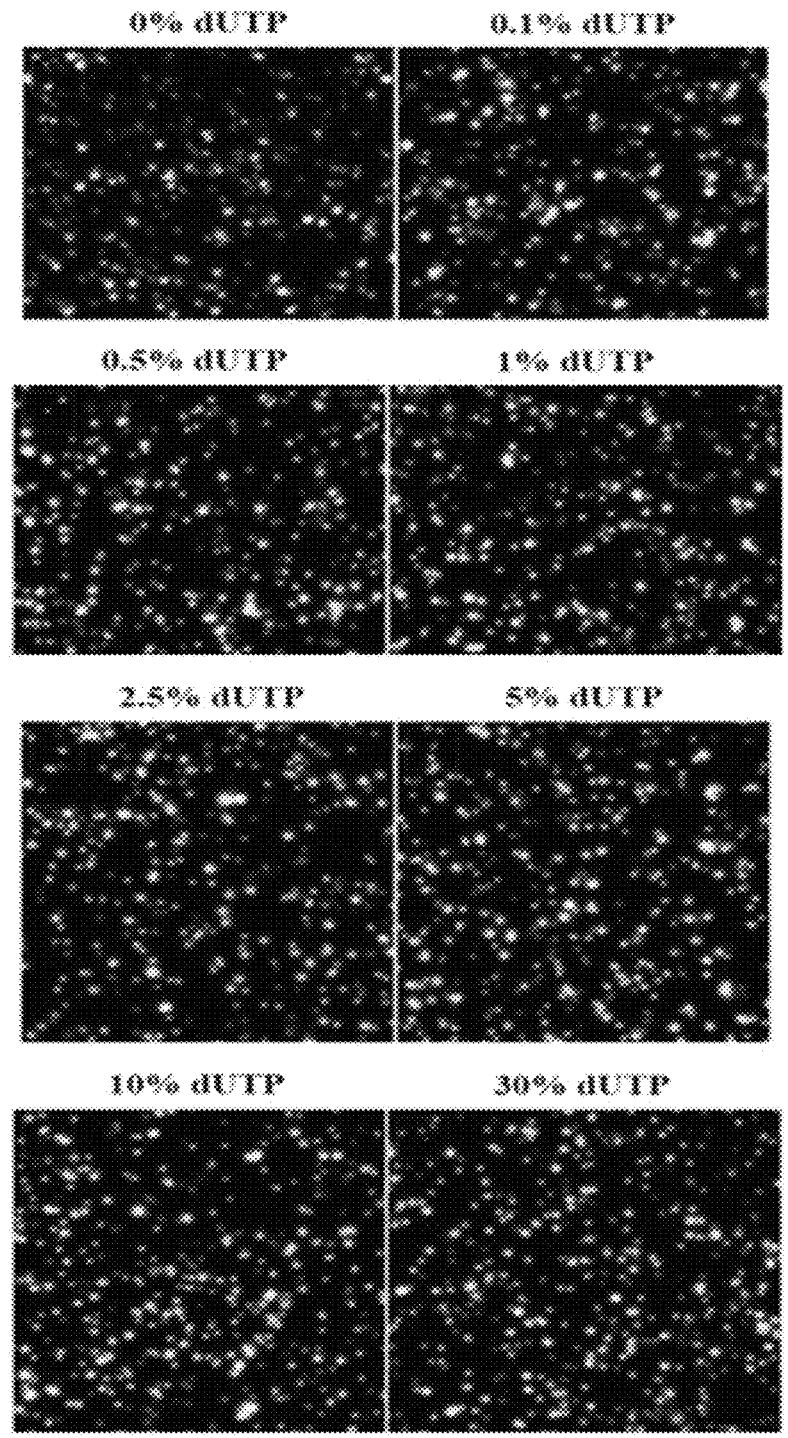

FIG. 72 shows a series of four color fluorescent images of second strand nanostructures immobilized to a support. The second strand nanostructures were generated from the first strand nanostructures described in FIG. 71. The second strand nanostructures were generated by conducting a primer extension reaction on the first strand nanostructures using a mixture of nucleotides lacking dUTP, and compaction oligonucleotides. The first strands were removed by enzymatic degradation while retaining the second strand molecules. Sequencing reagents were flowed onto the immobilized second template strands to form fluorescent binding complexes on the second strand nanostructures. Images of the resulting binding complexes were obtained. The procedure for obtaining the fluorescent images is described in Example 3.

Figure 73:
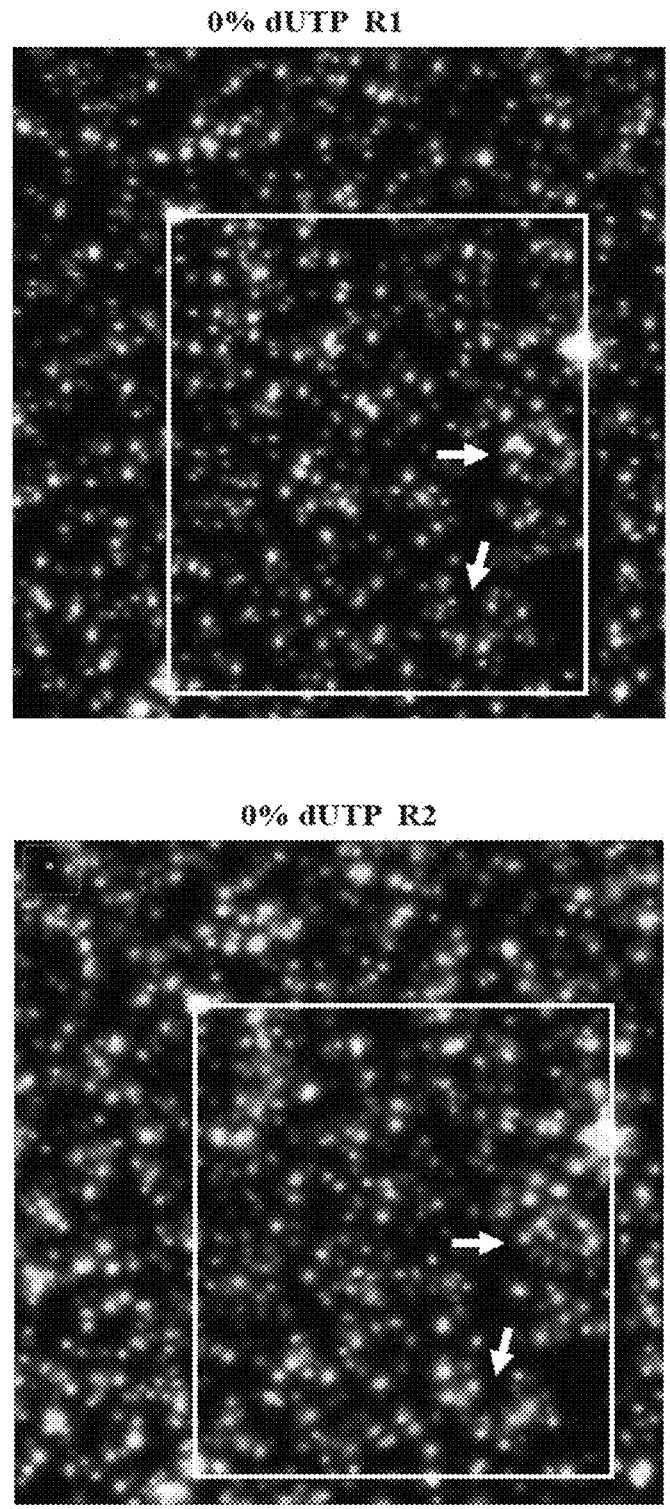

FIG. 73 shows four color fluorescent images of fluorescent binding complexes on immobilized first strand nanostructures (top), and fluorescent binding complexes on second strand nanostructures (bottom), where the second strands were generated from their respective first strands on the same flow cell. The outlined white boxes in the top and bottom images of FIG. 73 indicate the same field of view. The white arrows indicate the locations of groups of nanostructures that are easily identifiable and comparable in the top and bottom images.

DETAILED DESCRIPTION

Definitions

The headings provided herein are not limitations of the various aspects of the disclosure, which aspects can be understood by reference to the specification as a whole.

Unless defined otherwise, technical and scientific terms used herein have meanings that are commonly understood by those of ordinary skill in the art unless defined otherwise. Generally, terminologies pertaining to techniques of molecular biology, nucleic acid chemistry, protein chemistry, genetics, microbiology, transgenic cell production, and hybridization described herein are those well-known and commonly used in the art. Techniques and procedures described herein are generally performed according to conventional methods well known in the art and as described in various general and more specific references that are cited and discussed throughout the instant specification. For example, see Sambrook et al., Molecular Cloning: A Laboratory Manual (Third ed., Cold Spring Harbor Laboratory Press, Cold Spring Harbor, N.Y. 2000). See also Ausubel et al., Current Protocols in Molecular Biology, Greene Publishing Associates (1992). The nomenclatures utilized in connection with, and the laboratory procedures and techniques described herein are those well-known and commonly used in the art.

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative term (e.g., "or") is taken to mean either one or both or any combination thereof of the alternatives.

The term "and/or" used herein is to be taken mean specific disclosure of each of the specified features or components with or without the other. For example, the term "and/or" as used in a phrase such as "A and/or B" herein is intended to include: "A and B"; "A or B"; "A" (A alone); and "B" (B alone). In a similar manner, the term "and/or" as used in a phrase such as "A, B, and/or C" is intended to encompass each of the following aspects: "A, B, and C"; "A, B, or C"; "A or C"; "A or B"; "B or C"; "A and B"; "B and C"; "A and C"; "A" (A alone); "B" (B alone); and "C" (C alone).

As used herein and in the appended claims, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

As used herein, the terms "about" and "approximately" refer to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. Alternatively, "about" or "approximately" can mean a range of up to 10% (i.e., ±10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition. Also, where ranges and/or subranges of values are provided, the ranges and/or subranges can include the endpoints of the ranges and/or subranges.

The term "biological sample" refers to a single cell, a plurality of cells, a tissue, an organ, an organism, or section of any of these biological samples. The biological sample can be extracted (e.g., biopsied) from an organism, or obtained from a cell culture grown in liquid or in a culture dish. The biological sample comprises a sample that is fresh, frozen, fresh frozen, or archived (e.g., formalin-fixed paraffin-embedded; FFPE). The biological sample can be embedded in a wax, resin, epoxy or agar. The biological sample can be fixed, for example in any one or any combination of two or more of acetone, ethanol, methanol, formaldehyde, paraformaldehyde-Triton or glutaraldehyde. The biological sample can be sectioned or non-sectioned. The biological sample can be stained, de-stained or non-stained.

The nucleic acids of interest can be extracted from biological samples using any of a number of techniques known to those of skill in the art. For example, a typical DNA extraction procedure comprises (i) collection of the cell sample or tissue sample from which DNA is to be extracted, (ii) disruption of cell membranes (i.e., cell lysis) to release DNA and other cytoplasmic components, (iii) treatment of the lysed sample with a concentrated salt solution to precipitate proteins, lipids, and RNA, followed by centrifugation to separate out the precipitated proteins, lipids, and RNA, and (iv) purification of DNA from the supernatant to remove detergents, proteins, salts, or other reagents used during the cell membrane lysis. A variety of suitable commercial nucleic acid extraction and purification kits are consistent with the disclosure herein. Examples include, but are not limited to, the QIAamp kits (for isolation of genomic DNA from human samples) and DNAeasy kits (for isolation of genomic DNA from animal or plant samples) from Qiagen (Germantown, MD), or the Maxwell® and ReliaPrep™ series of kits from Promega (Madison, WI).

The terms "nucleic acid", "polynucleotide" and "oligonucleotide" and other related terms used herein are used interchangeably and refer to polymers of nucleotides and are not limited to any particular length. Nucleic acids include recombinant and chemically-synthesized forms. Nucleic acids can be isolated. Nucleic acids include DNA molecules (e.g., cDNA or genomic DNA), RNA molecules (e.g., mRNA), analogs of the DNA or RNA generated using nucleotide analogs (e.g., peptide nucleic acids (PNA) and non-naturally occurring nucleotide analogs), and chimeric forms containing DNA and RNA. Nucleic acids can be single-stranded or double-stranded. Nucleic acids comprise polymers of nucleotides, where the nucleotides include natural or non-natural bases and/or sugars. Nucleic acids comprise naturally-occurring internucleosidic linkages, for example phosphdiester linkages. Nucleic acids can lack a phosphate group. Nucleic acids comprise non-natural internucleoside linkages, including phosphorothioate, phosphorothiolate, or peptide nucleic acid (PNA) linkages. In some embodiments, nucleic acids comprise a one type of polynucleotides or a mixture of two or more different types of polynucleotides.

The term "universal sequence", "universal adaptor sequences" and related terms refers to a sequence in a nucleic acid molecule that is common among two or more polynucleotide molecules. For example, adaptors having the same universal sequence can be joined to a plurality of polynucleotides so that the population of co-joined molecules carry the same universal adaptor sequence. Examples of universal adaptor sequences include an amplification primer sequence, a sequencing primer sequence or a capture primer sequence (e.g., soluble or support-immobilized capture primers). Exemplary universal adaptor sequences are listed in Table 2 (FIG. 15).

The term "operably linked" and "operably joined" or related terms as used herein refers to juxtaposition of components. The juxtapositioned components can be linked together covalently. For example, two nucleic acid components can be enzymatically ligated together where the linkage that joins together the two components comprises phosphodiester linkage. A first and second nucleic acid component can be linked together, where the first nucleic acid component can confer a function on a second nucleic acid component. For example, linkage between a primer binding sequence and a sequence of interest forms a nucleic acid library molecule having a portion that can bind to a primer. In another example, a transgene (e.g., a nucleic acid encoding a polypeptide or a nucleic acid sequence of interest) can be ligated to a vector where the linkage permits expression or functioning of the transgene sequence contained in the vector. In some embodiments, a transgene is operably linked to a host cell regulatory sequence (e.g., a promoter sequence) that affects expression of the transgene. In some embodiments, the vector comprises at least one host cell regulatory sequence, including a promoter sequence, enhancer, transcription and/or translation initiation sequence, transcription and/or translation termination sequence, polypeptide secretion signal sequences, and the like. In some embodiments, the host cell regulatory sequence controls expression of the level, timing and/or location of the transgene.

The terms "linked", "joined", "attached", "appended" and variants thereof comprise any type of fusion, bond, adherence or association between any combination of compounds or molecules that is of sufficient stability to withstand use in the particular procedure. The procedure can include but are not limited to: nucleotide binding; nucleotide incorporation; de-blocking (e.g., removal of chain-terminating moiety); washing; removing; flowing; detecting; imaging and/or identifying. Such linkage can comprise, for example, covalent, ionic, hydrogen, dipole-dipole, hydrophilic, hydrophobic, or affinity bonding, bonds or associations involving van der Waals forces, mechanical bonding, and the like. In some embodiments, such linkage occurs intramolecularly, for example linking together the ends of a single-stranded or double-stranded linear nucleic acid molecule to form a circular molecule. In some embodiments, such linkage can occur between a combination of different molecules, or between a molecule and a non-molecule, including but not limited to: linkage between a nucleic acid molecule and a solid surface; linkage between a protein and a detectable reporter moiety; linkage between a nucleotide and detectable reporter moiety; and the like. Some examples of linkages can be found, for example, in Hermanson, G., "Bioconjugate Techniques", Second Edition (2008); Aslam, M., Dent, A., "Bioconjugation: Protein Coupling Techniques for the Biomedical Sciences", London: Macmillan (1998); Aslam, M., Dent, A., "Bioconjugation: Protein Coupling Techniques for the Biomedical Sciences", London: Macmillan (1998).

The term "adaptor" and related terms refers to oligonucleotides that can be operably linked (appended) to a target polynucleotide, where the adaptor confers a function to the co-joined adaptor-target molecule. Adaptors comprise DNA, RNA, chimeric DNA/RNA, or analogs thereof. Adaptors can include at least one ribonucleoside residue. Adaptors can be single-stranded, double-stranded, or have single-stranded and/or double-stranded portions. Adaptors can be configured to be linear, stem-looped, hairpin, or Y-shaped forms. Adaptors can be any length, including 4-100 nucleotides or longer. Adaptors can have blunt ends, overhang ends, or a combination of both. Overhang ends include 5' overhang and 3' overhang ends. The 5' end of a single-stranded adaptor, or one strand of a double-stranded adaptor, can have a 5' phosphate group or lack a 5' phosphate group. Adaptors can include a 5' tail that does not hybridize to a target polynucleotide (e.g., tailed adaptor), or adaptors can be non-tailed. An adaptor can include a sequence that is complementary to at least a portion of a primer, such as an amplification primer, a sequencing primer, or a capture primer (e.g., soluble or immobilized capture primers). Adaptors can include a random sequence or degenerate sequence. Adaptors can include at least one inosine residue. Adaptors can include at least one phosphorothioate, phosphorothiolate and/or phosphoramidate linkage. Adaptors can include a barcode sequence which can be used to distinguish polynucleotides (e.g., insert sequences) from different sample sources in a multiplex assay. Adaptors can include a unique identification sequence (e.g., unique molecular index, UMI; or a unique molecular tag) that can be used to uniquely identify a nucleic acid molecule to which the adaptor is appended. In some embodiments, a unique identification sequence can be used to increase error correction and accuracy, reduce the rate of false-positive variant calls and/or increase sensitivity of variant detection. Adaptors can include at least one restriction enzyme recognition sequence, including any one or any combination of two or more selected from a group consisting of type I, type II, type III, type IV, type Hs or type IIB.

The term "nucleic acid template", "template polynucleotide", "nucleic acid target" "target polynucleotide", "template strand" and other variations refer to a nucleic acid strand that serves as the basis nucleic acid molecule for any of the analysis methods describe herein (e.g., primer extension, amplifying and/or sequencing). The template nucleic acid can be single-stranded or double-stranded, or the template nucleic acid can have single-stranded or double-stranded portions. The template nucleic acid can be obtained from a naturally-occurring source, recombinant form, or chemically synthesized to include any type of nucleic acid analog. The template nucleic acid can be linear, circular, or other forms. The template nucleic acids can include an insert region having an insert sequence which is also known as a sequence of interest. The template nucleic acids can also include at least one adaptor sequence. The template nucleic acid can be a concatemer having two or tandem copies of a sequence of interest and at least one adaptor sequence. The insert region can be isolated in any form, including chromosomal, genomic, organellar (e.g., mitochondrial, chloroplast or ribosomal), recombinant molecules, cloned, amplified, cDNA, RNA such as precursor mRNA or mRNA, oligonucleotides, whole genomic DNA, obtained from fresh frozen paraffin embedded tissue, needle biopsies, circulating tumor cells, cell free circulating DNA, or any type of nucleic acid library. The insert region can be isolated from any source including from organisms such as prokaryotes, eukaryotes (e.g., humans, plants and animals), fungus, viruses cells, tissues, normal or diseased cells or tissues, body fluids including blood, urine, serum, lymph, tumor, saliva, anal and vaginal secretions, amniotic samples, perspiration, semen, environmental samples, culture samples, or synthesized nucleic acid molecules prepared using recombinant molecular biology or chemical synthesis methods. The insert region can be isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs. The template nucleic acid can be subjected to nucleic acid analysis, including sequencing and composition analysis.

The term "polymerase" and its variants, as used herein, comprises an enzyme comprising a domain that binds a nucleotide (or nucleoside) where the polymerase can form a complex having a template nucleic acid and a complementary nucleotide. The polymerase can have one or more activities including, but not limited to, base analog detection activities, DNA polymerization activity, reverse transcriptase activity, DNA binding, strand displacement activity, and nucleotide binding and recognition. A polymerase can be any enzyme that can catalyze polymerization of nucleotides (including analogs thereof) into a nucleic acid strand. Typically, but not necessarily, such nucleotide polymerization can occur in a template-dependent fashion. Typically, a polymerase comprises one or more active sites at which nucleotide binding and/or catalysis of nucleotide polymerization can occur. In some embodiments, a polymerase includes other enzymatic activities, such as for example, 3' to 5' exonuclease activity or 5' to 3' exonuclease activity. In some embodiments, a polymerase has strand displacing activity. A polymerase can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze nucleotide polymerization (e.g., catalytically active fragment). The polymerase includes catalytically inactive polymerases, catalytically active polymerases, reverse transcriptases, and other enzymes comprising a nucleotide binding domain. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof. A polymerase can be derived from a prokaryote, eukaryote, virus or phage. A polymerase comprises DNA-directed DNA polymerase and RNA-directed DNA polymerase.

The term "strand displacing" refers to the ability of a polymerase to locally separate strands of double-stranded nucleic acids and synthesize a new strand in a template-based manner. Strand displacing polymerases displace a complementary strand from a template strand and catalyze new strand synthesis. Strand displacing polymerases include mesophilic and thermophilic polymerases. Strand displacing polymerases include wild type enzymes, and variants including exonuclease minus mutants, mutant versions, chimeric enzymes and truncated enzymes. Examples of strand displacing polymerases include phi29 DNA polymerase, large fragment of Bst DNA polymerase, large fragment of Bsu DNA polymerase (exo-), Bca DNA polymerase (exo-), Klenow fragment of E. coli DNA polymerase, T5 polymerase, M-MuLV reverse transcriptase, HIV viral reverse transcriptase, Deep Vent DNA polymerase and KOD DNA polymerase. The phi29 DNA polymerase can be wild type phi29 DNA polymerase (e.g., MagniPhi from Expedeon™), or variant EquiPhi29 DNA polymerase (e.g., from Thermo Fisher Scientific™), or chimeric QualiPhi DNA polymerase (e.g., from 4basebio™).

As used herein, the term "fidelity" refers to the accuracy of DNA polymerization by template-dependent DNA polymerase. The fidelity of a DNA polymerase is typically measured by the error rate (the frequency of incorporating an inaccurate nucleotide, i.e., a nucleotide that is not complementary to the template nucleotide). The accuracy or fidelity of DNA polymerization is maintained by both the polymerase activity and the 3'-5' exonuclease activity of a DNA polymerase.

As used herein, the term "binding complex" refers to a complex formed by binding together a nucleic acid duplex, a polymerase, and a free nucleotide or a nucleotide unit of a multivalent molecule, where the nucleic acid duplex comprises a nucleic acid template molecule hybridized to a nucleic acid primer. In the binding complex, the free nucleotide or nucleotide unit may or may not be bound to the 3' end of the nucleic acid primer at a position that is opposite a complementary nucleotide in the nucleic acid template molecule. A "ternary complex" is an example of a binding complex which is formed by binding together a nucleic acid duplex, a polymerase, and a free nucleotide or nucleotide unit of a multivalent molecule, where the free nucleotide or nucleotide unit is bound to the 3' end of the nucleic acid primer (as part of the nucleic acid duplex) at a position that is opposite a complementary nucleotide in the nucleic acid template molecule.

The term "persistence time" and related terms refers to the length of time that a binding complex remains stable without dissociation of any of the components, where the components of the binding complex include a nucleic acid template and nucleic acid primer, a polymerase, a nucleotide unit of a multivalent molecule or a free (e.g., unconjugated) nucleotide. The nucleotide unit or the free nucleotide can be complementary or non-complementary to a nucleotide residue in the template molecule. The nucleotide unit or the free nucleotide can bind to the 3' end of the nucleic acid primer at a position that is opposite a complementary nucleotide residue in the nucleic acid template molecule. The persistence time is indicative of the stability of the binding complex and strength of the binding interactions. Persistence time can be measured by observing the onset and/or duration of a binding complex, such as by observing a signal from a labeled component of the binding complex. For example, a labeled nucleotide or a labeled reagent comprising one or more nucleotides may be present in a binding complex, thus allowing the signal from the label to be detected during the persistence time of the binding complex. One exemplary label is a fluorescent label. The binding complex (e.g., ternary complex) remains stable until subjected to a condition that causes dissociation of interactions between any of the polymerase, template molecule, primer and/or the nucleotide unit or the nucleotide. For example, a dissociating condition comprises contacting the binding complex with any one or any combination of a detergent, EDTA and/or water.

The term "primer" and related terms used herein refers to an oligonucleotide that is capable of hybridizing with a DNA and/or RNA polynucleotide template to form a duplex molecule. Primers comprise natural nucleotides and/or nucleotide analogs. Primers can be recombinant nucleic acid molecules. Primers may have any length, but typically range from 4-50 nucleotides. A typical primer comprises a 5' end and 3' end. The 3' end of the primer can include a 3' OH moiety which serves as a nucleotide polymerization initiation site in a polymerase-catalyzed primer extension reaction. Alternatively, the 3' end of the primer can lack a 3' OH moiety, or can include a terminal 3' blocking group that inhibits nucleotide polymerization in a polymerase-catalyzed reaction. Any one nucleotide, or more than one nucleotide, along the length of the primer can be labeled with a detectable reporter moiety. A primer can be in solution (e.g., a soluble primer) or can be immobilized to a support (e.g., a capture primer).

When used in reference to nucleic acid molecules, the terms "hybridize" or "hybridizing" or "hybridization" or other related terms refers to hydrogen bonding between two different nucleic acids to form a duplex nucleic acid. Hybridization also includes hydrogen bonding between two different regions of a single nucleic acid molecule to form a self-hybridizing molecule having a duplex region. Hybridization can comprise Watson-Crick or Hoogstein binding to form a duplex double-stranded nucleic acid, or a double-stranded region within a nucleic acid molecule. The double-stranded nucleic acid, or the two different regions of a single nucleic acid, may be wholly complementary, or partially complementary. Complementary nucleic acid strands need not hybridize with each other across their entire length. The complementary base pairing can be the standard A-T or C-G base pairing, or can be other forms of base-pairing interactions. Duplex nucleic acids can include mismatched base-paired nucleotides.

When used in reference to nucleic acids, the terms "extend", "extending", "extension" and other variants, refers to incorporation of one or more nucleotides into a nucleic acid molecule. Nucleotide incorporation comprises polymerization of one or more nucleotides into the terminal 3' OH end of a nucleic acid strand (e.g., a nucleic acid primer), resulting in extension of the nucleic acid strand (e.g., extended primer). Nucleotide incorporation can be conducted with natural nucleotides and/or nucleotide analogs. Typically, but not necessarily, nucleotide incorporation occurs in a template-dependent fashion. Any suitable method of extending a nucleic acid molecule may be used, including primer extension catalyzed by a DNA polymerase or RNA polymerase.

In some embodiments, any of the amplification primer sequences, sequencing primer sequences, capture primer sequences (capture oligonucleotides), target capture sequences, circularization anchor sequences, sample barcode sequences, spatial barcode sequences, or anchor region sequences can be about 3-50 nucleotides in length, or about 5-40 nucleotides in length, or about 5-25 nucleotides in length.

The term "nucleotides" and related terms refers to a molecule comprising an aromatic base, a five carbon sugar (e.g., ribose or deoxyribose), and at least one phosphate group. Canonical or non-canonical nucleotides are consistent with use of the term. The phosphate in some embodiments comprises a monophosphate, diphosphate, or triphosphate, or corresponding phosphate analog. The term "nucleoside" refers to a molecule comprising an aromatic base and a sugar. Nucleotides and nucleosides can be non-labeled or labeled with a detectable reporter moiety.

Nucleotides (and nucleosides) typically comprise a hetero cyclic base including substituted or unsubstituted nitrogen-containing parent heteroaromatic ring which are commonly found in nucleic acids, including naturally-occurring, substituted, modified, or engineered variants, or analogs of the same. The base of a nucleotide (or nucleoside) is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), etheno-adenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethyl-cytosines; 5-methycytosines; base (Y); as well as methylated, glycosylated, and acylated base moieties; and the like. Additional exemplary bases can be found in Fasman, 1989, in "Practical Handbook of Biochemistry and Molecular Biology", pp. 385-394, CRC Press, Boca Raton, Fla.

Nucleotides (and nucleosides) typically comprise a sugar moiety, such as carbocyclic moiety (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other sugar moieties (Joeng, et al., 1993 J. Med. Chem. 36: 2627-2638; Kim, et al., 1993 J. Med. Chem. 36: 30-7; Eschenmosser 1999 Science 284:2118-2124; and U.S. Pat. No. 5,558,991). The sugar moiety comprises: ribosyl; 2'-deoxyribosyl; 3'-deoxyribosyl; 2',3'-dideoxyribosyl; 2',3'-didehydrodideoxyribosyl; 2'-alkoxyribosyl; 2'-azidoribosyl; 2'-aminoribosyl; 2'-fluororibosyl; 2'-mercaptoriboxyl; 2'-alkylthioribosyl; 3'-alkoxyribosyl; 3'-azidoribosyl; 3'-aminoribosyl; 3'-fluororibosyl; 3'-mercaptoriboxyl; 3'-alkylthioribosyl carbocyclic; acyclic or other modified sugars.

In some embodiments, nucleotides comprise a chain of one, two or three phosphorus atoms where the chain is typically attached to the 5' carbon of the sugar moiety via an ester or phosphoramide linkage. In some embodiments, the nucleotide is an analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordithioate, and O-methylphosphoroamidite groups.

The term "reporter moiety", "reporter moieties" or related terms refers to a compound that generates, or causes to generate, a detectable signal. A reporter moiety is sometimes called a "label". Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. A reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. It is well known to one skilled in the art to select reporter moieties so that each absorbs excitation radiation and/or emits fluorescence at a wavelength distinguishable from the other reporter moieties to permit monitoring the presence of different reporter moieties in the same reaction or in different reactions. Two or more different reporter moieties can be selected having spectrally distinct emission profiles, or having minimal overlapping spectral emission profiles. Reporter moieties can be linked (e.g., operably linked) to nucleotides, nucleosides, nucleic acids, enzymes (e.g., polymerases or reverse transcriptases), or support (e.g., surfaces).

As used herein, a "nucleotide unit" or 'nucleotide moiety" refers to nucleotides (e.g., dATP, dTTP, dGTP, dCTP, or dUTP), or analogs thereof, comprising comprises a base, sugar and at least one phosphate group. Nucleotide units can be attached to the multivalent molecules used in the sequencing reactions described herein. In general, all nucleotide units attached to the same multivalent molecule will have the same identity (e.g., all A, all T, all C, or all G), although the skilled artisan will appreciate that there may be situations in which a multivalent molecule comprising nucleotide units of differing identity will be advantageous.

A reporter moiety (or label) comprises a fluorescent label or a fluorophore. Exemplary fluorescent moieties which may serve as fluorescent labels or fluorophores include, but are not limited to fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malachite green, stilbene, DEG dyes, NR dyes, near-infrared dyes and others known in the art such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and consist of two indolenin, benzoindolium, pyridium, thiozolium, and/or quinolinium groups separated by a polymethine bridge between two nitrogen atoms. Commercially available cyanine fluorophores include, for example, Cy3, (which may comprise 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy5 (which may comprise 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenin, and the benzo-derivatized Cy3.5, Cy5.5 and Cy7.5 are exceptions to this rule.

In some embodiments, the reporter moiety can be a FRET pair, such that multiple classifications can be performed under a single excitation and imaging step. As used herein, FRET may comprise excitation exchange (Forster) transfers, or electron-exchange (Dexter) transfers.

The term "support" as used herein refers to a substrate that is designed for deposition of biological molecules or biological samples for assays and/or analyses. Examples of biological molecules to be deposited onto a support include nucleic acids (e.g., DNA, RNA), polypeptides, saccharides, lipids, a single cell or multiple cells. Examples of biological samples include but are not limited to saliva, phlegm, mucus, blood, plasma, serum, urine, stool, sweat, tears and fluids from tissues or organs.

In some embodiments, the support is solid, semi-solid, or a combination of both. In some embodiments, the support is porous, semi-porous, non-porous, or any combination of porosity. In some embodiments, the support can be substantially planar, concave, convex, or any combination thereof. In some embodiments, the support can be cylindrical, for example comprising a capillary or interior surface of a capillary.

In some embodiments, the surface of the support can be substantially smooth. In some embodiments, the support can be regularly or irregularly textured, including bumps, etched, pores, three-dimensional scaffolds, or any combination thereof.

In some embodiments, the support comprises a bead having any shape, including spherical, hemi-spherical, cylindrical, barrel-shaped, toroidal, disc-shaped, rod-like, conical, triangular, cubical, polygonal, tubular or wire-like.

The support can be fabricated from any material, including but not limited to glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The support can have a plurality (e.g., two or more) of nucleic acid templates immobilized thereon. The plurality of immobilized nucleic acid templates has the same sequence or have different sequences. In some embodiments, individual nucleic acid template molecules in the plurality of nucleic acid templates are immobilized to a different site on the support. In some embodiments, two or more individual nucleic acid template molecules in the plurality of nucleic acid templates are immobilized to a site on the support.

The term "array" refers to a support comprising a plurality of sites located at pre-determined locations on the support to form an array of sites. The sites can be discrete and separated by interstitial regions. In some embodiments, the pre-determined sites on the support can be arranged in one dimension in a row or a column, or arranged in two dimensions in rows and columns. In some embodiments, the plurality of pre-determined sites is arranged on the support in an organized fashion. In some embodiments, the plurality of pre-determined sites is arranged in any organized pattern, including rectilinear, hexagonal patterns, grid patterns, patterns having reflective symmetry, patterns having rotational symmetry, or the like. The pitch between different pairs of sites can be that same or can vary. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are located at pre-determined locations on the support. In some embodiments, a plurality of pre-determined sites on the support (e.g., $10^2$-$10^{15}$ sites or more) are immobilized with nucleic acid templates to form a nucleic acid template array. In some embodiments, the nucleic acid templates that are immobilized at a plurality of pre-determined sites by hybridization to immobilized surface capture primers, or the nucleic acid templates are covalently attached to the surface capture primer. In some embodiments, the nucleic acid templates that are immobilized at a plurality of pre-determined sites, for example immobilized at $10^2$-$10^{15}$ sites (e.g., at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites) or more. In some embodiments, the immobilized nucleic acid templates are clonally-amplified to generate immobilized nucleic acid polonies at the plurality of pre-determined sites. In some embodiments, individual immobilized nucleic acid polonies comprise single-stranded or double-stranded concatemers.

In some embodiments, a support comprising a plurality of sites located at random locations on the support is referred to herein as a support having randomly located sites thereon. The location of the randomly located sites on the support are not pre-determined. The plurality of randomly-located sites is arranged on the support in a disordered and/or unpredictable fashion. In some embodiments, the support comprises at least $10^2$ sites, at least $10^3$ sites, at least 104 sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are randomly located on the support. In some embodiments, a plurality of randomly located sites on the support (e.g., $10^2$-$10^{15}$ sites or more) are immobilized with nucleic acid templates to form a support immobilized with nucleic acid templates. In some embodiments, the nucleic acid templates that are immobilized at a plurality of randomly located sites by hybridization to immobilized surface capture primers, or the nucleic acid templates are covalently attached to the surface capture primer. In some embodiments, the nucleic acid templates that are immobilized at a plurality of randomly located sites, for example immobilized at $10^2$-$10^{15}$ sites or more. In some embodiments, the immobilized nucleic acid templates are clonally-amplified to generate immobilized nucleic acid polonies at the plurality of randomly located sites. In some embodiments, individual immobilized nucleic acid polonies comprise single-stranded or double-stranded concatemers.

When used in reference to immobilized nucleic acids, the term "immobilized" and related terms refer to nucleic acid molecules that are attached to a support through covalent bond or non-covalent interaction, or attached to a coating on the support, or buried within a matrix formed by a coating on the support, where the nucleic acid molecules include surface capture primers, nucleic acid template molecules and extension products of capture primers. Extension products of capture primers includes nucleic acid concatemers that can form nucleic acid polonies.

In some embodiments, one or more nucleic acid templates are immobilized on the support, for example immobilized at the sites on the support. In some embodiments, the one or more nucleic acid templates are clonally-amplified. In some embodiments, the one or more nucleic acid templates are clonally-amplified off the support (e.g., in-solution) and then deposited onto the support and immobilized on the support. In some embodiments, the clonal amplification reaction of the one or more nucleic acid templates is conducted on the support resulting in immobilization on the support. In some embodiments, the one or more nucleic acid templates are clonally-amplified (e.g., in solution or on the support) using a nucleic acid amplification reaction, including any one or any combination of: polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification (RCA), circle-to-circle amplification, helicase-dependent amplification, recombinase-dependent amplification, and/or single-stranded binding (SSB) protein-dependent amplification.

The term "surface primer", "surface capture primer" and related terms refers to single-stranded oligonucleotides that are immobilized to a support and comprise a sequence that can hybridize to at least a portion of a nucleic acid template molecule. Surface primers can be used to immobilize template molecules to a support via hybridization. Surface primers can be immobilized to a support in a manner that resists primer removal during flowing, washing, aspirating, and changes in temperature, pH, salts, chemical and/or enzymatic conditions. Typically, but not necessarily, the 5' end of a surface primer can be immobilized to a support. Alternatively, an interior portion or the 3' end of a surface primer can be immobilized to a support.

In some embodiments, the surface primers comprise DNA, RNA, or analogs thereof. The surface primers can include a combination of DNA and RNA. The sequence of surface primers can be wholly complementary or partially complementary along their length to at least a portion of the nucleic acid template molecule (e.g., linear or circular template molecules). A support can include a plurality of immobilized surface primers having the same sequence, or having two or more different sequences. Surface primers can be any length, for example 4-50 nucleotides, or 50-100 nucleotides, or 100-150 nucleotides, or longer lengths, or any range therebetween.

A surface primer can include a terminal 3' nucleotide having a sugar 3' OH moiety which is extendible for nucleotide polymerization (e.g., polymerase catalyzed polymerization). A surface primer can include a terminal 3' nucleotide having a moiety that blocks polymerase-catalyzed extension. A surface primer can include a terminal 3' nucleotide having the 3' sugar position linked to a chain-terminating moiety that inhibits nucleotide polymerization. The 3' chain-terminating moiety can be removed (e.g., de-blocked) to convert the 3' end to an extendible 3' OH end using a de-blocking agent. Examples of chain terminating moieties include alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. Azide type chain terminating moieties including azide, azido and azidomethyl groups. Examples of de-blocking agents include a phosphine compound, such as Tris(2-carboxyethyl)phosphine (TCEP) and bis-sulfo triphenyl phosphine (BS-TPP), for chain-terminating groups azide, azido and azidomethyl groups. Examples of de-blocking agents include tetrakis(triphenylphosphine) palladium(0) (Pd(PPh$_3$)$_4$) with piperidine, or with 2,3-Dichloro-5,6-dicyano-1,4-benzo-quinone (DDQ), for chain-terminating groups alkyl, alkenyl, alkynyl and allyl. Examples of a de-blocking agent includes Pd/C for chain-terminating groups aryl and benzyl. Examples of de-blocking agents include phosphine, beta-mercaptoethanol or dithiothritol (DTT), for chain-terminating groups amine, amide, keto, isocyanate, phosphate, thio and disulfide. Examples of de-blocking agents include potassium carbonate (K$_2$CO$_3$) in MeOH, triethylamine in pyridine, and Zn in acetic acid (AcOH), for carbonate chain-terminating groups. Examples of de-blocking agents include tetrabutylammonium fluoride, pyridine-HF, with ammonium fluoride, and triethylamine trihydrofluoride, for chain-terminating groups urea and silyl.

In some embodiment, the plurality of immobilized surface capture primers on the support are in fluid communication with each other to permit flowing a solution of reagents (e.g., linear or circular nucleic acid template molecules, soluble primers, enzymes, nucleotides, divalent cations, buffers, reagents and the like) onto the support so that the plurality of immobilized surface capture primers on the support can be essentially simultaneously reacted with the reagents in a massively parallel manner. In some embodiments, the fluid communication of the plurality of immobilized surface capture primers can be used to conduct nucleic acid amplification reactions (e.g., RCA, MDA, PCR and bridge amplification) essentially simultaneously on the plurality of immobilized surface capture primers.

In some embodiment, the plurality of immobilized single stranded nucleic acid concatemer template molecules on the support are in fluid communication with each other to permit flowing a solution of reagents (e.g., soluble primers, enzymes, nucleotides, divalent cations, buffers, reagents and the like) onto the support so that the plurality of immobilized concatemer template molecules on the support can be essentially simultaneously reacted with the reagents in a massively parallel manner. In some embodiments, the fluid communication of the plurality of immobilized single stranded nucleic acid concatemer template molecules can be used to conduct nucleotide binding assays and/or conduct nucleotide polymerization reactions (e.g., primer extension or sequencing) essentially simultaneously on the plurality of immobilized single stranded nucleic acid concatemer template molecules, and optionally to conduct detection and imaging for massively parallel sequencing.

When used in reference to nucleic acids, the terms "amplify", "amplifying", "amplification", and other related terms include producing multiple copies of an original polynucleotide template molecule, where the copies comprise a sequence that is complementary to the template sequence, or the copies comprise a sequence that is the same as the template sequence. In some embodiments, the copies comprise a sequence that is substantially identical to a template sequence, or is substantially identical to a sequence that is complementary to the template sequence.

The present disclosure provides various pH buffering agents. The full name of the pH buffering agents is listed herein. The term "Tris" refers to a pH buffering agent Tris(hydroxymethyl)-aminomethane. The term "Tris-HCl" refers to a pH buffering agent Tris(hydroxymethyl)-aminomethane hydrochloride. The term "Tricine" refers to a pH buffering agent N-[tris(hydroxymethyl)methyl]glycine. The term "Bicine" refers to a pH buffering agent N,N-bis(2-hydroxyethyl)glycine. The term "Bis-Tris propane" refers to a pH buffering agent 1,3 Bis[tris(hydroxymethyl)methylamino]propane. The term "HEPES" refers to a pH buffering agent 4-(2-hydroxyethyl)-1-piperazineethanesulfonic acid. The term "MES" refers to a pH buffering agent 2-(N-morpholino)ethanesulfonic acid). The term "MOPS" refers to a pH buffering agent 3-(N-morpholino)propanesulfonic acid. The term "MOPSO" refers to a pH buffering agent 3-(N-morpholino)-2-hydroxypropanesulfonic acid. The term "BES" refers to a pH buffering agent N,N-bis(2-hydroxyethyl)-2-aminoethanesulfonic acid. The term "TES" refers to a pH buffering agent 2-[(2-Hydroxy-1,1bis(hydroxymethyl)ethyl)amino]ethanesulfonic acid). The term "CAPS" refers to a pH buffering agent 3-(cyclohexylamino)-1-propanesuhinic acid. The term "TAPS" refers to a pH buffering agent N-[Tris(hydroxymethyl)methyl]-3-amino propane sulfonic acid. The term "TAPSO" refers to a pH buffering agent N-[Tris(hydroxymethyl)methyl]-3-amino-2-hyidroxypropansulfonic acid. The term "ACES" refers to a pH buffering agent N-(2-Acetamido)-2-aminoethanesulfonic acid. The term "PIPES" refers to a pH buffering agent piperazine-1,4-bis(2-ethanesulfonic acid.

Introduction

The present disclosure provides compaction oligonucleotides and methods that employ compaction oligonucleotides for preparing nucleic acid nanostructures having compact size and shape.

In some embodiments, individual compaction oligonucleotides comprise two or more binding regions that are designed to hybridize to at least two regions of a nucleic acid molecule. In some embodiments, the different binding regions of a compaction oligonucleotide are designed to hybridize to distal portions of the same nucleic acid molecule and pull together the distal portions causing compaction of the nucleic acid molecule to form a compact nanostructure. For example, and without limitation, the different binding regions of a compaction oligonucleotide are designed to hybridize to distal portions of the same nucleic acid concatemer. In some embodiments, different binding regions of a compaction oligonucleotide hybridize to portions of universal adaptor sequences located at distal positions on the same concatemer and pull together the distal portions causing the concatemer to form into a DNA nanostructure having a more compact shape and size compared to a concatemer that is not hybridized to a compaction oligonucleotide.

In some embodiments, individual compaction oligonucleotides comprise two or more binding regions where each region is designed to hybridize to a region of two different nucleic acid molecules. In some embodiments, the different binding regions of a compaction oligonucleotide are designed to hybridize to two different nucleic acid molecules and form a compact nanostructure. For example, and without limitation, the different binding regions of a compaction oligonucleotide are designed to hybridize to a region of two different nucleic acid library molecule. In some embodiments, the nucleic acid library molecules comprise linear and/or circular library molecules. In some embodiments, different binding regions of a compaction oligonucleotide hybridize to portions of universal adaptor sequences on two different library molecules and form into a DNA nanostructure having a more compact shape and size compared to library molecules that are not hybridized to a compaction oligonucleotide.

In some embodiments, a compaction oligonucleotide comprises one or more oligonucleotides and can have any shape including for example linear, branched, star, comb, dendrimer or other shape.

In some embodiments, compaction oligonucleotides can include two, three, four or more binding regions (e.g., FIGS. 1-13). In some embodiments, the compaction oligonucleotides can be modified to increase resistance to exonuclease degradation.

In some embodiments, inclusion of compaction oligonucleotides during rolling circle amplification can promote formation of nanostructures having tighter size and shape compared to concatemers generated in the absence of the compaction oligonucleotides. The compact and stable characteristics of the nucleic acid nanostructures can improve sequencing accuracy by increasing signal intensity and they retain their shape and size and resist unraveling during multiple sequencing cycles.

Rolling circle amplification (RCA) can be conducted in the presence of compaction oligonucleotides to generate single stranded concatemer molecules having multiple copies of a polynucleotide unit arranged in tandem, where each polynucleotide unit comprises a sequence-of-interest and at least one universal adaptor sequence (e.g., at least one universal primer binding site). In some embodiments, individual compaction oligonucleotides hybridize to two or more regions of the same concatemer molecule.

Rolling circle amplification (RCA) can be conducted with compaction oligonucleotides to generate single stranded concatemer molecules having multiple copies of a polynucleotide unit arranged in tandem, where each polynucleotide unit comprises a sequence-of-interest and at least one universal adaptor sequence (e.g., at least one universal primer binding site). In some embodiments, the compaction oligonucleotides can have any shape (e.g., linear, branched, star, dendrimer or other shape) and can include two, three, four or more binding regions (e.g., FIGS. 1-13). In some embodiments, the binding regions of the compaction oligonucleotides are designed to hybridize to at least one universal adaptor sequence in a linear library molecule.

In some embodiments, the binding regions of the compaction oligonucleotides are designed to hybridize to at least one universal binding sequence in a concatemer molecule. In some embodiments, the binding regions of the compaction oligonucleotides can be modified to increase resistance to exonuclease degradation. The different binding regions of the compaction oligonucleotides can be designed to hybridize to distal portions of the same concatemer molecule and pull together the distal portions causing compaction of the concatemer to form a compact nanostructure. Inclusion of compaction oligonucleotides during RCA can promote formation of nanostructures having tighter size and shape compared to concatemers generated in the absence of the compaction oligonucleotides. Without wishing to be bound by theory, it is hypothesized that the compact and stable characteristics of the nucleic acid nanostructures improves sequencing accuracy, e.g., by increasing signal intensity, and the nanostructures retain their shape and size during multiple sequencing cycles.

As used herein, "nanostructures" or "nucleic acid nanostructures" are compacted concatemer molecules, where each nanostructure carries numerous copies of a polynucleotide unit along their lengths. Each polynucleotide unit can bind a sequencing primer, a sequencing polymerase and a detectably-labeled nucleotide reagent, to form a detectable sequencing complex. Each nanostructure can bind numerous detectable sequencing complexes. Thus, the compact size of the nanostructures can improve sequencing accuracy by increasing the local concentration of detectably-labeled nucleotide reagents that are used during the sequencing workflow, which increases the signal intensity emitted from a given nanostructure to give a discrete detectable signal.

Massively parallel sequencing workflows typically employ multiple steps including reagent flowing, microscopy imaging the detectable sequencing complexes, washing the template strands, and repeating the steps for hundreds of cycles. DNA template molecules immobilized on a flowcell can be subjected to numerous flow cycles of reagents where each flow is intended to change the reaction environment of the immobilized template molecules through changes in temperature, pH, salts and enzymes. The DNA template molecules can unravel or appear to drift positions during late-stage sequencing cycles, which causes a decrease in base call accuracy. Inclusion of compaction oligonucleotides during RCA generates compact nanostructures that are stable. The nanostructures as described in the present disclosure resist unraveling and drift, and retain their compact shape and size throughout multiple sequencing cycles, which improves base call accuracy of late-stage sequencing cycles.

The compositions and methods described herein can be used to prepare compact nanostructures immobilized at high density to random locations on a flow cell. The compact nanostructures are tightly-packed and fill much of the space on a flow cell. Yet the compact nanostructures are distinguishable from their near-neighbors which facilitates preparation of high density nanostructures for high throughput massively parallel nucleic acid sequencing. For example, fluorescently labeled nanostructures can be imaged as distinct nanoballs even at a density of about $6 \times 10^5/mm^2$ and arranged at random locations on a flow cell. Inclusion of compaction oligonucleotides during RCA may obviate the need to fabricate sequencing flow cells having an organized patterned array of nano-wells.

In some embodiments, the compaction oligonucleotides can be linear oligonucleotide molecules that can be adapted to integrate into existing library preparation workflows that employ rolling circle amplification. The first and second regions of the linear compaction oligonucleotides can be designed to hybridize to a universal binding sequence in a concatemer molecule. The linear compaction oligonucleotides described herein can be simpler than multi-branched dendrimers that are described, for example, in U.S. Pat. No. 8,445,194.

In some embodiments, the workflows described herein do not require special conditions or additives to generated stable compact nanostructures. For example, the workflows described herein do not require addition of proteins (e.g., streptavidin or histones) to generate stable nanostructures. Additives such as inorganic cation $Co(NH_3)_6^{3+}$, polyvinylpyrrolidone, or cationic liposomes, are not needed to generate stable nanostructures (e.g., see DNA condensation in U.S. Pat. No. 9,982,293). These additives may interfere with downstream reactions including DNA sequencing reactions.

Compositions

The present disclosure provides a plurality of nucleic acid nanostructures, wherein individual nucleic acid nanostructures comprise a nucleic acid concatemer molecule hybridized to at least one compaction oligonucleotide. In some embodiments, the nucleic acid nanostructures are in solution, immobilized to a support, or a mixture of nanostructures in solution and immobilized to a support.

In some embodiments, individual compaction oligonucleotides comprise at least a first binding region that can hybridize to a first portion of a concatemer molecule, and the compaction oligonucleotide comprise at least a second binding region that can hybridize to a second portion of the concatemer molecule (e.g., the same concatemer molecule) (e.g., FIGS. 1-13). In some embodiments, the first and second regions of individual compaction oligonucleotides can hybridize to two portions of the same concatemer to pull together distal portions of the concatemer causing compaction of the concatemer to form a nucleic acid nanostructure.

In some embodiments, hybridization of the compaction oligonucleotides to individual concatemer molecules causes the concatemer molecule to collapse or fold into a nucleic acid nanostructure. In some embodiments, the nucleic acid nanostructures can include one or more loops, or can have a spherical shape (e.g., nanoball), elongated shape (e.g., nanorod), proto-toroid shape or toroid shape (e.g., nanotoroid). A spot image of a nucleic acid nanostructure can be represented as a Gaussian spot and the size can be measured as a full width half maximum (FWHM). A smaller spot size as indicated by a smaller FWHM typically correlates with an improved image of the spot. In some embodiments, the FWHM of a nanostructure spot can be about 10 μm or smaller. The nucleic acid nanostructure can be a compact nucleic acid structure having a full width half maximum (FWHM) that is smaller compared to a concatemer that is not collapsed/folded into a nanostructure.

In some embodiments, individual compaction oligonucleotides in the plurality comprise nucleic acids and can have any shape including a linear, branched, star or dendrimer shape (e.g., bottle brush shape). In some embodiments, a compaction oligonucleotide can fold by forming intra-molecule base pairing having duplex portions via Watson-Crick base pairing, Hoogstein base pairing and/or a G-quadruplex structure. In some embodiments, the compaction oligonucleotides comprise nucleic acids that can fold into any shape having at least one hairpin, at least one stem-loop and/or at least one star shape.

In some embodiments, individual compaction oligonucleotides in the plurality comprise DNA, RNA, or a combination of DNA and RNA. The compaction oligonucleotide can be any length, including 20-200 nucleotides, 20-150 nucleotides, 30-100 nucleotides, 40-80 nucleotides in length, or any range therebetween.

Figure 1:
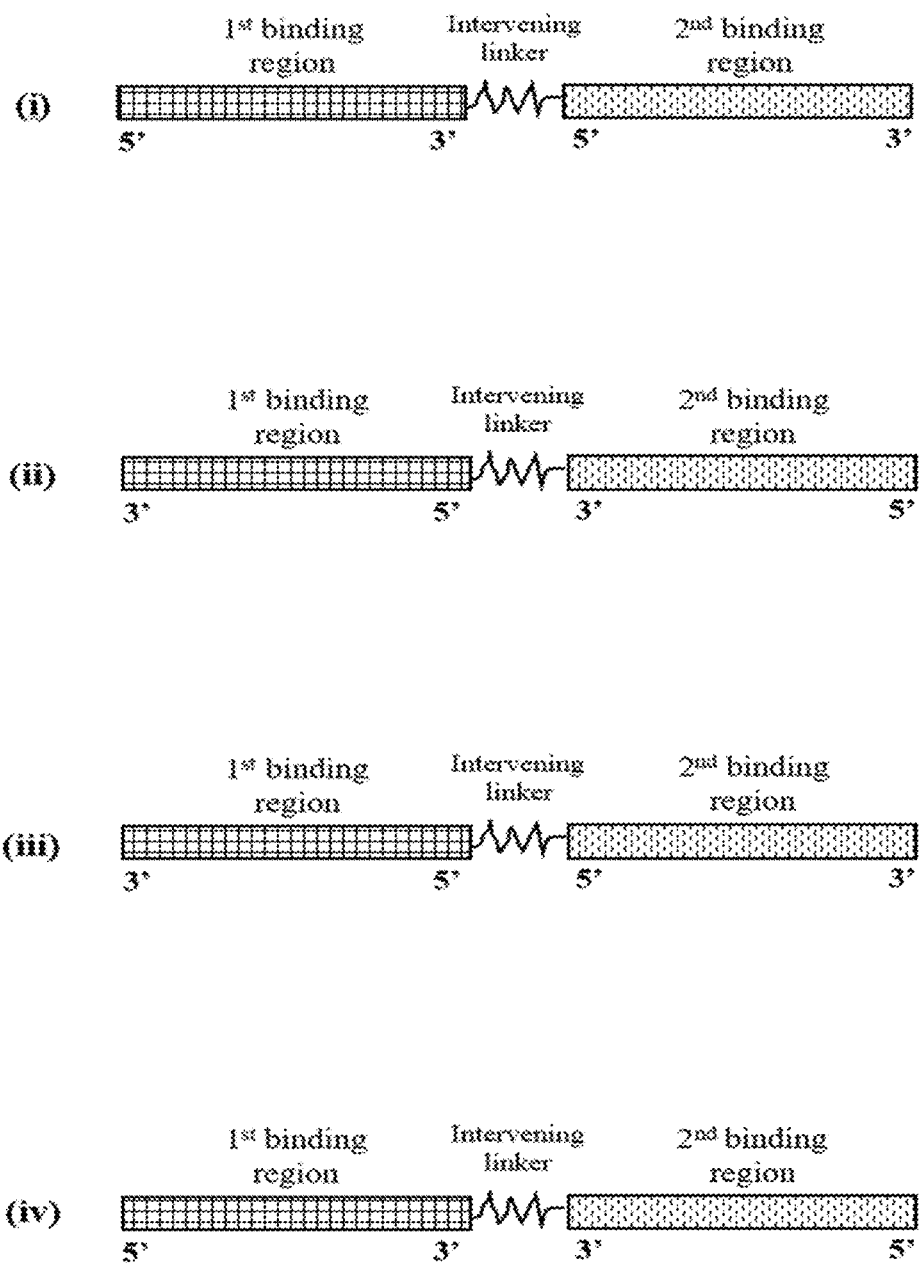
FIG. 1 shows schematics of several embodiments of linear compaction oligonucleotides each comprising a first binding region, an intervening linker, and a second binding region. In some embodiments, a compaction oligonucleotide comprises a first binding region arranged in a 5' to 3' orientation and a second binding region arranged in a 5' to 3' orientation (FIG. 1 (*i*)). In some embodiments, a compaction oligonucleotide comprises a first binding region arranged in a 3' to 5' orientation and a second binding region arranged in a 3' to 5' orientation (FIG. 1 (*ii*)). In some embodiments, a compaction oligonucleotide comprises a first binding region arranged in a 3' to 5' orientation and a second binding region arranged in a 5' to 3' orientation (FIG. 1 (*iii*)). In some embodiments, a compaction oligonucleotide comprises a first binding region arranged in a 5' to 3' orientation and a second binding region arranged in a 3' to 5' orientation (FIG. 1 (*iv*)).

In some embodiments, individual compaction oligonucleotides comprise a linear nucleic acid having a first binding region and a second binding region, and optionally an intervening linker between the first and second binding regions (e.g., FIG. 1). In some embodiments, the first binding region of a compaction oligonucleotide hybridizes to a first portion of a concatemer molecule. In some embodiments, the second binding region of the same compaction oligonucleotide hybridizes to a second portion of the same concatemer molecule. In some embodiments, the first binding region of the compaction oligonucleotide hybridizes to at least a portion of a first universal binding sequence in the concatemer molecule. In some embodiments, the second binding region of the compaction oligonucleotide hybridizes to at least a portion of a second universal binding sequence in the concatemer molecule. In some embodiments, the first and second binding regions of the compaction oligonucleotide comprise the same sequence or different sequences. In some embodiments, the second binding region of the compaction oligonucleotide comprises a reverse sequence of the first binding region of the compaction oligonucleotide. In some embodiments, the orientation of the first binding region of the compaction oligonucleotide is a 5' to 3' orientation or a 3' to 5' orientation. In some embodiments, the orientation of the second binding region of the compaction oligonucleotide is a 5' to 3' orientation or a 3' to 5' orientation (FIG. 1).

In some embodiments, a compaction oligonucleotide comprises a first binding region arranged in a 5' to 3' orientation and a second binding region arranged in a 5' to 3' orientation (FIG. 1(*i*)). In some embodiments, a compaction oligonucleotide comprises a first binding region arranged in a 3' to 5' orientation and a second binding region arranged in a 3' to 5' orientation (FIG. 1(*ii*)). In some embodiments, a compaction oligonucleotide comprises a first binding region arranged in a 3' to 5' orientation and a second binding region arranged in a 5' to 3' orientation (FIG. 1(*iii*)). In some embodiments, a compaction oligonucleotide comprises a first binding region arranged in a 5' to 3' orientation and a second binding region arranged in a 3' to 5' orientation (FIG. 1(*iv*)).

In some embodiments, the intervening linker of a compaction oligonucleotide is designed to be flexible. In some embodiments, the intervening linker of a compaction oligonucleotide is designed to be rigid. In some embodiments, the intervening linker of a compaction oligonucleotide comprises any one or any combination of nucleotides, nucleotide analogs and/or non-nucleotide linker. In some embodiments, the intervening linker of a compaction oligonucleotide exhibits little or no hybridization to any portion of the concatemer molecule.

In some embodiments, the compaction oligonucleotides comprise a linear nucleic acid having a first binding region, a second binding region, a third binding region, and optionally two intervening linkers. In some embodiments, the first intervening linker is located between the first and second binding regions. In some embodiments, the second intervening linker is located between the second and third binding regions (e.g., FIGS. 2A-2C). In some embodiments, the first binding region of the compaction oligonucleotide hybridizes to a first portion of a concatemer molecule. In some embodiments, the second binding region of the compaction oligonucleotide hybridizes to a second portion of the same concatemer molecule. In some embodiments, the third binding region of the compaction oligonucleotide hybridizes to a third portion of the same concatemer molecule.

Figure 2A:
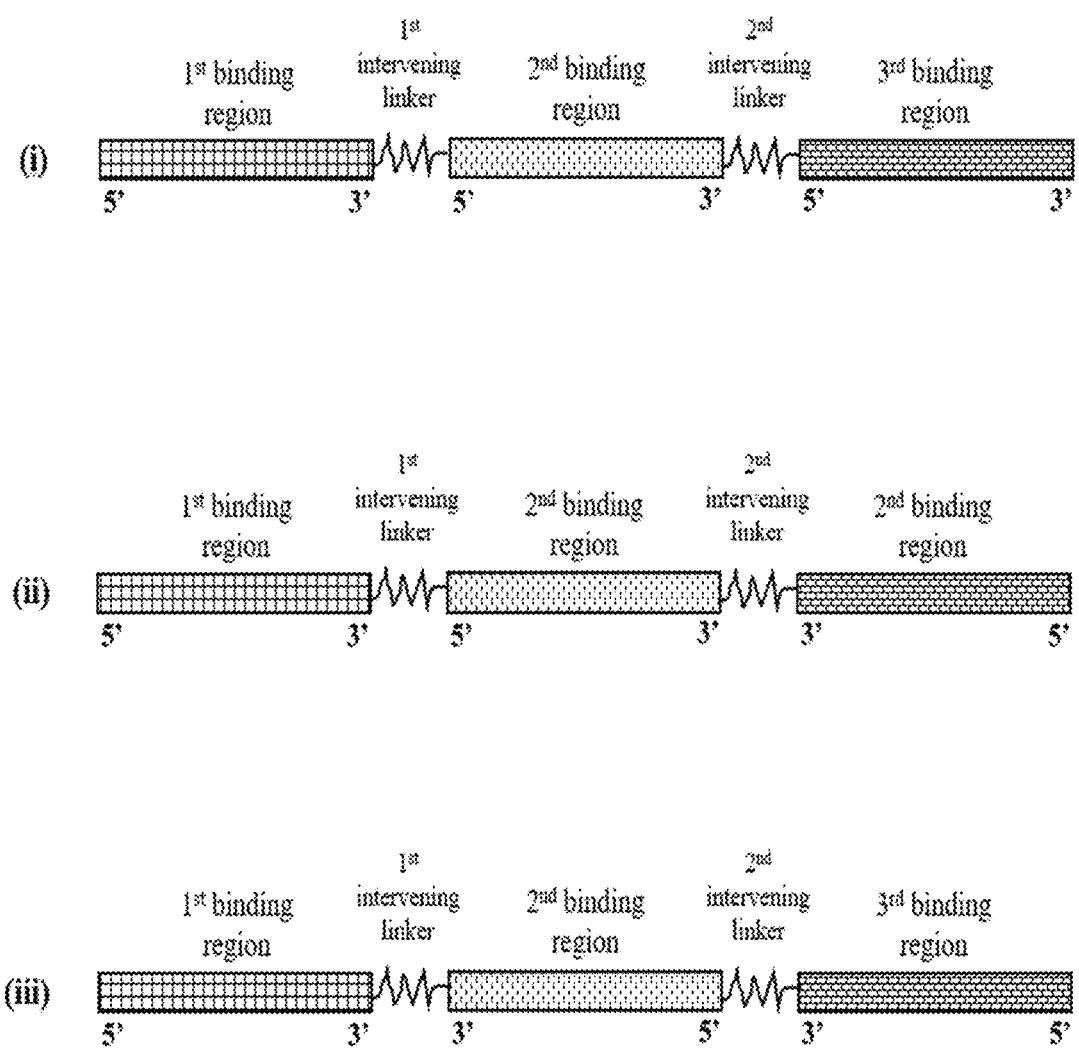
FIG. 2A shows schematics of several embodiments of linear compaction oligonucleotides each comprising a first binding region, a first intervening linker, a second binding region, a second intervening linker, and a third binding region. In some embodiments, a compaction oligonucleotide comprises a first binding region arranged in a 5' to 3' orientation, a second binding region arranged in a 5' to 3' orientation, and a third binding region arranged in a 5' to 3' orientation (FIG. 2A (i)). In some embodiments, a compaction oligonucleotide comprises a first binding region arranged in a 5' to 3' orientation, a second binding region arranged in a 5' to 3' orientation, and a third binding region arranged in a 3' to 5' orientation (FIG. 2A (ii)). In some embodiments, a compaction oligonucleotide comprises a first binding region arranged in a 5' to 3' orientation, a second binding region arranged in a 3' to 5' orientation, and a third binding region arranged in a 3' to 5' orientation (FIG. 2A (iii)).

In some embodiments, a compaction oligonucleotide comprises a first binding region arranged in a 5' to 3' orientation, a second binding region arranged in a 5' to 3' orientation, and a third binding region arranged in a 5' to 3' orientation (FIG. 2A(i)). In some embodiments, a compaction oligonucleotide comprises a first binding region arranged in a 5' to 3' orientation, a second binding region arranged in a 5' to 3' orientation, and a third binding region arranged in a 3' to 5' orientation (FIG. 2A(ii)).

In some embodiments, a compaction oligonucleotide comprises a first binding region arranged in a 5' to 3' orientation, a second binding region arranged in a 3' to 5' orientation, and a third binding region arranged in a 3' to 5' orientation (FIG. 2A(iii)).

Figure 2B:
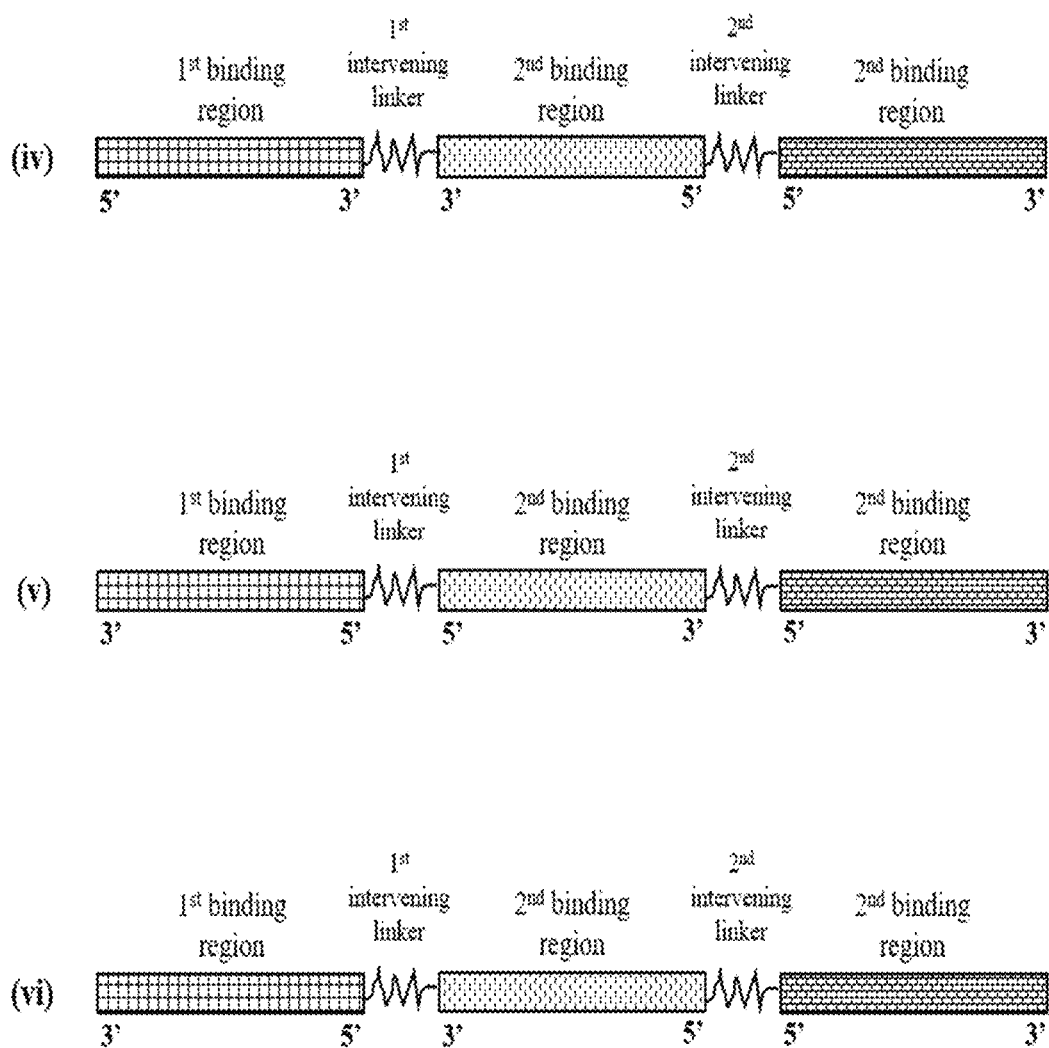
FIG. 2B shows schematics of several embodiments of linear compaction oligonucleotides each comprising a first binding region, a first intervening linker, a second binding region, a second intervening linker, and a third binding region. In some embodiments, a compaction oligonucleotide comprises a first binding region arranged in a 5' to 3' orientation, a second binding region arranged in a 3' to 5' orientation, and a third binding region arranged in a 5' to 3' orientation (FIG. 2B (iv)). In some embodiments, a compaction oligonucleotide comprises a first binding region arranged in a 3' to 5' orientation, a second binding region arranged in a 5' to 3' orientation, and a third binding region arranged in a 5' to 3' orientation (FIG. 2B (v)). In some embodiments, a compaction oligonucleotide comprises a first binding region arranged in a 3' to 5' orientation, a second binding region arranged in a 3' to 5' orientation, and a third binding region arranged in a 5' to 3' orientation (FIG. 2B (vi)).
Figure 3A:
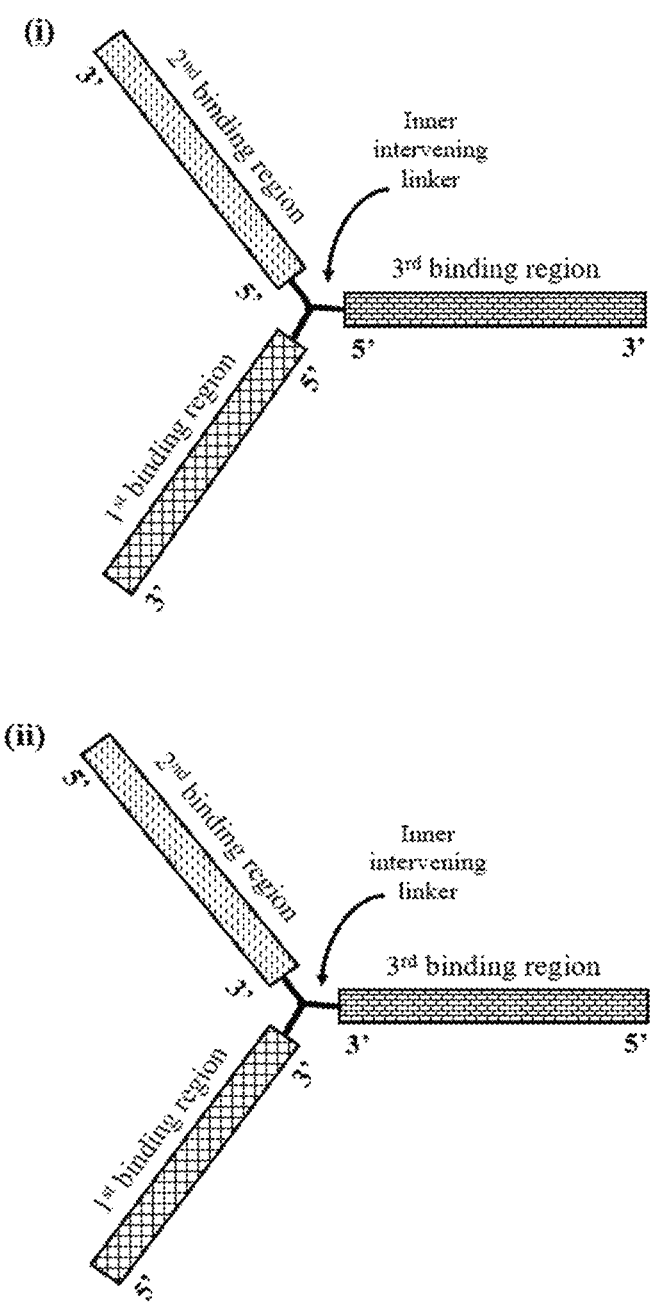
FIG. 3A shows schematics of several embodiments of compaction oligonucleotides each comprising three binding arms linked together by at least one inner intervening linker, wherein individual binding arms comprise a binding region. In some embodiments, a compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 5' to 3' orientation where the 3' end of the second binding region is directed away from the inner intervening linker; and (3) an inner intervening linker and a third binding region arranged in a 5' to 3' orientation where the 3' end of the third binding region is directed away from the inner intervening linker (FIG. 3A (i)). In some embodiments, a compaction oligonucleotide comprises: (1) an inner intervening linker and a first binding region arranged in a 3' to 5' orientation where the 5' end of the first binding region is directed away from the inner intervening linker; (2) an inner intervening linker and a second binding region arranged in a 3' to 5' orientation where the 5' end of the second binding region is directed away from the inner intervening linker; and (3) an inner intervening linker and a third binding region arranged in a 3' to 5' orientation where the 5' end of the third binding region is directed away from the inner intervening linker (FIG. 3A (ii)).
Figure 3B:
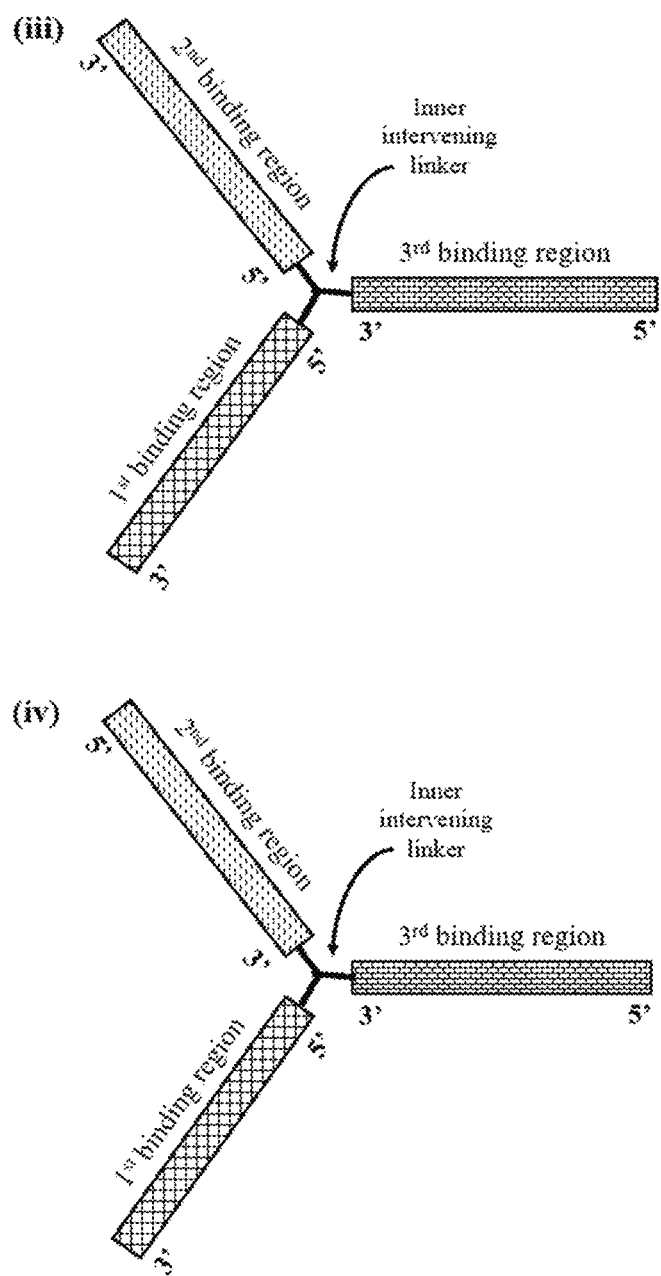
FIG. 3B shows schematics of several embodiments of compaction oligonucleotides each comprising three binding arms linked together by at least one inner intervening linker, wherein individual binding arms comprise a binding region. In some embodiments, a compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 5' to 3' orientation where the 3' end of the second binding region is directed away from the inner intervening linker; and (3) an inner intervening linker and a third binding region arranged in a 3' to 5' orientation where the 5' end of the third binding region is directed away from the inner intervening linker (FIG. 3B (iii)). In some embodiments, a compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 3' to 5' orientation where the 5' end of the second binding region is directed away from the inner intervening linker; and (3) an inner intervening linker and a third binding region arranged in a 3' to 5' orientation where the 5' end of the third binding region is directed away from the inner intervening linker (FIG. 3B (iv)).

In some embodiments, a compaction oligonucleotide comprises a first binding region arranged in a 5' to 3' orientation, a second binding region arranged in a 3' to 5' orientation, and a third binding region arranged in a 5' to 3' orientation (FIG. 2B(iv)). In some embodiments, a compaction oligonucleotide comprises a first binding region arranged in a 3' to 5' orientation, a second binding region arranged in a 5' to 3' orientation, and a third binding region arranged in a 5' to 3' orientation (FIG. 2B(v)). In some embodiments, a compaction oligonucleotide comprises a first binding region arranged in a 3' to 5' orientation, a second binding region arranged in a 3' to 5' orientation, and a third binding region arranged in a 5' to 3' orientation (FIG. 2B(vi)).

In some embodiments, a compaction oligonucleotide comprises a first binding region arranged in a 3' to 5' orientation, a second binding region arranged in a 5' to 3' orientation, and a third binding region arranged in a 5' to 3' orientation (FIG. 2C(vii)).

In some embodiments, a compaction oligonucleotide comprises a first binding region arranged in a 3' to 5' orientation, a second binding region arranged in a 3' to 5' orientation, and a third binding region arranged in a 5' to 3' orientation (FIG. 2C(viii)). In some embodiments, a compaction oligonucleotide comprises a first binding region arranged in a 3' to 5' orientation, a second binding region arranged in a 5' to 3' orientation, and a third binding region arranged in a 3' to 5' orientation (FIG. 2C(ix)).

In some embodiments, the first binding region of the compaction oligonucleotide hybridizes to at least a portion of a first universal binding sequence in the concatemer molecule. In some embodiments, the second binding region of the compaction oligonucleotide hybridizes to at least a portion of a second universal binding sequence in the same concatemer molecule. In some embodiments, the third binding region of the compaction oligonucleotide hybridizes to at least a portion of a third universal binding sequence in the same concatemer molecule.

In some embodiments, the first binding region, the second binding region, and the third binding region of the compaction oligonucleotide comprise the same sequence or different sequences. In some embodiments, the second and third binding regions of the compaction oligonucleotide have the same sequence, and the first binding region has a different sequence. In some embodiments, the first and second regions of the compaction oligonucleotide have the same sequence, and the third binding region has a different sequence. In some embodiments, the first and third binding regions of the compaction oligonucleotide have the same sequence, and the second binding region has a different sequence.

In some embodiments, the third binding region of the compaction oligonucleotide comprises a reverse sequence of the first binding region of the compaction oligonucleotide. In some embodiments, the second binding region of the compaction oligonucleotide comprises a sequence that is a reverse of the first binding region.

In some embodiments, the intervening linker of a compaction oligonucleotide is designed to be flexible. In some embodiments, the intervening linker of a compaction oligonucleotide is designed to be rigid. In some embodiments, the intervening linker of a compaction oligonucleotide comprises any one or any combination of nucleotides, nucleotide analogs and/or non-nucleotide linker. In some embodiments, the intervening linker of a compaction oligonucleotide exhibits little or no hybridization to any portion of the concatemer molecule.

In some embodiments, the compaction oligonucleotides comprise a star shaped nucleic acid having a first binding region, and internal region, and a second binding region, and optionally two intervening linkers. In some embodiments, the first intervening linker is located between the first binding and internal regions. In some embodiments, the second intervening linker is located between the internal and second binding regions (e.g., FIGS. 3A and B). In some embodiments, the first binding region of the compaction oligonucleotide hybridizes to a first portion of a concatemer molecule. In some embodiments, the internal region of the compaction oligonucleotide hybridizes to a second portion of the same concatemer molecule. In some embodiments, the second binding region of the compaction oligonucleotide hybridizes to a third portion of the same concatemer molecule.

In some embodiments, a compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 5' to 3' orientation where the 3' end of the second binding region is directed away from the inner intervening linker; and (3) an inner intervening linker and a third binding region arranged in a 5' to 3' orientation where the 3' end of the third binding region is directed away from the inner intervening linker (FIG. 3A(i)).

In some embodiments, a compaction oligonucleotide comprises: (1) an inner intervening linker and a first binding region arranged in a 3' to 5' orientation where the 5' end of the first binding region is directed away from the inner intervening linker; (2) an inner intervening linker and a second binding region arranged in a 3' to 5' orientation where the 5' end of the second binding region is directed away from the inner intervening linker; and (3) an inner intervening linker and a third binding region arranged in a 3' to 5' orientation where the 5' end of the third binding region is directed away from the inner intervening linker (FIG. 3A(ii)).

In some embodiments, a compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 5' to 3' orientation where the 3' end of the second binding region is directed away from the inner intervening linker; and (3) an inner intervening linker and a third binding region arranged in a 3' to 5' orientation where the 5' end of the third binding region is directed away from the inner intervening linker (FIG. 3B(iii)).

In some embodiments, a compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 3' to 5' orientation where the 5' end of the second binding region is directed away from the inner intervening linker; and (3) an inner intervening linker and a third binding region arranged in a 3' to 5' orientation where the 5' end of the third binding region is directed away from the inner intervening linker (FIG. 3B(iv)).

In some embodiments, the first binding region of the compaction oligonucleotide hybridizes to at least a portion of a first universal binding sequence in the concatemer molecule. In some embodiments, the internal region of the compaction oligonucleotide hybridizes to at least a portion of a second universal binding sequence in the concatemer molecule. In some embodiments, the second binding region of the compaction oligonucleotide hybridizes to at least a portion of a third universal binding sequence in the concatemer molecule. In some embodiments, the first binding region, the internal region, and the second binding region of the compaction oligonucleotide comprise the same sequence or different sequences. In some embodiments, the internal and second binding regions of the compaction oligonucleotide have the same sequence, and the first binding region has a different sequence. In some embodiments, the first binding and internal regions of the compaction oligonucleotide have the same sequence, and the second binding region has a different sequence. In some embodiments, the first binding and second binding regions of the compaction oligonucleotide have the same sequence, and the internal region has a different sequence. In some embodiments, the second binding region of the compaction oligonucleotide comprises a reverse sequence of the first binding region of the compaction oligonucleotide. In some embodiments, the internal region of the compaction oligonucleotide comprises a sequence that is a reverse of the first binding region.

In some embodiments, the intervening linker of a compaction oligonucleotide is designed to be flexible or rigid. In some embodiments, the intervening linker of a compaction oligonucleotide comprises any one or any combination of nucleotides, nucleotide analogs and/or non-nucleotide linker. In some embodiments, the intervening linker of a compaction oligonucleotide exhibits little or no hybridization to any portion of the concatemer molecule.

Figure 4:
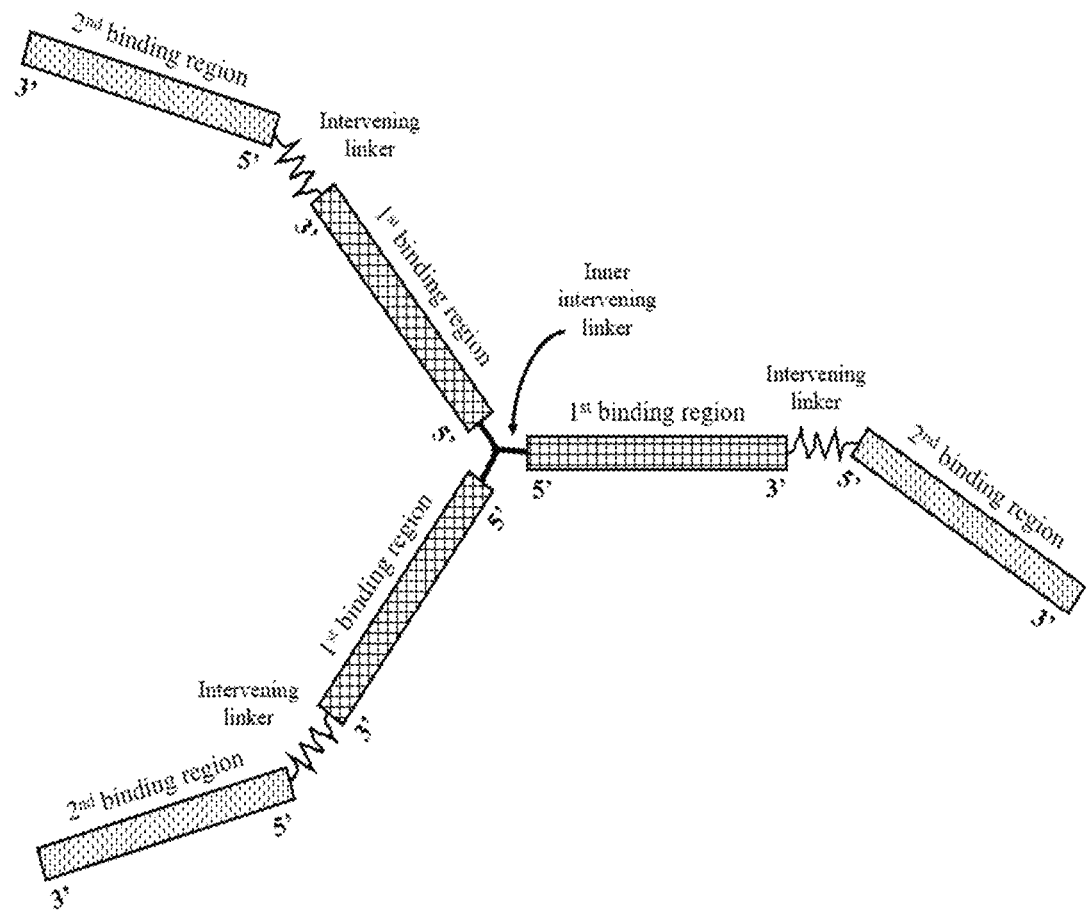
FIG. 4 shows a schematic of an embodiment of a compaction oligonucleotide comprising three binding arms linked together by at least one inner intervening linker, wherein individual binding arms comprise a first binding region, an intervening linker, and a second binding region. In some embodiments, a compaction oligonucleotide comprises three binding arms where each binding arm comprises: an inner intervening linker, a first binding region arranged in a 5' to 3' orientation, an intervening linker, and a second binding region arranged in a 5' to 3' direction, where the 3' end of the second binding region is directed away from the inner intervening linker.

In some embodiments, a compaction oligonucleotide comprises three binding arms where each binding arm comprises: an inner intervening linker, a first binding region arranged in a 5' to 3' orientation, an intervening linker, and a second binding region arranged in a 5' to 3' direction, where the 3' end of the second binding region is directed away from the inner intervening linker (FIG. 4).

In some embodiments, a compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 5' to 3' orientation where the 3' end of the second binding region is directed away from the inner intervening linker; (3) an inner intervening linker and a third binding region arranged in a 5' to 3' orientation where the 3' end of the third binding region is directed away from the inner intervening linker; and (4) an inner intervening linker and a fourth binding region arranged in a 5' to 3' orientation where the 3' end of the fourth binding region is directed away from the inner intervening linker (FIG. 5(i)).

In some embodiments, a compaction oligonucleotide comprises: (1) an inner intervening linker and a first binding region arranged in a 3' to 5' orientation where the 5' end of the first binding region is directed away from the inner intervening linker; (2) an inner intervening linker and a second binding region arranged in a 3' to 5' orientation where the 5' end of the second binding region is directed away from the inner intervening linker; (3) an inner intervening linker and a third binding region arranged in a 3' to 5' orientation where the 5' end of the third binding region is directed away from the inner intervening linker; and (4) an inner intervening linker and a fourth binding region arranged in a 3' to 5' orientation where the 5' end of the fourth binding region is directed away from the inner intervening linker (FIG. 5(ii)).

Figure 6A:
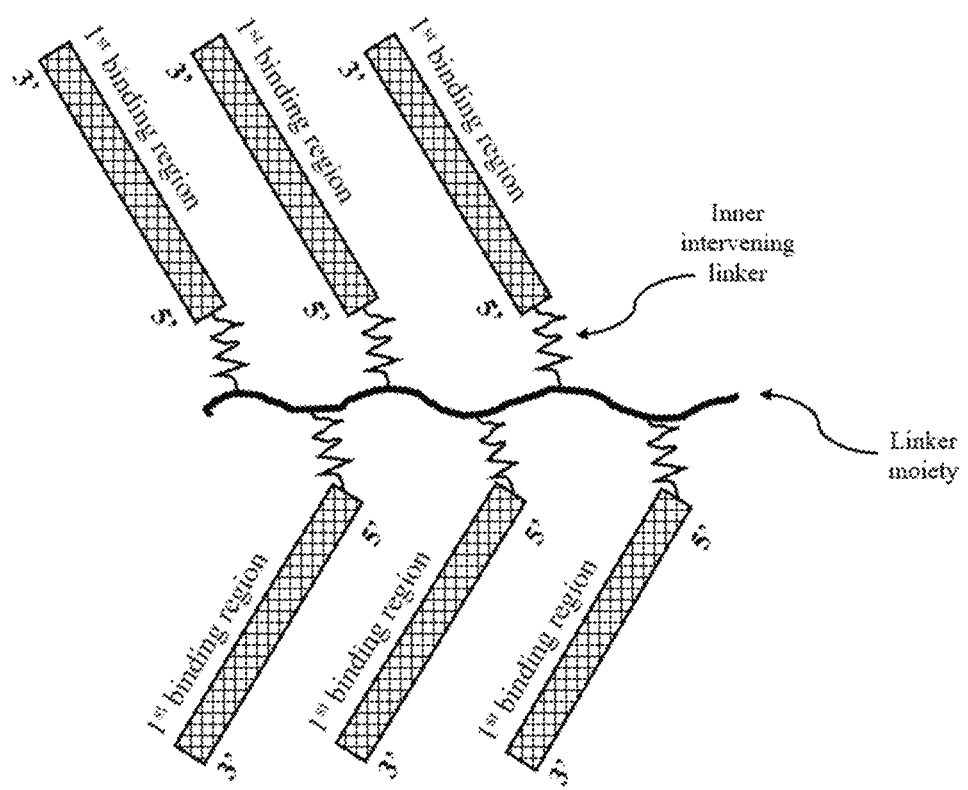
FIG. 6A shows a schematic of an embodiment of a double-sided comb shaped compaction oligonucleotide comprising a plurality of binding arms linked to a central linker moiety, wherein individual binding arms comprise a binding region. In some embodiments, the compaction oligonucleotide comprises at least three binding arms. In some embodiments, the compaction oligonucleotide comprises a plurality of binding arms having the same sequence. In some embodiments, individual binding arms comprise a first binding region arranged in a 5' to 3' orientation where the 3' end of the first binding region is directed away from the linker moiety. In some embodiments, individual binding arms are joined to the linker moiety by an inner intervening linker.

In some embodiments, the compaction oligonucleotide comprises at least three binding arms. In some embodiments, the compaction oligonucleotide comprises a plurality of binding arms having the same sequence. In some embodiments, individual binding arms comprise a first binding region arranged in a 5' to 3' orientation where the 3' end of the first binding region is directed away from the linker moiety. In some embodiments, individual binding arms are joined to the linker moiety by an inner intervening linker (FIG. 6A).

Figure 6B:
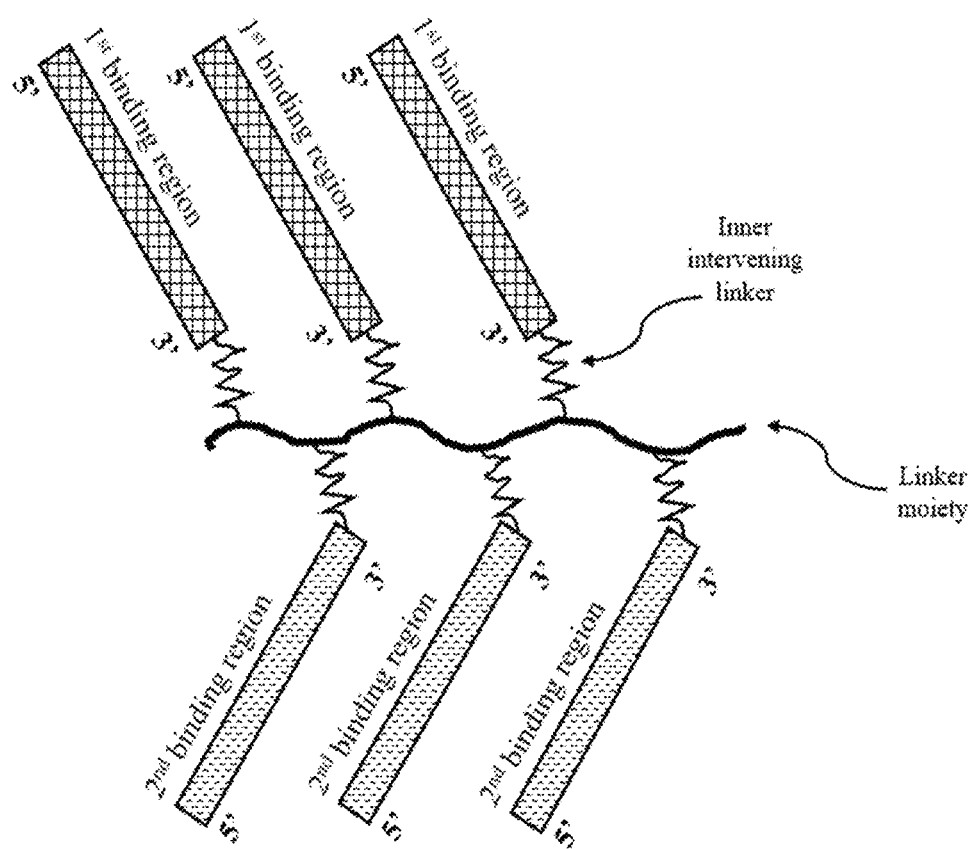
FIG. 6B shows a schematic of an embodiment of a double-sided comb shaped compaction oligonucleotide comprising a plurality of binding arms linked to a central linker moiety, wherein individual binding arms comprise a binding region. In some embodiments, the compaction oligonucleotide comprises at least three binding arms. In some embodiments, the compaction oligonucleotide comprises a plurality of binding arms having one of two different sequences. In some embodiments, individual binding arms comprise a first binding region arranged in a 5' to 3' orientation where the 3' end of the first binding region is directed away from the linker moiety. In some embodiments, individual binding arms comprise a second binding region arranged in a 5' to 3' orientation where the 3' end of the second binding region is directed away from the linker moiety. In some embodiments, individual binding arms are joined to the linker moiety by an inner intervening linker.

In some embodiments, the compaction oligonucleotide comprises at least three binding arms. In some embodiments, the compaction oligonucleotide comprises a plurality of binding arms having one of two different sequences. In some embodiments, individual binding arms comprise a first binding region arranged in a 5' to 3' orientation where the 3' end of the first binding region is directed away from the linker moiety. In some embodiments, individual binding arms comprise a second binding region arranged in a 5' to 3' orientation where the 3' end of the second binding region is directed away from the linker moiety. In some embodiments, individual binding arms are joined to the linker moiety by an inner intervening linker (FIG. 6B).

Figure 6C:
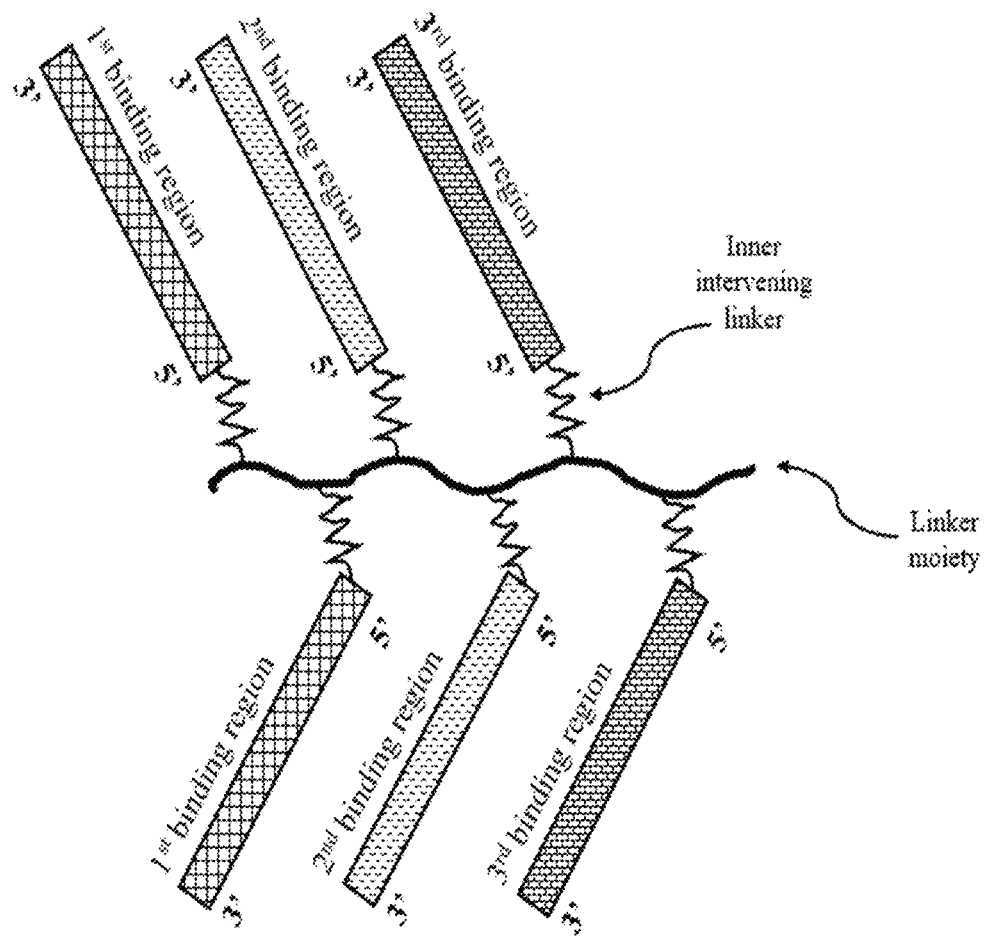
FIG. 6C shows a schematic of an embodiment of a double-sided comb shaped compaction oligonucleotide comprising a plurality of binding arms linked to a central linker moiety, wherein individual binding arms comprise a binding region. In some embodiments, the compaction oligonucleotide comprises at least three binding arms. In some embodiments, the compaction oligonucleotide comprises a plurality of binding arms having one of three different sequences. In some embodiments, individual binding arms comprise a first binding region arranged in a 5' to 3' orientation where the 3' end of the first binding region is directed away from the linker moiety. In some embodiments, individual binding arms comprise a second binding region arranged in a 5' to 3' orientation where the 3' end of the second binding region is directed away from the linker moiety. In some embodiments, individual binding arms comprise a third binding region arranged in a 5' to 3' orientation where the 3' end of the third binding region is directed away from the linker moiety. In some embodiments, individual binding arms are joined to the linker moiety by an inner intervening linker.

In some embodiments, the compaction oligonucleotide comprises at least three binding arms. In some embodiments, the compaction oligonucleotide comprises a plurality of binding arms having one of three different sequences. In some embodiments, individual binding arms comprise a first binding region arranged in a 5' to 3' orientation where the 3' end of the first binding region is directed away from the linker moiety. In some embodiments, individual binding arms comprise a second binding region arranged in a 5' to 3' orientation where the 3' end of the second binding region is directed away from the linker moiety. In some embodiments, individual binding arms comprise a third binding region arranged in a 5' to 3' orientation where the 3' end of the third binding region is directed away from the linker moiety. In some embodiments, individual binding arms are joined to the linker moiety by an inner intervening linker (FIG. 6C).

Figure 7A:
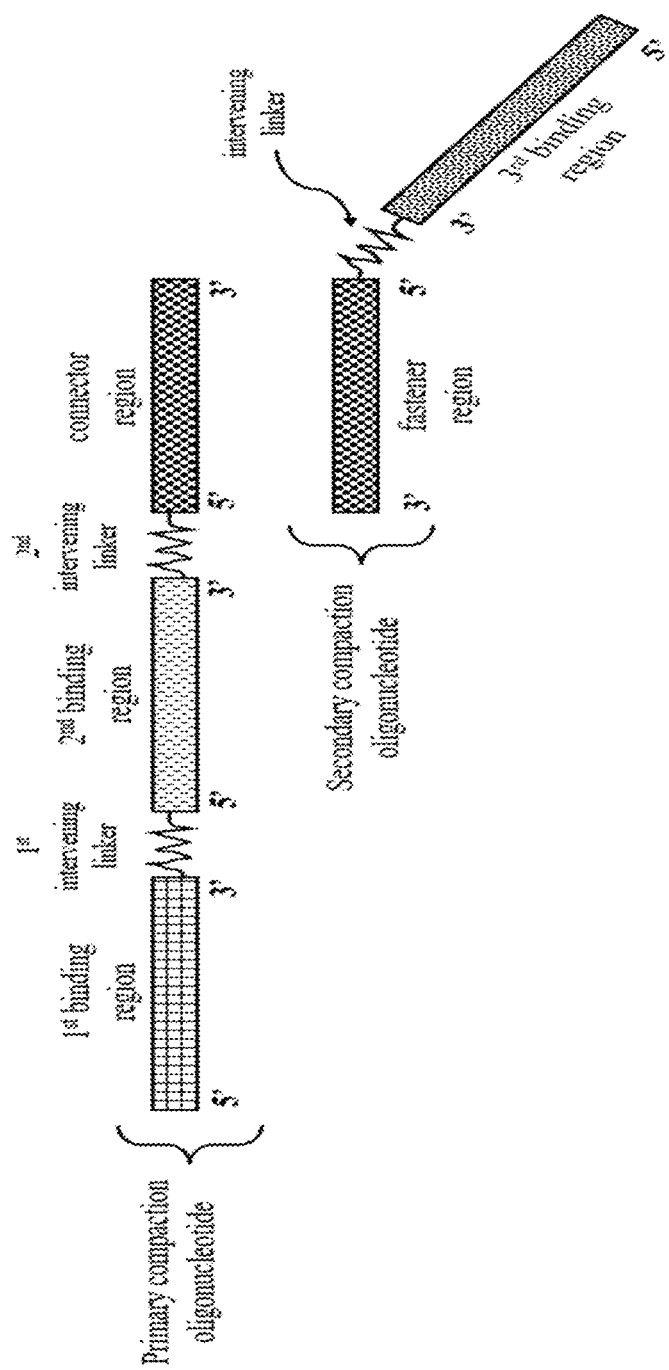
FIG. 7A shows a schematic of an embodiment of a multipart compaction oligonucleotide comprising a primary linear compaction oligonucleotide hybridized to a secondary linear compaction oligonucleotide. In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 5' to 3' orientation. In some embodiments, the secondary linear compaction oligonucleotide comprises a fastener region arranged in a 3' to 5' orientation, an intervening linker, and a third binding region arranged in a 3' to 5' orientation. In some embodiments, the connector region of the primary compaction oligonucleotide can hybridize to the fastener region of the secondary compaction oligonucleotide.

In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 5' to 3' orientation. In some embodiments, the secondary linear compaction oligonucleotide comprises a fastener region arranged in a 3' to 5' orientation, an intervening linker, and a third binding region arranged in a 3' to 5' orientation. In some embodiments, the connector region of the primary compaction oligonucleotide can hybridize to the fastener region of the secondary compaction oligonucleotide (FIG. 7A).

Figure 7B:
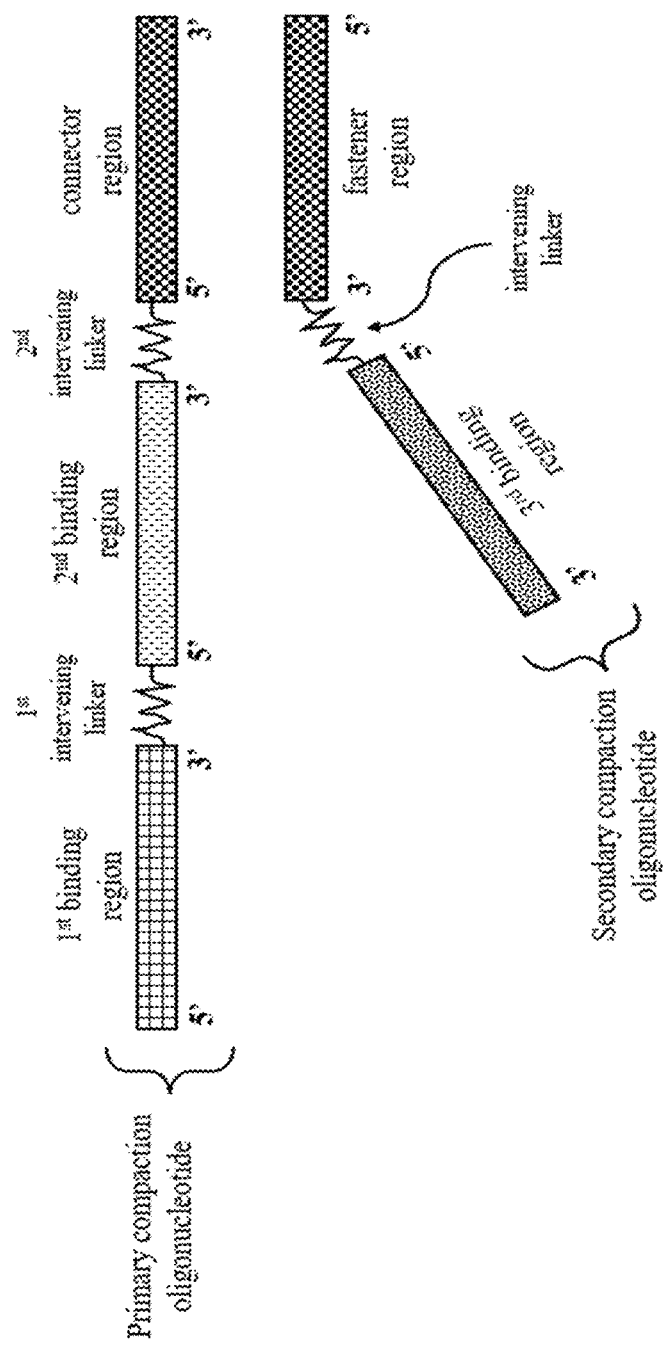
FIG. 7B shows a schematic of an embodiment of a multipart compaction oligonucleotide comprising a primary linear compaction oligonucleotide hybridized to a secondary linear compaction oligonucleotide. In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 5' to 3' orientation. In some embodiments, the secondary linear compaction oligonucleotide comprises a third binding region arranged in a 3' to 5' orientation, an intervening linker, and a fastener region arranged in a 3' to 5' orientation. In some embodiments, the connector region of the primary compaction oligonucleotide can hybridize to the fastener region of the secondary compaction oligonucleotide.

In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 5' to 3' orientation. In some embodiments, the secondary linear compaction oligonucleotide comprises a third binding region arranged in a 3' to 5' orientation, an intervening linker, and a fastener region arranged in a 3' to 5' orientation. In some embodiments, the connector region of the primary compaction oligonucleotide can hybridize to the fastener region of the secondary compaction oligonucleotide (FIG. 7B).

Figure 8A:
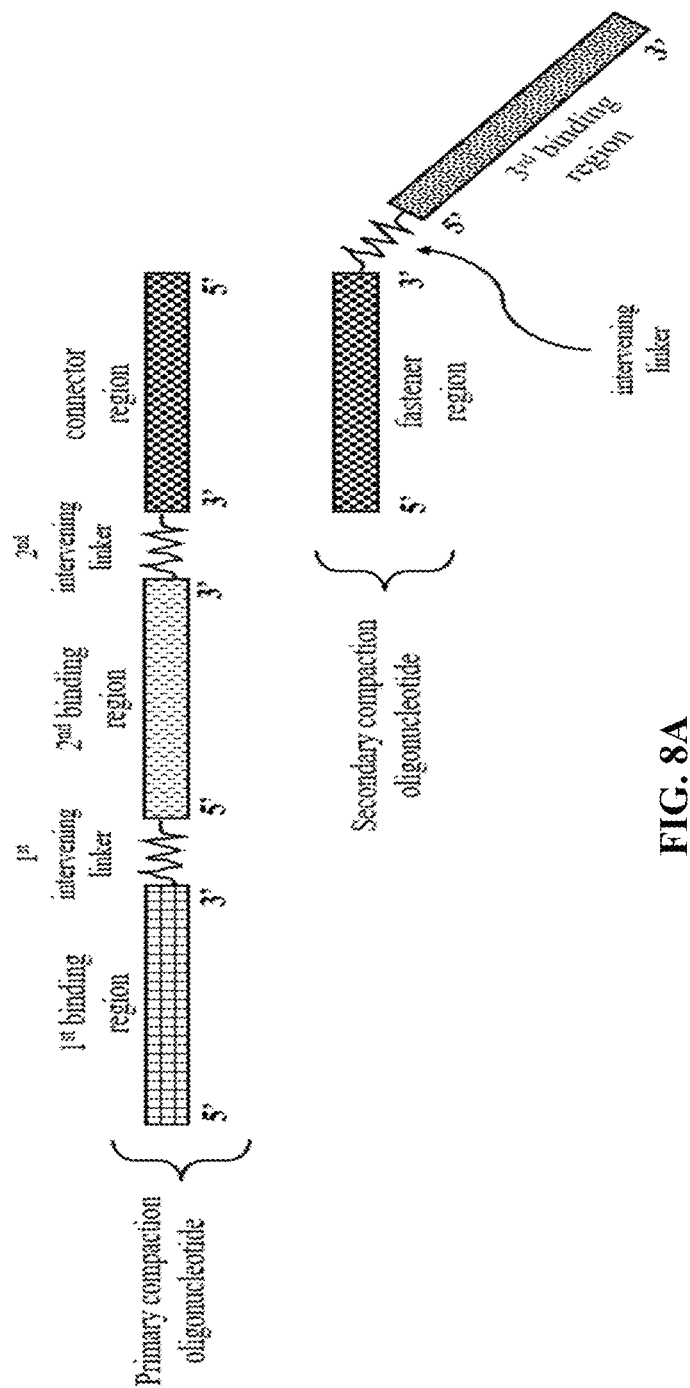
FIG. 8A shows a schematic of an embodiment of a multipart compaction oligonucleotide comprising a primary linear compaction oligonucleotide hybridized to a secondary linear compaction oligonucleotide. In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 3' to 5' orientation. In some embodiments, the secondary linear compaction oligonucleotide comprises a fastener region arranged in a 5' to 3' orientation, an intervening linker, and a third binding region arranged in a 5' to 3' orientation. In some embodiments, the connector region of the primary compaction oligonucleotide can hybridize to the fastener region of the secondary compaction oligonucleotide.

In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 3' to 5' orientation. In some embodiments, the secondary linear compaction oligonucleotide comprises a fastener region arranged in a 5' to 3' orientation, an intervening linker, and a third binding region arranged in a 5' to 3' orientation. In some embodiments, the connector region of the primary compaction oligonucleotide can hybridize to the fastener region of the secondary compaction oligonucleotide (FIG. 8A).

Figure 8B:
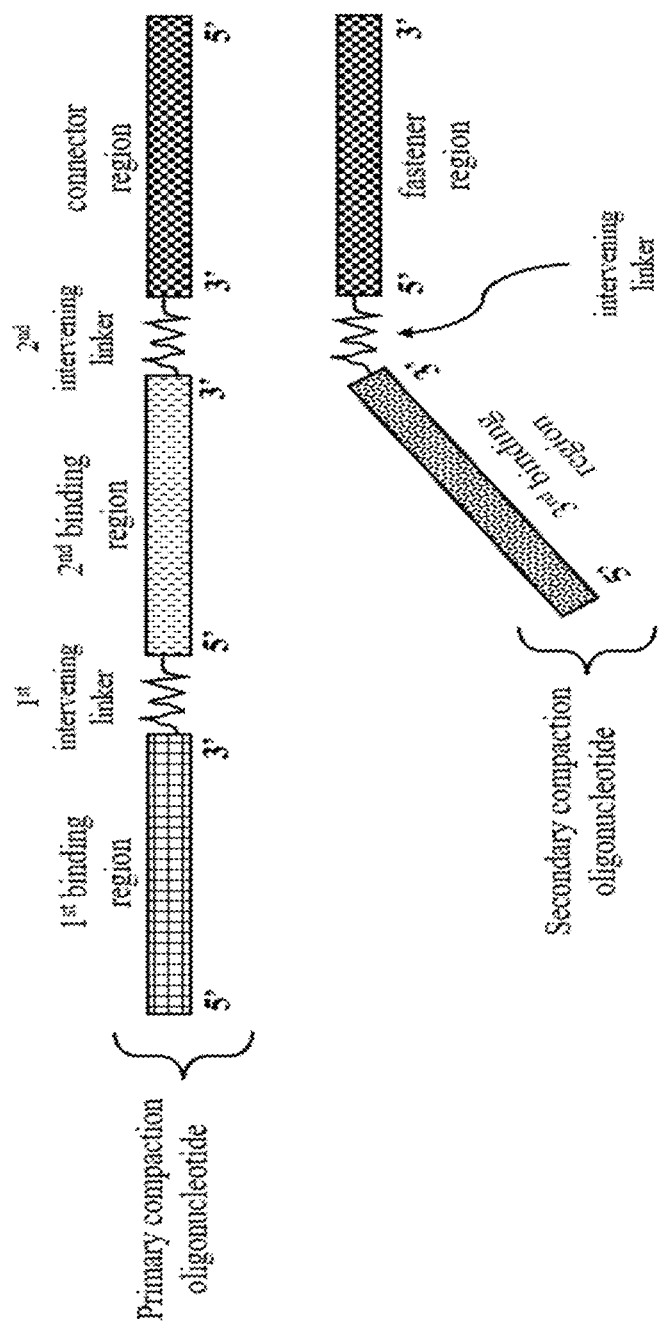
FIG. 8B shows a schematic of an embodiment of a multipart compaction oligonucleotide comprising a primary linear compaction oligonucleotide hybridized to a secondary linear compaction oligonucleotide. In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 3' to 5' orientation. In some embodiments, the secondary linear compaction oligonucleotide comprises a third binding region arranged in a 5' to 3' orientation, an intervening linker, and a fastener region arranged in a 5' to 3' orientation. In some embodiments, the connector region of the primary compaction oligonucleotide can hybridize to the fastener region of the secondary compaction oligonucleotide.

In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 3' to 5' orientation. In some embodiments, the secondary linear compaction oligonucleotide comprises a third binding region arranged in a 5' to 3' orientation, an intervening linker, and a fastener region arranged in a 5' to 3' orientation. In some embodiments, the connector region of the primary compaction oligonucleotide can hybridize to the fastener region of the secondary compaction oligonucleotide (FIG. 8B).

Figure 9:
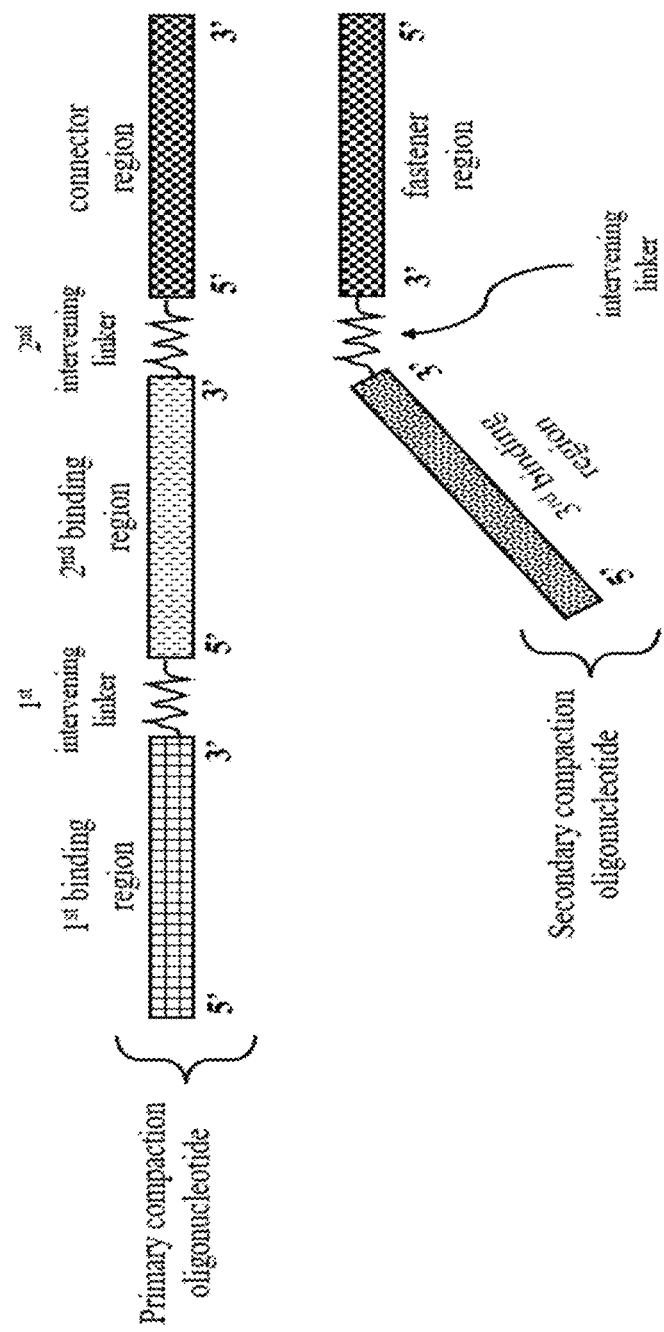
FIG. 9 shows a schematic of an embodiment of a multipart compaction oligonucleotide comprising a primary linear compaction oligonucleotide hybridized to a secondary linear compaction oligonucleotide. In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 5' to 3' orientation. In some embodiments, the secondary linear compaction oligonucleotide comprises a third binding region arranged in a 5' to 3' orientation, an intervening linker, and a fastener region arranged in a 3' to 5' orientation. In some embodiments, the connector region of the primary compaction oligonucleotide can hybridize to the fastener region of the secondary compaction oligonucleotide.

In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 5' to 3' orientation. In some embodiments, the secondary linear compaction oligonucleotide comprises a third binding region arranged in a 5' to 3' orientation, an intervening linker, and a fastener region arranged in a 3' to 5' orientation. In some embodiments, the connector region of the primary compaction oligonucleotide can hybridize to the fastener region of the secondary compaction oligonucleotide (FIG. 9).

Figure 10:
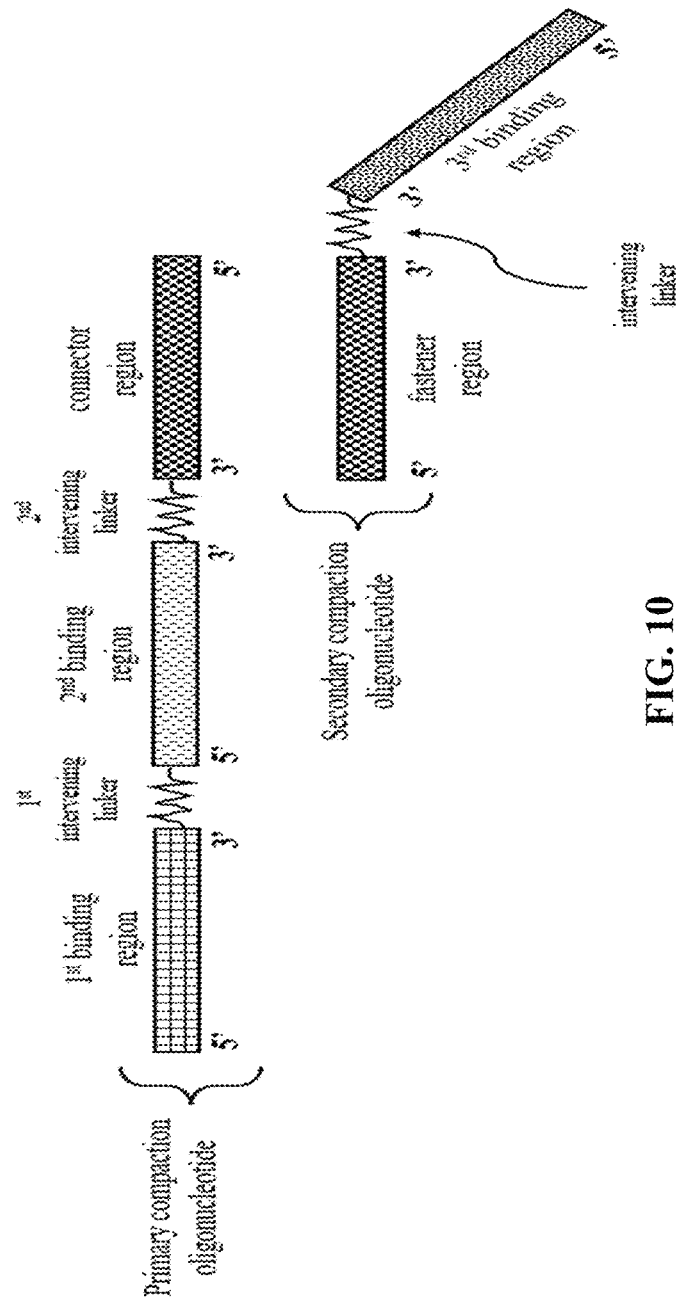
FIG. 10 shows a schematic of an embodiment of a multipart compaction oligonucleotide comprising a primary linear compaction oligonucleotide hybridized to a secondary linear compaction oligonucleotide. In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 3' to 5' orientation. In some embodiments, the secondary linear compaction oligonucleotide comprises a fastener region arranged in a 5' to 3' orientation, an intervening linker, and a third binding region arranged in a 3' to 5' orientation. In some embodiments, the connector region of the primary compaction oligonucleotide can hybridize to the fastener region of the secondary compaction oligonucleotide.

In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 3' to 5' orientation. In some embodiments, the secondary linear compaction oligonucleotide comprises a fastener region arranged in a 5' to 3' orientation, an intervening linker, and a third binding region arranged in a 3' to 5' orientation. In some embodiments, the connector region of the primary compaction oligonucleotide can hybridize to the fastener region of the secondary compaction oligonucleotide (FIG. 10).

Figure 11:
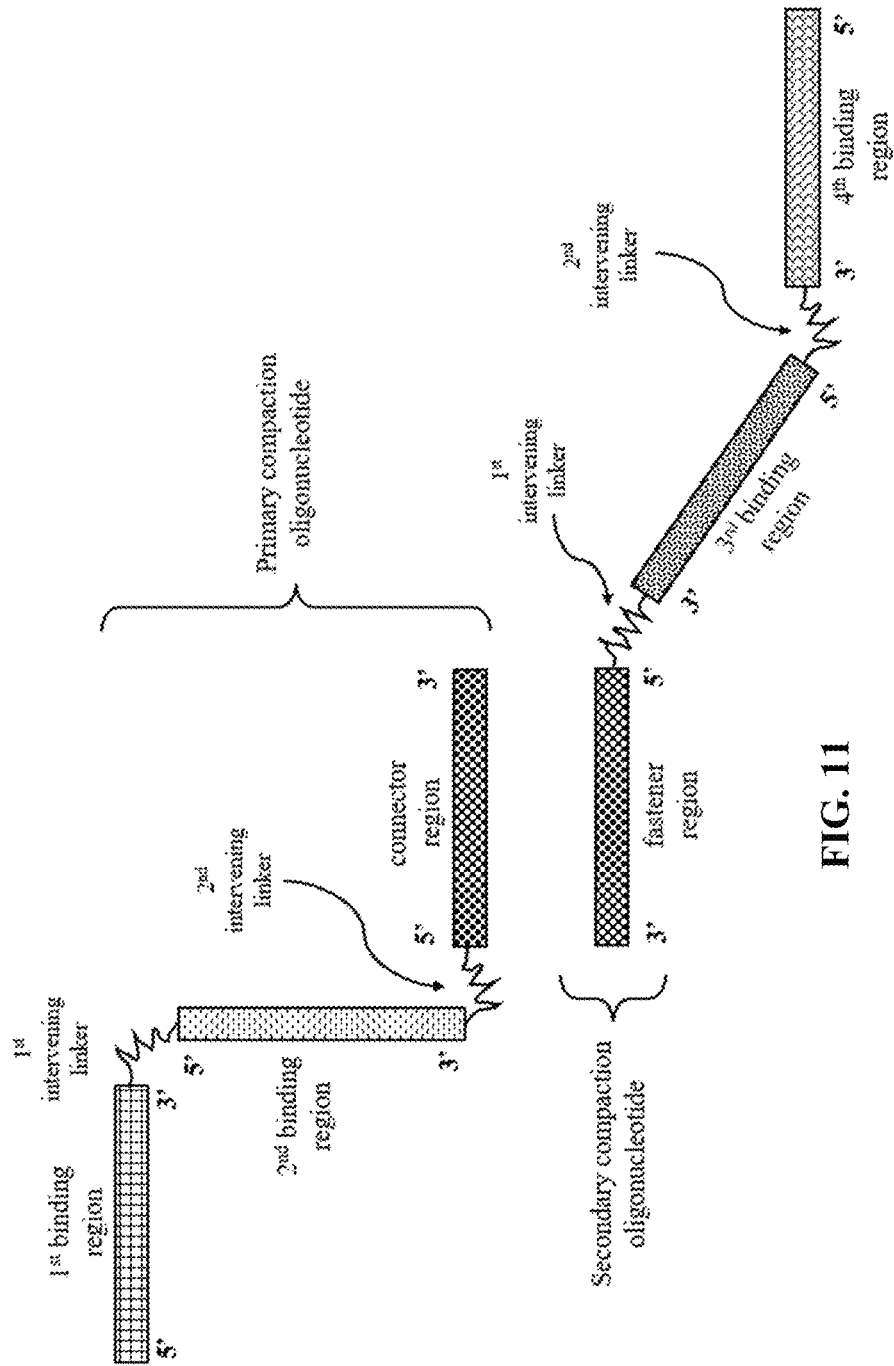
FIG. 11 shows a schematic of an embodiment of a multipart compaction oligonucleotide comprising a primary linear compaction oligonucleotide hybridized to a secondary linear compaction oligonucleotide. In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 5' to 3' orientation. In some embodiments, the secondary linear compaction oligonucleotide comprises a fastener region arranged in a 3' to 5' orientation, a first intervening linker, a third binding region arranged in a 3' to 5' orientation, a second intervening region, and a fourth binding region arranged in a 3' to 5' orientation. In some embodiments, the connector region of the primary compaction oligonucleotide can hybridize to the fastener region of the secondary compaction oligonucleotide.

In some embodiments, the primary linear compaction oligonucleotide comprises a first binding region arranged in a 5' to 3' orientation, a first intervening linker, a second binding region arranged in a 5' to 3' orientation, a second intervening linker and a connector region arranged in a 5' to 3' orientation. In some embodiments, the secondary linear compaction oligonucleotide comprises a fastener region arranged in a 3' to 5' orientation, a first intervening linker, a third binding region arranged in a 3' to 5' orientation, a second intervening region, and a fourth binding region arranged in a 3' to 5' orientation. In some embodiments, the connector region of the primary compaction oligonucleotide can hybridize to the fastener region of the secondary compaction oligonucleotide (FIG. 11).

Figure 12A:
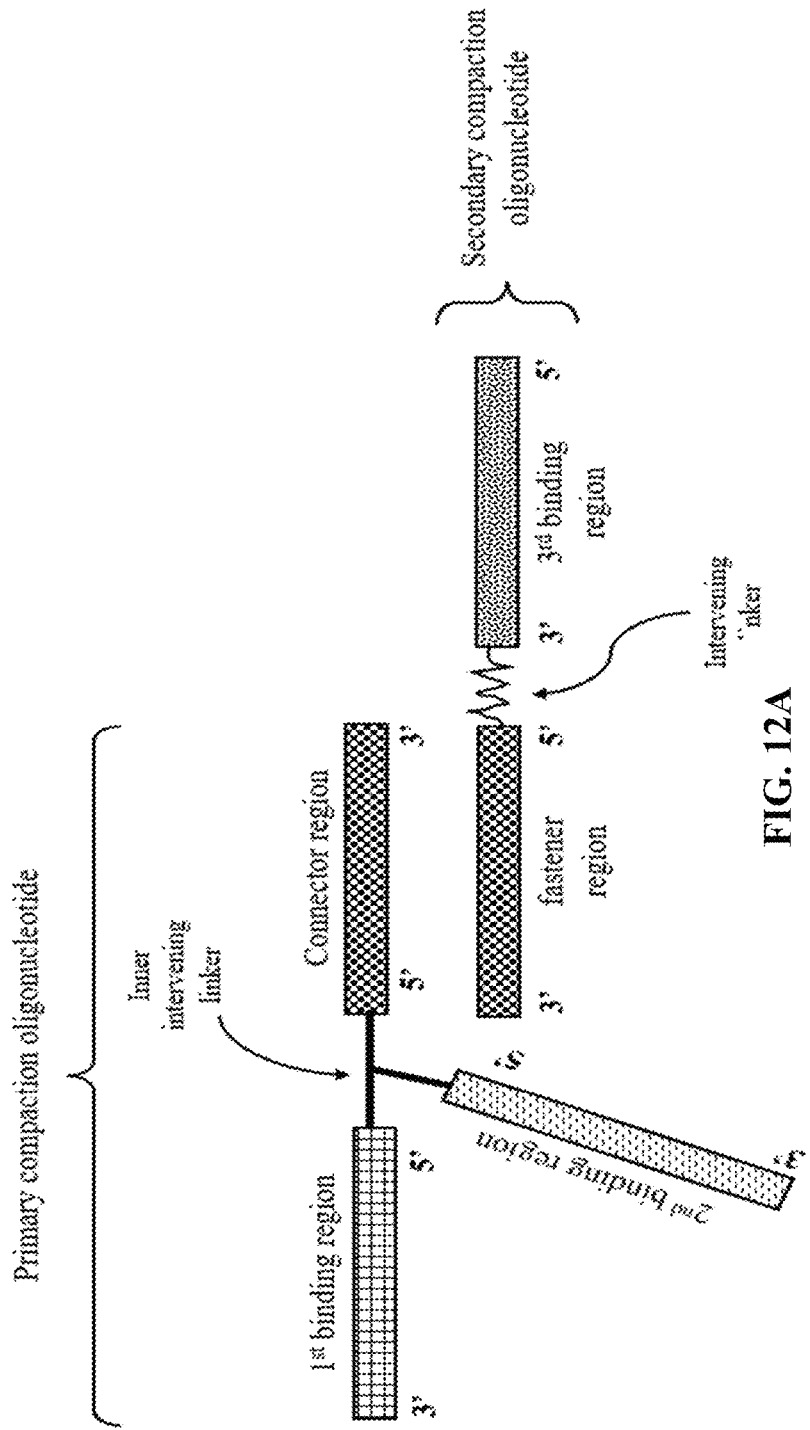
FIG. 12A shows a schematic of an embodiment of a multipart compaction oligonucleotide comprising a primary compaction oligonucleotide having three binding arms where one of the binding arms is hybridized to a secondary linear compaction oligonucleotide. In some embodiments, the primary compaction oligonucleotide comprises three binding arms linked together by at least one inner intervening linker, wherein individual binding arms comprise a binding region. In some embodiments, the primary compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 5' to 3' orientation where the 3' end of the second binding region is directed away from the inner intervening linker; and (3) an inner intervening linker and a connector region arranged in a 5' to 3' orientation where the 3' end of the connector region is directed away from the inner intervening linker. In some embodiments, the secondary linear compaction oligonucleotide comprises a fastener region arranged in a 5' to 3' orientation, an intervening linker, and a third binding region arranged in a 5' to 3' orientation. In some embodiments, the connector region of the primary compaction oligonucleotide can hybridize to the fastener region of the secondary compaction oligonucleotide.

In some embodiments, the primary compaction oligonucleotide comprises three binding arms linked together by at least one inner intervening linker, wherein individual binding arms comprise a binding region. In some embodiments, the primary compaction oligonucleotide comprises: (1) an inner intervening linker and a first binding region arranged in a 5' to 3' orientation where the 3' end of the first binding region is directed away from the inner intervening linker; (2) an inner intervening linker and a second binding region arranged in a 5' to 3' orientation where the 3' end of the second binding region is directed away from the inner intervening linker; and (3) an inner intervening linker and a connector region arranged in a 5' to 3' orientation where the 3' end of the connector region is directed away from the inner intervening linker. In some embodiments, the secondary linear compaction oligonucleotide comprises a fastener region arranged in a 5' to 3' orientation, an intervening linker, and a third binding region arranged in a 5' to 3' orientation. In some embodiments, the connector region of the primary compaction oligonucleotide can hybridize to the fastener region of the secondary compaction oligonucleotide (FIG. 12A).

Figure 12B:
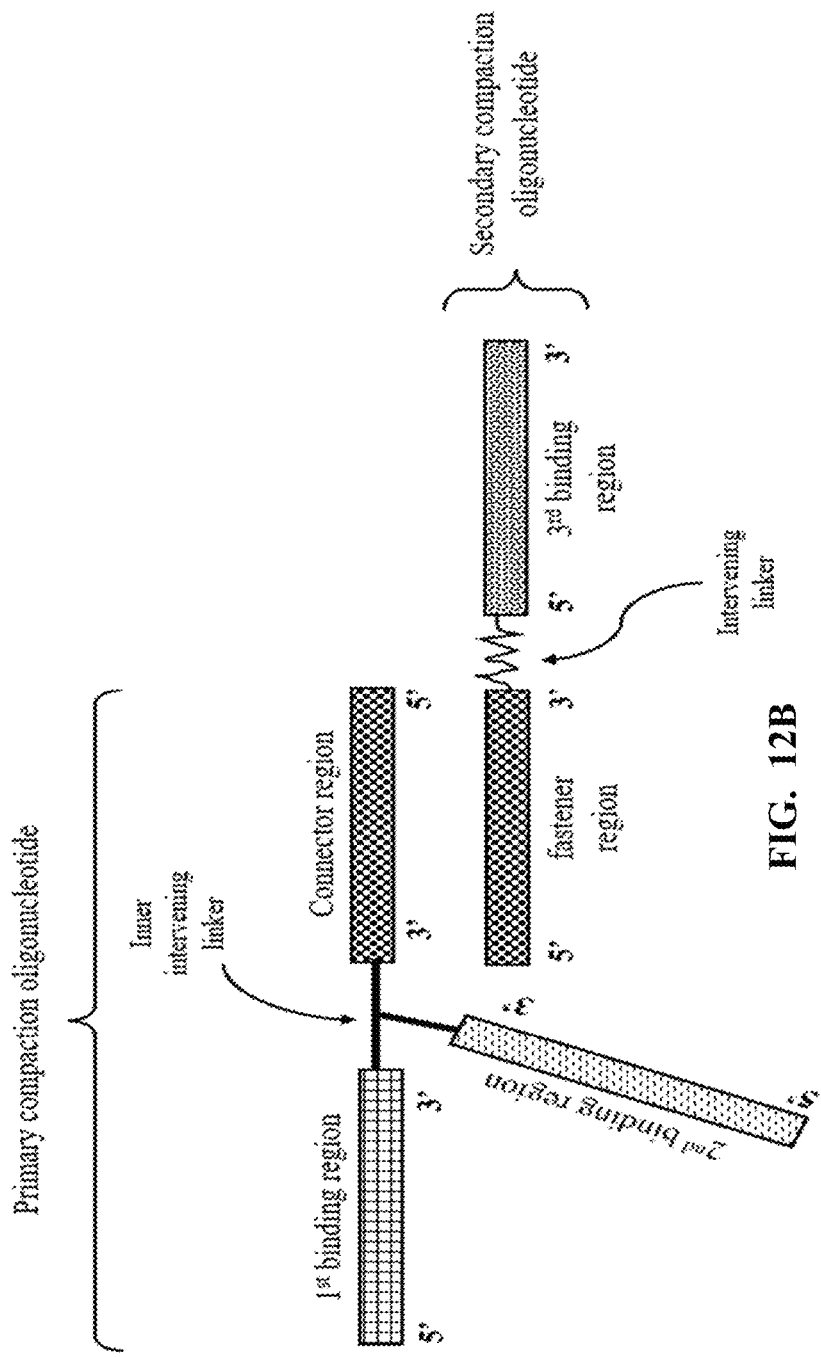
FIG. 12B shows a schematic of an embodiment of a multipart compaction oligonucleotide comprising a primary compaction oligonucleotide having three binding arms where one of the binding arms is hybridized to a secondary linear compaction oligonucleotide. In some embodiments, the primary compaction oligonucleotide comprises three binding arms linked together by at least one inner intervening linker, wherein individual binding arms comprise a binding region. In some embodiments, the primary compaction oligonucleotide comprises: (1) an inner intervening linker and a first binding region arranged in a 3' to 5' orientation where the 5' end of the first binding region is directed away from the inner intervening linker; (2) an inner intervening linker and a second binding region arranged in a 3' to 5' orientation where the 5' end of the second binding region is directed away from the inner intervening linker; and (3) an inner intervening linker and a connector region arranged in a 3' to 5' orientation where the 5' end of the connector region is directed away from the inner intervening linker. In some embodiments, the secondary linear compaction oligonucleotide comprises a fastener region arranged in a 5' to 3' orientation, an intervening linker, and a third binding region arranged in a 5' to 3' orientation. In some embodiments, the connector region of the primary compaction oligonucleotide can hybridize to the fastener region of the secondary compaction oligonucleotide.

In some embodiments, the primary compaction oligonucleotide comprises three binding arms linked together by at least one inner intervening linker, wherein individual binding arms comprise a binding region. In some embodiments, the primary compaction oligonucleotide comprises: (1) an inner intervening linker and a first binding region arranged in a 3' to 5' orientation where the 5' end of the first binding region is directed away from the inner intervening linker; (2) an inner intervening linker and a second binding region arranged in a 3' to 5' orientation where the 5' end of the second binding region is directed away from the inner intervening linker; and (3) an inner intervening linker and a connector region arranged in a 3' to 5' orientation where the 5' end of the connector region is directed away from the inner intervening linker. In some embodiments, the secondary linear compaction oligonucleotide comprises a fastener region arranged in a 5' to 3' orientation, an intervening linker, and a third binding region arranged in a 5' to 3' orientation. In some embodiments, the connector region of the primary compaction oligonucleotide can hybridize to the fastener region of the secondary compaction oligonucleotide (FIG. 12B).

Figure 13A:
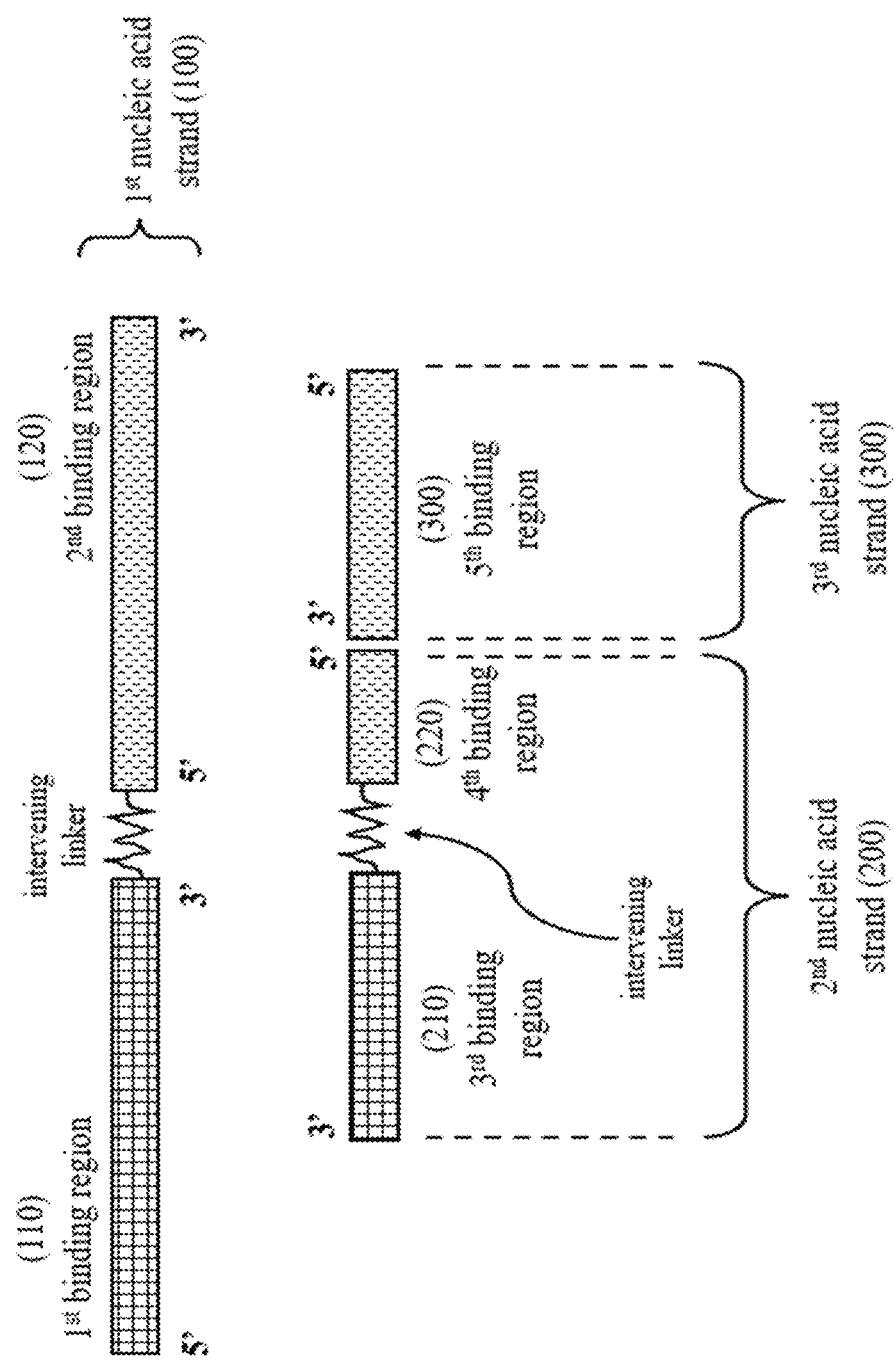
FIG. 13A shows a schematic of an embodiment of a multipart compaction oligonucleotide comprising a first nucleic acid strand (100) which is hybridized to a second nucleic acid strand (200) and a third nucleic acid strand (300). In some embodiments, the first nucleic acid strand comprises a first binding region (110) arranged in a 5' to 3' orientation, an intervening linker, and a second binding region arranged in a 5' to 3' orientation. In some embodiments, the second nucleic acid strand comprises a third binding region (210) arranged in a 3' to 5' orientation, an intervening linker, and a fourth binding region (220) arranged in a 3' to 5' orientation. In some embodiments, the third binding region (210) can hybridize to at least a portion of the first binding region (110) of the first nucleic acid strand (100). In some embodiments, the fourth binding region (220) can hybridize to at least a portion of the second binding region (120) of the first nucleic acid strand (100). In some embodiments, the third nucleic acid strand (300) comprises a fifth binding region (300) arranged in a 3' to 5' orientation. In some embodiments, the fifth binding region (300) can hybridize to at least a portion of the second binding region (120) of the first nucleic acid strand (100). In some embodiments, the fourth binding region (220) and the fifth binding region (300) do not hybridize to the same portions, or overlapping portions, of the second binding region (120).

In some embodiments, the first nucleic acid strand comprises a first binding region (110) arranged in a 5' to 3' orientation, an intervening linker, and a second binding region arranged in a 5' to 3' orientation. In some embodiments, the second nucleic acid strand comprises a third binding region (210) arranged in a 3' to 5' orientation, an intervening linker, and a fourth binding region (220) arranged in a 3' to 5' orientation. In some embodiments, the third binding region (210) can hybridize to at least a portion of the first binding region (110) of the first nucleic acid strand (100). In some embodiments, the fourth binding region (220) can hybridize to at least a portion of the second binding region (120) of the first nucleic acid strand (100). In some embodiments, the third nucleic acid strand (300) comprises a fifth binding region (300) arranged in a 3' to 5' orientation. In some embodiments, the fifth binding region (300) can hybridize to at least a portion of the second binding region (120) of the first nucleic acid strand (100). In some embodiments, the fourth binding region (220) and the fifth binding region (300) do not hybridize to the same portions, or overlapping portions, of the second binding region (120) (FIG. 13A).

Figure 13B:
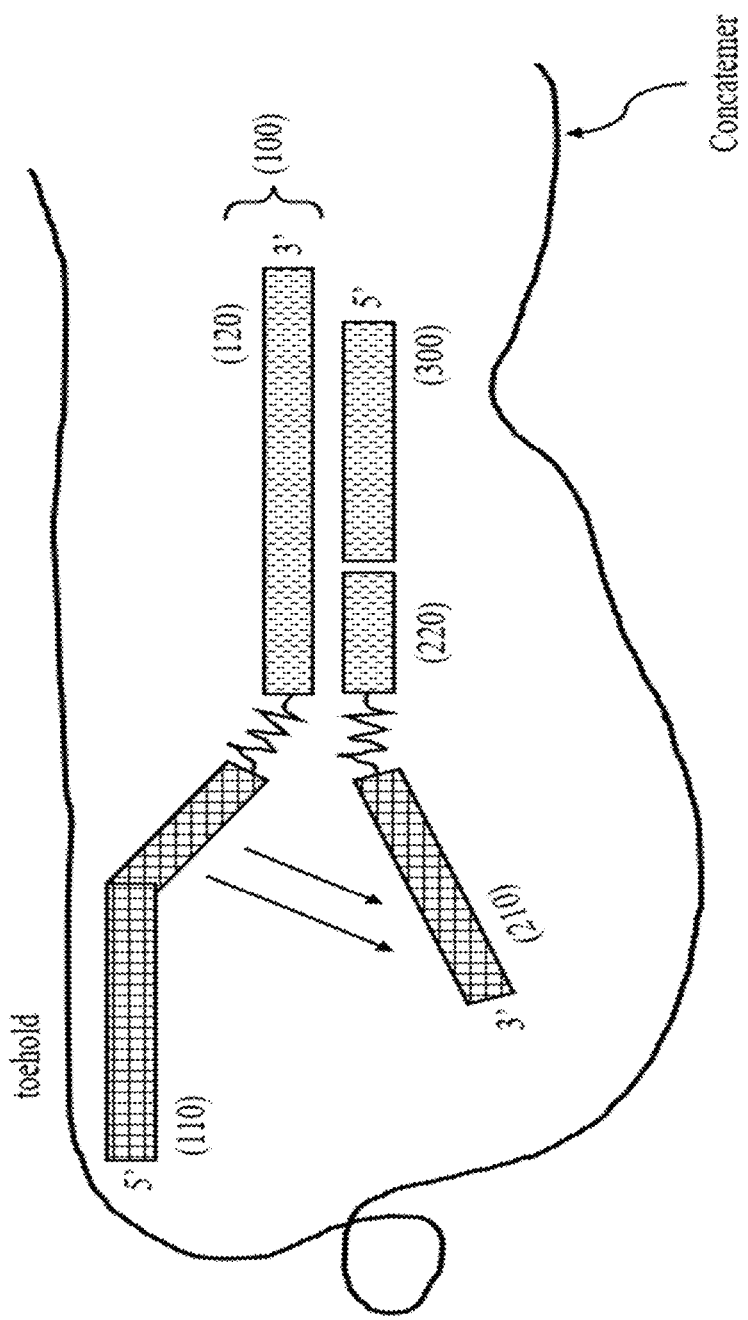
FIG. 13B shows a schematic of the multipart compaction oligonucleotide shown in FIG. 13A hybridizing to a portion of a nucleic acid concatemer.

In FIG. 13B a portion of the first binding region (110) of the first nucleic acid strand (100) hybridizes to a first portion of the concatemer which dissociates a portion of the third binding region (210) from the first binding region (110) as indicated by the two arrows. Hybridization of a portion of the first binding region (110) and the first portion of the concatemer forms a toehold duplex region. The second binding region (120) of the first nucleic acid strand (100) can remain hybridized to the fourth binding region (220) and the fifth binding region (300).

Figure 13C:
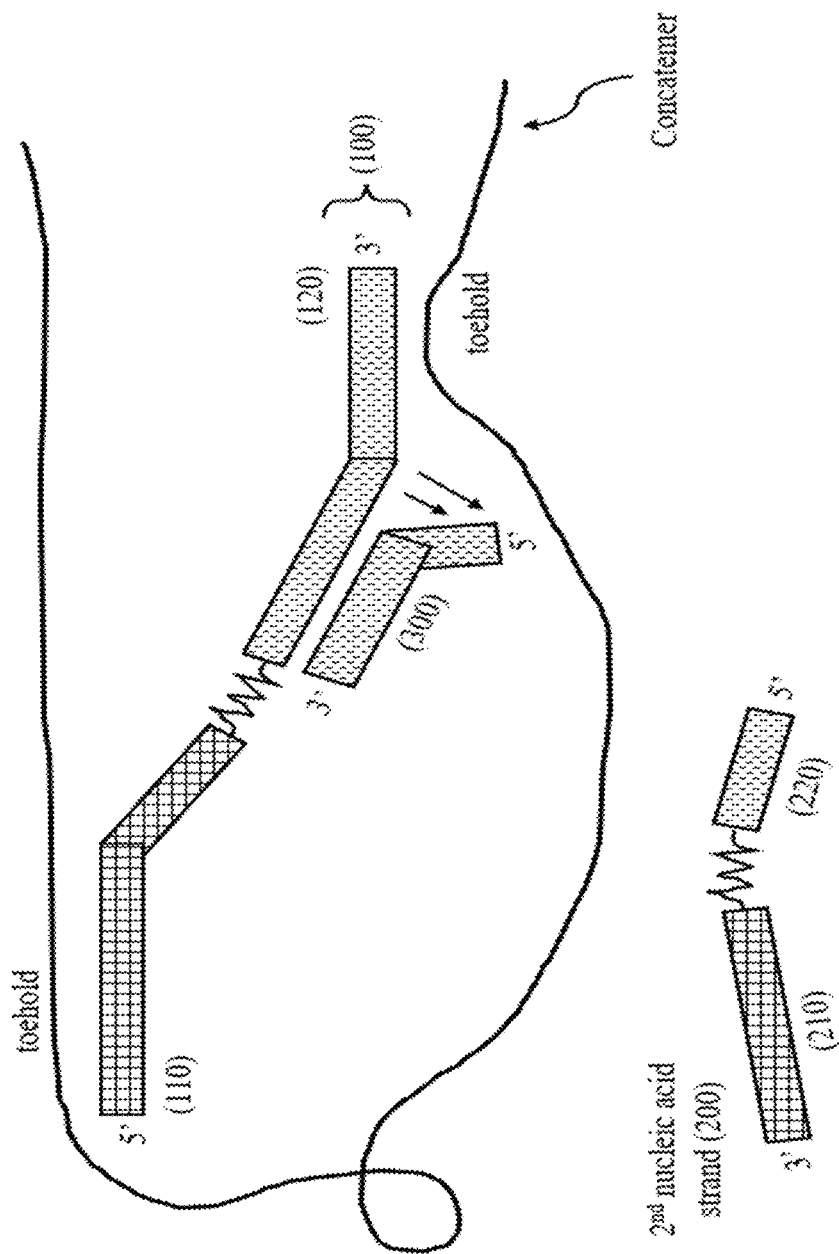
FIG. 13C shows a schematic of the multipart compaction oligonucleotide shown in FIG. 13B hybridizing to a different portion of the same nucleic acid concatemer.

In FIG. 13C a portion of the second binding region (120) of the first nucleic acid strand (100) hybridizes to a second portion of the concatemer which dissociates a portion of the fifth binding region (300) from the second binding region (120) as indicated by the two arrows. Hybridization of the portion of the second binding region (120) and the second portion of the concatemer forms another toehold duplex region. The second nucleic acid strand (200) is completely dissociated from the first binding region (110) of the first nucleic acid strand (100).

Figure 13D:
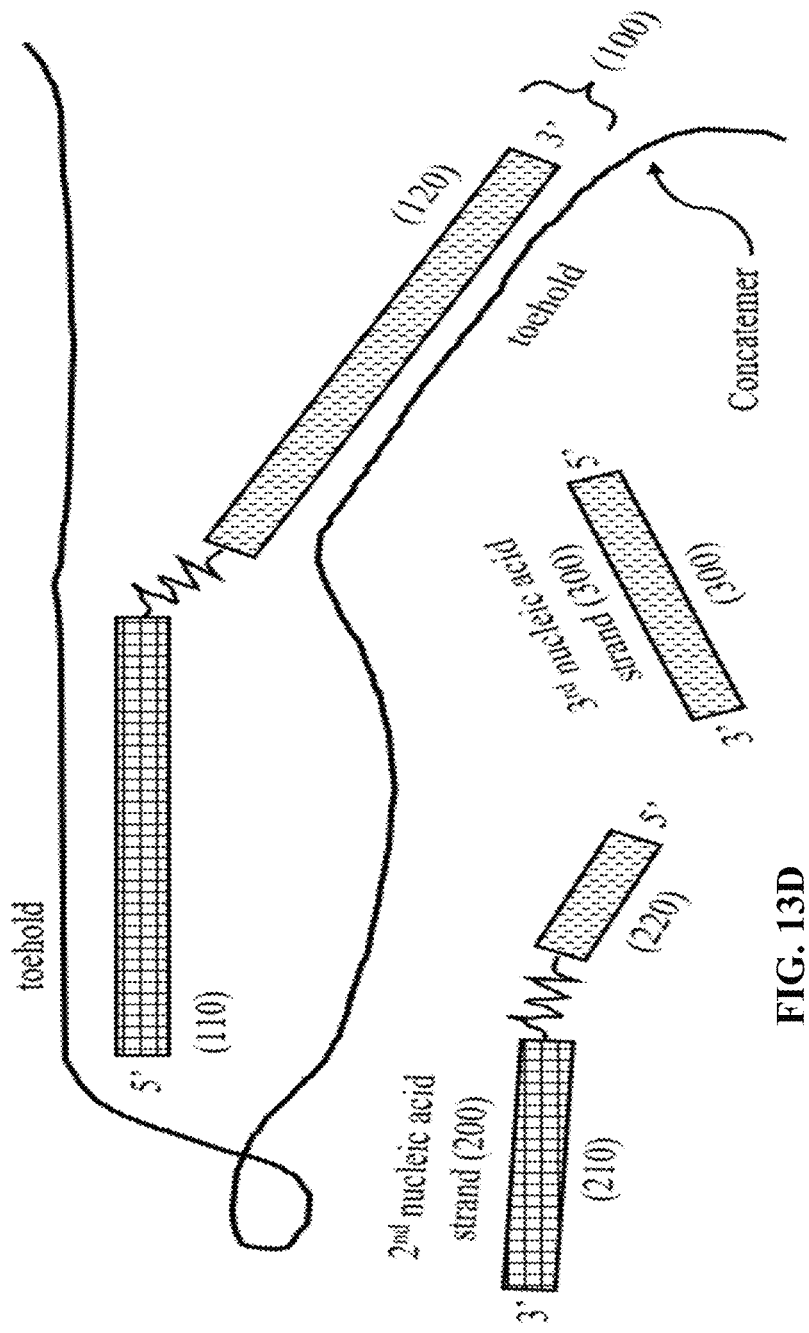
FIG. 13D shows a schematic of the multipart compaction oligonucleotide shown in FIG. 13C where the full length of the first binding region (110) is hybridized to a first portion of the nucleic acid concatemer thereby forming a first toehold duplex region, and the full length of the second binding region (120) is hybridized to a second portion of the same nucleic acid concatemer thereby forming a second toehold duplex region. The second nucleic acid strand (200) is completely dissociated from the first binding region (110) of the first nucleic acid strand (100). The third nucleic acid strand (300) is completely dissociated from the second binding region (120) of the first nucleic acid strand (100).

In FIG. 13D, the second nucleic acid strand (200) is completely dissociated from the first binding region (110) of the first nucleic acid strand (100). The third nucleic acid strand (300) is completely dissociated from the second binding region (120) of the first nucleic acid strand (100).

In some embodiments, the intervening linker of any of the compaction oligonucleotides described herein can be any length, for example about 2-20 nucleotides in length. The intervening linker comprises a homopolymer having consecutive identical bases (e.g., AAA, GGG, CCC, TTT or UUU). The intervening linker comprises a non-homopolymer sequence. In some embodiments, the intervening linker comprises at least one inosine. In some embodiments, the intervening linker comprises a homopolymer having consecutive identical bases (e.g., inosine).

In some embodiments, the intervening linker comprises a spacer. In some embodiments, the spacer comprises a non-nucleotide linker. In some embodiments, the spacer comprises an 18-carbon spacer (e.g., comprising a hexa-ethyleneglycol spacer), multiple C3 spacer phosphoramidites, or a spacer 9 which comprises a trimethylene glycol spacer. In some embodiments, the spacer comprises a polyethylene glycol spacer, including a PEG2, PEG3 or PEG4 spacer.

In some embodiments, the intervening linker comprises at least one non-nucleotide linker and at least one PEG spacer in any arrangement. For example, the intervening linker comprises 5'-right arm-([PEG-spacer]-[C18-spacer])$_n$-left arm-3' where "n" is 1-10. In another example, the intervening linker comprises 5'-right arm-([C18-spacer]-[PEG-spacer])$_n$-left arm-3' where "n" is 1-10.

Any of the binding regions of a compaction oligonucleotide can be wholly complementary or partially complementary along their length to a portion of a concatemer molecule. In some embodiments, the binding regions of a compaction oligonucleotide are designed to hybridize to a universal binding sequencing in a concatemer molecule.

In some embodiments, the first binding region of the compaction oligonucleotide can hybridize to a first portion of the concatemer molecule, where the first portion of the concatemer molecule comprises a universal adaptor sequence according to any one of SEQ ID NOs:157-176, or a complementary sequence thereof (see Table 2)).

In some embodiments, the second binding region of the compaction oligonucleotide can hybridize to a second portion of the concatemer molecule, where the second portion of the concatemer molecule comprises a universal adaptor sequence according to any one of SEQ ID NOs:157-176, or a complementary sequence thereof (see Table 2)).

In some embodiments, any binding region of the compaction oligonucleotide (e.g., first, second, third, fourth, fifth, sixth, or other binding regions) can hybridize to a portion of the concatemer molecule, where the portion of the concatemer molecule comprises a universal adaptor sequence according to any one of SEQ ID NOs:157-176, or a complementary sequence thereof (see Table 2)).

In some embodiments, the compaction oligonucleotide comprises two or more binding regions and all of the binding regions have the same sequence. In some embodiments, the compaction oligonucleotide comprises two binding regions having different sequences. In some embodiments, the compaction oligonucleotide comprises three or more binding regions and at least two of the binding regions have different sequences.

The first binding region of the compaction oligonucleotide can have the same sequence as the second binding region.

The first binding region of the compaction oligonucleotide can have a sequence that is different from the second binding region.

In some embodiments, the first binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, the second, third, fourth, fifth or any subsequent binding region of the compaction oligonucleotide comprises a sequence that is a reverse sequence of the first binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, the first binding region of a compaction oligonucleotide comprises a sequence according to any of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, the second, third, fourth, fifth or any subsequent binding region of the compaction oligonucleotide comprises a sequence that is a reverse sequence of the first binding region, where the second, third, fourth, fifth or any subsequence binding region comprises any of one of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, first binding region of the compaction oligonucleotide can have a sequence that is a reverse sequence of the second binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, the second binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, the third binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, the fourth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, the fifth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, the subsequent binding region(s) of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, the compaction oligonucleotides comprise a full-length sequence according to any one of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156 (see Table 1).

In some embodiments, the terminal 3' end of any of the compaction oligonucleotides can include at least one additional base comprising one or more 2'-O-methyl RNA bases (e.g., designated mUmUmU) or the terminal 3' end lacks additional 2'-O-methyl RNA bases.

In some embodiments, the compaction oligonucleotides comprise one or more modified bases or linkages at their 5' or 3' ends to confer certain functionalities. In some embodiments, the compaction oligonucleotides comprise at least one phosphorothioate linkages at their 5' and/or 3' ends to confer exonuclease resistance. In some embodiments, at least one nucleotide at or near the 3' end comprises a 2' fluoro base which confers exonuclease resistance. In some embodiments, the 3' end of the compaction oligonucleotides comprise at least one 2'-O-methyl RNA base which blocks polymerase-catalyzed extension. For example, the 3' end of the compaction oligonucleotide comprises at least one base comprising 2'-O-methyl RNA base (e.g., designated mUmUmU). In some embodiments, the compaction oligonucleotides comprise a 3' inverted dT at their 3' ends which blocks polymerase-catalyzed extension. In some embodiments, the compaction oligonucleotides comprise 3' phosphorylation which blocks polymerase-catalyzed extension. In some embodiments, the compaction oligonucleotides comprise at least one locked nucleic acid (LNA) which increases the thermal stability of duplexes formed by hybridizing a compaction oligonucleotide to a concatemer molecule.

The compaction oligonucleotides can include at least one region (e.g., hybridization/binding region) having consecutive guanines. For example, the compaction oligonucleotides can include at least one region having 2, 3, 4, 5, 6 or more consecutive guanines. In some embodiments, the compaction oligonucleotides comprise four consecutive guanines which can form a guanine tetrad structure (see FIG. 64). The guanine tetrad structure can be stabilized via Hoogsteen hydrogen bonding. The guanine tetrad structure can be stabilized by a central cation including potassium, sodium, lithium, rubidium, or cesium.

At least one compaction oligonucleotide can form a guanine tetrad (FIG. 64) and hybridize to the universal binding sequences in a concatemer which can cause the concatemer to fold to form an intramolecular G-quadruplex structure (FIG. 65). The concatemers can self-collapse to form compact nanostructures. Formation of the guanine tetrads and G-quadruplexes in the nanostructures may increase the stability of the nanostructures to retain their compact size and shape which can withstand changes in pH, temperature and/or repeated flows of reagents.

In some embodiments, the plurality of compaction oligonucleotides comprises the same sequence. In some embodiments, the plurality of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156. In some embodiments, the plurality of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156, where the 3' end of the compaction oligonucleotide also includes three bases comprising 2'-O-methyl RNA base (e.g., designated mUmUmU).

In some embodiments, the plurality of compaction oligonucleotides comprises a mixture of two or more different populations of compaction oligonucleotides having different sequences. In some embodiments, the plurality of compaction oligonucleotides comprises a mixture of 2, 3, 4, 5, 6, 7, 8, 9 or 10 different populations of compaction oligonucleotides wherein the compaction oligonucleotides in the different populations have different sequences. In some embodiments, in the mixture of different compaction oligonucleotides, any given population of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156.

In some embodiments, individual nucleic acid concatemers comprise a single-stranded nucleic acid molecule. Individual concatemer molecules comprise at least two copies of a polynucleotide unit arranged in tandem. In some embodiments, each polynucleotide unit comprises a sequence-of-interest. In some embodiments, each polynucleotide unit comprises at least one universal adaptor sequence. In some embodiments, each polynucleotide unit comprises a sequence-of-interest and at least one universal adaptor sequence. In some embodiments, individual concatemer molecules comprise 2-100 copies of a polynucleotide unit, or 100-250 copies of a polynucleotide unit, or 250-500 copies of a polynucleotide unit, or 500-750 copies of a polynucleotide unit, or 750-1000 copies of a polynucleotide unit, or more than 1000 copies of a polynucleotide unit. In some embodiments, individual concatemer molecules comprise 1000-10,000 copies of a polynucleotide unit. In some embodiments, the concatemer molecule can be generated by conducting a rolling circle amplification reaction using a circular library molecule as a library template molecule, an amplification primer (e.g., immobilized primer or soluble primer), amplification polymerase (e.g., having strand-displacing activity) and a plurality of nucleotides. In some embodiments, the concatemer comprises a plurality of tandem polynucleotide units where the sequence of each polynucleotide unit of a given concatemer molecule is complementary to the sequence of a circular library molecule that served as the template library molecule.

In some embodiments, the concatemer can be generated by conducting a rolling circle amplification reaction using a plurality of nucleotides which comprises any combination of two or more nucleotides including dATP, dGTP, dCTP, dTTP and/or dUTP. In some embodiments, individual concatemer in a plurality of concatemer molecules include at least two uracil bases that are distributed at random positions along individual concatemer template molecules, where the uracil bases can be distributed at different positions in the different concatemer molecules.

In some embodiments, the 5' end or the 3' end of individual concatemers can be immobilized to the support or coating. In some embodiments, an internal region of individual concatemers can be immobilized to the support or coating. In some embodiments, the concatemer remains immobilized to the support or coating upon collapsing/folding into the nanostructure.

In some embodiments, the coating comprises at least one hydrophilic polymer layer and a plurality of surface capture primers having a sequence that can hybridize to at least a portion of the circular library molecule. The surface capture primers can be immobilized to the coating and/or embedded in the coating. The surface capture primers can be covalently linked to a monomer compound that forms the polymer layer. In some embodiments, the density of surface capture primers can be about $10^2$-$10^{15}$ per mm$^2$. The coating can include a plurality of one or more types of surface capture primers. One type of surface capture primer can be used for conducting an on-support rolling circle amplification workflow. Another type of surface capture primer can be used for conducting an in-solution rolling circle amplification workflow.

In some embodiments, individual concatemer molecules can be generated by hybridizing a circular library molecule with an immobilized surface capture primer and conducting an on-support rolling circle amplification reaction with an amplification polymerase (e.g., having strand-displacing activity) and a plurality of nucleotides to generate a concatemer that is covalently joined to the surface primer which is immobilized to the coating or embedded in the coating (e.g., FIGS. 21-23, 39-40). The surface capture primers used to conduct on-support rolling circle amplification can hybridize to at least a portion of a circular library molecule.

In some embodiments, individual concatemer molecules can be generated by hybridizing a circular library molecule with a soluble amplification primer and conducting an in-solution rolling circle amplification reaction with an amplification polymerase (e.g., having strand-displacing activity) and a plurality of nucleotides to generate a duplex comprising a concatemer hybridized to the circular library molecule. The duplex can be distributed onto a support having at least on hydrophilic polymer layer and a plurality of surface capture primers having a sequence that can hybridize to at least a portion of the concatemer molecule. A portion of the concatemer can hybridize to a surface capture primer to generate a concatemer that is immobilized by hybridization to a surface primer. The rolling circle amplification reaction can continue after distribution onto the coated support (e.g., FIGS. 30-32, 46-48).

In some embodiments, the support comprises a planar or non-planar support. The support can be solid or semi-solid. In some embodiments, the support can be porous, semi-porous or non-porous. The support can be made of any material such as glass, plastic or a polymer material.

In some embodiments, the surface of the support can be coated with one or more compounds to produce a passivated layer on the support. In some embodiments, the passivated layer forms a porous or semi-porous layer. In some embodiments, individual concatemer molecules can be attached to the support, or to the passivated layer, to immobilize the concatemer molecule to the support. In some embodiments, the support comprises a low non-specific binding surface that enables improved nucleic acid hybridization, amplification and sequencing performance on the support. In general, the support may comprise one or more layers of a covalently or non-covalently attached low-binding, chemical modification layers, e.g., silane layers, polymer films, and one or more covalently or non-covalently attached oligonucleotides that can be used for immobilizing a plurality of nucleic acid template molecules to the support. In some embodiments, the support can comprise a functionalized polymer coating layer covalently bound at least to a portion of the support via a chemical group on the support, a primer grafted to the functionalized polymer coating, and a water-soluble protective coating on the primer and the functionalized polymer coating. In some embodiments, the functionalized polymer coating comprises a poly(N-(5-azidoacet-amidylpentyl)acrylamide-co-acrylamide (PAZAM). In some embodiments, the support comprises a surface coating having at least one hydrophilic polymer coating layer. The surface coating can further comprise at least one layer of a plurality of oligonucleotides (e.g., surface primers). The hydrophilic polymer coating layer can comprise polyethylene glycol (PEG). The hydrophilic polymer coating layer can comprise branched PEG having at least 4 branches. In some embodiments, the low non-specific binding coating has a degree of hydrophilicity which can be measured as a water contact angle, where the water contact angle is no more than 45 degrees.

In some embodiments, the plurality of concatemer molecules is immobilized to the support or immobilized to the coating on the support. In some embodiments, the support comprises a density of about $10^2$-$10^{15}$ immobilized concatemer molecules per mm$^2$. In some embodiments, the plurality of concatemers remain immobilized to the support upon collapsing or folding into the nanostructure. Thus, the support comprises a density of about $10^2$-$10^{15}$ immobilized nanostructures per mm$^2$.

In some embodiments, the concatemers are immobilized at different sites on the support. In some embodiments, the plurality of concatemer molecules is immobilized to pre-determined sites (e.g., locations) on the support. The plurality of concatemers can be arranged in an organized pre-determined pattern on the support. In some embodiments, the plurality of concatemer molecules is immobilized to random non-pre-determined sites (e.g., locations) on the support. In some embodiments, the plurality of concatemers remain immobilized to the support upon collapsing or folding into the nanostructure. Thus, the plurality of nanostructures can be immobilized to the support at pre-determined sites on the support or at random sites on the support.

In some embodiments, the plurality of immobilized concatemer molecules is in fluid communication with each other to permit flowing a solution of reagents (e.g., enzymes including polymerases, multivalent molecules, nucleotides and/or divalent cations, and the like) onto the support so that the plurality of immobilized concatemer molecules on the support can be reacted with the solution of reagents in a massively parallel manner.

In some embodiments, the plurality of immobilized nanostructures is in fluid communication with each other to permit flowing a solution of reagents (e.g., enzymes including polymerases, multivalent molecules, nucleotides and/or divalent cations, and the like) onto the support so that the plurality of immobilized nanostructures on the support can be reacted with the solution of reagents in a massively parallel manner.

In some embodiments, the plurality of immobilized nucleic acid nanostructures further comprises a plurality of circular nucleic acid library molecules. In some embodiments, the plurality of circular nucleic acid library molecules is soluble and are not hybridized to the immobilized nucleic acid nanostructures. In some embodiments, at least one of the immobilized nucleic acid nanostructures is hybridized to a circular nucleic acid library molecule. In some embodiments, the nucleic acid nanostructure comprises a plurality of tandem polynucleotide units where the sequence of each polynucleotide unit of a given nanostructure molecule is complementary to the sequence of a circular library molecule.

In some embodiments, the plurality of immobilized nucleic acid nanostructures further comprises a plurality of circular nucleic acid library molecules, a plurality of amplification polymerases (e.g., having strand-displacing activity) and a plurality of nucleotides. In some embodiments, the plurality of circular nucleic acid library molecules is soluble and are not hybridized to the immobilized nucleic acid nanostructures. In some embodiments, at least one of the immobilized nucleic acid nanostructures is hybridized to a circular nucleic acid library molecule to form a nucleic acid amplification duplex having a template molecule (e.g., circular library molecule) and a 3' primer initiation site (e.g., 3' end of the nucleic acid nanostructure). In some embodiments, the nucleic acid amplification duplex is bound with an amplification polymerase to form a complexed amplification polymerase. In some embodiments, in the complexed amplification polymerase, a complementary nucleotide can be bound to the 3' primer initiation site at a position that is opposite a complementary nucleotide in the template molecule (e.g., circular library molecule). In some embodiments, the plurality of nucleotides comprises any combination of two or more nucleotides including dATP, dGTP, dCTP, dTTP and/or dUTP.

In some embodiments, the plurality of immobilized nucleic acid nanostructures further comprises a plurality of sequencing primers, a plurality of sequencing polymerases, and a plurality of nucleotide reagents. In some embodiments, the plurality of sequencing primers is soluble and are not hybridized to the immobilized nucleic acid nanostructures. In some embodiments, at least one of the immobilized nucleic acid nanostructures is hybridized to at least one sequencing primer to form a nucleic acid sequencing duplex having a template molecule (e.g., nanostructure molecule) and a 3' primer initiation site (e.g., 3' end of the sequencing primer). In some embodiments, the nucleic acid sequencing duplex is bound with a sequencing polymerase to form a complexed sequencing polymerase. In some embodiments, the complexed sequencing polymerase is bound with a nucleotide reagent which comprises a canonical nucleotide, a nucleotide analog, or a multivalent molecule.

In some embodiments, the canonical nucleotide can include an aromatic base, a five-carbon sugar and at least one phosphate group. The canonical nucleotide can be unlabeled or can be labeled with a detectable reporter moiety (e.g., fluorophore). In some embodiments, a complementary canonical nucleotide can be bound to the 3' primer initiation site at a position that is opposite a complementary nucleotide in the template molecule (e.g., nanostructure molecule). In some embodiments, the plurality of immobilized nucleic acid nanostructures further comprises a catalytic or non-catalytic divalent cation. An exemplary catalytic divalent cation comprises magnesium and/or manganese which promotes polymerase-catalyzed nucleotide incorporation. An exemplary non-catalytic divalent cation comprises strontium, barium and/or calcium which inhibits polymerase-catalyzed nucleotide incorporation.

In some embodiments, the nucleotide analogs can include an aromatic base, a five-carbon sugar having a 3' chain terminating moiety that inhibits polymerase-catalyzed nucleotide incorporation, and at least one phosphate group. The nucleotide analog can be unlabeled or can be labeled with a detectable reporter moiety (e.g., fluorophore). In some embodiments, a complementary nucleotide analog can be bound to the 3' primer initiation site at a position that is opposite a complementary nucleotide in the template molecule (e.g., nanostructure molecule). In some embodiments, the plurality of immobilized nucleic acid nanostructures further comprises a catalytic or non-catalytic divalent cation. An exemplary catalytic divalent cation comprises magnesium and/or manganese which promotes polymerase-catalyzed nucleotide incorporation. An exemplary non-catalytic divalent cation comprises strontium, barium and/or calcium which inhibits polymerase-catalyzed nucleotide incorporation.

In some embodiments, the multivalent molecule can include (1) a core; and (2) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit (see FIGS. 56-59). In some embodiments, the nucleotide unit comprises an aromatic base, a five-carbon sugar and at least one phosphate group, and the linker is attached to the nucleotide unit through the base. The multivalent molecule can be unlabeled or can be labeled with a detectable reporter moiety (e.g., fluorophore). In some embodiments, a complementary nucleotide unit of a multivalent molecule can be bound to the 3' primer initiation site at a position that is opposite a complementary nucleotide in the template molecule (e.g., nanostructure molecule). In some embodiments, the plurality of immobilized nucleic acid nanostructures further comprises a catalytic or non-catalytic divalent cation. An exemplary catalytic divalent cation comprises magnesium and/or manganese which promotes polymerase-catalyzed nucleotide incorporation. An exemplary non-catalytic divalent cation comprises strontium, barium and/or calcium which inhibits polymerase-catalyzed nucleotide incorporation.

In some embodiments, the plurality of immobilized nucleic acid nanostructures further comprise a plurality of binding complexes including at least a first and second binding complex, wherein (i) the first binding complex comprises a first nucleic acid primer, a first polymerase, and a first multivalent molecule, bound to a first portion of a nucleic acid nanostructure thereby forming a first binding complex, wherein a first nucleotide unit of the multivalent molecule is bound to the first polymerase, and (ii) the second binding complex comprises a second nucleic acid primer, a second polymerase, and the first multivalent molecule, bound to a second portion of the same nucleic acid nanostructure thereby forming a second binding complex, wherein a second nucleotide unit of the multivalent molecule is bound to the second polymerase, wherein the first and second binding complexes which include the same multivalent molecule forms an avidity complex. In some embodiments, the first multivalent molecule is unlabeled or is labeled with a detectable reporter moiety.

In some embodiments, the first nucleic acid primer comprises a first sequencing primer, and the second nucleic acid primer comprises a second sequencing primer. In some embodiments, the first polymerase comprises a first sequencing polymerase, and the second polymerase comprises a second sequencing polymerase.

In some embodiments, the first nucleic acid primer comprises a first amplification primer, and the second nucleic acid primer comprises a second amplification primer. In some embodiments, the first polymerase comprises a first amplification polymerase, and the second polymerase comprises a second amplification polymerase.

In some embodiments, the plurality of immobilized nucleic acid nanostructures further comprises a cellular biological sample which is positioned on the immobilized nanostructures.

In some embodiments, the cellular biological sample comprises a single cell, a plurality of cells, a tissue, an organ, an organism, or a section from any of these cellular biological samples. The cellular biological sample comprises a sample that is fresh, frozen, fresh-frozen, or archived (e.g., formalin-fixed paraffin-embedded; FFPE). The cellular biological sample can be embedded in a matrix material. The cellular biological sample can be stained, de-stained or non-stained. The cellular biological sample can be permeabilized to permit the nucleic acids within the cellular sample to migrate from the cell(s) to the plurality of immobilized nanostructures.

On-Support Methods
Generating High Density Immobilized Nanostructures

Figure 21:
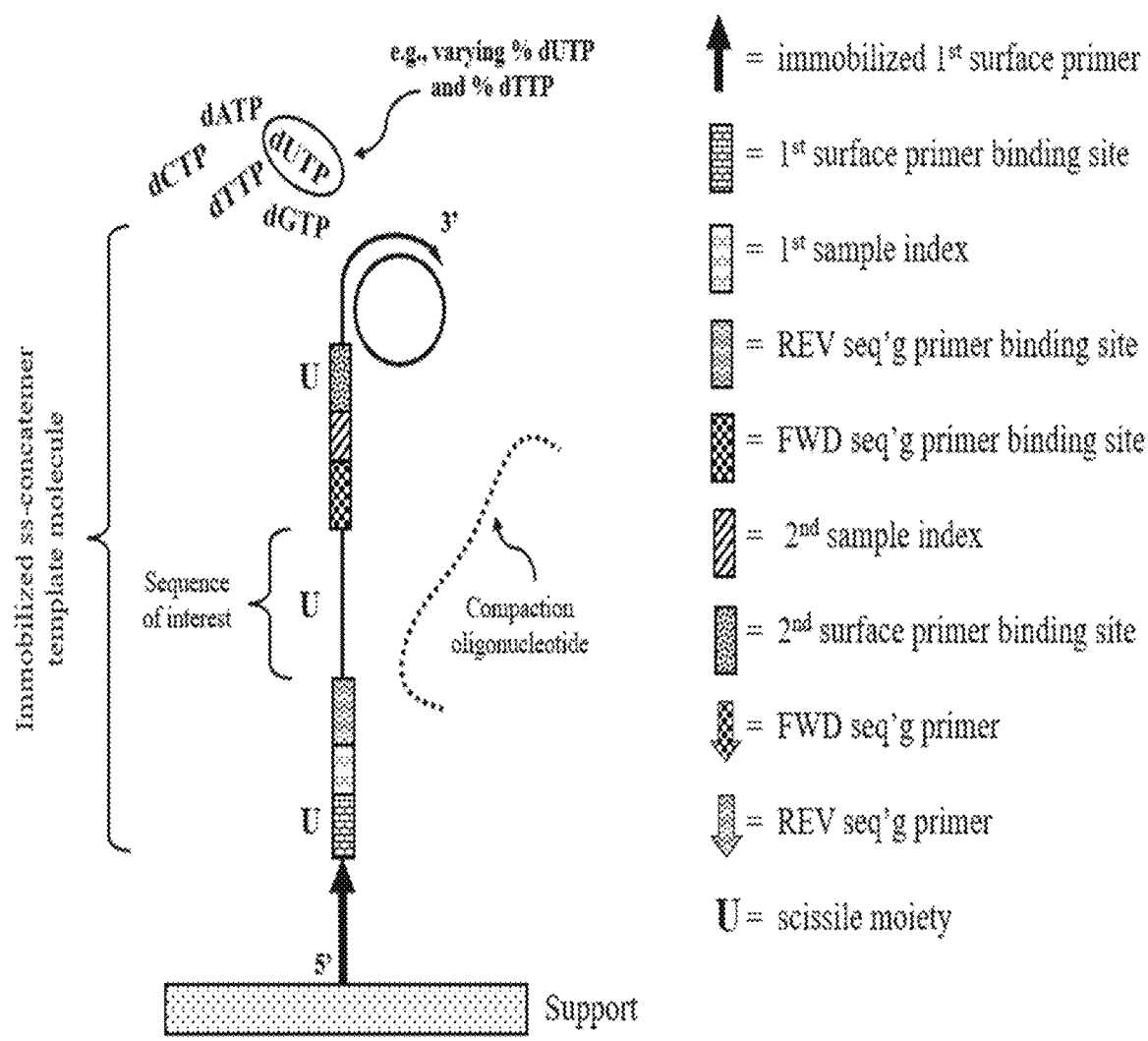
FIG. 21 is a schematic showing an exemplary on-support rolling circle amplification reaction using (i) an immobilized first surface primer, (ii) a nucleic acid circular library molecule, (iii) a mixture of nucleotides including nucleotides having a scissile moiety that can be cleaved to generate an abasic site, (iv) a strand-displacing polymerase, and (iv) a compaction oligonucleotide. The rolling circle amplification reaction generates an immobilized single stranded nucleic acid concatemer template molecule having at least one nucleotide with a scissile moiety which can be cleaved to generate an abasic site in the immobilized concatemer template molecule. The arrangement of the various primer binding sequences in the nucleic acid circular library molecule is for illustration purposes. The skilled artisan will appreciate that many other arrangements are possible.

The present disclosure provides methods for generating high density nucleic acid nanostructures immobilized on a support, comprising: (a) providing a support having a plurality of first universal surface primers immobilized thereon, wherein the density of the first universal surface primers on the support is about $10^2$-$10^{15}$ per mm$^2$; and (b) generating a plurality of immobilized single stranded nucleic acid concatemer template molecules by hybridizing a plurality of single stranded circular nucleic acid library molecules to the plurality of immobilized first universal surface primers and conducting an on-support rolling circle amplification reaction with (i) a plurality of strand-displacing polymerases, (ii) a plurality of nucleotides, and (iii) a plurality of compaction oligonucleotides, thereby generating a plurality of immobilized single stranded nucleic acid concatemer template molecules (FIGS. 21 and 39). In some embodiments, individual compaction oligonucleotides comprise a single-stranded linear oligonucleotide having a 5' region that can hybridize to a first portion of a concatemer molecule and the compaction oligonucleotide having a 3' region that can hybridize to a second portion of the concatemer molecule (e.g., the same concatemer) (FIGS. 23 and 40), wherein the plurality of immobilized concatemer molecules collapse or fold into a compact nucleic acid nanostructure upon binding to the compaction oligonucleotides, and wherein the plurality of concatemers remain immobilized to the support upon collapsing or folding into the nanostructure, thereby generating a support having a density of about $10^2$-$10^{15}$ per $mm^2$ of nanostructures immobilized to the support.

In some embodiments, the nucleic acid nanostructures can include one or more loops, or can have a spherical shape (e.g., nanoball), elongated shape (e.g., nanorod), protoroid shape or toroid shape (e.g., nano-toroid).

Inclusion of the plurality of compaction oligonucleotides in the on-support rolling circle amplification reaction can improve the FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 um or smaller.

The nucleic acid nanostructure can be a compact nucleic acid structure having a full width half maximum (FWHM) that is smaller compared to a concatemer that is not collapsed/folded into a nanostructure.

In some embodiments, the compaction oligonucleotides comprise single stranded oligonucleotides comprising DNA, RNA, or a combination of DNA and RNA. The compaction oligonucleotides can be any length, including 20-150 nucleotides, or 30-100 nucleotides, or 40-80 nucleotides in length, or any range therebetween.

In some embodiments, the compaction oligonucleotide comprises a first binding region and a second binding region, and optionally an intervening linker between the 5' and 3' regions. The intervening linker can be any length, for example. About 2-20 nucleotides in length. The intervening linker can comprise a homopolymer having consecutive identical bases (e.g., AAA, GGG, CCC, TTT or UUU). The intervening linker can comprise a non-homopolymer sequence.

The first binding region of the compaction oligonucleotides can be wholly complementary or partially complementary along its length to a first portion of a concatemer molecule. The second binding region of the compaction oligonucleotides can be wholly complementary or partially complementary along its length to a second portion of a concatemer molecule. The first binding region of the compaction oligonucleotides can hybridize to a first universal sequence portion of a concatemer molecule having a sequence of any one of SEQ ID NOs:157-176 (see Table 2). The second binding region of the compaction oligonucleotides can hybridize to a second universal sequence portion of a concatemer molecule having a sequence of any one of SEQ ID NOs:157-176 (see Table 2). The first and second binding regions of the compaction oligonucleotide can hybridize to the concatemer to pull together distal portions of the concatemer causing compaction of the concatemer to form a nanostructure.

In some embodiments, any binding region of the compaction oligonucleotide (e.g., first, second, third, fourth, fifth, sixth, or other binding regions) can hybridize to a portion of the concatemer molecule, where the portion of the concatemer molecule comprises a universal adaptor sequence according to any one of SEQ ID NOs:157-176, or a complementary sequence thereof (see Table 2)).

In some embodiments, in step (b), the first binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the second, third, fourth, fifth or any subsequent binding region of the compaction oligonucleotide comprises a sequence that is a reverse sequence of the first binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the first binding region of a compaction oligonucleotide comprises a sequence according to any of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the second, third, fourth, fifth or any subsequent binding region of the compaction oligonucleotide comprises a sequence that is a reverse sequence of the first binding region, where the second, third, fourth, fifth or any subsequence binding region comprises any of one of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), first binding region of the compaction oligonucleotide can have a sequence that is a reverse sequence of the second binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the second binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the third binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the fourth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the fifth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the subsequent binding region(s) of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the compaction oligonucleotides comprise a full-length sequence according to any one of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156 (see Table 1).

In some embodiments, the 3' region of any of the compaction oligonucleotides can include an additional three bases at the terminal 3' end which comprises 2'-O-methyl RNA bases (e.g., designated mUmUmU) or the terminal 3' end lacks additional 2'-O-methyl RNA bases.

In some embodiments, the compaction oligonucleotides comprise one or more modified bases or linkages at their 5' or 3' ends to confer certain functionalities. In some embodiments, the compaction oligonucleotides comprise at least one phosphorothioate linkages at their 5' and/or 3' ends to confer exonuclease resistance. In some embodiments, at least one nucleotide at or near the 3' end comprises a 2' fluoro base which confers exonuclease resistance. In some embodiments, the 3' end of the compaction oligonucleotides comprise at least one 2'-O-methyl RNA base which blocks polymerase-catalyzed extension. For example, the 3' end of the compaction oligonucleotide can comprise three bases comprising 2'-O-methyl RNA base (e.g., designated mUmUmU). In some embodiments, the compaction oligonucleotides comprise a 3' inverted dT at their 3' ends which blocks polymerase-catalyzed extension. In some embodiments, the compaction oligonucleotides comprise 3' phosphorylation which blocks polymerase-catalyzed extension. In some embodiments, the internal region of the compaction oligonucleotides comprises at least one locked nucleic acid (LNA) which increases the thermal stability of duplexes formed by hybridizing a compaction oligonucleotide to a concatemer molecule.

The compaction oligonucleotides can include at least one region having consecutive guanines. For example, the compaction oligonucleotides can include at least one region having 2, 3, 4, 5, 6 or more consecutive guanines. In some embodiments, the compaction oligonucleotides comprise four consecutive guanines which can form a guanine tetrad structure (see FIG. 64). The guanine tetrad structure can be stabilized via Hoogsteen hydrogen bonding. The guanine tetrad structure can be stabilized by a central cation including potassium, sodium, lithium, rubidium or cesium.

The rolling circle amplification reaction can be conducted in the presence of a plurality of compaction oligonucleotides having at least four consecutive guanines. The resulting concatemers comprise repeat copies of the universal binding sequence for the compaction oligonucleotide. At least one compaction oligonucleotide can form a guanine tetrad (FIG. 64) and hybridize to the universal binding sequences for the compaction oligonucleotide, and the resulting concatemer can fold to form an intramolecular G-quadruplex structure (FIG. 65). The concatemers can self-collapse to form compact nanostructures. Formation of the guanine tetrads and G-quadruplexes in the nanostructures may increase the stability of the nanostructures to retain their compact size and shape which can withstand changes in pH, temperature and/or repeated flows of reagents.

In some embodiments, the plurality of compaction oligonucleotides in step (b) comprise the same sequence. In some embodiments, the plurality of compaction oligonucleotides in step (b) comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156. In some embodiments, the plurality of compaction oligonucleotides comprise a sequence according to any one of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156, where the 3' end of the compaction oligonucleotide also includes three bases comprising 2'-O-methyl RNA base (e.g., designated mUmUmU).

In some embodiments, the plurality of compaction oligonucleotides in step (b) comprise a mixture of two or more different populations of compaction oligonucleotides having different sequences. In some embodiments, the plurality of compaction oligonucleotides in step (b) comprise a mixture of 2, 3, 4, 5, 6, 7, 8, 9 or 10 different populations of compaction oligonucleotides wherein the compaction oligonucleotides in the different populations have different sequences. In some embodiments, in the mixture of different compaction oligonucleotides in step (b), any given population of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156.

The support can be passivated with at least one layer of a hydrophilic polymer coating which includes the plurality of first universal surface primers (FIG. 54).

In some embodiments, the plurality of immobilized first universal surface primers are located on the support or coating at random positions. When the immobilized universal surface primers are located on the support or the coated support at random positions, the nucleic acid nanostructures are also located at random positions. The randomly-located nucleic acid nanostructures can be tightly packed and fill much of the space on the coated support. Upon binding the immobilized nanostructures to detectably labeled oligonucleotides or nucleotide reagents the signal intensity can be concentrated in a smaller space which markedly increases signal intensity and color distinction, compared to binding detectably labeled oligonucleotides or nucleotide reagents to concatemers that are not collapsed/folded into a nanostructure. Thus, the nanostructures described herein, and the methods employed to generate them, improve signal intensity without the need for preparing a support (e.g., flowcell) having a pre-determined organized pattern array.

In some embodiments, the plurality of immobilized first universal surface primers are located on the support or coating at pre-determined positions. For example, the immobilized first universal surface primers are arranged in an organized pattern. When the immobilized universal surface primers are located on the support or the coated support at pre-determined positions, the nucleic acid nanostructures are also located at pre-determined positions.

In some embodiment, the first universal surface primers lack a scissile moiety (for example the first universal surface primers lack a scissile moiety that can be converted into abasic sites). In some embodiments, the first universal surface primers lack a scissile moiety comprising uridine, 8-oxo-7,8-dihydroguanine (e.g., 8oxoG) or deoxyinosine.

In some embodiments, the plurality of nucleotides which are used to conduct the rolling circle amplification reaction comprise: dATP, dCTP, dGTP and dTTP, and wherein none of the nucleotides have a scissile moiety (for example the scissile moiety in a nucleotide can be converted into an abasic site).

In some embodiments, the plurality of nucleotides which are used to conduct the rolling circle amplification reaction comprise: dATP, dCTP, dGTP, dTTP and nucleotides having a scissile moiety. In some embodiments, the nucleotide having the scissile moiety comprises uridine, 8-oxo-7,8-dihydroguanine (e.g., 8oxoG) or deoxyinosine. The scissile moiety of the nucleotides can be converted into an abasic site.

Figure 22:
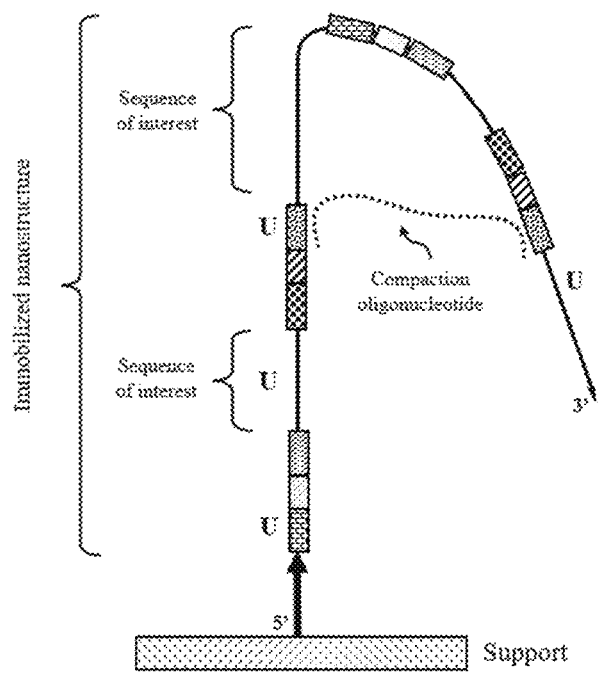

In some embodiments, the rolling circle amplification reaction, which is conducted with nucleotides having a scissile moiety, generates a plurality of single stranded nucleic acid concatemer template molecules wherein individual concatemer template molecules include at least two nucleotides each having a scissile moiety that are distributed at random positions along individual immobilized concatemer template molecules (FIGS. 21-22). In some embodiments, the nucleotides having a scissile moiety are distributed at different positions in the different immobilized concatemer template molecules.

In some embodiments, individual concatemer template molecules in the plurality comprise at least two copies of a polynucleotide unit arranged in tandem. In some embodiments, each polynucleotide unit comprises a sequence-of-interest. In some embodiments, each polynucleotide unit comprises at least one universal adaptor sequence. In some embodiments, each polynucleotide unit comprises a sequence-of-interest and at least one universal adaptor sequence. In some embodiments, individual concatemer molecules comprise 2-100 copies of a polynucleotide unit, or 100-250 copies of a polynucleotide unit, or 250-500 copies of a polynucleotide unit, or 500-750 copies of a polynucleotide unit, or 750-1000 copies of a polynucleotide unit, or more than 1000 copies of a polynucleotide unit. In some embodiments, individual concatemer molecules comprise 1000-2000 copies of a polynucleotide unit, or 1000-10,000 copies of a polynucleotide unit. In some embodiments, individual concatemers comprise a plurality of tandem polynucleotide units where the sequence of each polynucleotide unit of a given concatemer molecule is complementary to the sequence of a circular library molecule that served as the template library molecule.

In some embodiments, individual concatemer molecules comprise two or more copies of a sequence of interest, and wherein the immobilized concatemer template molecules further comprise any one or any combination of two or more of: (i) two or more copies of a universal binding sequence (or a complementary sequence thereof) for a soluble forward sequencing primer, (ii) two or more copies of a universal binding sequence (or a complementary sequence thereof) for a soluble reverse sequencing primer, (iii) two or more copies of a universal binding sequence (or a complementary sequence thereof) for an immobilized first universal surface primer, (iv) two or more copies of a universal binding sequence (or a complementary sequence thereof) for an immobilized second universal surface primer, (v) two or more copies of a universal binding sequence (or a complementary sequence thereof) for a first soluble amplification primer, (vi) two or more copies of a universal binding sequence (or a complementary sequence thereof) for a second soluble amplification primer, (vii) two or more copies of a universal binding sequence (or a complementary sequence thereof) for a soluble compaction oligonucleotide, (viii) two or more copies of a sample barcode sequence and/or (ix) two or more copies of a unique molecular index sequence.

In some embodiments, the methods for generating high density nucleic acid nanostructures immobilized on a support further comprise: positioning a cellular biological sample on the immobilized nanostructures.

In some embodiments, the cellular biological sample comprises a single cell, a plurality of cells, a tissue, an organ, an organism, or a section from any of these cellular biological samples. The cellular biological sample comprises a sample that is fresh, frozen, fresh-frozen, or archived (e.g., formalin-fixed paraffin-embedded; FFPE). The cellular biological sample can be embedded in a matrix material. The cellular biological sample can be stained, de-stained or non-stained. The cellular biological sample can be permeabilized to permit the nucleic acids within the cellular sample to migrate from the cell(s) to the plurality of immobilized nanostructures.

On-Support Methods
Generating High Density Immobilized Nanostructures Comprising Scissile Moieties The present disclosure provides methods for generating a plurality of immobilized nucleic acid nanostructures, comprising step (a): providing a support having a plurality of first universal surface primers immobilized thereon, wherein the support is passivated with at least one hydrophilic polymer layer which includes a plurality of first universal surface primers, wherein each of the first universal surface primers comprises a 3' OH extendible end and lacks a nucleotide having a scissile moiety and wherein the density of the first universal surface primers is about $10^2$-$10^{15}$ per mm$^2$. The first universal surface primers can lack a scissile moiety that can be converted into an abasic site in a nucleic acid strand. For example, the first universal surface primers can lack uridine, 8-oxo-7,8-dihydroguanine (e.g., 8oxoG) and deoxyinosine. In some embodiments, the support lacks a plurality of second universal surface primers or includes a plurality of second universal surface primers. In some embodiments, the support comprises a plurality of first and second universal surface primers.

In some embodiments, the immobilized first universal surface primers comprise single stranded oligonucleotides comprising DNA, RNA or a combination of DNA and RNA. The first universal surface primers can comprise a sequence that is wholly complementary or partially complementary along their lengths to at least a portion of a circular nucleic acid library molecule. The first universal surface primers can include a terminal 3' nucleotide having a sugar 3' OH moiety which is extendible for nucleotide polymerization (e.g., polymerase catalyzed polymerization).

In some embodiments, the immobilized first universal surface primers can be immobilized to the support or immobilized to a coating on the support. The immobilized first universal surface primers can be embedded and attached (coupled) to the coating on the support. In some embodiments, the 5' end of the immobilized first universal surface primers are immobilized to a support or immobilized to a coating on the support. Alternatively, an interior portion or the 3' end of the immobilized first universal surface primers can be immobilized to a support or immobilized to a coating on the support. The support can comprise a plurality of immobilized first universal surface primers having the same sequence. The immobilized first universal surface primers can be any length, for example 4-50 nucleotides, or 50-100 nucleotides, or 100-150 nucleotides, or longer lengths, or any range therebetween.

In some embodiments, the plurality of immobilized first universal surface primers are located on the coated support at random positions (e.g., non-pre-determined positions). When the immobilized universal surface primers are located on the coated support at random positions, the immobilized nucleic acid nanostructures are also located at random positions. The randomly-located nucleic acid nanostructures can be tightly packed and fill much of the space on the coated support.

In some embodiments, the plurality of immobilized first universal surface primers are located on the coated support at pre-determined positions. For example, the immobilized first universal surface primers are arranged in an organized pattern. When the immobilized universal surface primers are located on the support or the coated support at pre-determined positions, the nucleic acid nanostructures are also located at pre-determined positions.

In some embodiments, the plurality of immobilized first universal surface primers comprise at least one phosphorothioate diester bond at their 5' ends which can render the first universal surface primers resistant to exonuclease degradation. In some embodiments, the plurality of immobilized first universal surface primers comprise 2-5 or more consecutive phosphorothioate diester bonds at their 5' ends. In some embodiments, the plurality of immobilized first universal surface primers comprise at least one ribonucleotide and/or at least one 2'-O-methyl or 2'-O-methoxyethyl (MOE) nucleotide which can render the first universal surface primers resistant to exonuclease degradation.

In some embodiments, the immobilized first universal surface primers comprise at least one locked nucleic acid (LNA) which comprises a methylene bridge bond between a 2' oxygen and 4' carbon of the pentose ring. Immobilized first universal surface primers that include at least one LNA can be resistant to nuclease digestions and can exhibit increased melting temperature when hybridized to the circular nucleic acid library molecules.

Figure 29:
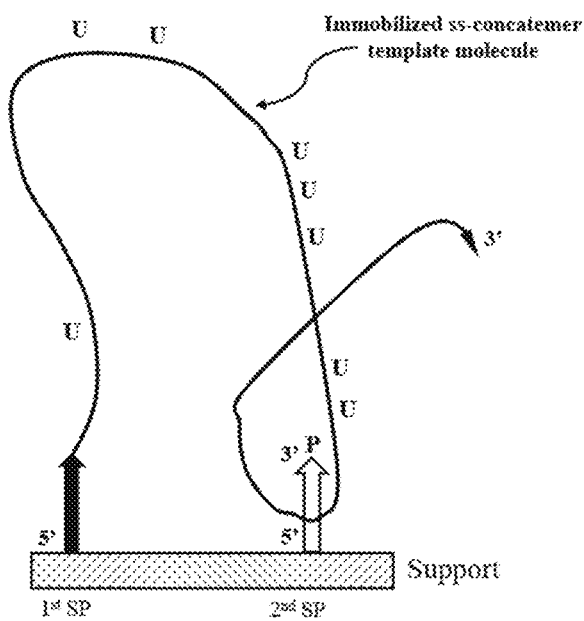
FIG. 29 is a schematic showing an exemplary support having a first and second surface primers immobilized thereon, and an immobilized concatemer which was generated by the on-support RCA workflow depicted in FIG. 21. A portion of the concatemer is hybridized to the immobilized second surface primer. The immobilized concatemer template molecule has two or more copies of a universal binding sequence for an immobilized second surface primer. The portion of the immobilized concatemer template molecule that includes the universal binding sequence for an immobilized second surface primer can hybridize to the immobilized second surface primer.

In some embodiments, the support further comprises a plurality of a second universal surface primer immobilized thereon (FIG. 29). The second universal surface primers have a sequence that differs from the first universal immobilized surface primer. The immobilized second universal surface primers of step (a) comprise single stranded oligonucleotides comprising DNA, RNA or a combination of DNA and RNA. The second universal surface primers comprise a sequence that is wholly complementary or partially complementary along their lengths to at least a portion of an immobilized single stranded concatemer template molecule. The immobilized second universal surface primers can be immobilized to the support or immobilized to a coating on the support. The immobilized second universal surface primers can be embedded and attached (coupled) to the coating on the support. In some embodiments, the 5' end of the second universal surface primers are immobilized to a support or immobilized to a coating on the support. Alternatively, an interior portion or the 3' end of the immobilized second universal surface primers can be immobilized to a support or immobilized to a coating on the support. The support can comprise a plurality of immobilized second universal surface primers having the same sequence. The immobilized second universal surface primers can be any length, for example 4-50 nucleotides, or 50-100 nucleotides, or 100-150 nucleotides, or longer lengths. In some embodiments, the 3' terminal end of the immobilized second universal surface primers comprise an extendible 3' OH moiety. In some embodiments, the 3' terminal end of the immobilized second universal surface primers comprise a 3' non-extendible moiety. The 3' terminal end of the immobilized second universal surface primers can comprise a moiety that blocks primer extension, such as for example a phosphate group, a dideoxycytidine group, an inverted dT, or an amino group; these immobilized second universal surface primers are not extendible in a primer extension reaction. The immobilized second universal surface primers can lack a nucleotide having a scissile moiety.

In some embodiments, the plurality of immobilized second universal surface primers comprise at least one phosphorothioate diester bond at their 5' ends which can render the second universal surface primers resistant to exonuclease degradation. In some embodiments, the plurality of immobilized second universal surface primers comprise 2-5 or more consecutive phosphorothioate diester bonds at their 5' ends. In some embodiments, the plurality of immobilized second universal surface primers comprise at least one ribonucleotide and/or at least one 2'-O-methyl or 2'-O-methoxyethyl (MOE) nucleotide which can render the second universal surface primers resistant to exonuclease degradation.

In some embodiments, individual immobilized single stranded nucleic acid concatemer template molecules are covalently joined to an immobilized first universal surface primer, and at least one portion of the individual concatemer template molecule is hybridized to an immobilized second universal surface primer (FIG. 29). The immobilized second universal surface primers can serve to pin down a portion of the immobilized concatemer template molecules to the support. In some embodiments, the immobilized concatemer template molecule has two or more copies of a universal binding sequence for an immobilized second universal surface primer. The portion of the immobilized concatemer template molecule that includes the universal binding sequence for an immobilized second universal surface primer can hybridize to the immobilized second universal surface primer. In some embodiments, the second universal surface primers include a terminal 3' blocking group that renders them non-extendible. In some embodiments, the second universal surface primers have terminal 3' extendible ends.

In some embodiments, the support comprises about $10^2$-$10^{15}$ immobilized first universal surface primers per $mm^2$. In some embodiments, the support comprises about $10^2$-$10^{15}$ immobilized second universal surface primers per $mm^2$. In some embodiments, the support comprises about $10^2$-$10^{15}$ immobilized first universal surface primers and immobilized second universal surface primers per $mm^2$.

The immobilized surface primers (e.g., first and second universal surface primers) can be in fluid communication with each other to permit flowing various solutions of linear or circular nucleic acid template molecules, soluble primers, enzymes, nucleotides, divalent cations, buffers, reagents, and the like, onto the support so that the plurality of immobilized surface primers (and the primer extension products generated from the immobilized surface primers) react with the solutions in a massively parallel manner.

Figure 23:
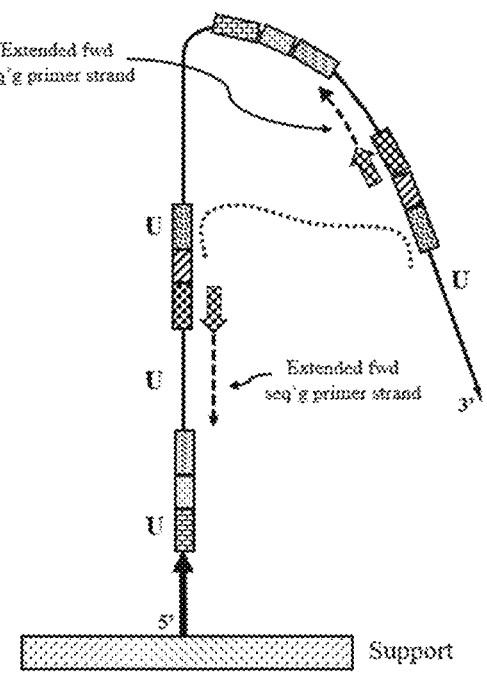

In some embodiments, the methods for generating a plurality of immobilized nucleic acid nanostructures, further comprise step (b): generating a plurality of immobilized single stranded nucleic acid concatemer template molecules wherein individual concatemer template molecules are covalently joined to an immobilized first universal surface primer by hybridizing a plurality of single stranded covalently closed circular nucleic acid library molecules to the plurality of immobilized first universal surface primers and conducting an on-support rolling circle amplification reaction with (i) a plurality of strand-displacing polymerases, (ii) a plurality of nucleotides which include dATP, dCTP, dGTP, dTTP and a nucleotide having a scissile moiety, and (iii) a plurality of compaction oligonucleotides, thereby generating a plurality of immobilized single stranded nucleic acid concatemer template molecules (e.g., FIGS. 22-23). In some embodiments, individual compaction oligonucleotides comprise a single-stranded linear oligonucleotide having a first binding region that can hybridize to a first portion of a concatemer molecule and the compaction oligonucleotide having a second binding region that can hybridize to a second portion of the concatemer molecule. In some embodiments, individual immobilized concatemer molecules collapse or fold into a compact nucleic acid nanostructure (e.g., first strand nanostructure). In some embodiments, the plurality of concatemers remain immobilized to the support upon collapsing or folding into nanostructures, thereby generating a support having a density of about $10^2$-$10^{15}$ per mm$^2$ of nanostructures immobilized to the support. In some embodiments, individual immobilized nanostructures comprise a plurality of tandem polynucleotide units and each polynucleotide unit has a sequence that is complementary to the sequence of a covalently closed circular nucleic acid library molecule.

The plurality of immobilized nucleic acid nanostructures can be in fluid communication with each other to permit flowing various reagents in solution including soluble primers, enzymes, nucleotides, divalent cations, buffers and the like, onto the support so that the plurality of immobilized nanostructures react with the solutions in a massively parallel manner.

In some embodiments, in step (b), the first binding region of the compaction oligonucleotides can hybridize to a first portion of the concatemer molecule, where the first portion of the concatemer molecule comprises a universal adaptor sequence according to any one of SEQ ID NOs:157-176, or a complementary sequence thereof (see Table 2)).

In some embodiments, in step (b), the second binding region of the compaction oligonucleotides can hybridize to a second portion of the concatemer molecule, where the second portion of the concatemer molecule comprises a universal adaptor sequence according to any one of SEQ ID NOs:157-176, or a complementary sequence thereof (see Table 2)).

In some embodiments, in step (b), the compaction oligonucleotides comprise a first, second, third, fourth, fifth, sixth, or other binding regions.

In some embodiments, in step (b), any binding region of the compaction oligonucleotide (e.g., first, second, third, fourth, fifth, sixth, or other binding regions) can hybridize to a portion of the concatemer molecule, where the portion of the concatemer molecule comprises a universal adaptor sequence according to any one of SEQ ID NOs:157-176, or a complementary sequence thereof (see Table 2)).

In some embodiments, in step (b), the compaction oligonucleotide comprises two or more binding regions and all of the binding regions have the same sequence. In some embodiments, the compaction oligonucleotide comprises two binding regions having different sequences. In some embodiments, the compaction oligonucleotide comprises three or more binding regions and at least two of the binding regions have different sequences.

In some embodiments, in step (b), the first binding region of the compaction oligonucleotide can have the same sequence as the second binding region.

In some embodiments, in step (b), the first binding region of the compaction oligonucleotide can have a sequence that is different from the second binding region.

In some embodiments, in step (b), the first binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the second, third, fourth, fifth or any subsequent binding region of the compaction oligonucleotide comprises a sequence that is a reverse sequence of the first binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the first binding region of a compaction oligonucleotide comprises a sequence according to any of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the second, third, fourth, fifth or any subsequent binding region of the compaction oligonucleotide comprises a sequence that is a reverse sequence of the first binding region, where the second, third, fourth, fifth or any subsequence binding region comprises any of one of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), first binding region of the compaction oligonucleotide can have a sequence that is a reverse sequence of the second binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the second binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the third binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the fourth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the fifth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the subsequent binding region(s) of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the compaction oligonucleotides comprise a full-length sequence according to any one of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156 (see Table 1).

In some embodiments, in step (b), the terminal 3' end of any of the compaction oligonucleotides can include at least one additional base comprising one or more 2'-O-methyl RNA bases (e.g., designated mUmUmU) or the terminal 3' end lacks additional 2'-O-methyl RNA bases.

In some embodiments, in step (b), the compaction oligonucleotides comprise one or more modified bases or linkages at their 5' or 3' ends to confer certain functionalities. In some embodiments, the compaction oligonucleotides comprise at least one phosphorothioate linkages at their 5' and/or 3' ends to confer exonuclease resistance. In some embodiments, at least one nucleotide at or near the 3' end comprises a 2' fluoro base which confers exonuclease resistance. In some embodiments, the 3' end of the compaction oligonucleotides comprise at least one 2'-O-methyl RNA base which blocks polymerase-catalyzed extension. For example, the 3' end of the compaction oligonucleotide comprises at least one base comprising 2'-O-methyl RNA base (e.g., designated mUmUmU). In some embodiments, the compaction oligonucleotides comprise a 3' inverted dT at their 3' ends which blocks polymerase-catalyzed extension. In some embodiments, the compaction oligonucleotides comprise 3' phosphorylation which blocks polymerase-catalyzed extension. In some embodiments, the compaction oligonucleotides comprise at least one locked nucleic acid (LNA) which increases the thermal stability of duplexes formed by hybridizing a compaction oligonucleotide to a concatemer molecule.

In some embodiments, in step (b), the compaction oligonucleotides can include at least one region (e.g., hybridization/binding region) having consecutive guanines. For example, the compaction oligonucleotides can include at least one region having 2, 3, 4, 5, 6 or more consecutive guanines. In some embodiments, the compaction oligonucleotides comprise four consecutive guanines which can form a guanine tetrad structure (see FIG. 64). The guanine tetrad structure can be stabilized via Hoogsteen hydrogen bonding. The guanine tetrad structure can be stabilized by a central cation including potassium, sodium, lithium, rubidium, or cesium.

In some embodiments, in step (b), at least one compaction oligonucleotide can form a guanine tetrad (FIG. 64) and hybridize to the universal binding sequences in a concatemer which can cause the concatemer to fold to form an intramolecular G-quadruplex structure (FIG. 65). The concatemers can self-collapse to form compact nanostructures. Formation of the guanine tetrads and G-quadruplexes in the nanostructures may increase the stability of the nanostructures to retain their compact size and shape which can withstand changes in pH, temperature and/or repeated flows of reagents.

In some embodiments, the plurality of compaction oligonucleotides in step (b) comprises a mixture of two or more different populations of compaction oligonucleotides having different sequences. In some embodiments, the plurality of compaction oligonucleotides in step (b) comprise a mixture of 2, 3, 4, 5, 6, 7, 8, 9 or 10 different populations of compaction oligonucleotides wherein the compaction oligonucleotides in the different populations have different sequences. In some embodiments, in the mixture of different compaction oligonucleotides in step (b), any given population of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156.

In some embodiments, in the methods for generating a plurality of immobilized nucleic acid nanostructures of step (b), the nucleic acid nanostructures can include one or more loops, or can have a spherical shape (e.g., nanoball), elongated shape (e.g., nanorod), proto-toroid shape or toroid shape (e.g., nano-toroid). The nucleic acid nanostructure can be a compact nucleic acid structure having a full width half maximum (FWHM) that is smaller compared to a concatemer that is not collapsed/folded into a nanostructure. Inclusion of the plurality of compaction oligonucleotides in the on-support rolling circle amplification reaction can improve the FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

Figure 18:
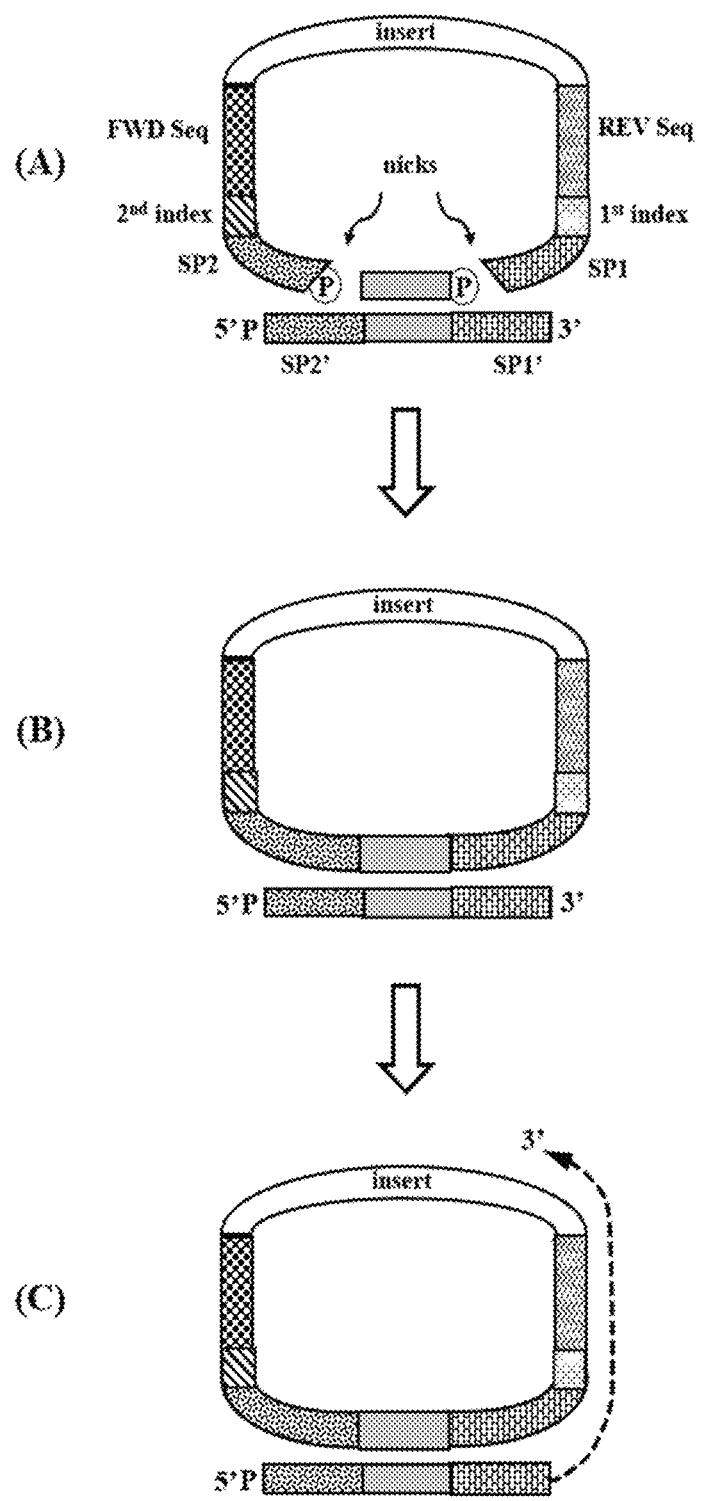
FIG. 18 is a schematic showing an exemplary workflow for generating a covalently closed circular library molecule using a double-stranded splint molecule. A library-splint complex (A) is subjected to a ligation reaction to close the two nicks to form a covalently closed circular library molecule (B) which is hybridized to a first splint strand. The first splint strand can be used as an amplification primer to conduct a rolling circle amplification reaction (C). The dotted line represents the nascent extension product.
Figure 20:
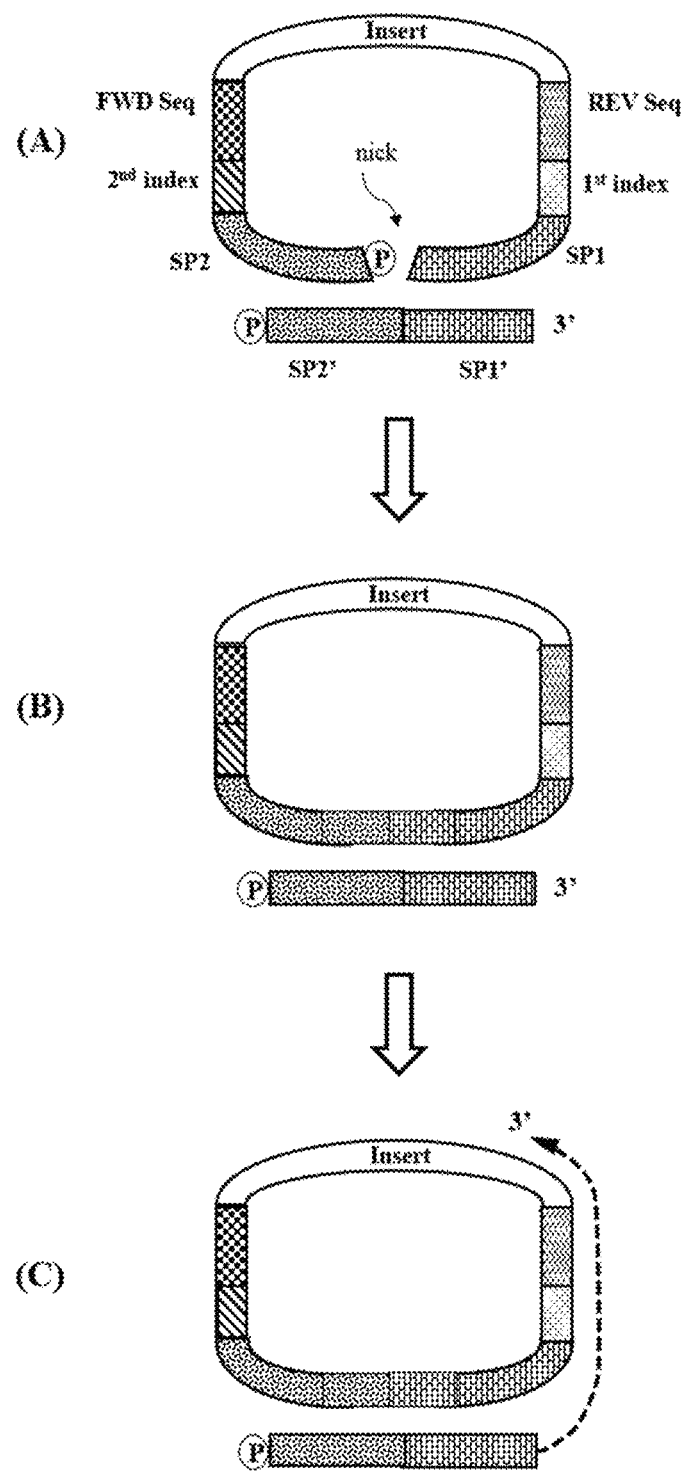
FIG. 20 is a schematic showing an exemplary workflow for generating a covalently closed circular library molecule using a single-stranded splint molecule. A library-splint complex (A) is subjected to a ligation reaction to close the one nick to form a covalently closed circular library molecule (B) which is hybridized to the single-stranded strand. The single-stranded splint strand can be used as an amplification primer to conduct a rolling circle amplification reaction (C). The dotted line represents the nascent extension product.

In some embodiments, in the methods for generating a plurality of immobilized nucleic acid nanostructures of step (b), individual single stranded covalently closed circular nucleic acid library molecules in the plurality comprise a sequence of interest, and any one or any combination of two or more of (i) a universal binding sequence (or complementary sequence thereof) for a soluble forward sequencing primer, (ii) a universal binding sequence (or complementary sequence thereof) for a soluble reverse sequencing primer, (iii) a universal binding sequence (or complementary sequence thereof) for an immobilized first universal surface primer, (iv) a universal binding sequence (or complementary sequence thereof) for an immobilized second universal surface primer, (v) a universal binding sequence (or complementary sequence thereof) for a first soluble amplification primer, (vi) a universal binding sequence (or complementary sequence thereof) for a second soluble amplification primer, (vii) a universal binding sequence (or complementary sequence thereof) for a soluble compaction oligonucleotide, (viii) a sample barcode sequence and/or (ix) a unique molecular index sequence (e.g., FIGS. 18A and B; FIGS. 20A and B).

In some embodiments, in the methods for generating a plurality of immobilized nucleic acid nanostructures of step (b), the rolling circle amplification reaction generates a plurality of immobilized single stranded nucleic acid concatemer template molecules (e.g., first strand nanostructures) wherein individual concatemer template molecules comprise at least two copies of a polynucleotide unit arranged in tandem. In some embodiments, each polynucleotide unit comprises a sequence-of-interest. In some embodiments, each polynucleotide unit comprises at least one universal adaptor sequence. In some embodiments, each polynucleotide unit comprises a sequence-of-interest and at least one universal adaptor sequence (e.g., FIG. 21). In some embodiments, individual concatemer molecules comprise 2-100 copies of a polynucleotide unit, or 100-250 copies of a polynucleotide unit, or 250-500 copies of a polynucleotide unit, or 500-750 copies of a polynucleotide unit, or 750-1000 copies of a polynucleotide unit, or more than 1000 copies of a polynucleotide unit. In some embodiments, individual concatemer molecules comprise 1000-10,000 copies of a polynucleotide unit. In some embodiments, individual concatemers comprise a plurality of tandem polynucleotide units where the sequence of each polynucleotide unit of a given concatemer molecule is complementary to the sequence of a circular library molecule that served as the template library molecule.

In some embodiments, individual concatemer molecules comprise two or more copies of a sequence of interest, wherein the immobilized concatemer template molecules further comprise any one or any combination of two or more of: (i) two or more copies of a universal binding sequence (or a complementary sequence thereof) for a soluble forward sequencing primer, (ii) two or more copies of a universal binding sequence (or a complementary sequence thereof) for a soluble reverse sequencing primer, (iii) two or more copies of a universal binding sequence (or a complementary sequence thereof) for an immobilized first universal surface primer, (iv) two or more copies of a universal binding sequence (or a complementary sequence thereof) for an immobilized second universal surface primer, (v) two or more copies of a universal binding sequence (or a complementary sequence thereof) for a first soluble amplification primer, (vi) two or more copies of a universal binding sequence (or a complementary sequence thereof) for a second soluble amplification primer, (vii) two or more copies of a universal binding sequence (or a complementary sequence thereof) for a soluble compaction oligonucleotide, (viii) two or more copies of a sample barcode sequence and/or (ix) two or more copies of a unique molecular index sequence.

In some embodiments, in the methods for generating a plurality of immobilized nucleic acid nanostructures of step (b), the rolling circle amplification reaction generates concatemer molecules comprising universal binding sequences that can hybridize/bind to certain primers. In some embodiments, the universal binding sequence (or a complementary sequence thereof) for the forward sequencing primer can hybridize to at least a portion of the forward sequencing primer. In some embodiments, the universal binding sequence (or a complementary sequence thereof) for the reverse sequencing primer can hybridize to at least a portion of the reverse sequencing primer. In some embodiments, the universal binding sequence (or a complementary sequence thereof) for the immobilized first universal surface primer can hybridize to at least a portion of the immobilized first universal surface primer. In some embodiments, the universal binding sequence (or a complementary sequence thereof) for the immobilized second universal surface primer can hybridize to at least a portion of the immobilized second universal surface primer. In some embodiments, the universal binding sequence (or a complementary sequence thereof) for the first soluble amplification primer can hybridize to at least a portion of the first soluble amplification primer. In some embodiments, the universal binding sequence (or a complementary sequence thereof) for the second soluble amplification primer can hybridize to at least a portion of the second soluble amplification primer. In some embodiments, the universal binding sequence (or a complementary sequence thereof) for the soluble compaction oligonucleotide can hybridize to at least a portion of the soluble compaction oligonucleotide.

In some embodiments, in the methods for generating a plurality of immobilized nucleic acid nanostructures of step (b), the plurality of immobilized single stranded nucleic acid concatemer template molecules (e.g., first strand nanostructures) comprise two or more copies of a universal binding sequence (or complementary sequence thereof) for immobilized second sequence surface primers. In some embodiments, individual immobilized single stranded nucleic acid concatemer template molecules are joined (e.g., covalently joined) to an immobilized first universal surface primer, and at least one portion of the individual concatemer template molecule is hybridized to an immobilized second universal surface primer. The immobilized second universal surface primers can serve to pin down a portion of the immobilized concatemer template molecules to the support (see FIG. 29). In some embodiments, the second universal surface primers include a terminal 3' blocking group that renders them non-extendible.

In some embodiments, in the methods for generating a plurality of immobilized nucleic acid nanostructures of step (b), the rolling circle amplification reaction can be conducted with a nucleotide mixture containing dATP, dCTP, dGTP, dTTP and a nucleotide having a scissile moiety to generate immobilized concatemer template molecules (e.g., first strand nanostructures) which includes at least one nucleotide having a scissile moiety (e.g., FIGS. 21-22). The scissile moieties in the immobilized concatemer template molecules can be converted into abasic sites. In some embodiments, in the nucleotide mixture, the nucleotide having the scissile moiety comprises uridine, 8-oxo-7,8-dihydroguanine (e.g., 8oxoG) or deoxyinosine. In the immobilized concatemer template molecules, the uridine can be converted to an abasic site using uracil DNA glycosylase (UDG), the 8oxoG can be converted to an abasic site using FPG glycosylase, and the deoxyinosine can be converted to an abasic site using 3-Methyladenine DNA glycosylase II (AlkA) glycosylase.

In some embodiments, the nucleotide mixture can include an amount of dUTP so that a target percent of the thymidine in the resulting concatemer molecules are replaced with dUTP. For example, when 30% of dTTP in the concatemer molecules are to be replaced with dUTP (e.g., 30% is the target percent) then the nucleotide mixture can contain 7.5% dUTP (e.g., 30/4=7.5%), 17.5% dTTP, and 25% each for dATP, dCTP and dGTP. The target percent of dTTP to be replaced by dUTP can be about 0.1-1%, or about 1-5%, or about 5-10%, or about 10-20%, or about 20-30%, or about 30-45%, or about 45-50%, or a higher percent of the dTTP in the immobilized concatemer template molecules are replaced with nucleotides having a scissile moiety.

In some embodiments, the nucleotide mixture can include an amount of deoxyinosine so that a target percent of the guanosine in the resulting concatemer molecules are replaced with deoxyinosine. For example, when 30% of dGTP in the concatemer molecules are to be replaced with deoxyinosine (e.g., 30% is the target percent) then the nucleotide mixture can contain 7.5% deoxyinosine (e.g., 30/4=7.5%), 17.5% dGTP, and 25% each for dATP, dCTP and dTTP. The target percent of dGTP to be replaced by deoxyinosine can be about 0.1-1%, or about 1-5%, or about 5-10%, or about 10-20%, or about 20-30%, or about 30-45%, or about 45-50%, or a higher percent of the dGTP in the immobilized concatemer template molecules are replaced with nucleotides having a scissile moiety.

In some embodiments, the nucleotide mixture can include an amount of 8oxoG so that a target percent of the guanosine in the resulting concatemer molecules are replaced with 8oxoG. For example, when 30% of dGTP in the concatemer molecules are to be replaced with 8oxoG (e.g., 30% is the target percent) then the nucleotide mixture can contain 7.5% 8oxoG (e.g., 30/4=7.5%), 17.5% dGTP, and 25% each for dATP, dCTP and dTTP. The target percent of dGTP to be replaced by 8oxoG can be about 0.1-1%, or about 1-5%, or about 5-10%, or about 10-20%, or about 20-30%, or about 30-45%, or about 45-50%, or a higher percent of the dGTP in the immobilized concatemer template molecules are replaced with nucleotides having a scissile moiety.

In some embodiments, in the methods for generating a plurality of immobilized nucleic acid nanostructures of step (b), the rolling circle amplification reaction generates a plurality of single stranded nucleic acid concatemer template molecules (e.g., first strand nanostructures) wherein individual concatemer template molecules have at least two nucleotides each having a scissile moiety that are distributed at random positions along the individual immobilized concatemer template molecule. In some embodiments, the nucleotides having a scissile moiety are distributed at different positions in the different immobilized concatemer template molecules.

In some embodiments, in the methods for generating a plurality of immobilized nucleic acid nanostructures of step (b), the method can further comprise removing the single-stranded covalently closed circular nucleic acid library molecules from the concatemer template molecules with at least one washing step which is conducted under a condition suitable to retain the single stranded nucleic acid concatemer template molecules where individual concatemer template molecules are operably joined to an immobilized first universal surface primer.

In some embodiments, the methods for generating a plurality of immobilized nucleic acid nanostructures, further comprise step (c): sequencing the plurality of immobilized concatemer template molecules (e.g., first strand nanostructures) thereby generating a plurality of extended forward sequencing primer strands. The sequencing of step (c) can comprise contacting the plurality of immobilized concatemer template molecules with a plurality of soluble forward sequencing primers under a condition suitable to hybridize at least one forward sequencing primer to at least one of the forward sequencing primer binding sites/sequences of the immobilized concatemer template molecules, and conducting forward sequencing reactions to generate a plurality of forward sequencing products using one or more types of sequencing polymerases, a plurality of nucleotide reagents, and the hybridized first forward sequencing primers (FIG. 23). In some embodiments, the plurality of nucleotide reagents is detectably labeled. In some embodiments, the sequencing of step (c) further comprises detecting and imaging the plurality of forward sequencing products.

In some embodiments, in the sequencing of step (c) further comprises contacting the plurality of immobilized concatemer template molecules with a plurality of compaction oligonucleotides under a condition suitable to hybridize the 5' end of at least one compaction oligonucleotide to a first portion of a concatemer molecule and to hybridize the second binding of the same compaction oligonucleotide to a second portion of the same concatemer molecule. In some embodiments, the plurality of compaction oligonucleotides of step (c) comprises any of the sequences as described in step (b) above.

In some embodiments, in the sequencing of step (c), the soluble forward sequencing primers comprise 3' OH extendible ends. In some embodiments, the soluble forward sequencing primers comprise a 3' blocking moiety which can be removed to generate a 3' OH extendible end. In some embodiments, the soluble forward sequencing primers lack a nucleotide having a scissile moiety. The forward sequencing reactions can generate a plurality of extended forward sequencing primer strands. In some embodiments, individual immobilized concatemer template molecules have multiple copies of the forward sequencing primer binding sites, wherein each forward sequencing primer binding site is capable of hybridizing to a first forward sequencing primer. Individual forward sequencing primer binding sites in a given immobilized concatemer template molecule can be hybridized to a forward sequencing primer and can undergo a sequencing reaction. Individual immobilized concatemer template molecules can undergo two or more sequence reactions, where each sequencing reaction is initiated from a first forward sequencing primer that is hybridized to a forward sequencing primer binding site (e.g., see FIG. 23).

In some embodiments, in the sequencing of step (c), the nucleotide reagent comprises a plurality of nucleotides, a plurality of nucleotide analogs, or a plurality of multivalent molecules.

In some embodiments, in the sequencing of step (c), individual nucleotides in the plurality of nucleotides comprises an aromatic base, a five carbon sugar and at least one phosphate group. In some embodiments, the plurality of nucleotides is unlabeled. In some embodiments, at least one nucleotide in the plurality can be labeled with a detectable reporter moiety (e.g., fluorophore). In some embodiments, the sequencing of step (c) further comprises contacting the plurality of immobilized concatemer template molecules with a catalytic or non-catalytic divalent cation. An exemplary catalytic divalent cation comprises magnesium and/or manganese which promotes polymerase-catalyzed nucleotide incorporation. An exemplary non-catalytic divalent cation comprises strontium, barium and/or calcium which inhibits polymerase-catalyzed nucleotide incorporation.

In some embodiments, in the sequencing of step (c), individual nucleotide analogs in the plurality comprise an aromatic base, a five carbon sugar having a 3' chain terminating moiety that inhibits polymerase-catalyzed nucleotide incorporation, and at least one phosphate group. In some embodiments, the plurality of nucleotide analogs is unlabeled. In some embodiments, at least one nucleotide analog in the plurality can be labeled with a detectable reporter moiety (e.g., fluorophore). In some embodiments, the sequencing of step (c) further comprises contacting the plurality of immobilized concatemer template molecules with a catalytic or non-catalytic divalent cation. An exemplary catalytic divalent cation can comprise magnesium and/or manganese, which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (c), individual multivalent molecules in the plurality comprise (1) a core; and (2) a plurality of nucleotide arms each comprising (i) a core attachment moiety, (ii) a spacer, (iii) a linker, and (iv) a nucleotide unit, wherein the core is attached to the plurality of nucleotide arms, wherein the spacer is attached to the linker, wherein the linker is attached to the nucleotide unit (e.g., see FIGS. 55A-C, 56-59). In some embodiments, the nucleotide unit comprises an aromatic base, a five carbon sugar and at least one phosphate group, and the linker is attached to the nucleotide unit through the base. In some embodiments, the plurality of multivalent molecules is unlabeled. In some embodiments, at least one multivalent molecule in the plurality is labeled with a detectable reporter moiety (e.g., fluorophore). In some embodiments, the sequencing of step (c) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium, which inhibits polymerase-catalyzed nucleotide incorporation.

In some embodiments, in the sequencing of step (c), the method further comprises forming at least one avidity complex, by contacting the plurality of immobilized concatemer template molecules (e.g., first strand nanostructures) with a plurality of soluble forward sequencing primers, a plurality of sequencing polymerases, and a plurality of multivalent molecules, to form a plurality of binding complexes including at least a first and second binding complex, wherein (i) the first binding complex comprises a first forward sequencing primer, a first sequencing polymerase, and a first multivalent molecule, bound to a first portion of the immobilized concatemer template molecule (e.g., first strand nanostructure) thereby forming the first binding complex, wherein a first nucleotide unit of the multivalent molecule is bound to the first polymerase, and (ii) the second binding complex comprises a second forward sequencing primer, a second sequencing polymerase, and the first multivalent molecule, bound to a second portion of the same immobilized concatemer template molecule thereby forming the second binding complex, wherein a second nucleotide unit of the multivalent molecule is bound to the second polymerase, and wherein the first and second binding complexes which include the same multivalent molecule forms an avidity complex. In some embodiments, the multivalent molecule is unlabeled or is labeled with a detectable reporter moiety.

In some embodiments, in the on-support rolling circle amplification reaction of step (b), the first binding region of the compaction oligonucleotides hybridize to the concatemer template molecules at a first portion that does not interfere (e.g., little or no overlap) with hybridizing the soluble forward sequencing primers to the forward sequencing primer binding sites of the plurality of concatemer template molecules of step (c).

In some embodiments, in the on-support rolling circle amplification reaction of step (b), the second binding region of the compaction oligonucleotides hybridize to the concatemer template molecules at a second portion that does not interfere (e.g., little or no overlap) with hybridizing the soluble forward sequencing primers to the forward sequencing primer binding sites of the plurality of concatemer template molecules of step (c).

In some embodiments, the methods for generating a plurality of immobilized nucleic acid nanostructures, further comprise step (d): retaining the plurality of immobilized concatemer template molecules (e.g., first strand nanostructures) and replacing the plurality of extended forward sequencing primer strands with a plurality of forward extension strands that are hybridized to the retained immobilized nucleic acid concatemer template molecules. The plurality of extended forward sequencing primer strands can be removed and replaced with a plurality of forward extension strands by conducting a primer extension reaction to synthesize a second strand, a forward extension strand (e.g., see FIGS. 24-25). The primer extension reaction can be conducted with a plurality of compaction oligonucleotides to collapse/fold the forward extension strands generate second strand nanostructures. One skilled in the art will recognize that there are several methods for conducting the primer extension reaction, some of which are described below.

Figure 24:
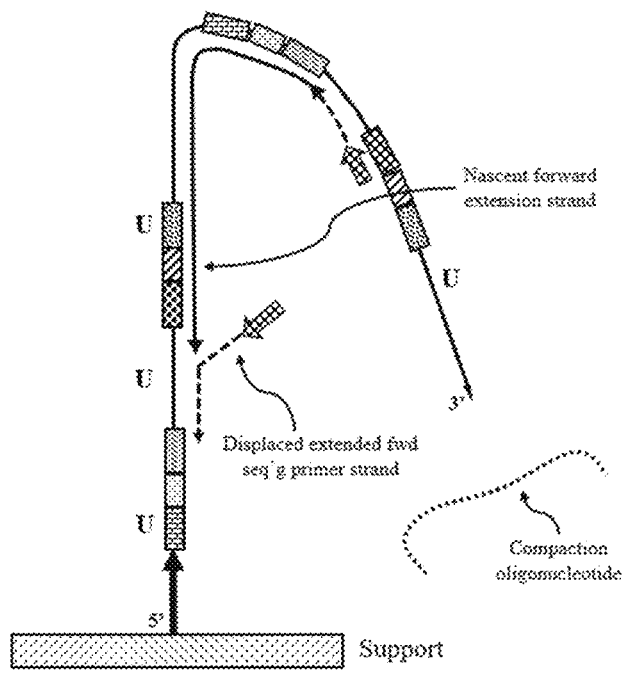
Figure 25:
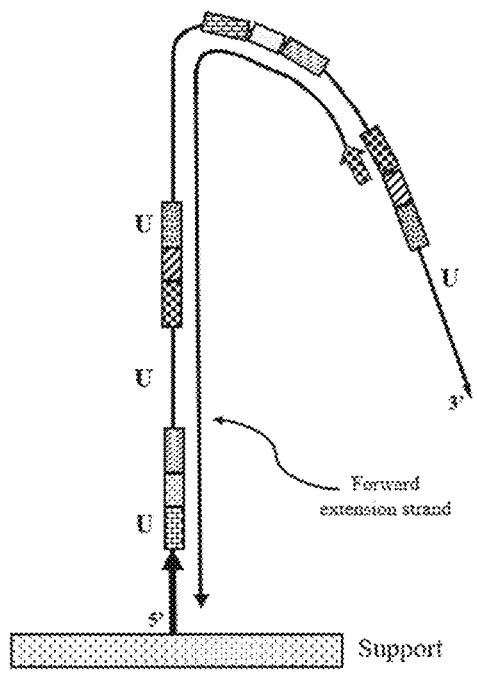

In some embodiments, the primer extension reaction of step (d) comprises contacting at least one extended forward sequencing primer strand with a plurality of strand displacing polymerases and a plurality of nucleotides and in the absence of soluble amplification primers, under a condition suitable to conduct a strand displacing primer extension reaction using the at least one extended forward sequencing primers strand to initiate the primer extension reaction thereby generating a forward extension strand that is covalently joined to the extended forward sequencing primers strand, wherein the forward extension strand is hybridized to the immobilized concatemer template molecule (e.g., first strand nanostructures) (FIGS. 24-25). For example, one of the extended forward sequencing primer strands can serve as a primer for the strand displacing polymerase. The strand displacing polymerase can extend the extended forward sequencing primer strand, and displace downstream extended forward sequencing primer strands while synthesizing an extended strand that replaces the downstream extended forward sequencing primer strands. The newly extended strand is covalently joined to an extended forward sequencing primer strand. The immobilized concatemer template molecules are then retained. In some embodiments, the plurality of nucleotides in the primer extension reaction of step (d) lack a nucleotide having a scissile moiety. The primer extension reaction can include a plurality of compaction oligonucleotides to generate forward extension strands that form nanostructures (e.g., second strand nanostructures). Individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of the forward extension strand and the compaction oligonucleotide having a 3' region that can hybridize to a second portion of the forward extension strand (e.g., the same forward extension strand).

In some embodiments, any of the embodiments of step (d) can be conducted in the presence of a plurality of compaction oligonucleotides. In some embodiments, the plurality of compaction oligonucleotides in any of the embodiments of step (d) comprise any of the sequences as described in step (b) above.

Without wishing to be bound by theory, it is believed that inclusion of compaction oligonucleotides in the primer extension reaction of step (d) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 µm or smaller.

Examples of strand displacing polymerases include, without limitation, phi29 DNA polymerase, large fragment of Bst DNA polymerase, large fragment of Bsu DNA polymerase (exo-), Bca DNA polymerase (exo-), Klenow fragment of E. coli DNA polymerase, T5 polymerase, M-MuLV reverse transcriptase, HIV viral reverse transcriptase, Deep Vent DNA polymerase and KOD DNA polymerase. The phi29 DNA polymerase can be wild type phi29 DNA polymerase (e.g., MagniPhi from Expedeon™), or variant EquiPhi29 DNA polymerase (e.g., from Thermo Fisher Scientific™), or chimeric QualiPhi DNA polymerase (e.g., from 4basebio™).

In some embodiments, the primer extension reaction of step (d) comprises: (i) removing the plurality of extended forward sequencing primer strands while retaining the immobilized concatemer template molecules (e.g., first strand nanostructures); and (ii) contacting the plurality of retained immobilized concatemer molecules with a plurality of soluble forward sequencing primers (e.g., a second plurality of soluble forward sequencing primers), a plurality of nucleotides (e.g., a second plurality of nucleotides) and a plurality of primer extension polymerases, under a condition suitable to hybridize the plurality of soluble forward sequencing primers to the plurality of retained immobilized concatemer template molecules and suitable for conducting polymerase-catalyzed primer extension reactions thereby generating a plurality of forward extension strands, wherein the soluble sequencing primers hybridize with the forward sequencing primer binding sequence in the retained immobilized concatemer molecules. The plurality of nucleotides in the primer extension reaction of step (d) lack a nucleotide having a scissile moiety. The primer extension reaction of step (d) can include a plurality of compaction oligonucleotides to generate forward extension strands that form nanostructures (e.g., second strand nanostructures). Individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of the forward extension strand and the compaction oligonucleotide having a 3' region that can hybridize to a second portion of the forward extension strand (e.g., the same forward extension strand).

Without wishing to be bound by theory, it is believed that inclusion of compaction oligonucleotides in the primer extension reaction of step (d) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 µm or smaller.

In some embodiments, the primer extension reaction of step (d) comprises: (i) removing the plurality of extended forward sequencing primer strand while retaining the immobilized concatemer template molecules (e.g., first strand nanostructures); and (ii) contacting the plurality of retained immobilized concatemer molecules with a plurality of soluble amplification primers, a plurality of nucleotides (e.g., a second plurality of nucleotides) and a plurality of primer extension polymerases, under a condition suitable to hybridize the plurality of soluble amplification primers to the plurality of retained immobilized concatemer template molecules and suitable for conducting polymerase-catalyzed primer extension reactions thereby generating a plurality of forward extension strands, wherein the soluble amplification primers hybridize with the soluble amplification primer binding sequence in the retained immobilized concatemer molecules. The plurality of nucleotides in the primer extension reaction of step (d) can lack a nucleotide having a scissile moiety. The primer extension reaction of step (d) can include a plurality of compaction oligonucleotides to generate forward extension strands that form nanostructures (e.g., second strand nanostructures). Individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of the forward extension strand and the compaction oligonucleotide having a 3' region that can hybridize to a second portion of the forward extension strand (e.g., the same forward extension strand).

Without wishing to be bound by theory, it is believed that inclusion of compaction oligonucleotides in the primer extension reaction of step (d) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 µm or smaller.

In some embodiments, in any embodiment of step (d) described above, the condition suitable to hybridize the plurality of soluble forward sequencing primers to the plurality of retained immobilized single stranded nucleic acid concatemer template molecules, or the condition suitable to hybridize the plurality of soluble amplification primers to the plurality of retained immobilized single stranded nucleic acid concatemer template molecules, comprises hybridizing the retained immobilized concatemer template molecules with the soluble forward sequencing primers in the presence of a primer extension polymerase, a plurality of nucleotides, and a high efficiency hybridization buffer. In some embodiment, the high efficiency hybridization buffer comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids;

(iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In some embodiments, in any embodiment of step (d) described above, the plurality of extended forward sequencing primer strands can be removed from the immobilized concatemer template molecules (e.g., first strand nanostructures) using an enzyme or a chemical reagent. For example, the plurality of extended forward sequencing primer strands can be enzymatically degraded using a 5' to 3' double-stranded DNA exonuclease, including T7 exonuclease (e.g., from New England Biolabs™, catalog #M0263S). In some embodiments, the plurality of extended forward sequencing primer strands can be removed with a temperature that favors nucleic acid denaturation.

In some embodiments, in any embodiment of step (d) described above, a denaturation reagent can be used to remove the plurality of extended forward sequencing primer strands, wherein the denaturation reagent comprises any one or any combination of compounds such as formamide, acetonitrile, guanidinium chloride and/or a buffering agent (e.g., Tris-HCl, MES, HEPES, or the like).

In some embodiments, in any embodiment of step (d) described above, the plurality of extended forward sequencing primer strands can be removed using an elevated temperature (e.g., heat) with or without a nucleic acid denaturation reagent. The plurality of extended forward sequencing primer strands can be subjected to a temperature of about 45-50° C., or about 50-60° C., or about 60-70° C., or about 70-80° C., or about 80-90° C., or about 90-95° C., or higher temperature.

In some embodiments, in any embodiment of step (d) described above, the plurality of extended forward sequencing primer strands can be removed using 100% formamide at a temperature of about 65° C. for about 3 minutes, and washing with a reagent comprising about 50 mM NaCl or equivalent ionic strength and having a pH of about 6.5-8.5.

In some embodiments, in any embodiment of step (d) described above, the primer extension polymerase comprises a high fidelity polymerase. In some embodiments, the primer extension polymerase of step (d) comprises a DNA polymerase capable of catalyzing a primer extension reaction using a uracil-containing template molecule (e.g., a uracil-tolerant polymerase). Exemplary polymerases include, but are not limited to, Q5U Hot Start high-fidelity DNA polymerase (e.g., catalog #M0515S from New England Biolabs™) Taq DNA polymerase, One Taq DNA polymerase (e.g., mixture of Taq and Deep Vent DNA polymerases, catalog #M0480S from New England Biolabs™), LongAmp Taq DNA polymerase (e.g., catalog #M0323S from New England Biolabs™), Epimark Hot Start Taq DNA polymerase (e.g., catalog #M0490S from New England Biolabs™), Bst DNA polymerase (e.g., large fragment, catalog #M0275S from New England Biolabs™), Bsu DNA polymerase (e.g., large fragment, catalog #M0330S from New England Biolabs™), Phi29 DNA polymerase (e.g., catalog #M0269S from New England Biolabs™), E. coli DNA polymerase (e.g., catalog #M0209S from New England Biolabs™), Therminator DNA polymerase (e.g., catalog #M0261S from New England Biolabs), Vent DNA polymerase and Deep Vent DNA polymerase.

Figure 26:
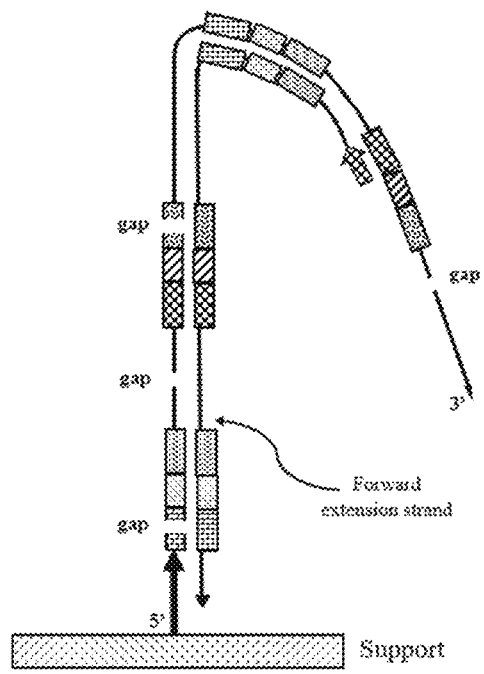
Figure 27:
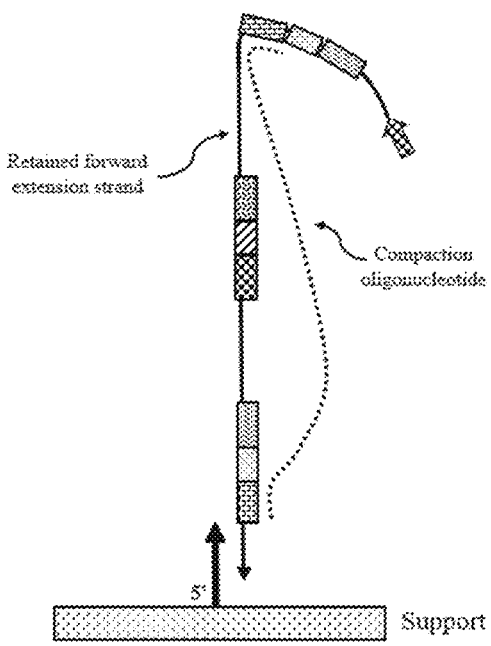

In some embodiments, the methods for generating a plurality of immobilized nucleic acid nanostructures, further comprise step (e): removing the retained immobilized concatemer template molecules (e.g., first strand nanostructures) by generating abasic sites in the immobilized single stranded concatemer template molecules at the nucleotide(s) having the scissile moiety and generating gaps at the abasic sites to generate a plurality of gap-containing single stranded nucleic acid concatemer template molecules while retaining the plurality of forward extension strands (second strand nanostructures) and retaining the plurality of immobilized surface primers (FIGS. 26-27).

The abasic sites are generated on the retained concatemer template strands that contain nucleotides having scissile moieties. In some embodiments, the scissile moieties in the retained concatemer template molecules comprises uridine, 8-oxo-7,8-dihydroguanine (e.g., 8oxoG) or deoxyinosine. The abasic sites can be removed to generate a plurality of single stranded nucleic acid template molecules having gaps while retaining the plurality of forward extension strands. The abasic sites can be generated by contacting the immobilized concatemer template molecules with an enzyme that removes the nucleo-base at the nucleotide having the scissile moiety. The uracil in the retained concatemer template strands can be converted to an abasic site using uracil DNA glycosylase (UDG). The 8oxoG in the retained concatemer template strands can be converted to an abasic site using FPG glycosylase. The deoxyinosine in the retained concatemer template strands can be converted to an abasic site using AlkA glycosylase.

In some embodiments, in the methods for generating a plurality of immobilized nucleic acid nanostructures of step (e), the gaps can be generated by contacting the abasic sites in the immobilized concatemer template molecules with an enzyme or a mixture of enzymes having lyase activity that breaks the phosphodiester backbone at the 5' and 3' sides of the abasic site to release the base-free deoxyribose and generate a gap (FIG. 26). The abasic sites can be removed using AP lyase, Endo IV endonuclease, FPG glycosylase/AP lyase, Endo VIII glycosylase/AP lyase. In some embodiments, generating the abasic sites and removal of the abasic sites to generate gaps can be achieved using a mixture of uracil DNA glycosylase and DNA glycosylase-lyase endonuclease VIII, for example, and without limitation, USER™ (Uracil-Specific Excision Reagent Enzyme from New England Biolabs™) or thermolabile USER™ (also from New England Biolabs™).

In some embodiments, in the methods for generating a plurality of immobilized nucleic acid nanostructures of step (e), the plurality of gap-containing template molecules can be removed using an enzyme, chemical compound and/or heat. After the gap-removal procedure, the plurality of retained forward extension strands are hybridized to the retained immobilized surface primers (FIG. 27). For example, the plurality of gap-containing template molecules can be enzymatically degraded using a 5' to 3' double-stranded DNA exonuclease, including T7 exonuclease (e.g., from New England Biolabs, catalog #M0263S). When a 5' to 3' double-stranded DNA exonuclease is used for removing gap-containing template molecules, then the plurality of soluble amplification primers in step (e) can comprise at least one phosphorothioate diester bond at their 5' ends which can render the soluble amplification primers resistant to exonuclease degradation. In some embodiments, the plurality of soluble amplification primers in step (d) comprise 2-5 or more consecutive phosphorothioate diester bonds at their 5' ends. In some embodiments, the plurality soluble amplification primers in step (d) comprise at least one ribonucleotide and/or at least one 2'-O-methyl or 2'-O-methoxyethyl (MOE) nucleotide which can render the forward sequencing primers resistant to exonuclease degradation.

In some embodiments, the plurality of gap-containing template molecules can be removed using a chemical reagent that favors nucleic acid denaturation. The denaturation reagent can include any one or any combination of compounds such as formamide, acetonitrile, guanidinium chloride and/or a buffering agent (e.g., Tris-HCl, MES, HEPES, or the like).

In some embodiments, the plurality of gap-containing template molecules can be removed using an elevated temperature (e.g., heat) with or without a nucleic acid denaturation reagent. The gap-containing template molecules can be subjected to a temperature of about 45-50° C., or about 50-60° C., or about 60-70° C., or about 70-80° C., or about 80-90° C., or about 90-95° C., or higher temperature.

In some embodiments, the plurality of gap-containing template molecules can be removed using 100% formamide at a temperature of about 65° C. for about 3 minutes, and washing with a reagent comprising about 50 mM NaCl or equivalent ionic strength and having a pH of about 6.5-8.5.

Figure 28:
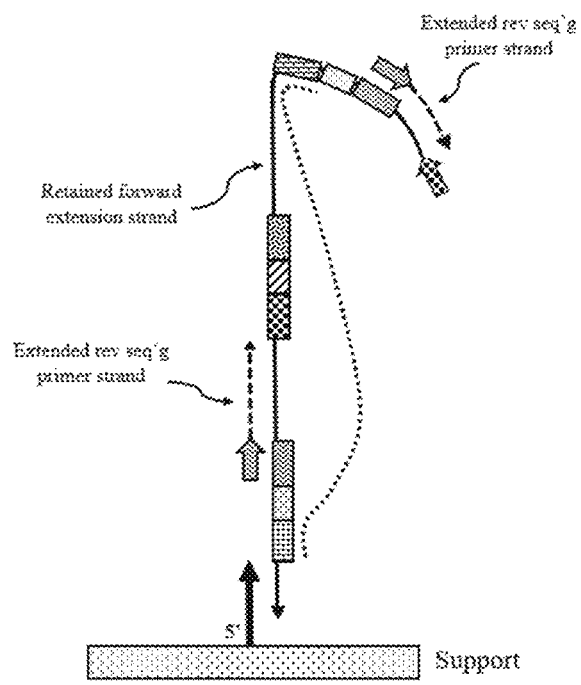

In some embodiments, the methods for generating a plurality of immobilized nucleic acid nanostructures, further comprise step (f): sequencing the plurality of retained forward extension strands (e.g., second strand nanostructures) thereby generating a plurality of extended reverse sequencing primer strands. In some embodiments, the sequencing of step (f) comprises contacting the plurality of retained forward extension strands with a plurality of soluble reverse sequencing primers under a condition suitable to hybridize the reverse sequencing primers to the reverse sequencing primer binding site of the retained forward extension strands, and conducting reverse sequencing reactions to generate a plurality of reverse sequencing products using one or more types of sequencing polymerases, a plurality of nucleotide reagents, and the hybridized reverse sequencing primers (FIG. 28). In some embodiments, the plurality of nucleotide reagents is detectably labeled. In some embodiments, the sequencing of step (f) further comprises detecting and imaging the plurality of reverse sequencing products. The universal adaptor sequence can be part of a concatemer molecule having multiple copies of a polynucleotide unit arranged in tandem, where each polynucleotide unit comprises a sequence-of-interest and at least one universal adaptor sequence. The first binding region of a compaction oligonucleotide can hybridize to at least a portion of any one of the universal adaptor sequences listed in Table 2. The second binding region of a compaction oligonucleotide sequence can hybridize to at least a portion of any one of the universal adaptor sequences listed in Table 2.

In some embodiments, the sequencing of step (f) further comprises contacting the plurality of plurality of retained forward extension strands with a plurality of compaction oligonucleotides under a condition suitable to hybridize the 5' end of at least one compaction oligonucleotide to a first portion of plurality of retained forward extension strand and to hybridize the second binding region of the same compaction oligonucleotide to a second portion of the same plurality of retained forward extension strand.

In some embodiments, in step (f), the plurality of compaction oligonucleotides comprises any of the sequences as described in step (b) above.

In some embodiments, in the sequencing of step (f), the extended reverse sequencing primer strands are hybridized to the retained forward extension strand. The retained forward extension strand is hybridized to the first universal surface primer. The extended reverse sequencing primer strands are not hybridized to the first universal surface primer, or covalently joined to the first universal surface primer. Therefore, the extended reverse sequencing primer strands are not immobilized to the support (e.g., see FIG. 28).

In some embodiments, in the sequencing of step (f), the soluble reverse sequencing primers comprise 3' OH extendible ends. In some embodiments, the soluble reverse sequencing primers comprise a 3' blocking moiety which can be removed to generate a 3' OH extendible end. In some embodiments, the soluble reverse sequencing primers lack a nucleotide having a scissile moiety. The reverse sequencing reactions can generate a plurality of extended reverse sequencing primer strands. In some embodiments, individual retained forward extension strand have multiple copies of the reverse sequencing primer binding sites/sequences, wherein each reverse sequencing primer binding site is capable of hybridizing to a reverse sequencing primer. Individual reverse sequencing primer binding sites in a given retained forward extension strand can then be hybridized to a reverse sequencing primer and can undergo a sequencing reaction. Individual retained forward extension strands can undergo two or more reverse sequencing reactions, where each sequencing reaction is initiated from a reverse sequencing primer that is hybridized to a reverse sequencing primer binding site (e.g., see FIG. 28).

In some embodiments, in the sequencing of step (f), the nucleotide reagent comprises a plurality of nucleotides, a plurality of nucleotide analogs, or a plurality of multivalent molecules.

In some embodiments, in the sequencing of step (f), individual nucleotides in the plurality of nucleotides comprises an aromatic base, a five carbon sugar and at least one phosphate group. In some embodiments, the plurality of nucleotides is unlabeled. In some embodiments, at least one nucleotide in the plurality can be labeled with a detectable reporter moiety (e.g., fluorophore). In some embodiments, the sequencing of step (f) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (f), individual nucleotide analogs in the plurality comprise an aromatic base, a five carbon sugar having a 3' chain terminating moiety that inhibits polymerase-catalyzed nucleotide incorporation, and at least one phosphate group. In some embodiments, the plurality of nucleotide analogs is unlabeled. In some embodiments, at least one nucleotide analog in the plurality can be labeled with a detectable reporter moiety (e.g., fluorophore). In some embodiments, the sequencing of step (f) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (f), individual multivalent molecules in the plurality comprise (1) a core; and (2) a plurality of nucleotide arms each comprising (i) a core attachment moiety, (ii) a spacer, (iii) a linker, and (iv) a nucleotide unit, wherein the core is attached to the plurality of nucleotide arms, wherein the spacer is attached to the linker, wherein the linker is attached to the nucleotide unit (e.g., see FIGS. 56-59). In some embodiments, the nucleotide unit comprises an aromatic base, a five carbon sugar and at least one phosphate group, and the linker is attached to the nucleotide unit through the base. In some embodiments, the plurality of multivalent molecules is unlabeled. In some embodiments, at least one multivalent molecule in the plurality is labeled with a detectable reporter moiety (e.g., fluorophore). In some embodiments, the sequencing of step (f) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (f), the method further comprises forming at least one avidity complex, by contacting the plurality of immobilized concatemer template molecules (e.g., second strand nanostructures) with a plurality of soluble reverse sequencing primers, a plurality of sequencing polymerases, and a plurality of multivalent molecules, to form a plurality of binding complexes including at least a first and second binding complex, wherein (i) the first binding complex comprises a first reverse sequencing primer, a first sequencing polymerase, and a first multivalent molecule, bound to a first portion of the immobilized concatemer template molecule (e.g., second strand nanostructure) thereby forming the first binding complex, wherein a first nucleotide unit of the multivalent molecule is bound to the first polymerase, and (ii) the second binding complex comprises a second reverse sequencing primer, a second sequencing polymerase, and the first multivalent molecule, bound to a second portion of the same immobilized concatemer template molecule thereby forming the second binding complex, wherein a second nucleotide unit of the multivalent molecule is bound to the second polymerase, and wherein the first and second binding complexes which include the same multivalent molecule forms an avidity complex. In some embodiments, the multivalent molecule is unlabeled or is labeled with a detectable reporter moiety.

In some embodiments, in any of the primer extension reactions of step (d), the first binding region of the compaction oligonucleotides hybridize to the forward extension strand at a first portion that does not interfere (e.g., little or no overlap) with hybridizing the reverse sequencing primers to the reverse sequencing primer binding sites of the plurality of forward extension strands of step (f).

In some embodiments, in any of the primer extension reactions of step (d), the second binding region of the compaction oligonucleotides hybridize to the forward extension strand at a second portion that does not interfere (e.g., little or no overlap) with hybridizing the reverse sequencing primers to the reverse sequencing primer binding sites of the plurality of forward extension strands of step (f).

In some embodiments, in the methods for generating a plurality of immobilized nucleic acid nanostructures, the compaction oligonucleotides of steps (b), (c), (e) and (f), comprise single stranded oligonucleotides comprising DNA, RNA, or a combination of DNA and RNA. The compaction oligonucleotides can be any length, including 20-150 nucleotides, or 30-100 nucleotides, or 40-80 nucleotides in length, or any range therebetween.

In some embodiments, the compaction oligonucleotide comprises a first binding region and a 3' region, and optionally an intervening linker between the first and second binding regions. The intervening linker can be any length, for example about 2-20 nucleotides in length. The intervening linker can comprise a homopolymer having consecutive identical bases (e.g., AAA, GGG, CCC, TTT or UUU). The intervening linker can comprise a non-homopolymer sequence.

The first binding region of the compaction oligonucleotides can be wholly complementary or partially complementary along its length to a first portion of a concatemer molecule. The second binding region of the compaction oligonucleotides can be wholly complementary or partially complementary along its length to a second portion of a concatemer molecule. The first binding region of the compaction oligonucleotides can hybridize to a first universal sequence portion of a concatemer molecule having a sequence of any one of SEQ ID NOs:157-176 (see Table 2). The second binding region of the compaction oligonucleotides can hybridize to a second universal sequence portion of a concatemer molecule having a sequence of any one of SEQ ID NOs:157-176 (see Table 2). The first binding region and second binding regions of the compaction oligonucleotide can hybridize to the concatemer to pull together distal portions of the concatemer causing compaction of the concatemer to form a nanostructure.

In some embodiments, the methods for generating a plurality of immobilized nucleic acid nanostructures further comprise: positioning a cellular biological sample on the immobilized nanostructures after step (b). For example, the cellular biological sample can be placed on the immobilized nucleic acid nanostructures after step (b) and prior to step (c).

In some embodiments, the cellular biological sample comprises a single cell, a plurality of cells, a tissue, an organ, an organism, or a section from any of these cellular biological samples. In some embodiments, the cellular biological sample comprises a sample that is fresh, frozen, fresh-frozen, or archived (e.g., formalin-fixed paraffin-embedded; FFPE). The cellular biological sample can be embedded in a matrix material. The cellular biological sample can be stained, de-stained or non-stained. The cellular biological sample can be permeabilized to permit the nucleic acid within the cellular sample to migrate from the cell(s) to the plurality of immobilized nanostructures.

In some embodiments, in step (f), the condition suitable to hybridize the reverse sequencing primers to the reverse sequencing primer binding sequences of the retained forward extension strands comprises contacting the plurality of soluble reverse sequencing primers and the retained forward extension strands with a high efficiency hybridization buffer. In some embodiments, the high efficiency hybridization buffer comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In an alternative embodiment, the sequencing of step (f) comprises using the immobilized surface primer as a sequencing primer and conducting sequencing reactions to generate a plurality of reverse sequencing strands.

In some embodiments, at least one washing step can be conducted after any of steps (a)-(f). The washing step can be conducted with a wash buffer comprising a pH buffering agent, a metal chelating agent, a salt, and a detergent.

In some embodiments, the pH buffering compound in the wash buffer comprises any one or any combination of two or more of Tris, Tris-HCl, Tricine, Bicine, Bis-Tris propane, HEPES, MES, MOPS, MOPSO, BES, TES, CAPS, TAPS, TAPSO, ACES, PIPES, ethanolamine (a.k.a 2-amino methanol; MEA), a citrate compound, a citrate mixture, NaOH and/or KOH. In some embodiments, the pH buffering agent can be present in the wash buffer at a concentration of about 1-100 mM, or about 10-50 mM, or about 10-25 mM. In some embodiments, the pH of the pH buffering agent which is present in any of the reagents described here in can be adjusted to a pH of about 4-9, or a pH of about 5-9, or a pH of about 5-8.

In some embodiments, the metal chelating agent in the wash buffer comprises EDTA (ethylenediaminetetraacetic acid), EGTA (ethylene glycol tetraacetic acid), HEDTA (hydroxyethylethylenediaminetriacetic acid), DPTA (diethylene triamine pentaacetic acid), NTA (N,N-bis(carboxymethyl)glycine), citrate anhydrous, sodium citrate, calcium citrate, ammonium citrate, ammonium bicitrate, citric acid, potassium citrate, or magnesium citrate. In some embodiments, the wash buffer comprises a chelating agent at a concentration of about 0.01-50 mM, or about 0.1-20 mM, or about 0.2-10 mM.

In some embodiments, the salt in the wash buffer comprises NaCl, KCl, $NH_2SO_4$ or potassium glutamate. In some embodiments, the detergent comprises an ionic detergent such as SDS (sodium dodecyl sulfate). The wash buffer can include a monovalent salt at a concentration of about 25-500 mM, or about 50-250 mM, or about 100-200 mM.

In some embodiments, the detergent in the wash buffer comprises a non-ionic detergent such as Triton X-100, Tween 20, Tween 80 or Nonidet P-40. In some embodiments, the detergent comprises a zwitterionic detergent such as CHAPS (3-[(3-cholamidopropyl)dimethylammonio]-1-propanesulfonate) or N-Dodecyl-N,N-dimethyl-3-amonio-1-propanesulfate (DetX). In some embodiments, the detergent comprises LDS (lithium dodecyl sulfate), sodium taurodeoxycholate, sodium taurocholate, sodium glycocholate, sodium deoxycholate or sodium cholate. In some embodiments, the detergent is included in the wash buffer at a concentration of about 0.01-0.05%, or about 0.05-0.1%, or about 0.1-0.15%, or about 0.15-0.2%, or about 0.2-0.25%.

In some embodiments, the methods for generating a plurality of immobilized nucleic acid nanostructures using an on-support rolling circle amplification reaction, the methods comprise: step (a) providing a support having a plurality of first universal surface primers immobilized thereon; step (b) conducting on-support RCA; and step (c) forward sequencing. In some embodiments, the methods do not include steps (d)-(f). For example, the methods do not include: synthesis of second strand nanostructures (step (d)); generating abasic sites and gaps (step (e)); and reverse sequencing (step (f)).

In some embodiments, the methods for generating a plurality of immobilized nucleic acid nanostructures using an on-support rolling circle amplification reaction, the methods comprise: step (a) providing a support having a plurality of first universal surface primers immobilized thereon; and step (b) conducting on-support RCA. In some embodiments, the methods do not include steps (c)-(f). For example, the methods do not include: forward sequencing (step (c)); synthesis of second strand nanostructures (step (d)); generating abasic sites and gaps (step (e)); and reverse sequencing (step (f)).

On-Support Methods
Generating High Density Immobilized Nanostructures Lacking Scissile Moieties The present disclosure provides methods for generating a plurality of immobilized nucleic acid nanostructures, comprising step (a): providing a support having a plurality of first universal surface primers immobilized thereon, wherein the support is passivated with at least one hydrophilic polymer layer which includes a plurality of first universal surface primers, wherein each of the first universal surface primers comprises a 3' OH extendible end and wherein the density of the first universal surface primers is about $10^2$-$10^{15}$ per $mm^2$. The first universal surface primers lack a scissile moiety that can be converted into an abasic site in a nucleic acid strand. For example, the first universal surface primers lack uridine, 8-oxo-7,8-dihydroguanine (e.g., 8oxoG) and deoxyinosine. In some embodiments, the support lacks a plurality of second universal surface primers or includes a plurality of second universal surface primers. In some embodiments, the support comprises a plurality of first and second universal surface primers.

In some embodiments, the immobilized first universal surface primers comprise single stranded oligonucleotides comprising DNA, RNA or a combination of DNA and RNA. The first universal surface primers comprise a sequence that is wholly complementary or partially complementary along their lengths to at least a portion of a circular nucleic acid library molecule. The first universal surface primers can include a terminal 3' nucleotide having a sugar 3' OH moiety which is extendible for nucleotide polymerization (e.g., polymerase catalyzed polymerization).

In some embodiments, the immobilized first universal surface primers can be immobilized to the support or immobilized to a coating on the support. The immobilized first universal surface primers can be embedded and attached (coupled) to the coating on the support. In some embodiments, the 5' end of the immobilized first universal surface primers are immobilized to a support or immobilized to a coating on the support. Alternatively, an interior portion or the 3' end of the immobilized first universal surface primers can be immobilized to a support or immobilized to a coating on the support. The support comprises a plurality of immobilized first universal surface primers having the same sequence. The immobilized first universal surface primers can be any length, for example 4-50 nucleotides, or 50-100 nucleotides, or 100-150 nucleotides, or longer lengths, or any length therebetween.

In some embodiments, the plurality of immobilized first universal surface primers are located on the coated support at random positions (e.g., non-pre-determined positions). When the immobilized universal surface primers are located on the coated support at random positions, the immobilized nucleic acid nanostructures are also located at random positions. The randomly-located nucleic acid nanostructures can be tightly packed and fill much of the space on the coated support.

In some embodiments, the plurality of immobilized first universal surface primers are located on the coated support at pre-determined positions. For example, the immobilized first universal surface primers are arranged in an organized pattern. When the immobilized universal surface primers are located on the support or the coated support at pre-determined positions, the nucleic acid nanostructures are also located at pre-determined positions.

In some embodiments, the plurality of immobilized first universal surface primers comprise at least one phosphorothioate diester bond at their 5' ends which can render the first universal surface primers resistant to exonuclease degradation. In some embodiments, the plurality of immobilized first universal surface primers comprise 2-5 or more consecutive phosphorothioate diester bonds at their 5' ends. In some embodiments, the plurality of immobilized first universal surface primers comprise at least one ribonucleotide and/or at least one 2'-O-methyl or 2'-O-methoxyethyl (MOE) nucleotide which can render the first universal surface primers resistant to exonuclease degradation.

In some embodiments, the immobilized first universal surface primers comprise at least one locked nucleic acid (LNA) which comprises a methylene bridge bond between a 2' oxygen and 4' carbon of the pentose ring. Immobilized first universal surface primers that include at least one LNA can be resistant to nuclease digestions and can exhibit increased melting temperature when hybridized to the circular nucleic acid library molecules.

In some embodiments, the support further comprises a plurality of a second universal surface primer immobilized thereon (e.g., FIG. 29 but in this embodiment the immobilized concatemer lacks uracil). The second universal surface primers have a sequence that differs from the first universal immobilized surface primer. The immobilized second universal surface primers of step (a) comprise single stranded oligonucleotides comprising DNA, RNA or a combination of DNA and RNA. The second universal surface primers comprise a sequence that is wholly complementary or partially complementary along their lengths to at least a portion of an immobilized single stranded concatemer template molecule. The immobilized second universal surface primers can be immobilized to the support or immobilized to a coating on the support. The immobilized second universal surface primers can be embedded and attached (coupled) to the coating on the support. In some embodiments, the 5' end of the second universal surface primers are immobilized to a support or immobilized to a coating on the support. Alternatively, an interior portion or the 3' end of the immobilized second universal surface primers can be immobilized to a support or immobilized to a coating on the support. The support comprises a plurality of immobilized second universal surface primers having the same sequence. The immobilized second universal surface primers can be any length, for example 4-50 nucleotides, or 50-100 nucleotides, or 100-150 nucleotides, or longer lengths, or any length therebetween. In some embodiments, the 3' terminal end of the immobilized second universal surface primers comprise an extendible 3' OH moiety. In some embodiments, the 3' terminal end of the immobilized second universal surface primers comprise a 3' non-extendible moiety. The 3' terminal end of the immobilized second universal surface primers comprise a moiety that blocks primer extension, such as for example a phosphate group, a dideoxycytidine group, an inverted dT, or an amino group. The immobilized second universal surface primers are not extendible in a primer extension reaction. The immobilized second universal surface primers can lack a nucleotide having a scissile moiety.

In some embodiments, the plurality of immobilized second universal surface primers comprises at least one phosphorothioate diester bond at their 5' ends which can render the second universal surface primers resistant to exonuclease degradation. In some embodiments, the plurality of immobilized second universal surface primers comprise 2-5 or more consecutive phosphorothioate diester bonds at their 5' ends. In some embodiments, the plurality of immobilized second universal surface primers comprise at least one ribonucleotide and/or at least one 2'-O-methyl or 2'-O-methoxyethyl (MOE) nucleotide which can render the second universal surface primers resistant to exonuclease degradation.

In some embodiments, individual immobilized single stranded nucleic acid concatemer template molecules are covalently joined to an immobilized first universal surface primer, and at least one portion of the individual concatemer template molecule is hybridized to an immobilized second universal surface primer (e.g., FIG. 29 but in this embodiment the immobilized concatemer lacks uracil). The immobilized second universal surface primers can serve to pin down a portion of the immobilized concatemer template molecules to the support. The immobilized concatemer template molecule has two or more copies of a universal binding sequence for an immobilized second universal surface primer. The portion of the immobilized concatemer template molecule that includes the universal binding sequence for an immobilized second universal surface primer can hybridize to the immobilized second universal surface primer. In some embodiments, the second universal surface primers include a terminal 3' blocking group that renders them non-extendible. In some embodiments, the second universal surface primers have terminal 3' extendible ends.

In some embodiments, the support comprises about $10^2$-$10^{15}$ immobilized first universal surface primers per mm$^2$. In some embodiments, the support comprises about $10^2$-$10^{15}$ immobilized second universal surface primers per mm$^2$. In some embodiments, the support comprises about $10^2$-$10^{15}$ immobilized first universal surface primers and immobilized second universal surface primers per mm$^2$.

In some embodiments, the immobilized surface primers (e.g., first and second universal surface primers) are in fluid communication with each other to permit flowing various solutions of linear or circular nucleic acid template molecules, soluble primers, enzymes, nucleotides, divalent cations, buffers, reagents, and the like, onto the support so that the plurality of immobilized surface primers (and the primer extension products generated from the immobilized surface primers) react with the solutions in a massively parallel manner.

In some embodiments, the methods for generating a plurality of immobilized nucleic acid nanostructures, further comprise step (b): generating a plurality of immobilized single stranded nucleic acid concatemer template molecules wherein individual concatemer template molecules are covalently joined to an immobilized first universal surface primer by hybridizing a plurality of single stranded covalently closed circular nucleic acid library molecules to the plurality of immobilized first universal surface primers and conducting an on-support rolling circle amplification reaction with (i) a plurality of strand-displacing polymerases, (ii) a plurality of nucleotides which include dATP, dCTP, dGTP, dTTP, and (iii) a plurality of compaction oligonucleotides, thereby generating a plurality of immobilized single stranded nucleic acid concatemer template molecules (e.g., FIGS. 39-40). In some embodiments, individual compaction oligonucleotides comprise a single-stranded linear oligonucleotide having a 5' region that can hybridize to a first portion of a concatemer molecule and the compaction oligonucleotide having a 3' region that can hybridize to a second portion of the concatemer molecule (e.g., FIG. 40). In some embodiments, individual immobilized concatemer molecules collapse or fold into a compact nucleic acid nanostructure (e.g., first strand nanostructure). In some embodiments, the plurality of concatemers remain immobilized to the support upon collapsing or folding into nanostructures, thereby generating a support having a density of about $10^2$-$10^{15}$ per mm$^2$ of nanostructures immobilized to the support. In some embodiments, individual immobilized nanostructures comprise a plurality of tandem polynucleotide units and each polynucleotide unit has a sequence that is complementary to the sequence of a covalently closed circular nucleic acid library molecule.

The rolling circle amplification reaction can include a mixture of nucleotides that lack a scissile moiety. Exemplary nucleotides having a scissile moiety include, without limitation, uridine, 8-oxo-7,8-dihydroguanine (e.g., 8oxoG) and deoxyinosine. In some embodiments, the rolling circle amplification reaction generates a plurality of immobilized single stranded nucleic acid concatemer template molecules that lack a nucleotide having a scissile moiety.

In some embodiments, the plurality of immobilized nucleic acid nanostructures is in fluid communication with each other to permit flowing various reagents in solution including soluble primers, enzymes, nucleotides, divalent cations, buffers and the like, onto the support so that the plurality of immobilized nanostructures react with the solutions in a massively parallel manner.

In some embodiments, in step (b), the first binding region of the compaction oligonucleotides can hybridize to a first portion of the concatemer molecule, where the first portion of the concatemer molecule comprises a universal adaptor sequence according to any one of SEQ ID NOs:157-176, or a complementary sequence thereof (see Table 2).

In some embodiments, in step (b), the second binding region of the compaction oligonucleotides can hybridize to a second portion of the concatemer molecule, where the second portion of the concatemer molecule comprises a universal adaptor sequence according to any one of SEQ ID NOs:157-176, or a complementary sequence thereof (see Table 2).

In some embodiments, in step (b), the compaction oligonucleotides comprise a first, second, third, fourth, fifth, sixth, or other binding regions.

In some embodiments, in step (b), any binding region of the compaction oligonucleotide (e.g., first, second, third, fourth, fifth, sixth, or other binding regions) can hybridize to a portion of the concatemer molecule, where the portion of the concatemer molecule comprises a universal adaptor sequence according to any one of SEQ ID NOs:157-176, or a complementary sequence thereof (see Table 2).

In some embodiments, in step (b), the compaction oligonucleotide comprises two or more binding regions and all of the binding regions have the same sequence. In some embodiments, the compaction oligonucleotide comprises two binding regions having different sequences. In some embodiments, the compaction oligonucleotide comprises three or more binding regions and at least two of the binding regions have different sequences.

In some embodiments, in step (b), the first binding region of the compaction oligonucleotide can have the same sequence as the second binding region.

In some embodiments, in step (b), the first binding region of the compaction oligonucleotide can have a sequence that is different from the second binding region.

In some embodiments, in step (b), the first binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the second, third, fourth, fifth or any subsequent binding region of the compaction oligonucleotide comprises a sequence that is a reverse sequence of the first binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the first binding region of a compaction oligonucleotide comprises a sequence according to any of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the second, third, fourth, fifth or any subsequent binding region of the compaction oligonucleotide comprises a sequence that is a reverse sequence of the first binding region, where the second, third, fourth, fifth or any subsequence binding region comprises any of one of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), first binding region of the compaction oligonucleotide can have a sequence that is a reverse sequence of the second binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the second binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the third binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the fourth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the fifth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the subsequent binding region(s) of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the compaction oligonucleotides comprise a full-length sequence according to any one of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156 (see Table 1).

In some embodiments, in step (b), the terminal 3' end of any of the compaction oligonucleotides can include at least one additional base comprising one or more 2'-O-methyl RNA bases (e.g., designated mUmUmU) or the terminal 3' end lacks additional 2'-O-methyl RNA bases.

In some embodiments, in step (b), the compaction oligonucleotides comprise one or more modified bases or linkages at their 5' or 3' ends to confer certain functionalities. In some embodiments, the compaction oligonucleotides comprise at least one phosphorothioate linkages at their 5' and/or 3' ends to confer exonuclease resistance. In some embodiments, at least one nucleotide at or near the 3' end comprises a 2' fluoro base which confers exonuclease resistance. In some embodiments, the 3' end of the compaction oligonucleotides comprise at least one 2'-O-methyl RNA base which blocks polymerase-catalyzed extension. For example, the 3' end of the compaction oligonucleotide comprises at least one base comprising 2'-O-methyl RNA base (e.g., designated mUmUmU). In some embodiments, the compaction oligonucleotides comprise a 3' inverted dT at their 3' ends which blocks polymerase-catalyzed extension. In some embodiments, the compaction oligonucleotides comprise 3' phosphorylation which blocks polymerase-catalyzed extension. In some embodiments, the compaction oligonucleotides comprise at least one locked nucleic acid (LNA) which increases the thermal stability of duplexes formed by hybridizing a compaction oligonucleotide to a concatemer molecule.

In some embodiments, in step (b), the compaction oligonucleotides can include at least one region (e.g., hybridization/binding region) having consecutive guanines. For example, the compaction oligonucleotides can include at least one region having 2, 3, 4, 5, 6 or more consecutive guanines. In some embodiments, the compaction oligonucleotides comprise four consecutive guanines which can form a guanine tetrad structure (see FIG. 64). The guanine tetrad structure can be stabilized via Hoogsteen hydrogen bonding. The guanine tetrad structure can be stabilized by a central cation including potassium, sodium, lithium, rubidium, or cesium.

In some embodiments, in step (b), at least one compaction oligonucleotide can form a guanine tetrad (FIG. 64) and hybridize to the universal binding sequences in a concatemer which can cause the concatemer to fold to form an intramolecular G-quadruplex structure (FIG. 65). The concatemers can self-collapse to form compact nanostructures. Formation of the guanine tetrads and G-quadruplexes in the nanostructures may increase the stability of the nanostructures to retain their compact size and shape which can withstand changes in pH, temperature and/or repeated flows of reagents.

In some embodiments, the plurality of compaction oligonucleotides in step (b) comprises a mixture of two or more different populations of compaction oligonucleotides having different sequences. In some embodiments, the plurality of compaction oligonucleotides in step (b) comprise a mixture of 2, 3, 4, 5, 6, 7, 8, 9 or 10 different populations of compaction oligonucleotides wherein the compaction oligonucleotides in the different populations have different sequences. In some embodiments, in the mixture of different compaction oligonucleotides in step (b), any given population of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156.

In some embodiments, in the methods for generating a plurality of immobilized nucleic acid nanostructures of step (b), the nucleic acid nanostructures can include one or more loops, or can have a spherical shape (e.g., nanoball), elongated shape (e.g., nanorod), proto-toroid shape or toroid shape (e.g., nano-toroid). The nucleic acid nanostructure can be a compact nucleic acid structure having a full width half maximum (FWHM) that is smaller compared to a concatemer that is not collapsed/folded into a nanostructure. Inclusion of the plurality of compaction oligonucleotides in the on-support rolling circle amplification reaction can improve the FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, in the methods for generating a plurality of immobilized nucleic acid nanostructures of step (b), individual single stranded covalently closed circular nucleic acid library molecules in the plurality comprise a sequence of interest, and any one or any combination of two or more of (i) a universal binding sequence (or complementary sequence thereof) for a soluble forward sequencing primer, (ii) a universal binding sequence (or complementary sequence thereof) for a soluble reverse sequencing primer, (iii) a universal binding sequence (or complementary sequence thereof) for an immobilized first universal surface primer, (iv) a universal binding sequence (or complementary sequence thereof) for an immobilized second universal surface primer, (v) a universal binding sequence (or complementary sequence thereof) for a first soluble amplification primer, (vi) a universal binding sequence (or complementary sequence thereof) for a second soluble amplification primer, (vii) a universal binding sequence (or complementary sequence thereof) for a soluble compaction oligonucleotide, (viii) at least one sample barcode sequence and/or (ix) a unique molecular index sequence (e.g., FIGS. 18A-B, FIGS. 20A-B).

In some embodiments, in the methods for generating a plurality of immobilized nucleic acid nanostructures of step (b), the rolling circle amplification reaction generates a plurality of immobilized single stranded nucleic acid concatemer template molecules (e.g., first strand nanostructures) wherein individual concatemer template molecules comprise at least two copies of a polynucleotide unit arranged in tandem. In some embodiments, each polynucleotide unit comprises a sequence-of-interest. In some embodiments, each polynucleotide unit comprises at least one universal adaptor sequence. In some embodiments, each polynucleotide unit comprises a sequence-of-interest and at least one universal adaptor sequence (e.g., FIG. 39). In some embodiments, individual concatemer molecules comprise 2-100 copies of a polynucleotide unit, or 100-250 copies of a polynucleotide unit, or 250-500 copies of a polynucleotide unit, or 500-750 copies of a polynucleotide unit, or 750-1000 copies of a polynucleotide unit, or more than 1000 copies of a polynucleotide unit. In some embodiments, individual concatemer molecules comprise 1000-2000 copies of a polynucleotide unit, or 1000-10,000 copies of a polynucleotide unit. In some embodiments, individual concatemers comprise a plurality of tandem polynucleotide units where the sequence of each polynucleotide unit of a given concatemer molecule is complementary to the sequence of a circular library molecule that served as the template library molecule.

In some embodiments, individual concatemer molecules comprise two or more copies of a sequence of interest, and wherein the immobilized concatemer template molecules further comprise any one or any combination of two or more of: (i) two or more copies of a universal binding sequence (or a complementary sequence thereof) for a soluble forward sequencing primer, (ii) two or more copies of a universal binding sequence (or a complementary sequence thereof) for a soluble reverse sequencing primer, (iii) two or more copies of a universal binding sequence (or a complementary sequence thereof) for an immobilized first universal surface primer, (iv) two or more copies of a universal binding sequence (or a complementary sequence thereof) for an immobilized second universal surface primer, (v) two or more copies of a universal binding sequence (or a complementary sequence thereof) for a first soluble amplification primer, (vi) two or more copies of a universal binding sequence (or a complementary sequence thereof) for a second soluble amplification primer, (vii) two or more copies of a universal binding sequence (or a complementary sequence thereof) for a soluble compaction oligonucleotide, (viii) two or more copies of a sample barcode sequence and/or (ix) two or more copies of a unique molecular index sequence.

In some embodiments, in the methods for generating a plurality of immobilized nucleic acid nanostructures of step (b), the rolling circle amplification reaction generates concatemer molecules comprising universal binding sequences that can hybridize/bind to certain primers. In some embodiments, the universal binding sequence (or a complementary sequence thereof) for the forward sequencing primer can hybridize to at least a portion of the forward sequencing primer. In some embodiments, the universal binding sequence (or a complementary sequence thereof) for the reverse sequencing primer can hybridize to at least a portion of the reverse sequencing primer. In some embodiments, the universal binding sequence (or a complementary sequence thereof) for the immobilized first universal surface primer can hybridize to at least a portion of the immobilized first universal surface primer. In some embodiments, the universal binding sequence (or a complementary sequence thereof) for the immobilized second universal surface primer can hybridize to at least a portion of the immobilized second universal surface primer. In some embodiments, the universal binding sequence (or a complementary sequence thereof) for the first soluble amplification primer can hybridize to at least a portion of the first soluble amplification primer. In some embodiments, the universal binding sequence (or a complementary sequence thereof) for the second soluble amplification primer can hybridize to at least a portion of the second soluble amplification primer. In some embodiments, the universal binding sequence (or a complementary sequence thereof) for the soluble compaction oligonucleotide can hybridize to at least a portion of the soluble compaction oligonucleotide.

In some embodiments, in the methods for generating a plurality of immobilized nucleic acid nanostructures of step (b), the plurality of immobilized single stranded nucleic acid concatemer template molecules (e.g., first strand nanostructures) comprise two or more copies of a universal binding sequence (or complementary sequence thereof) for immobilized second sequence surface primers. In some embodiments, individual immobilized single stranded nucleic acid concatemer template molecules are joined (e.g., covalently joined) to an immobilized first universal surface primer, and at least one portion of the individual concatemer template molecule is hybridized to an immobilized second universal surface primer. The immobilized second universal surface primers serve to pin down a portion of the immobilized concatemer template molecules to the support (see FIG. 29 but in this embodiment the immobilized concatemer lacks uracil). In some embodiments, the second universal surface primers include a terminal 3' blocking group that renders them non-extendible.

In some embodiments, in the methods for generating a plurality of immobilized nucleic acid nanostructures of step (b), the method can further comprise removing the single-stranded covalently closed circular nucleic acid library molecules from the concatemer template molecules with at least one washing step which is conducted under a condition suitable to retain the single stranded nucleic acid concatemer template molecules where individual concatemer template molecules are operably joined to an immobilized first universal surface primer.

In some embodiments, the methods for generating a plurality of immobilized nucleic acid nanostructures, further comprise step (c): sequencing the plurality of immobilized concatemer template molecules (e.g., first strand nanostructures) thereby generating a plurality of extended forward sequencing primer strands. The sequencing of step (c) comprises contacting the plurality of immobilized concatemer template molecules with a plurality of soluble forward sequencing primers under a condition suitable to hybridize at least one forward sequencing primer to at least one of the forward sequencing primer binding sites/sequences of the immobilized concatemer template molecules, and conducting forward sequencing reactions to generate a plurality of forward sequencing products using one or more types of sequencing polymerases, a plurality of nucleotide reagents, and the hybridized first forward sequencing primers (FIG. 41). In some embodiments, the plurality of nucleotide reagents is detectably labeled. In some embodiments, the sequencing of step (c) further comprises detecting and imaging the plurality of forward sequencing products.

In some embodiments, in the sequencing of step (c) further comprises contacting the plurality of immobilized concatemer template molecules with a plurality of compaction oligonucleotides under a condition suitable to hybridize the 5' end of at least one compaction oligonucleotide to a first portion of a concatemer molecule and to hybridize the second binding region of the same compaction oligonucleotide to a second portion of the same concatemer molecule. In some embodiments, the plurality of compaction oligonucleotides of step (c) comprise any of the sequences as described in step (b) above.

In some embodiments, in the sequencing of step (c), the soluble forward sequencing primers comprise 3' OH extendible ends. In some embodiments, the soluble forward sequencing primers comprise a 3' blocking moiety which can be removed to generate a 3' OH extendible end. In some embodiments, the soluble forward sequencing primers lack a nucleotide having a scissile moiety. The forward sequencing reactions can generate a plurality of extended forward sequencing primer strands. In some embodiments, individual immobilized concatemer template molecules have multiple copies of the forward sequencing primer binding sites, wherein each forward sequencing primer binding site is capable of hybridizing to a first forward sequencing primer. Individual forward sequencing primer binding sites in a given immobilized concatemer template molecule can be hybridized to a forward sequencing primer and can undergo a sequencing reaction. Individual immobilized concatemer template molecules can undergo two or more sequence reactions, where each sequencing reaction is initiated from a first forward sequencing primer that is hybridized to a forward sequencing primer binding site (e.g., see FIG. 41).

In some embodiments, in the sequencing of step (c), the nucleotide reagent comprises a plurality of nucleotides, a plurality of nucleotide analogs, or a plurality of multivalent molecules.

In some embodiments, in the sequencing of step (c), individual nucleotides in the plurality of nucleotides comprises an aromatic base, a five carbon sugar and at least one phosphate group. In some embodiments, the plurality of nucleotides is unlabeled. In some embodiments, at least one nucleotide in the plurality can be labeled with a detectable reporter moiety (e.g., fluorophore). In some embodiments, the sequencing of step (c) further comprises contacting the plurality of immobilized concatemer template molecules with a catalytic or non-catalytic divalent cation. An exemplary catalytic divalent cation comprises magnesium and/or manganese which promotes polymerase-catalyzed nucleotide incorporation. An exemplary non-catalytic divalent cation comprises strontium, barium and/or calcium which inhibits polymerase-catalyzed nucleotide incorporation.

In some embodiments, in the sequencing of step (c), individual nucleotide analogs in the plurality comprise an aromatic base, a five carbon sugar having a 3' chain terminating moiety that inhibits polymerase-catalyzed nucleotide incorporation, and at least one phosphate group. In some embodiments, the plurality of nucleotide analogs is unlabeled. In some embodiments, at least one nucleotide analog in the plurality can be labeled with a detectable reporter moiety (e.g., fluorophore). In some embodiments, the sequencing of step (c) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (c), individual multivalent molecules in the plurality comprise (1) a core; and (2) a plurality of nucleotide arms each comprising (i) a core attachment moiety, (ii) a spacer, (iii) a linker, and (iv) a nucleotide unit, wherein the core is attached to the plurality of nucleotide arms, wherein the spacer is attached to the linker, wherein the linker is attached to the nucleotide unit (e.g., see FIGS. 56-59). In some embodiments, the nucleotide unit comprises an aromatic base, a five carbon sugar and at least one phosphate group, and the linker is attached to the nucleotide unit through the base. In some embodiments, the plurality of multivalent molecules is unlabeled. In some embodiments, at least one multivalent molecule in the plurality is labeled with a detectable reporter moiety (e.g., fluorophore). In some embodiments, the sequencing of step (c) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (c), the method further comprises forming at least one avidity complex, by contacting the plurality of immobilized concatemer template molecules (e.g., first strand nanostructures) with a plurality of soluble forward sequencing primers, a plurality of sequencing polymerases, and a plurality of multivalent molecules, to form a plurality of binding complexes including at least a first and second binding complex, wherein (i) the first binding complex comprises a first forward sequencing primer, a first sequencing polymerase, and a first multivalent molecule, bound to a first portion of the immobilized concatemer template molecule (e.g., first strand nanostructure) thereby forming the first binding complex, wherein a first nucleotide unit of the multivalent molecule is bound to the first polymerase, and (ii) the second binding complex comprises a second forward sequencing primer, a second sequencing polymerase, and the first multivalent molecule, bound to a second portion of the same immobilized concatemer template molecule thereby forming the second binding complex, wherein a second nucleotide unit of the multivalent molecule is bound to the second polymerase, and wherein the first and second binding complexes which include the same multivalent molecule forms an avidity complex. In some embodiments, the multivalent molecule is unlabeled or is labeled with a detectable reporter moiety.

In some embodiments, in the on-support rolling circle amplification reaction of step (b), the first binding region of the compaction oligonucleotides hybridize to the concatemer template molecules at a first portion that does not interfere (e.g., little or no overlap) with hybridizing the soluble forward sequencing primers to the forward sequencing primer binding sites of the plurality of concatemer template molecules of step (c).

In some embodiments, in the on-support rolling circle amplification reaction of step (b), the second binding region of the compaction oligonucleotides hybridize to the concatemer template molecules at a second portion that does not interfere (e.g., little or no overlap) with hybridizing the soluble forward sequencing primers to the forward sequencing primer binding sites of the plurality of concatemer template molecules of step (c).

In some embodiments, the methods for generating a plurality of immobilized nucleic acid nanostructures, further comprise step (d): retaining the plurality of immobilized concatemer template molecules (e.g., first strand nanostructures) and replacing the plurality of extended forward sequencing primer strands with a plurality of forward extension strands that are hybridized to the retained immobilized nucleic acid concatemer template molecules. The plurality of extended forward sequencing primer strands can be removed and replaced with a plurality of forward extension strands by conducting a primer extension reaction to synthesize a second strand, a forward extension strand (e.g., see FIGS. 42-43). The primer extension reaction can be conducted with a plurality of compaction oligonucleotides to collapse/fold the forward extension strands generate second strand nanostructures. One skilled in the art will recognize that there are several methods for conducting the primer extension reaction, some of which are described below.

In some embodiments, the primer extension reaction of step (d) comprises contacting at least one extended forward sequencing primer strand with (1) a plurality of strand displacing polymerases, (2) a plurality of nucleotides, and (3) a plurality of compaction oligonucleotides, in the absence of soluble amplification primers, under a condition suitable to conduct a strand displacing primer extension reaction using the at least one extended forward sequencing primers strand to initiate the primer extension reaction thereby generating a forward extension strand that is covalently joined to the extended forward sequencing primers strand, wherein the forward extension strand is hybridized to the immobilized concatemer template molecule (e.g., first strand nanostructures) (FIG. 42). For example, one of the extended forward sequencing primer strands can serve as a primer for the strand displacing polymerase. The strand displacing polymerase can extend the extended forward sequencing primer strand, and displace downstream extended forward sequencing primer strands while synthesizing an extended strand that replaces the downstream extended forward sequencing primer strands. The newly extended strand is covalently joined to an extended forward sequencing primer strand. The immobilized concatemer template molecules are retained. The plurality of nucleotides in the primer extension reaction of step (d) lack a nucleotide having a scissile moiety. The strand displacing primer extension reaction can also generate a plurality of partially displaced forward extension strands that are hybridized to the immobilized concatemer template molecules to form a plurality of immobilized amplicons (FIG. 43). The strand displacing primer extension reaction can also generate a plurality of detached forward extension strands that are not hybridized to the immobilized concatemer template molecules (FIG. 43). The primer extension reaction can include a plurality of compaction oligonucleotides to generate forward extension strands that form nanostructures (e.g., second strand nanostructures). Individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of the forward extension strand and the compaction oligonucleotide having a 3' region that can hybridize to a second portion of the forward extension strand (e.g., the same forward extension strand or a different forward extension strand). A compaction oligonucleotide can hybridize to a forward extension strand and a partially displaced forward extension strand (FIG. 44). A compaction oligonucleotide can hybridize to a partially displaced forward extension strand and a detached forward extension strand thereby immobilizing the detached forward extension strand (FIG. 44). A compaction oligonucleotide can hybridize to a forward extension strand (e.g., which is hybridized to an immobilized concatemer template molecule) and a detached forward extension strand thereby immobilizing the detached forward extension strand (FIG. 44).

Inclusion of compaction oligonucleotides in the primer extension reaction of step (d) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, step (d) comprises: (i) removing the plurality of extended forward sequencing primer strand while retaining the immobilized concatemer template molecules; and (ii) contacting the plurality of retained immobilized concatemer molecules with (1) a plurality of soluble amplification primers, (2) a plurality of nucleotides, (3) a plurality of strand displacing polymerases, and (4) a plurality of compaction oligonucleotides, under a condition suitable to hybridize the plurality of soluble amplification primers to the plurality of retained immobilized concatemer template molecules and suitable for conducting a strand displacing primer extension reaction thereby generating different types of forward extension strands, including a plurality of forward extension strands that are hybridized along at least a portion of their length to the immobilized concatemer template molecules, a plurality of partially displaced forward extension strands that are partially hybridized to the immobilized concatemer template molecules to form a plurality of immobilized amplicons, and a plurality of detached forward extension strands that are not hybridized to the immobilized concatemer template molecules. The soluble amplification primers hybridize with the amplification primer binding sequence in the retained immobilized concatemer molecules. The immobilized concatemer template molecules are retained. The plurality of nucleotides in the primer extension reaction of step (d) lack a nucleotide having a scissile moiety.

The strand displacing primer extension reaction can include a plurality of compaction oligonucleotides that bind to the forward extension strands to form nanostructures (e.g., second strand nanostructures). Upon binding to at least one compaction oligonucleotide, individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of a forward extension strand and the compaction oligonucleotide having a 3' region that can hybridize to a second portion of a forward extension strand (e.g., the same forward extension strand or a different forward extension strand). A compaction oligonucleotide can hybridize to a forward extension strand and a partially displaced forward extension strand. A compaction oligonucleotide can hybridize to a partially displaced forward extension strand and a detached forward extension strand thereby immobilizing the detached forward extension strand. A compaction oligonucleotide can hybridize to a forward extension strand (e.g., which is hybridized to an immobilized concatemer template molecule) and a detached forward extension strand thereby immobilizing the detached forward extension strand.

Inclusion of compaction oligonucleotides in the primer extension reaction of step (d) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, step (d) comprises: (i) removing the plurality of extended forward sequencing primer strand while retaining the immobilized concatemer template molecules; and (ii) contacting the plurality of retained immobilized concatemer molecules with (1) a plurality of soluble forward sequencing primers, (2) a plurality of nucleotides, (3) a plurality of strand displacing polymerases, and (4) a plurality of compaction oligonucleotides, under a condition suitable to hybridize the plurality of soluble forward sequencing primers to the plurality of retained immobilized concatemer template molecules and suitable for conducting a strand displacing primer extension reaction thereby generating different types of forward extension strands, including a plurality of forward extension strands that are hybridized along at least a portion of their length to the immobilized concatemer template molecules, a plurality of partially displaced forward extension strands that are partially hybridized to the immobilized concatemer template molecules to form a plurality of immobilized amplicons, and a plurality of detached forward extension strands that are not hybridized to the immobilized concatemer template molecules. The soluble forward sequencing primers hybridize with the forward sequencing primer binding sequence in the retained immobilized concatemer molecules. The immobilized concatemer template molecules are retained. The plurality of nucleotides in the primer extension reaction of step (d) lack a nucleotide having a scissile moiety.

The strand displacing primer extension reaction can include a plurality of compaction oligonucleotides that bind to the forward extension strands to form nanostructures (e.g., second strand nanostructures). Upon binding to at least one compaction oligonucleotide, individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of a forward extension strand and the compaction oligonucleotide having a 3' region that can hybridize to a second portion of a forward extension strand (e.g., the same forward extension strand or a different forward extension strand). A compaction oligonucleotide can hybridize to a forward extension strand and a partially displaced forward extension strand. A compaction oligonucleotide can hybridize to a partially displaced forward extension strand and a detached forward extension strand thereby immobilizing the detached forward extension strand. A compaction oligonucleotide can hybridize to a forward extension strand (e.g., which is hybridized to an immobilized concatemer template molecule) and a detached forward extension strand thereby immobilizing the detached forward extension strand.

Inclusion of compaction oligonucleotides in the primer extension reaction of step (d) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, step (d) can be conducted in the presence of a plurality of compaction oligonucleotides. In some embodiments, the plurality of compaction oligonucleotides of step (d) comprise any of the sequences as described in step (b) above.

In some embodiments, in any embodiment of step (d) described above, the plurality of strand displacing polymerases comprise phi29 DNA polymerase, large fragment of Bst DNA polymerase, large fragment of Bsu DNA polymerase (exo-), Bca DNA polymerase (exo-), Klenow fragment of E. coli DNA polymerase, T5 polymerase, M-MuLV reverse transcriptase, HIV viral reverse transcriptase, Deep Vent DNA polymerase and KOD DNA polymerase. The phi29 DNA polymerase can be wild type phi29 DNA polymerase (e.g., MagniPhi from Expedeon™), or variant EquiPhi29 DNA polymerase (e.g., from Thermo Fisher Scientific™), or chimeric QualiPhi DNA polymerase (e.g., from 4basebio™).

In some embodiments, in any embodiment of step (d) described above, the condition suitable to hybridize the plurality of soluble forward sequencing primers to the plurality of retained immobilized single stranded nucleic acid concatemer template molecules, or the condition suitable to hybridize the plurality of soluble amplification primers to the plurality of retained immobilized single stranded nucleic acid concatemer template molecules, comprises hybridizing the retained immobilized concatemer template molecules with the soluble forward sequencing primers in the presence of a primer extension polymerase, a plurality of nucleotides, and a high efficiency hybridization buffer. In some embodiment, the high efficiency hybridization buffer comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In some embodiments, in any embodiment of step (d) described above, the plurality of extended forward sequencing primer strands can be removed from the immobilized concatemer template molecules (e.g., first strand nanostructures) using an enzyme or a chemical reagent. For example, the plurality of extended forward sequencing primer strands can be enzymatically degraded using a 5' to 3' double-stranded DNA exonuclease, including, without limitation, T7 exonuclease (e.g., from New England Biolabs™, catalog #M0263S). In some embodiments, the plurality of extended forward sequencing primer strands can be removed with a temperature that favors nucleic acid denaturation.

In some embodiments, in any embodiment of step (d) described above, a denaturation reagent can be used to remove the plurality of extended forward sequencing primer strands, wherein the denaturation reagent comprises any one or any combination of compounds such as formamide, acetonitrile, guanidinium chloride and/or a buffering agent (e.g., Tris-HCl, MES, HEPES, or the like).

In some embodiments, in any embodiment of step (d) described above, the plurality of extended forward sequencing primer strands can be removed using an elevated temperature (e.g., heat) with or without a nucleic acid denaturation reagent. The plurality of extended forward sequencing primer strands can be subjected to a temperature of about 45-50° C., or about 50-60° C., or about 60-70° C., or about 70-80° C., or about 80-90° C., or about 90-95° C., or higher temperatures.

In some embodiments, in any embodiment of step (d) described above, the plurality of extended forward sequencing primer strands can be removed using 100% formamide at a temperature of about 65° C. for about 3 minutes, and washing with a reagent comprising about 50 mM NaCl or equivalent ionic strength and having a pH of about 6.5-8.5.

In some embodiments, in any embodiment of step (d) described above, the primer extension polymerase comprises a high fidelity polymerase. In some embodiments, the primer extension polymerase of step (d) comprises a DNA polymerase capable of catalyzing a primer extension reaction using a uracil-containing template molecule (e.g., a uracil-tolerant polymerase). Exemplary polymerases include, but are not limited to, Q5U Hot Start high-fidelity DNA polymerase (e.g., catalog #M0515S from New England Biolabs™) Taq DNA polymerase, One Taq DNA polymerase (e.g., mixture of Taq and Deep Vent DNA polymerases, catalog #M0480S from New England Biolabs™), LongAmp Taq DNA polymerase (e.g., catalog #M0323S from New England Biolabs™), Epimark Hot Start Taq DNA polymerase (e.g., catalog #M0490S from New England Biolabs™), Bst DNA polymerase (e.g., large fragment, catalog #M0275S from New England Biolabs™), Bsu DNA polymerase (e.g., large fragment, catalog #M0330S from New England Biolabs™), Phi29 DNA polymerase (e.g., catalog #M0269S from New England Biolabs™), *E. coli* DNA polymerase (e.g., catalog #M0209S from New England Biolabs™), Therminator DNA polymerase (e.g., catalog #M0261S from New England Biolabs™), Vent DNA polymerase and Deep Vent DNA polymerase.

In some embodiments, the methods for generating a plurality of immobilized nucleic acid nanostructures, further comprise step (e): sequencing the plurality of immobilized partially displaced forward extension strands thereby generating a first plurality of extended reverse sequencing primer strands. In some embodiments, step (e) further comprises sequencing the plurality of immobilized detached forward extension strands thereby generating a second plurality of extended reverse sequencing primer strands (FIG. 45). In some embodiments, individual immobilized partially displaced forward extension strands have two or more extended reverse sequencing primer strands hybridized thereon. In some embodiments, individual immobilized detached forward extension strands have two or more extended reverse sequencing primer strands hybridized thereon.

In some embodiments, the sequencing of step (e) comprises contacting the plurality of immobilized partially displaced forward extension strands (e.g., that are hybridized to the immobilized concatemer template molecules), and contacting the plurality of immobilized detached forward extension strands, with a plurality of soluble reverse sequencing primers under a condition suitable to hybridize the reverse sequencing primers to the reverse sequencing primer binding site of the forward extension strands (FIG. 45). The sequencing of step (e) comprises conducting sequencing reactions using the hybridized reverse sequencing primers wherein the reverse sequencing reactions generates a plurality of extended reverse sequencing primer strands (FIG. 45). The plurality of first extended reverse sequencing primer strands is hybridized to an immobilized partially displaced forward extension strand. The plurality of second extended reverse sequencing primer strands is hybridized to an immobilized detached forward extension strand.

During the sequencing of step (e), the immobilized partially displaced forward extension strands remain hybridized to the retained immobilized concatemer template molecules (FIG. 45). During the sequencing of step (e), the immobilized detached forward extension strands remain hybridized to the immobilized partially displaced forward extension strands (FIG. 45). As shown in FIG. 45, the reverse sequencing reaction can be conducted with a plurality of soluble reverse sequencing primers on the partially displaced forward extension strand and the immobilized detached forward extension strand. The reverse sequencing reaction generates extended reverse sequencing primer strands. For the sake of simplicity, FIG. 45 shows one copy of an extended reverse sequencing primer strand on the partially displaced forward extension strand, and one copy of an extended reverse sequencing primer strand on the immobilized detached forward extension strand. The skilled artisan will appreciate that the partially displaced forward extension strand and the immobilized detached forward extension strand can include two or more extended reverse sequencing primer strands hybridized thereon.

In some embodiments, the sequencing of step (e) comprises contacting the plurality of hybridized reverse sequencing primers with (1) a plurality of sequencing polymerases, (2) a plurality of nucleotide reagents, and (3) a plurality of compaction oligonucleotides, under a condition suitable for conducting reverse sequencing reactions to generate a plurality of reverse sequencing products (FIG. 45). In some embodiments, the plurality of nucleotide reagents is detectably labeled. In some embodiments, the sequencing of step (e) further comprises detecting and imaging the plurality of reverse sequencing products.

In some embodiments, the sequencing of step (e) comprises contacting the plurality of immobilized forward extension strands with a plurality of compaction oligonucleotides, under a condition suitable to hybridize the 5' end of at least one compaction oligonucleotide to a first portion of a forward extension strand and to hybridize the second binding region of the same compaction oligonucleotide to a second portion of the same forward extension strand. The immobilized forward extension strands then include the immobilized partially displaced forward extension strands and the immobilized detached forward extension strands.

In some embodiments, the sequencing of step (e) further comprises contacting the plurality of immobilized forward extension strands with a plurality of compaction oligonucleotides, under a condition suitable to hybridize the 5' end of at least one compaction oligonucleotide to an immobilized partially displaced forward extension strand and to hybridize the second binding region of the same compaction oligonucleotide to an immobilized detached forward extension strand. The immobilized forward extension strands then include the immobilized partially displaced forward extension strands and the of immobilized detached forward extension strands.

In some embodiments, in the sequencing of step (e), the soluble reverse sequencing primers comprise 3' OH extendible ends. In some embodiments, the soluble reverse sequencing primers comprise a 3' blocking moiety which can be removed to generate a 3' OH extendible end. In some embodiments, the soluble reverse sequencing primers lack a nucleotide having a scissile moiety. The reverse sequencing reactions can generate a plurality of extended reverse sequencing primer strands. In some embodiments, individual immobilized forward extension strands have multiple copies of the reverse sequencing primer binding sites/sequences, wherein each reverse sequencing primer binding site is capable of hybridizing to a reverse sequencing primer. Individual reverse sequencing primer binding sites in a given immobilized forward extension strand can be hybridized to a reverse sequencing primer and can undergo a sequencing reaction. Individual immobilized forward extension strands can undergo two or more reverse sequencing reactions, where each sequencing reaction is initiated from a reverse sequencing primer that is hybridized to a reverse sequencing primer binding site (e.g., see FIG. 45).

In some embodiments, in the sequencing of step (e), the nucleotide reagent comprises a plurality of nucleotides, a plurality of nucleotide analogs, or a plurality of multivalent molecules.

In some embodiments, in the sequencing of step (e), individual nucleotides in the plurality of nucleotides comprises an aromatic base, a five carbon sugar and at least one phosphate group. In some embodiments, the plurality of nucleotides is unlabeled. In some embodiments, at least one nucleotide in the plurality can be labeled with a detectable reporter moiety (e.g., fluorophore). In some embodiments, the sequencing of step (e) further comprises contacting the plurality of immobilized forward extension strands with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (e), individual nucleotide analogs in the plurality comprise an aromatic base, a five carbon sugar having a 3' chain terminating moiety that inhibits polymerase-catalyzed nucleotide incorporation, and at least one phosphate group. In some embodiments, the plurality of nucleotide analogs is unlabeled. In some embodiments, at least one nucleotide analog in the plurality can be labeled with a detectable reporter moiety (e.g., fluorophore). In some embodiments, the sequencing of step (e) further comprises contacting the plurality of immobilized forward extension strands with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (e), individual multivalent molecules in the plurality comprise (1) a core; and (2) a plurality of nucleotide arms each comprising (i) a core attachment moiety, (ii) a spacer, (iii) a linker, and (iv) a nucleotide unit, wherein the core is attached to the plurality of nucleotide arms, wherein the spacer is attached to the linker, wherein the linker is attached to the nucleotide unit (e.g., see FIGS. 56-59). In some embodiments, the nucleotide unit comprises an aromatic base, a five carbon sugar and at least one phosphate group, and the linker is attached to the nucleotide unit through the base. In some embodiments, the plurality of multivalent molecules is unlabeled. In some embodiments, at least one multivalent molecule in the plurality is labeled with a detectable reporter moiety (e.g., fluorophore). In some embodiments, the sequencing of step (e) further comprises contacting the plurality of immobilized forward extension strands with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (e), the method further comprises forming at least one avidity complex, by contacting the plurality of immobilized forward extension strands (e.g., second strand nanostructures) with a plurality of soluble reverse sequencing primers, a plurality of sequencing polymerases, and a plurality of multivalent molecules, to form a plurality of binding complexes including at least a first and second binding complex, wherein (i) the first binding complex comprises a first reverse sequencing primer, a first sequencing polymerase, and a first multivalent molecule, bound to a first portion of the immobilized forward extension strand (e.g., second strand nanostructure) thereby forming the first binding complex, wherein a first nucleotide unit of the multivalent molecule is bound to the first polymerase, and (ii) the second binding complex comprises a second reverse sequencing primer, a second sequencing polymerase, and the first multivalent molecule, bound to a second portion of the same immobilized forward extension strand thereby forming the second binding complex, wherein a second nucleotide unit of the multivalent molecule is bound to the second polymerase, and wherein the first and second binding complexes which include the same multivalent molecule forms an avidity complex. In some embodiments, the multivalent molecule is unlabeled or is labeled with a detectable reporter moiety.

In some embodiments, in any of the primer extension reactions of step (d), the first binding region of the compaction oligonucleotides hybridize to any of the immobilized forward extension strands at a first portion that does not interfere (e.g., little or no overlap) with hybridizing the reverse sequencing primers to the reverse sequencing primer binding sites of the plurality of immobilized forward extension strands of step (e).

In some embodiments, in any of the primer extension reactions of step (d), the second binding region of the compaction oligonucleotides hybridize to any of the immobilized forward extension strands at a second portion that does not interfere (e.g., little or no overlap) with hybridizing the reverse sequencing primers to the reverse sequencing primer binding sites of the plurality of immobilized forward extension strands of step (e).

In some embodiments, in any of the methods described above for generating a plurality of immobilized nucleic acid nanostructures, the compaction oligonucleotides of steps (b), (c), (d) and (e), comprise single stranded oligonucleotides comprising DNA, RNA, or a combination of DNA and RNA. The compaction oligonucleotides can be any length, including 20-150 nucleotides, or 30-100 nucleotides, or 40-80 nucleotides in length, or any range therebetween.

In some embodiments, the compaction oligonucleotide comprises a 5' region and a 3' region, and optionally an intervening linker between the 5' and 3' regions. The intervening linker can be any length, for example about 2-20 nucleotides in length. The intervening linker can comprise a homopolymer having consecutive identical bases (e.g., AAA, GGG, CCC, TTT or UUU). The intervening linker can comprise a non-homopolymer sequence.

The first binding region of the compaction oligonucleotides can be wholly complementary or partially complementary along its length to a first portion of a concatemer molecule. The second binding region of the compaction oligonucleotides can be wholly complementary or partially complementary along its length to a second portion of a concatemer molecule. The first binding region of the compaction oligonucleotides can hybridize to a first universal sequence portion of a concatemer molecule having a sequence of any one of SEQ ID NOs:157-176 (see Table 2). The second binding region of the compaction oligonucleotides can hybridize to a second universal sequence portion of a concatemer molecule having a sequence of any one of SEQ ID NOs:157-176 (see Table 2). The first and second regions of the compaction oligonucleotide can hybridize to the concatemer to pull together distal portions of the concatemer causing compaction of the concatemer to form a nanostructure.

In some embodiments, the methods for generating a plurality of immobilized nucleic acid nanostructures further comprise: positioning a cellular biological sample on the immobilized nanostructures after step (b). For example, the cellular biological sample can be placed on the immobilized nucleic acid nanostructures, e.g., after step (b) and prior to step (c). In some embodiments, the cellular biological sample comprises a single cell, a plurality of cells, a tissue, an organ, an organism, or a section from any of these cellular biological samples. The cellular biological sample can comprise a sample that is fresh, frozen, fresh-frozen, or archived (e.g., formalin-fixed paraffin-embedded; FFPE). The cellular biological sample can be embedded in a matrix material. The cellular biological sample can be stained, de-stained or non-stained. The cellular biological sample can be permeabilized to permit the nucleic acids within the cellular sample to migrate from the cell(s) to the plurality of immobilized nanostructures.

In some embodiments, in step (e), the condition suitable to hybridize the reverse sequencing primers to the reverse sequencing primer binding sequences of the retained forward extension strands comprises contacting the plurality of soluble reverse sequencing primers and the retained forward extension strands with a high efficiency hybridization buffer. In some embodiments, the high efficiency hybridization buffer comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In an alternative embodiment, the sequencing of step (e) comprises using the immobilized surface primer as a sequencing primer and conducting sequencing reactions to generate a plurality of reverse sequencing strands.

In some embodiments, at least one washing step can be conducted after any of steps (a)-(e). The washing step can be conducted with a wash buffer comprising a pH buffering agent, a metal chelating agent, a salt, and a detergent.

In some embodiments, the pH buffering compound in the wash buffer comprises any one or any combination of two or more of Tris, Tris-HCl, Tricine, Bicine, Bis-Tris propane, HEPES, MES, MOPS, MOPSO, BES, TES, CAPS, TAPS, TAPSO, ACES, PIPES, ethanolamine (i.e., 2-amino methanol; MEA), a citrate compound, a citrate mixture, NaOH and/or KOH. In some embodiments, the pH buffering agent can be present in the wash buffer at a concentration of about 1-100 mM, or about 10-50 mM, or about 10-25 mM. In some embodiments, the pH of the pH buffering agent which is present in any of the reagents described here in can be adjusted to a pH of about 4-9, or a pH of about 5-9, or a pH of about 5-8.

In some embodiments, the metal chelating agent in the wash buffer comprises EDTA (ethylenediaminetetraacetic acid), EGTA (ethylene glycol tetraacetic acid), HEDTA (hydroxyethylethylenediaminetriacetic acid), DPTA (diethylene triamine pentaacetic acid), NTA (N,N-bis(carboxymethyl)glycine), citrate anhydrous, sodium citrate, calcium citrate, ammonium citrate, ammonium bicitrate, citric acid, potassium citrate, or magnesium citrate. In some embodiments, the wash buffer comprises a chelating agent at a concentration of about 0.01-50 mM, or about 0.1-20 mM, or about 0.2-10 mM.

In some embodiments, the salt in the wash buffer comprises NaCl, KCl, $NH_2SO_4$ or potassium glutamate. In some embodiments, the detergent comprises an ionic detergent such as SDS (sodium dodecyl sulfate). The wash buffer can include a monovalent salt at a concentration of about 25-500 mM, or about 50-250 mM, or about 100-200 mM.

In some embodiments, the detergent in the wash buffer comprises a non-ionic detergent such as Triton X-100, Tween 20, Tween 80 or Nonidet P-40. In some embodiments, the detergent comprises a zwitterionic detergent such as CHAPS (3-[(3-cholamidopropyl)dimethylammonio]-1-propanesulfonate) or N-Dodecyl-N,N-dimethyl-3-amonio-1-propanesulfate (DetX). In some embodiments, the detergent comprises LDS (lithium dodecyl sulfate), sodium taurodeoxycholate, sodium taurocholate, sodium glycocholate, sodium deoxycholate or sodium cholate. In some embodiments, the detergent is included in the wash buffer at a concentration of about 0.01-0.05%, or about 0.05-0.1%, or about 0.1-0.15%, or about 0.15-0.2%, or about 0.2-0.25%.

In some embodiments, the methods for generating a plurality of immobilized nucleic acid nanostructures using an on-support rolling circle amplification reaction which lacks nucleotides having a scissile moiety, the methods comprise: step (a) providing a support having a plurality of first universal surface primers immobilized thereon; step (b) conducting on-support RCA; and step (c) conducting forward sequencing. In some embodiments, the methods do not include steps (d)-(e). For example, the methods do not include: synthesis of second strand nanostructures (step (d)); and reverse sequencing (step (e)).

In some embodiments, the methods for generating a plurality of immobilized nucleic acid nanostructures using an on-support rolling circle amplification reaction, the methods comprise: step (a) providing a support having a plurality of first universal surface primers immobilized thereon; and step (b) conducting on-support RCA. In some embodiments, the methods do not include steps (c)-(e). For example, in some embodiments, the methods do not include: forward sequencing (step (c)); synthesis of second strand nanostructures (step (d)); and reverse sequencing (step (e)).

In-Solution Methods
Generating High Density Immobilized Nanostructures

The present disclosure provides methods for generating high density nucleic acid nanostructures immobilized on a support, comprising:
  (a) generating a plurality of single stranded nucleic acid concatemer template molecules by hybridizing a plurality of single-stranded circular nucleic acid library molecules to a plurality of soluble first amplification primers and conducting an in-solution rolling circle amplification reaction with, (i) a plurality of a strand displacing polymerase, (ii) a plurality of nucleotides, thereby generating a plurality of single stranded nucleic acid concatemer template molecules in solution (e.g., FIGS. 30 and 46),
  (b) distributing the rolling circle amplification reaction from step (a) onto a support having a plurality of first universal surface primers immobilized thereon, wherein the density of the first universal surface primers on the support is about $10^2$-$10^{15}$ per mm$^2$, wherein one or more portions of individual single stranded concatemers hybridize to one or more immobilized first universal surface primers (e.g., FIGS. 31 and 47);
  (c) continuing the rolling circle amplification reaction on the support with (i) a plurality of strand-displacing polymerases, (ii) a plurality of nucleotides, and (iii) a plurality of compaction oligonucleotides, to generate a plurality of extended concatemer template molecules that are immobilized via hybridization to the immobilized first surface primers (e.g., FIGS. 32 and 48), wherein individual compaction oligonucleotides comprise a single-stranded linear oligonucleotide having a 5' region that can hybridize to a first portion of a concatemer molecule and/or an extended concatemer molecule, and the compaction oligonucleotide having a 3' region that can hybridize to a second portion of the concatemer molecule (e.g., the same concatemer) and/or the extended concatemer molecule (e.g., the same extended concatemer), wherein the plurality of immobilized extended concatemer molecules collapse or fold into a compact nucleic acid nanostructure upon binding to the compaction oligonucleotides, and wherein the plurality of concatemers remain immobilized to the support upon collapsing or folding into the nanostructure, thereby generating a support having a density of about $10^2$-$10^{15}$ per mm$^2$ of nanostructures immobilized to the support.

In some embodiments, the nucleic acid nanostructures can include one or more loops, or can have a spherical shape (e.g., nanoball), elongated shape (e.g., nanorod), proto-toroid shape or toroid shape (e.g., nano-toroid).

Inclusion of the plurality of compaction oligonucleotides in the on-support rolling circle amplification reaction can improve the FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 µm or smaller.

In some embodiments, the nucleic acid nanostructure can be a compact nucleic acid structure having a full width half maximum (FWHM) that is smaller compared to a concatemer that is not collapsed/folded into a nanostructure.

In some embodiments, the compaction oligonucleotides comprise single stranded oligonucleotides comprising DNA, RNA, or a combination of DNA and RNA. The compaction oligonucleotides can be any length, including 20-150 nucleotides, or 30-100 nucleotides, or 40-80 nucleotides in length, or any range therebetween.

In some embodiments, the compaction oligonucleotide comprises a first binding region and a second binding region, and optionally an intervening linker between the first binding region and second binding region. The intervening linker can be any length, for example about 2-20 nucleotides in length. The intervening linker can comprise a homopolymer having consecutive identical bases (e.g., AAA, GGG, CCC, TTT or UUU). The intervening linker can comprise a non-homopolymer sequence.

The first binding region of the compaction oligonucleotides can be wholly complementary or partially complementary along its length to a first portion of a concatemer molecule. The second binding region of the compaction oligonucleotides can be wholly complementary or partially complementary along its length to a second portion of a concatemer molecule. The first binding region of the compaction oligonucleotides can hybridize to a first universal sequence portion of a concatemer molecule having a sequence of any one of SEQ ID NOs:157-176 (see Table 2). The second binding region of the compaction oligonucleotides can hybridize to a second universal sequence portion of a concatemer molecule having a sequence of any one of SEQ ID NOs:157-176 (see Table 2). The first binding region and second binding region of the compaction oligonucleotide can hybridize to the concatemer to pull together distal portions of the concatemer, causing compaction of the concatemer, to form a nanostructure.

In some embodiments, any binding region of the compaction oligonucleotide (e.g., first, second, third, fourth, fifth, sixth, or other binding regions) can hybridize to a portion of the concatemer molecule, where the portion of the concatemer molecule comprises a universal adaptor sequence according to any one of SEQ ID NOs:157-176, or a complementary sequence thereof (see Table 2)).

In some embodiments, in step (b), the first binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the second, third, fourth, fifth or any subsequent binding region of the compaction oligonucleotide comprises a sequence that is a reverse sequence of the first binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the first binding region of a compaction oligonucleotide comprises a sequence according to any of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the second, third, fourth, fifth or any subsequent binding region of the compaction oligonucleotide comprises a sequence that is a reverse sequence of the first binding region, where the second, third, fourth, fifth or any subsequence binding region comprises any of one of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), first binding region of the compaction oligonucleotide can have a sequence that is a reverse sequence of the second binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (b), the second binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the third binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the fourth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the fifth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the subsequent binding region(s) of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (b), the compaction oligonucleotides comprise a full-length sequence according to any one of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156 (see Table 1).

In some embodiments, the second binding 3' region of any of the compaction oligonucleotides can include an additional three bases at the terminal 3' end which comprises 2'-O-methyl RNA bases (e.g., designated mUmUmU) or the terminal 3' end lacks additional 2'-O-methyl RNA bases.

In some embodiments, the compaction oligonucleotides comprise one or more modified bases or linkages at their 5' or 3' ends to confer certain functionalities. In some embodiments, the compaction oligonucleotides comprise at least one phosphorothioate linkages at their 5' and/or 3' ends to confer exonuclease resistance. In some embodiments, at least one nucleotide at or near the 3' end comprises a 2' fluoro base which confers exonuclease resistance. In some embodiments, the 3' end of the compaction oligonucleotides comprise at least one 2'-O-methyl RNA base which blocks polymerase-catalyzed extension. For example, the 3' end of the compaction oligonucleotide comprises three bases comprising 2'-O-methyl RNA base (e.g., designated mUmUmU). In some embodiments, the compaction oligonucleotides comprise a 3' inverted dT at their 3' ends which blocks polymerase-catalyzed extension. In some embodiments, the compaction oligonucleotides comprise 3' phosphorylation which blocks polymerase-catalyzed extension. In some embodiments, the internal region of the compaction oligonucleotides comprises at least one locked nucleic acid (LNA) which increases the thermal stability of duplexes formed by hybridizing a compaction oligonucleotide to a concatemer molecule.

The compaction oligonucleotides can include at least one region having consecutive guanines. For example, the compaction oligonucleotides can include at least one region having 2, 3, 4, 5, 6 or more consecutive guanines. In some embodiments, the compaction oligonucleotides comprise four consecutive guanines which can form a guanine tetrad structure (see FIG. 64). The guanine tetrad structure can be stabilized via Hoogsteen hydrogen bonding. The guanine tetrad structure can be stabilized by a central cation including potassium, sodium, lithium, rubidium or cesium.

The rolling circle amplification reaction can be conducted in the presence of a plurality of compaction oligonucleotides having at least four consecutive guanines. The resulting concatemers comprise repeat copies of the universal binding sequence for the compaction oligonucleotide. At least one compaction oligonucleotide can form a guanine tetrad (FIG. 64) and hybridize to the universal binding sequences for the compaction oligonucleotide, and the resulting concatemer can fold to form an intramolecular G-quadruplex structure (FIG. 65). The concatemers can self-collapse to form compact nanostructures. Formation of the guanine tetrads and G-quadruplexes in the nanostructures may increase the stability of the nanostructures to retain their compact size and shape which can withstand changes in pH, temperature and/or repeated flows of reagents.

In some embodiments, the plurality of compaction oligonucleotides in step (b) comprise the same sequence. In some embodiments, the plurality of compaction oligonucleotides in step (b) comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156. In some embodiments, the plurality of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156, where the 3' end of the compaction oligonucleotide also includes three bases comprising 2'-O-methyl RNA base (e.g., designated mUmUmU).

In some embodiments, the plurality of compaction oligonucleotides in step (b) comprise a mixture of two or more different populations of compaction oligonucleotides having different sequences. In some embodiments, the plurality of compaction oligonucleotides in step (b) comprise a mixture of 2, 3, 4, 5, 6, 7, 8, 9 or 10 different populations of compaction oligonucleotides wherein the compaction oligonucleotides in the different populations have different sequences. In some embodiments, in the mixture of different compaction oligonucleotides in step (b), any given population of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156.

In some embodiments, the support is passivated with at least one layer of a hydrophilic polymer coating which includes the plurality of first universal surface primers.

In some embodiments, the plurality of immobilized first universal surface primers are located on the support or coating at random positions. When the immobilized universal surface primers are located on the support or the coated support at random positions, the nucleic acid nanostructures are also located at random positions. The randomly-located nucleic acid nanostructures can be tightly packed and fill much of the space on the coated support. Upon binding the immobilized nanostructures to detectably labeled oligonucleotides or nucleotide reagents the signal intensity can be concentrated in a smaller space which markedly increases signal intensity and color distinction, compared to binding detectably labeled oligonucleotides or nucleotide reagents to concatemers that are not collapsed/folded into a nanostructure. Thus, the nanostructures described herein, and the methods employed to generate them, improve signal intensity without the need for preparing a support (e.g., flowcell) having a pre-determined organized pattern array.

In some embodiments, the plurality of immobilized first universal surface primers are located on the support or coating at pre-determined positions. For example, the immobilized first universal surface primers are arranged in an organized pattern. When the immobilized universal surface primers are located on the support or the coated support at pre-determined positions, the nucleic acid nanostructures are also located at pre-determined positions.

In some embodiments, the first universal surface primers lack a scissile moiety (for example, the first universal surface primers lack a scissile moiety that can be converted into abasic sites). In some embodiments, the first universal surface primers lack a scissile moiety comprising uridine, 8-oxo-7,8-dihydroguanine (e.g., 8oxoG) or deoxyinosine.

In some embodiments, the plurality of nucleotides which are used to conduct the rolling circle amplification reaction of steps (a) and/or (c) comprise dATP, dCTP, dGTP and dTTP, and wherein none of the nucleotides have a scissile moiety (for example the scissile moiety in a nucleotide can be converted into an abasic site).

In some embodiments, the plurality of nucleotides which are used to conduct the rolling circle amplification reaction of steps (a) and/or (c) comprise dATP, dCTP, dGTP, dTTP and nucleotides having a scissile moiety. For example, the nucleotide having the scissile moiety comprises uridine, 8-oxo-7,8-dihydroguanine (e.g., 8oxoG) or deoxyinosine. In some embodiments, the scissile moiety of the nucleotides can be converted into an abasic site.

In some embodiments, the rolling circle amplification reaction of steps (a) and/or (c), which are conducted with nucleotides having a scissile moiety, generates a plurality of single stranded nucleic acid concatemer template molecules wherein individual concatemer template molecules include at least two nucleotides each having a scissile moiety that are distributed at random positions along individual immobilized concatemer template molecules. In some embodiments, the nucleotides having a scissile moiety are distributed at different positions in the different immobilized concatemer template molecules.

In some embodiments, individual concatemer template molecules in the plurality comprise at least two copies of a polynucleotide unit arranged in tandem. In some embodiments, each polynucleotide unit comprises a sequence-of-interest. In some embodiments, each polynucleotide unit comprises at least one universal adaptor sequence. In some embodiments, each polynucleotide unit comprises a sequence-of-interest and at least one universal adaptor sequence. In some embodiments, individual concatemer molecules comprise 2-100 copies of a polynucleotide unit, or 100-250 copies of a polynucleotide unit, or 250-500 copies of a polynucleotide unit, or 500-750 copies of a polynucleotide unit, or 750-1000 copies of a polynucleotide unit, or more than 1000 copies of a polynucleotide unit. In some embodiments, individual concatemer molecules comprise 1000-2000 copies of a polynucleotide unit, or 1000-10,000 copies of a polynucleotide unit. In some embodiments, individual concatemers comprise a plurality of tandem polynucleotide units where the sequence of each polynucleotide unit of a given concatemer molecule is complementary to the sequence of a circular library molecule that served as the template library molecule.

In some embodiments, individual concatemer molecules comprise two or more copies of a sequence of interest, and wherein the immobilized concatemer template molecules further comprise any one or any combination of two or more of: (i) two or more copies of a universal binding sequence (or a complementary sequence thereof) for a soluble forward sequencing primer, (ii) two or more copies of a universal binding sequence (or a complementary sequence thereof) for a soluble reverse sequencing primer, (iii) two or more copies of a universal binding sequence (or a complementary sequence thereof) for an immobilized first universal surface primer, (iv) two or more copies of a universal binding sequence (or a complementary sequence thereof) for an immobilized second universal surface primer, (v) two or more copies of a universal binding sequence (or a complementary sequence thereof) for a first soluble amplification primer, (vi) two or more copies of a universal binding sequence (or a complementary sequence thereof) for a second soluble amplification primer, (vii) two or more copies of a universal binding sequence (or a complementary sequence thereof) for a soluble compaction oligonucleotide, (viii) two or more copies of a sample barcode sequence and/or (ix) two or more copies of a unique molecular index sequence.

In some embodiments, the methods for generating high density nucleic acid nanostructures immobilized on a support further comprise: positioning a cellular biological sample on the immobilized nanostructures.

In some embodiments, the cellular biological sample comprises a single cell, a plurality of cells, a tissue, an organ, an organism, or a section from any of these cellular biological samples. The cellular biological sample can comprise a sample that is fresh, frozen, fresh-frozen, or archived (e.g., formalin-fixed paraffin-embedded; FFPE). The cellular biological sample can be embedded in a matrix material. The cellular biological sample can be stained, de-stained or non-stained. The cellular biological sample can be permeabilized to permit the nucleic acids within the cellular sample to migrate from the cell(s) to the plurality of immobilized nanostructures.

In-Solution Methods

Generating High Density Immobilized Nanostructures Comprising Scissile Moieties

The present disclosure provides methods for generating high density nucleic acid nanostructures immobilized on a support, comprising step (a): contacting a plurality of single-stranded circular nucleic acid library molecules to (i) a plurality of soluble first amplification primers, (ii) a plurality of a strand displacing polymerase, and (iii) a plurality of nucleotides which include dATP, dCTP, dGTP, dTTP and a nucleotide having a scissile moiety, under a condition suitable to form a plurality of library-primer duplexes and suitable for conducting an in-solution rolling circle amplification reaction, thereby generating a plurality of single stranded nucleic acid concatemers having at least one nucleotide with a scissile moiety (FIG. 30). In some embodiments, the soluble first amplification primer comprises a sequence that selectively hybridizes to a universal binding sequence in the circular nucleic acid library molecules, such as for example a universal binding sequence (or a complementary sequence thereof) for the first soluble amplification primer. Alternatively, the soluble first amplification primer comprises a random sequence that binds non-selectively to a sequence in the circular nucleic acid library molecules. In some embodiments in step (a), individual single stranded circular nucleic acid library molecules in the plurality comprises a sequence of interest and wherein the individual library molecules further comprise any one or any combination of two or more of (i) a universal binding sequence (or a complementary sequence thereof) for a soluble forward sequencing primer, (ii) a universal binding sequence (or a complementary sequence thereof) for a soluble reverse sequencing primer, (iii) a universal binding sequence (or a complementary sequence thereof) for an immobilized first surface primer, (iv) a universal binding sequence (or a complementary sequence thereof) for an immobilized second surface primer, (v) a universal binding sequence (or a complementary sequence thereof) for a first soluble amplification primer, (vi) a universal binding sequence (or a complementary sequence thereof) for a second soluble amplification primer, (vii) a universal binding sequence (or a complementary sequence thereof) for a soluble compaction oligonucleotide, (viii) at least one sample barcode sequence and/or (ix) a unique molecular index sequence. In some embodiments, the single-stranded circular nucleic acid library molecules comprise covalently closed circular molecules.

In some embodiments, the rolling circle amplification reaction of step (a) generates a plurality of single stranded nucleic acid concatemer molecules in solution, comprising a concatemer having at least one nucleotide having a scissile moiety. In some embodiments, individual concatemer template molecules in the plurality comprise two or more copies of a sequence of interest, and wherein the individual immobilized concatemer template molecules further comprise any one or any combination of two or more of: (i) two or more copies of a universal binding sequence for a soluble forward sequencing primer, (ii) two or more copies of a universal binding sequence for a soluble reverse sequencing primer, (iii) two or more copies of a universal binding sequence for an immobilized first surface primer, (iv) two or more copies of a universal binding sequence for an immobilized second surface primer, (v) two or more copies of a universal binding sequence for a first soluble amplification primer, (vi) two or more copies of a universal binding sequence for a second soluble amplification primer, (vii) two or more copies of a universal binding sequence for a soluble compaction oligonucleotide, (viii) two or more copies of a sample barcode sequence and/or (ix) two or more copies of a unique molecular index sequence.

In some embodiments in step (a), the universal binding sequence (or a complementary sequence thereof) for the forward sequencing primer can hybridize to at least a portion of the forward sequencing primer. In some embodiments, the universal binding sequence (or a complementary sequence thereof) for the reverse sequencing primer can hybridize to at least a portion of the reverse sequencing primer. In some embodiments, the universal binding sequence (or a complementary sequence thereof) for the immobilized first surface primer can hybridize to at least a portion of the immobilized first surface primer. In some embodiments, the universal binding sequence (or a complementary sequence thereof) for the immobilized second surface primer can hybridize to at least a portion of the immobilized second surface primer. In some embodiments, the universal binding sequence (or a complementary sequence thereof) for the first soluble amplification primer can hybridize to at least a portion of the first soluble amplification primer. In some embodiments, the universal binding sequence (or a complementary sequence thereof) for the second soluble amplification primer can hybridize to at least a portion of the second soluble amplification primer. In some embodiments, the universal binding sequence (or a complementary sequence thereof) for the soluble compaction oligonucleotide can hybridize to at least a portion of the soluble compaction oligonucleotide.

The in-solution rolling circle amplification reaction of step (a) can be conducted with a nucleotide mixture containing dATP, dCTP, dGTP, dTTP and a nucleotide having a scissile moiety to generate the concatemer molecules which includes at least one nucleotide having a scissile moiety. The scissile moieties in the concatemer molecules can be converted into abasic sites. In some embodiments, in the nucleotide mixture, the nucleotide having the scissile moiety comprises uridine, 8-oxo-7,8-dihydroguanine (e.g., 8oxoG) or deoxyinosine. In the concatemer molecules, the uridine can be converted to an abasic site using uracil DNA glycosylase (UDG), the 8oxoG can be converted to an abasic site using FPG glycosylase, and the deoxyinosine can be converted to an abasic site using AlkA glycosylase.

In some embodiments, the nucleotide mixture can include an amount of dUTP so that a target percent of the thymidine in the resulting concatemer molecules are replaced with dUTP. For example, when 30% of dTTP in the concatemer molecules are to be replaced with dUTP (e.g., 30% is the target percent) then the nucleotide mixture can contain 7.5% dUTP (e.g., 30/4=7.5%), 17.5% dTTP, and 25% each for dATP, dCTP and dGTP. The target percent of dTTP to be replaced by dUTP can be about 0.1-1%, or about 1-5%, or about 5-10%, or about 10-20%, or about 20-30%, or about 30-45%, or about 45-50%, or a higher percent of the dTTP in the concatemer molecules are replaced with nucleotides having a scissile moiety.

In some embodiments, the nucleotide mixture can include an amount of deoxyinosine so that a target percent of the guanosine in the resulting concatemer molecules are replaced with deoxyinosine. For example, when 30% of dGTP in the concatemer molecules are to be replaced with deoxyinosine (e.g., 30% is the target percent) then the nucleotide mixture can contain 7.5% deoxyinosine (e.g., 30/4=7.5%), 17.5% dGTP, and 25% each for dATP, dCTP and dTTP. The target percent of dGTP to be replaced by deoxyinosine can be about 0.1-1%, or about 1-5%, or about 5-10%, or about 10-20%, or about 20-30%, or about 30-45%, or about 45-50%, or a higher percent of the dGTP in the concatemer molecules are replaced with nucleotides having a scissile moiety.

In some embodiments, the nucleotide mixture can include an amount of 8oxoG so that a target percent of the guanosine in the resulting concatemer molecules are replaced with 8oxoG. For example, when 30% of dGTP in the concatemer molecules are to be replaced with 8oxoG (e.g., 30% is the target percent) then the nucleotide mixture can contain 7.5% 8oxoG (e.g., 30/4=7.5%), 17.5% dGTP, and 25% each for dATP, dCTP and dTTP. The target percent of dGTP to be replaced by 8oxoG can be about 0.1-1%, or about 1-5%, or about 5-10%, or about 10-20%, or about 20-30%, or about 30-45%, or about 45-50%, or a higher percent of the dGTP in the concatemer molecules are replaced with nucleotides having a scissile moiety.

In some embodiments, the in-solution rolling circle amplification reaction generates concatemer molecules with incorporated nucleotides having a scissile moiety that are distributed at random positions along individual immobilized concatemer template molecules. In some embodiments, the nucleotides having a scissile moiety are distributed at different positions in the different concatemer molecules.

In some embodiments, the methods for generating high density nucleic acid nanostructures immobilized on a support further comprises step (b): distributing the rolling circle amplification reaction from step (a) onto a support having a plurality of first universal surface primers immobilized thereon, under a condition suitable for hybridizing one or more portions of individual single stranded concatemers to one or more immobilized first universal surface primers (FIG. 31). The concatemers are immobilized to the support by hybridization to the immobilized first universal surface primers. In some embodiments, the support is passivated with at least one hydrophilic polymer layer which includes a plurality of first universal surface primers, wherein each of the first universal surface primers comprises a 3' OH extendible end and lacks a nucleotide having a scissile moiety and wherein the density of the first universal surface primers is about $10^2$-$10^{15}$ per mm$^2$. The first universal surface primers lack a scissile moiety that can be converted into an abasic site in a nucleic acid strand. For example, the first universal surface primers lack uridine, 8-oxo-7,8-dihydroguanine (e.g., 8oxoG) and deoxyinosine. In some embodiments, the support lacks a plurality of second universal surface primers. In some embodiments, the support comprises a plurality of first and second universal surface primers.

In some embodiments, the methods for generating high density nucleic acid nanostructures immobilized on a support further comprises step (c): continuing the rolling circle amplification reaction on the support to generate a plurality of extended concatemer template molecules that are immobilized via hybridization to the immobilized first surface primers (FIGS. 31-32). The on-support RCA reaction can be conducted with a (i) plurality of a strand displacing polymerase, (ii) a plurality of nucleotides which include dATP, dCTP, dGTP, dTTP and a nucleotide having a scissile moiety, and (iii) a plurality of compaction oligonucleotides, under a condition suitable to generate a plurality of extended concatemers having at least one nucleotide with a scissile moiety (FIG. 32).

In some embodiments, individual compaction oligonucleotides comprise a single-stranded linear oligonucleotide having a 5' region that can hybridize to a first portion of an extended concatemer molecule and the compaction oligonucleotide having a 3' region that can hybridize to a second portion of the extended concatemer molecule (FIG. 32).

In some embodiments, individual immobilized concatemer molecules bind a plurality of compaction oligonucleotides which causes the concatemer molecules to collapse or fold into a compact nucleic acid nanostructure (e.g., first strand nanostructure).

In some embodiments, the plurality of extended concatemers remain immobilized to the support upon collapsing or folding into nanostructures, thereby generating a support having a density of about $10^2$-$10^{15}$ per mm$^2$ of nanostructures immobilized to the support.

In some embodiments, individual immobilized nanostructures comprise a plurality of tandem polynucleotide units and each polynucleotide unit has a sequence that is complementary to the sequence of a covalently closed circular nucleic acid library molecule.

In some embodiments, the on-support rolling circle amplification reaction generates immobilized concatemer template molecules with incorporated nucleotides having a scissile moiety that are distributed at random positions along individual immobilized concatemer template molecules. In some embodiments, the nucleotides having a scissile moiety are distributed at different positions in the different immobilized concatemer template molecules.

The plurality of immobilized nucleic acid nanostructures is in fluid communication with each other to permit flowing various reagents in solution including soluble primers, enzymes, nucleotides, divalent cations, buffers and the like, onto the support so that the plurality of immobilized nanostructures react with the solutions in a massively parallel manner.

In some embodiments, the density of the first universal surface primers on the support is about $10^2$-$10^{15}$ per mm$^2$. In some embodiments, the immobilized first universal surface primers comprise single stranded oligonucleotides comprising DNA, RNA or a combination of DNA and RNA. The first universal surface primers comprise a sequence that is wholly complementary or partially complementary along their lengths to at least a portion of a circular nucleic acid library molecule. The first universal surface primers can include a terminal 3' nucleotide having a sugar 3' OH moiety which is extendible for nucleotide polymerization (e.g., polymerase catalyzed polymerization).

In some embodiments, the immobilized first universal surface primers can be immobilized to the support or immobilized to a coating on the support. The immobilized first universal surface primers can be embedded and attached (coupled) to the coating on the support. In some embodiments, the 5' end of the immobilized first universal surface primers are immobilized to a support or immobilized to a coating on the support. Alternatively, an interior portion or the 3' end of the immobilized first universal surface primers can be immobilized to a support or immobilized to a coating on the support. The support comprises a plurality of immobilized first universal surface primers having the same sequence. The immobilized first universal surface primers can be any length, for example 4-50 nucleotides, or 50-100 nucleotides, or 100-150 nucleotides, or longer lengths, or any range therebetween.

In some embodiments, the plurality of immobilized first universal surface primers are located on the coated support at random positions (e.g., non-pre-determined positions). When the immobilized universal surface primers are located on the coated support at random positions, the immobilized nucleic acid nanostructures are also located at random positions. The randomly-located nucleic acid nanostructures can be tightly packed and fill much of the space on the coated support.

In some embodiments, the plurality of immobilized first universal surface primers are located on the coated support at pre-determined positions. For example, the immobilized first universal surface primers are arranged in an organized pattern. When the immobilized universal surface primers are located on the support or the coated support at pre-determined positions, the nucleic acid nanostructures are also located at pre-determined positions.

In some embodiments, the plurality of immobilized first universal surface primers comprise at least one phosphorothioate diester bond at their 5' ends which can render the first universal surface primers resistant to exonuclease degradation. In some embodiments, the plurality of immobilized first universal surface primers comprise 2-5 or more consecutive phosphorothioate diester bonds at their 5' ends. In some embodiments, the plurality of immobilized first universal surface primers comprise at least one ribonucleotide and/or at least one 2'-O-methyl or 2'-O-methoxyethyl (MOE) nucleotide which can render the first universal surface primers resistant to exonuclease degradation.

In some embodiments, the immobilized first universal surface primers comprise at least one locked nucleic acid (LNA) which comprises a methylene bridge bond between a 2' oxygen and 4' carbon of the pentose ring. Immobilized first universal surface primers that include at least one LNA can be resistant to nuclease digestions and can exhibit increased melting temperature when hybridized to the circular nucleic acid library molecules or the nucleic acid concatemer molecules.

In some embodiments, the support further comprises a plurality of a second universal surface primer immobilized thereon (FIG. 38). The second universal surface primers have a sequence that differs from the first universal immobilized surface primer. In some embodiments, the density of the second universal surface primers on the support is about $10^2$-$10^{15}$ per mm$^2$. The immobilized second universal surface primers of step (a) comprise single stranded oligonucleotides comprising DNA, RNA or a combination of DNA and RNA. The second universal surface primers can comprise a sequence that is wholly complementary or partially complementary along their lengths to at least a portion of an immobilized single stranded concatemer template molecule. The immobilized second universal surface primers can be immobilized to the support or immobilized to a coating on the support. The immobilized second universal surface primers can be embedded and attached (coupled) to the coating on the support. In some embodiments, the 5' end of the second universal surface primers are immobilized to a support or immobilized to a coating on the support. Alternatively, an interior portion or the 3' end of the immobilized second universal surface primers can be immobilized to a support or immobilized to a coating on the support. The support comprises a plurality of immobilized second universal surface primers having the same sequence. The immobilized second universal surface primers can be any length, for example 4-50 nucleotides, or 50-100 nucleotides, or 100-150 nucleotides, or longer lengths, or any range therebetween. In some embodiments, the 3' terminal end of the immobilized second universal surface primers comprise an extendible 3' OH moiety. In some embodiments, the 3' terminal end of the immobilized second universal surface primers comprise a 3' non-extendible moiety. The 3' terminal end of the immobilized second universal surface primers comprise a moiety that blocks primer extension, such as for example a phosphate group, a dideoxycytidine group, an inverted dT, or an amino group. These immobilized second universal surface primers are not extendible in a primer extension reaction. The immobilized second universal surface primers can lack a nucleotide having a scissile moiety.

In some embodiments, the plurality of immobilized second universal surface primers comprise at least one phosphorothioate diester bond at their 5' ends which can render the second universal surface primers resistant to exonuclease degradation. In some embodiments, the plurality of immobilized second universal surface primers comprise 2-5 or more consecutive phosphorothioate diester bonds at their 5' ends. In some embodiments, the plurality of immobilized second universal surface primers comprise at least one ribonucleotide and/or at least one 2'-O-methyl or 2'-O-methoxyethyl (MOE) nucleotide which can render the second universal surface primers resistant to exonuclease degradation.

In some embodiments, individual immobilized single stranded nucleic acid concatemer template molecules are hybridized to an immobilized first universal surface primer, and at least one portion of the individual concatemer template molecule is hybridized to an immobilized second universal surface primer (FIG. 38). The immobilized second universal surface primers can serve to pin down a portion of the immobilized concatemer template molecules to the support. The immobilized concatemer template molecule has two or more copies of a universal binding sequence for an immobilized second universal surface primer. The portion of the immobilized concatemer template molecule that includes the universal binding sequence for an immobilized second universal surface primer can hybridize to the immobilized second universal surface primer. In some embodiments, the second universal surface primers include a terminal 3' blocking group that renders them non-extendible. In some embodiments, the second universal surface primers have terminal 3' extendible ends.

The immobilized surface primers (e.g., first and second universal surface primers) are in fluid communication with each other to permit flowing various solutions of linear or circular nucleic acid template molecules, soluble primers, enzymes, nucleotides, divalent cations, buffers, reagents, and the like, onto the support so that the plurality of immobilized surface primers (and the primer extension products generated from the immobilized surface primers) react with the solutions in a massively parallel manner.

In some embodiments, in step (c), the first binding region of the compaction oligonucleotides can hybridize to a first portion of the concatemer molecule, where the first portion of the concatemer molecule comprises a universal adaptor sequence according to any one of SEQ ID NOs:157-176, or a complementary sequence thereof (see Table 2)).

In some embodiments, in step (c), the second binding region of the compaction oligonucleotides can hybridize to a second portion of the concatemer molecule, where the second portion of the concatemer molecule comprises a universal adaptor sequence according to any one of SEQ ID NOs:157-176, or a complementary sequence thereof (see Table 2)).

In some embodiments, in step (c), the compaction oligonucleotides comprise a first, second, third, fourth, fifth, sixth, or other binding regions.

In some embodiments, in step (c), any binding region of the compaction oligonucleotide (e.g., first, second, third, fourth, fifth, sixth, or other binding regions) can hybridize to a portion of the concatemer molecule, where the portion of the concatemer molecule comprises a universal adaptor sequence according to any one of SEQ ID NOs:157-176, or a complementary sequence thereof (see Table 2)).

In some embodiments, in step (c), the compaction oligonucleotide comprises two or more binding regions and all of the binding regions have the same sequence. In some embodiments, the compaction oligonucleotide comprises two binding regions having different sequences. In some embodiments, the compaction oligonucleotide comprises three or more binding regions and at least two of the binding regions have different sequences.

In some embodiments, in step (c), the first binding region of the compaction oligonucleotide can have the same sequence as the second binding region.

In some embodiments, in step (c), the first binding region of the compaction oligonucleotide can have a sequence that is different from the second binding region.

In some embodiments, in step (c), the first binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the second, third, fourth, fifth or any subsequent binding region of the compaction oligonucleotide comprises a sequence that is a reverse sequence of the first binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (c), the first binding region of a compaction oligonucleotide comprises a sequence according to any of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (c), the second, third, fourth, fifth or any subsequent binding region of the compaction oligonucleotide comprises a sequence that is a reverse sequence of the first binding region, where the second, third, fourth, fifth or any subsequence binding region comprises any of one of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), first binding region of the compaction oligonucleotide can have a sequence that is a reverse sequence of the second binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (c), the second binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the third binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the fourth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the fifth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the subsequent binding region(s) of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the compaction oligonucleotides comprise a full-length sequence according to any one of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156 (see Table 1).

In some embodiments, in step (c), the terminal 3' end of any of the compaction oligonucleotides can include at least one additional base comprising one or more 2'-O-methyl RNA bases (e.g., designated mUmUmU) or the terminal 3' end lacks additional 2'-O-methyl RNA bases.

In some embodiments, in step (c), the compaction oligonucleotides comprise one or more modified bases or linkages at their 5' or 3' ends to confer certain functionalities. In some embodiments, the compaction oligonucleotides comprise at least one phosphorothioate linkages at their 5' and/or 3' ends to confer exonuclease resistance. In some embodiments, at least one nucleotide at or near the 3' end comprises a 2' fluoro base which confers exonuclease resistance. In some embodiments, the 3' end of the compaction oligonucleotides comprise at least one 2'-O-methyl RNA base which blocks polymerase-catalyzed extension. For example, the 3' end of the compaction oligonucleotide comprises at least one base comprising 2'-O-methyl RNA base (e.g., designated mUmUmU). In some embodiments, the compaction oligonucleotides comprise a 3' inverted dT at their 3' ends which blocks polymerase-catalyzed extension. In some embodiments, the compaction oligonucleotides comprise 3' phosphorylation which blocks polymerase-catalyzed extension. In some embodiments, the compaction oligonucleotides comprise at least one locked nucleic acid (LNA)

which increases the thermal stability of duplexes formed by hybridizing a compaction oligonucleotide to a concatemer molecule.

In some embodiments, in step (c), the compaction oligonucleotides can include at least one region (e.g., hybridization/binding region) having consecutive guanines. For example, the compaction oligonucleotides can include at least one region having 2, 3, 4, 5, 6 or more consecutive guanines. In some embodiments, the compaction oligonucleotides comprise four consecutive guanines which can form a guanine tetrad structure (see FIG. 64). The guanine tetrad structure can be stabilized via Hoogsteen hydrogen bonding. The guanine tetrad structure can be stabilized by a central cation including potassium, sodium, lithium, rubidium, or cesium.

In some embodiments, in step (c), at least one compaction oligonucleotide can form a guanine tetrad (FIG. 64) and hybridize to the universal binding sequences in a concatemer which can cause the concatemer to fold to form an intramolecular G-quadruplex structure (FIG. 65). The concatemers can self-collapse to form compact nanostructures. Formation of the guanine tetrads and G-quadruplexes in the nanostructures may increase the stability of the nanostructures to retain their compact size and shape which can withstand changes in pH, temperature and/or repeated flows of reagents.

In some embodiments, the plurality of compaction oligonucleotides in step (c) comprises a mixture of two or more different populations of compaction oligonucleotides having different sequences. In some embodiments, the plurality of compaction oligonucleotides in step (c) comprise a mixture of 2, 3, 4, 5, 6, 7, 8, 9 or 10 different populations of compaction oligonucleotides wherein the compaction oligonucleotides in the different populations have different sequences. In some embodiments, in the mixture of different compaction oligonucleotides in step (c), any given population of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156.

In some embodiments, in the methods for generating a plurality of immobilized nucleic acid nanostructures of step (c), the nucleic acid nanostructures can include one or more loops, or can have a spherical shape (e.g., nanoball), elongated shape (e.g., nanorod), proto-toroid shape or toroid shape (e.g., nano-toroid). The nucleic acid nanostructure can be a compact nucleic acid structure having a full width half maximum (FWHM) that is smaller compared to a concatemer that is not collapsed/folded into a nanostructure. Inclusion of the plurality of compaction oligonucleotides in the on-support rolling circle amplification reaction can improve the FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, in the methods for generating a plurality of immobilized nucleic acid nanostructures of step (c), individual single stranded covalently closed circular nucleic acid library molecules in the plurality comprise a sequence of interest, and any one or any combination of two or more of (i) a universal binding sequence (or complementary sequence thereof) for a soluble forward sequencing primer, (ii) a universal binding sequence (or complementary sequence thereof) for a soluble reverse sequencing primer, (iii) a universal binding sequence (or complementary sequence thereof) for an immobilized first universal surface primer, (iv) a universal binding sequence (or complementary sequence thereof) for an immobilized second universal surface primer, (v) a universal binding sequence (or complementary sequence thereof) for a first soluble amplification primer, (vi) a universal binding sequence (or complementary sequence thereof) for a second soluble amplification primer, (vii) a universal binding sequence (or complementary sequence thereof) for a soluble compaction oligonucleotide, (viii) at least one sample barcode sequence and/or (ix) a unique molecular index sequence (e.g., FIGS. 18A-B, FIGS. 20A-B).

In some embodiments, in the methods for generating a plurality of immobilized nucleic acid nanostructures of step (c), the rolling circle amplification reaction generates a plurality of immobilized single stranded nucleic acid concatemer template molecules (e.g., first strand nanostructures) wherein individual concatemer template molecules comprise at least two copies of a polynucleotide unit arranged in tandem. In some embodiments, each polynucleotide unit comprises a sequence-of-interest. In some embodiments, each polynucleotide unit comprises at least one universal adaptor sequence. In some embodiments, each polynucleotide unit comprises a sequence-of-interest and at least one universal adaptor sequence. In some embodiments, individual concatemer molecules comprise 2-100 copies of a polynucleotide unit, or 100-250 copies of a polynucleotide unit, or 250-500 copies of a polynucleotide unit, or 500-750 copies of a polynucleotide unit, or 750-1000 copies of a polynucleotide unit, or more than 1000 copies of a polynucleotide unit. In some embodiments, individual concatemer molecules comprise 1000-10,000 copies of a polynucleotide unit. In some embodiments, individual concatemers comprise a plurality of tandem polynucleotide units where the sequence of each polynucleotide unit of a given concatemer molecule is complementary to the sequence of a circular library molecule that served as the template library molecule.

In some embodiments, individual immobilized concatemer molecules comprise two or more copies of a sequence of interest, and wherein the immobilized concatemer template molecules further comprise any one or any combination of two or more of: (i) two or more copies of a universal binding sequence (or a complementary sequence thereof) for a soluble forward sequencing primer, (ii) two or more copies of a universal binding sequence (or a complementary sequence thereof) for a soluble reverse sequencing primer, (iii) two or more copies of a universal binding sequence (or a complementary sequence thereof) for an immobilized first universal surface primer, (iv) two or more copies of a universal binding sequence (or a complementary sequence thereof) for an immobilized second universal surface primer, (v) two or more copies of a universal binding sequence (or a complementary sequence thereof) for a first soluble amplification primer, (vi) two or more copies of a universal binding sequence (or a complementary sequence thereof) for a second soluble amplification primer, (vii) two or more copies of a universal binding sequence (or a complementary sequence thereof) for a soluble compaction oligonucleotide, (viii) two or more copies of a sample barcode sequence and/or (ix) two or more copies of a unique molecular index sequence (e.g., FIG. 32).

In some embodiments, in the methods for generating a plurality of immobilized nucleic acid nanostructures of step (c), the rolling circle amplification reaction generates concatemer molecules comprising universal binding sequences that can hybridize/bind to certain primers. In some embodiments, the universal binding sequence (or a complementary sequence thereof) for the forward sequencing primer can hybridize to at least a portion of the forward sequencing primer. In some embodiments, the universal binding sequence (or a complementary sequence thereof) for the reverse sequencing primer can hybridize to at least a portion of the reverse sequencing primer. In some embodiments, the universal binding sequence (or a complementary sequence thereof) for the immobilized first universal surface primer can hybridize to at least a portion of the immobilized first universal surface primer. In some embodiments, the universal binding sequence (or a complementary sequence thereof) for the immobilized second universal surface primer can hybridize to at least a portion of the immobilized second universal surface primer. In some embodiments, the universal binding sequence (or a complementary sequence thereof) for the first soluble amplification primer can hybridize to at least a portion of the first soluble amplification primer. In some embodiments, the universal binding sequence (or a complementary sequence thereof) for the second soluble amplification primer can hybridize to at least a portion of the second soluble amplification primer. In some embodiments, the universal binding sequence (or a complementary sequence thereof) for the soluble compaction oligonucleotide can hybridize to at least a portion of the soluble compaction oligonucleotide.

In some embodiments, in the methods for generating a plurality of immobilized nucleic acid nanostructures of step (c), the plurality of immobilized single stranded nucleic acid concatemer template molecules (e.g., first strand nanostructures) comprise two or more copies of a universal binding sequence (or complementary sequence thereof) for immobilized second sequence surface primers. In some embodiments, individual immobilized single stranded nucleic acid concatemer template molecules are hybridized to an immobilized first universal surface primer, and at least one portion of the individual concatemer template molecule is hybridized to an immobilized second universal surface primer. The immobilized second universal surface primers can serve to pin down a portion of the immobilized concatemer template molecules to the support (see FIG. 38). In some embodiments, the second universal surface primers include a terminal 3' blocking group that renders them non-extendible.

In some embodiments, in the methods for generating a plurality of immobilized nucleic acid nanostructures of step (c), the rolling circle amplification reaction can be conducted with a nucleotide mixture containing dATP, dCTP, dGTP, dTTP and a nucleotide having a scissile moiety to generate immobilized concatemer template molecules (e.g., first strand nanostructures) which includes at least one nucleotide having a scissile moiety (FIG. 32). The scissile moieties in the immobilized concatemer template molecules can be converted into abasic sites. In some embodiments, in the nucleotide mixture, the nucleotide having the scissile moiety comprises uridine, 8-oxo-7,8-dihydroguanine (e.g., 8oxoG) or deoxyinosine. In the immobilized concatemer template molecules, the uridine can be converted to an abasic site using uracil DNA glycosylase (UDG), the 8oxoG can be converted to an abasic site using FPG glycosylase, and the deoxyinosine can be converted to an abasic site using AlkA glycosylase.

In some embodiments, the nucleotide mixture can include an amount of dUTP so that a target percent of the thymidine in the resulting concatemer molecules are replaced with dUTP. For example, when 30% of dTTP in the concatemer molecules are to be replaced with dUTP (e.g., 30% is the target percent) then the nucleotide mixture can contain 7.5% dUTP (e.g., 30/4=7.5%), 17.5% dTTP, and 25% each for dATP, dCTP and dGTP. The target percent of dTTP to be replaced by dUTP can be about 0.1-1%, or about 1-5%, or about 5-10%, or about 10-20%, or about 20-30%, or about 30-45%, or about 45-50%, or a higher percent of the dTTP in the immobilized concatemer template molecules are replaced with nucleotides having a scissile moiety.

In some embodiments, the nucleotide mixture can include an amount of deoxyinosine so that a target percent of the guanosine in the resulting concatemer molecules are replaced with deoxyinosine. For example, when 30% of dGTP in the concatemer molecules are to be replaced with deoxyinosine (e.g., 30% is the target percent) then the nucleotide mixture can contain 7.5% deoxyinosine (e.g., 30/4=7.5%), 17.5% dGTP, and 25% each for dATP, dCTP and dTTP. The target percent of dGTP to be replaced by deoxyinosine can be about 0.1-1%, or about 1-5%, or about 5-10%, or about 10-20%, or about 20-30%, or about 30-45%, or about 45-50%, or a higher percent of the dGTP in the immobilized concatemer template molecules are replaced with nucleotides having a scissile moiety.

In some embodiments, the nucleotide mixture can include an amount of 8oxoG so that a target percent of the guanosine in the resulting concatemer molecules are replaced with 8oxoG. For example, when 30% of dGTP in the concatemer molecules are to be replaced with 8oxoG (e.g., 30% is the target percent) then the nucleotide mixture can contain 7.5% 8oxoG (e.g., 30/4=7.5%), 17.5% dGTP, and 25% each for dATP, dCTP and dTTP. The target percent of dGTP to be replaced by 8oxoG can be about 0.1-1%, or about 1-5%, or about 5-10%, or about 10-20%, or about 20-30%, or about 30-45%, or about 45-50%, or a higher percent of the dGTP in the immobilized concatemer template molecules are replaced with nucleotides having a scissile moiety.

In some embodiments, in the methods for generating a plurality of immobilized nucleic acid nanostructures of step (c), the rolling circle amplification reaction generates a plurality of single stranded nucleic acid concatemer template molecules (e.g., first strand nanostructures) wherein individual concatemer template molecules have at least two nucleotides each having a scissile moiety that are distributed at random positions along the individual immobilized concatemer template molecule. In some embodiments, the nucleotides having a scissile moiety are distributed at different positions in the different immobilized concatemer template molecules.

In some embodiments, in the methods for generating a plurality of immobilized nucleic acid nanostructures of step (c), the method can further comprise removing the single-stranded covalently closed circular nucleic acid library molecules from the concatemer template molecules with at least one washing step which is conducted under a condition suitable to retain the single stranded nucleic acid concatemer template molecules where individual concatemer template molecules are operably joined to an immobilized first universal surface primer.

Figure 33:
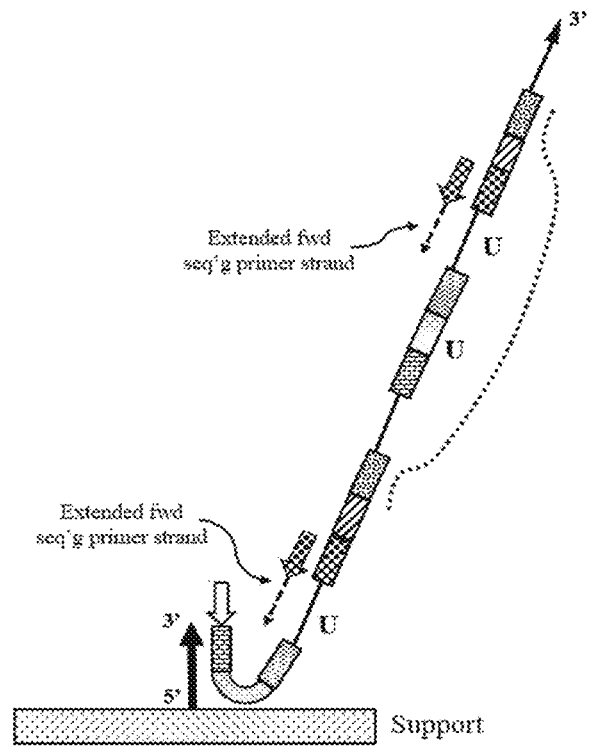

In some embodiments, the methods for generating a plurality of immobilized nucleic acid nanostructures, further comprise step (d): sequencing the plurality of immobilized concatemer template molecules (e.g., first strand nanostructures) thereby generating a plurality of extended forward sequencing primer strands. The sequencing of step (d) comprises contacting the plurality of immobilized concatemer template molecules with a plurality of soluble forward sequencing primers under a condition suitable to hybridize at least one forward sequencing primer to at least one of the forward sequencing primer binding sites/sequences of the immobilized concatemer template molecules, and conducting forward sequencing reactions to generate a plurality of forward sequencing products using one or more types of sequencing polymerases, a plurality of nucleotide reagents, and the hybridized first forward sequencing primers (FIG. 33). In some embodiments, the plurality of nucleotide reagents is detectably labeled. In some embodiments, the sequencing of step (d) further comprises detecting and imaging the plurality of forward sequencing products.

In some embodiments, in the sequencing of step (d) further comprises contacting the plurality of immobilized concatemer template molecules with a plurality of compaction oligonucleotides under a condition suitable to hybridize the 5' end of at least one compaction oligonucleotide to a first portion of a concatemer molecule and to hybridize the second binding region of the same compaction oligonucleotide to a second portion of the same concatemer molecule. In some embodiments, the plurality of compaction oligonucleotides of step (d) comprise any of the sequences as described in step (c) above.

In some embodiments, in the sequencing of step (d), the soluble forward sequencing primers comprise 3' OH extendible ends. In some embodiments, the soluble forward sequencing primers comprise a 3' blocking moiety which can be removed to generate a 3' OH extendible end. In some embodiments, the soluble forward sequencing primers lack a nucleotide having a scissile moiety. The forward sequencing reactions can generate a plurality of extended forward sequencing primer strands. In some embodiments, individual immobilized concatemer template molecules have multiple copies of the forward sequencing primer binding sites, wherein each forward sequencing primer binding site is capable of hybridizing to a first forward sequencing primer. Individual forward sequencing primer binding sites in a given immobilized concatemer template molecule can be hybridized to a forward sequencing primer and can undergo a sequencing reaction. Individual immobilized concatemer template molecules can undergo two or more sequence reactions, where each sequencing reaction is initiated from a first forward sequencing primer that is hybridized to a forward sequencing primer binding site (e.g., see FIG. 33).

In some embodiments, in the sequencing of step (d), the nucleotide reagent comprises a plurality of nucleotides, a plurality of nucleotide analogs, or a plurality of multivalent molecules.

In some embodiments, in the sequencing of step (d), individual nucleotides in the plurality of nucleotides comprises an aromatic base, a five carbon sugar and at least one phosphate group. In some embodiments, the plurality of nucleotides is unlabeled. In some embodiments, at least one nucleotide in the plurality can be labeled with a detectable reporter moiety (e.g., fluorophore). In some embodiments, the sequencing of step (d) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (d), individual nucleotide analogs in the plurality comprise an aromatic base, a five carbon sugar having a 3' chain terminating moiety that inhibits polymerase-catalyzed nucleotide incorporation, and at least one phosphate group. In some embodiments, the plurality of nucleotide analogs are unlabeled. In some embodiments, at least one nucleotide analog in the plurality can be labeled with a detectable reporter moiety (e.g., fluorophore). In some embodiments, the sequencing of step (d) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (d), individual multivalent molecules in the plurality comprise (1) a core; and (2) a plurality of nucleotide arms each comprising (i) a core attachment moiety, (ii) a spacer, (iii) a linker, and (iv) a nucleotide unit, wherein the core is attached to the plurality of nucleotide arms, wherein the spacer is attached to the linker, wherein the linker is attached to the nucleotide unit (e.g., see FIGS. 56-59). In some embodiments, the nucleotide unit comprises an aromatic base, a five carbon sugar and at least one phosphate group, and the linker is attached to the nucleotide unit through the base. In some embodiments, the plurality of multivalent molecules is unlabeled. In some embodiments, at least one multivalent molecule in the plurality is labeled with a detectable reporter moiety (e.g., fluorophore). In some embodiments, the sequencing of step (d) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (d), the method further comprises forming at least one avidity complex, by contacting the plurality of immobilized concatemer template molecules (e.g., first strand nanostructures) with a plurality of soluble forward sequencing primers, a plurality of sequencing polymerases, and a plurality of multivalent molecules, to form a plurality of binding complexes including at least a first and second binding complex, wherein (i) the first binding complex comprises a first forward sequencing primer, a first sequencing polymerase, and a first multivalent molecule, bound to a first portion of the immobilized concatemer template molecule (e.g., first strand nanostructure) thereby forming the first binding complex, wherein a first nucleotide unit of the multivalent molecule is bound to the first polymerase, and (ii) the second binding complex comprises a second forward sequencing primer, a second sequencing polymerase, and the first multivalent molecule, bound to a second portion of the same immobilized concatemer template molecule thereby forming the second binding complex, wherein a second nucleotide unit of the multivalent molecule is bound to the second polymerase, and wherein the first and second binding complexes which include the same multivalent molecule forms an avidity complex. In some embodiments, the multivalent molecule is unlabeled or is labeled with a detectable reporter moiety.

In some embodiments, in the rolling circle amplification reaction of step (c), the first binding region of the compaction oligonucleotides hybridize to the concatemer template molecules at a first portion that does not interfere (e.g., little or no overlap) with hybridizing the soluble forward sequencing primers to the forward sequencing primer binding sites of the plurality of concatemer template molecules of step (d).

In some embodiments, in the rolling circle amplification reaction of step (c), the second binding region of the compaction oligonucleotides hybridize to the concatemer template molecules at a second portion that does not interfere (e.g., little or no overlap) with hybridizing the soluble forward sequencing primers to the forward sequencing primer binding sites of the plurality of concatemer template molecules of step (d).

In some embodiments, the methods for generating a plurality of immobilized nucleic acid nanostructures, further comprise step (e): retaining the plurality of immobilized concatemer template molecules (e.g., first strand nanostructures) and replacing the plurality of extended forward sequencing primer strands with a plurality of forward extension strands that are hybridized to the retained immobilized nucleic acid concatemer template molecules. The plurality of extended forward sequencing primer strands can be removed and replaced with a plurality of forward extension strands by conducting a primer extension reaction to synthesize a second strand, a forward extension strand (e.g., see FIG. 34). The primer extension reaction can be conducted with a plurality of compaction oligonucleotides to collapse/fold the forward extension strands generate second strand nanostructures. One skilled in the art will recognize that there are several methods for conducting the primer extension reaction, some of which are described below.

In some embodiments, the primer extension reaction of step (e) comprises contacting at least one extended forward sequencing primer strand with a plurality of strand displacing polymerases and a plurality of nucleotides and in the absence of soluble amplification primers, under a condition suitable to conduct a strand displacing primer extension reaction using the at least one extended forward sequencing primers strand to initiate the primer extension reaction thereby generating a forward extension strand that is covalently joined to the extended forward sequencing primers strand, wherein the forward extension strand is hybridized to the immobilized concatemer template molecule (e.g., first strand nanostructures) (FIG. 35). For example, one of the extended forward sequencing primer strands can serve as a primer for the strand displacing polymerase. The strand displacing polymerase can extend the extended forward sequencing primer strand, and displace downstream extended forward sequencing primer strands while synthesizing an extended strand that replaces the downstream extended forward sequencing primer strands. The newly extended strand is covalently joined to an extended forward sequencing primer strand. The immobilized concatemer template molecules are retained. The plurality of nucleotides in the primer extension reaction of step (e) lack a nucleotide having a scissile moiety. The primer extension reaction can include a plurality of compaction oligonucleotides to generate forward extension strands that form nanostructures (e.g., second strand nanostructures). Individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of the forward extension strand and the compaction oligonucleotide having a 3' region that can hybridize to a second portion of the forward extension strand (e.g., the same forward extension strand). In some embodiments, the plurality of compaction oligonucleotides of step (e) comprise any of the sequences as described in step (c) above.

Inclusion of compaction oligonucleotides in the primer extension reaction of step (e) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 µm or smaller.

Examples of strand displacing polymerases include phi29 DNA polymerase, large fragment of Bst DNA polymerase, large fragment of Bsu DNA polymerase (exo-), Bca DNA polymerase (exo-), Klenow fragment of E. coli DNA polymerase, T5 polymerase, M-MuLV reverse transcriptase, HIV viral reverse transcriptase, Deep Vent DNA polymerase and KOD DNA polymerase. The phi29 DNA polymerase can be wild type phi29 DNA polymerase (e.g., MagniPhi from Expedeon™), or variant EquiPhi29 DNA polymerase (e.g., from Thermo Fisher Scientific™), or chimeric QualiPhi DNA polymerase (e.g., from 4basebio™).

In some embodiments, the primer extension reaction of step (e) comprises: (i) removing the plurality of extended forward sequencing primer strands while retaining the immobilized concatemer template molecules (e.g., first strand nanostructures); and (ii) contacting the plurality of retained immobilized concatemer molecules with a plurality of soluble forward sequencing primers (e.g., a second plurality of soluble forward sequencing primers), a plurality of nucleotides (e.g., a second plurality of nucleotides) and a plurality of primer extension polymerases, under a condition suitable to hybridize the plurality of soluble forward sequencing primers to the plurality of retained immobilized concatemer template molecules and suitable for conducting polymerase-catalyzed primer extension reactions thereby generating a plurality of forward extension strands, wherein the soluble sequencing primers hybridize with the forward sequencing primer binding sequence in the retained immobilized concatemer molecules. The plurality of nucleotides in the primer extension reaction of step (e) lack a nucleotide having a scissile moiety. The primer extension reaction of step (e) can include a plurality of compaction oligonucleotides to generate forward extension strands that form nanostructures (e.g., second strand nanostructures). Individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of the forward extension strand and the compaction oligonucleotide having a 3' region that can hybridize to a second portion of the forward extension strand (e.g., the same forward extension strand). In some embodiments, the plurality of compaction oligonucleotides of step (e) comprise any of the sequences as described in step (c) above.

Inclusion of compaction oligonucleotides in the primer extension reaction of step (e) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, the primer extension reaction of step (e) comprises: (i) removing the plurality of extended forward sequencing primer strand while retaining the immobilized concatemer template molecules (e.g., first strand nanostructures); and (ii) contacting the plurality of retained immobilized concatemer molecules with a plurality of soluble amplification primers, a plurality of nucleotides (e.g., a second plurality of nucleotides) and a plurality of primer extension polymerases, under a condition suitable to hybridize the plurality of soluble amplification primers to the plurality of retained immobilized concatemer template molecules and suitable for conducting polymerase-catalyzed primer extension reactions thereby generating a plurality of forward extension strands, wherein the soluble amplification primers hybridize with the soluble amplification primer binding sequence in the retained immobilized concatemer molecules. The plurality of nucleotides in the primer extension reaction of step (e) lack a nucleotide having a scissile moiety. The primer extension reaction of step (e) can include a plurality of compaction oligonucleotides to generate forward extension strands that form nanostructures (e.g., second strand nanostructures). Individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of the forward extension strand and the compaction oligonucleotide having a 3' region that can hybridize to a second portion of the forward extension strand (e.g., the same forward extension strand).

Inclusion of compaction oligonucleotides in the primer extension reaction of step (e) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, in any embodiment of step (e) described above, the condition suitable to hybridize the plurality of soluble forward sequencing primers to the plurality of retained immobilized single stranded nucleic acid concatemer template molecules, or the condition suitable to hybridize the plurality of soluble amplification primers to the plurality of retained immobilized single stranded nucleic acid concatemer template molecules, comprises hybridizing the retained immobilized concatemer template molecules with the soluble forward sequencing primers in the presence of a primer extension polymerase, a plurality of nucleotides, and a high efficiency hybridization buffer. In some embodiment, the high efficiency hybridization buffer comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In some embodiments, in any embodiment of step (e) described above, the plurality of extended forward sequencing primer strands can be removed from the immobilized concatemer template molecules (e.g., first strand nanostructures) using an enzyme or a chemical reagent. For example, the plurality of extended forward sequencing primer strands can be enzymatically degraded using a 5' to 3' double-stranded DNA exonuclease, including T7 exonuclease (e.g., from New England Biolabs™, catalog #M0263S). In some embodiments, the plurality of extended forward sequencing primer strands can be removed with a temperature that favors nucleic acid denaturation.

In any embodiment of step (e) described above, a denaturation reagent can be used to remove the plurality of extended forward sequencing primer strands, wherein the denaturation reagent comprises any one or any combination of compounds such as formamide, acetonitrile, guanidinium chloride and/or a buffering agent (e.g., Tris-HCl, MES, HEPES, or the like).

In some embodiments, in any embodiment of step (e) described above, the plurality of extended forward sequencing primer strands can be removed using an elevated temperature (e.g., heat) with or without a nucleic acid denaturation reagent. The plurality of extended forward sequencing primer strands can be subjected to a temperature of about 45-50° C., or about 50-60° C., or about 60-70° C., or about 70-80° C., or about 80-90° C., or about 90-95° C., or higher temperatures, or any range therebetween.

In some embodiments, in any embodiment of step (e) described above, the plurality of extended forward sequencing primer strands can be removed using 100% formamide at a temperature of about 65° C. for about 3 minutes, and washing with a reagent comprising about 50 mM NaCl or equivalent ionic strength and having a pH of about 6.5-8.5.

In some embodiments, in any embodiment of step (e) described above, the primer extension polymerase comprises a high fidelity polymerase. In some embodiments, the primer extension polymerase of step (e) comprises a DNA polymerase capable of catalyzing a primer extension reaction using a uracil-containing template molecule (e.g., a uracil-tolerant polymerase). Exemplary polymerases include, but are not limited to, Q5U Hot Start high-fidelity DNA polymerase (e.g., catalog #M0515S from New England Biolabs™) Taq DNA polymerase, One Taq DNA polymerase (e.g., mixture of Taq and Deep Vent DNA polymerases, catalog #M0480S from New England Biolabs™), LongAmp Taq DNA polymerase (e.g., catalog #M0323S from New England Biolabs™), Epimark Hot Start Taq DNA polymerase (e.g., catalog #M0490S from New England Biolabs™), Bst DNA polymerase (e.g., large fragment, catalog #M0275S from New England Biolabs™), Bsu DNA polymerase (e.g., large fragment, catalog #M0330S from New England Biolabs™), Phi29 DNA polymerase (e.g., catalog #M0269S from New England Biolabs™), *E. coli* DNA polymerase (e.g., catalog #M0209S from New England Biolabs™), Therminator DNA polymerase (e.g., catalog #M0261S from New England Biolabs™), Vent DNA polymerase and Deep Vent DNA polymerase.

In some embodiments, the methods for generating a plurality of immobilized nucleic acid nanostructures, further comprise step (f): removing the retained immobilized concatemer template molecules (e.g., first strand nanostructures) by generating abasic sites in the immobilized single stranded concatemer template molecules at the nucleotide(s) having the scissile moiety and generating gaps at the abasic sites to generate a plurality of gap-containing single stranded nucleic acid concatemer template molecules while retaining the plurality of forward extension strands (second strand nanostructures) and retaining the plurality of immobilized surface primers (FIG. 36).

The abasic sites are generated on the retained concatemer template strands that contain nucleotides having scissile moieties. In some embodiments, the scissile moieties in the retained concatemer template molecules comprises uridine, 8-oxo-7,8-dihydroguanine (e.g., 8oxoG) or deoxyinosine. The abasic sites can be removed to generate a plurality of single stranded nucleic acid template molecules having gaps while retaining the plurality of forward extension strands. The abasic sites can be generated by contacting the immobilized concatemer template molecules with an enzyme that removes the nucleo-base at the nucleotide having the scissile moiety. The uracil in the retained concatemer template strands can be converted to an abasic site using uracil DNA glycosylase (UDG). The 8oxoG in the retained concatemer template strands can be converted to an abasic site using FPG glycosylase. The deoxyinosine in the retained concatemer template strands can be converted to an abasic site using AlkA glycosylase.

In some embodiments, in the methods for generating a plurality of immobilized nucleic acid nanostructures of step (f), the gaps can be generated by contacting the abasic sites in the immobilized concatemer template molecules with an enzyme or a mixture of enzymes having lyase activity that breaks the phosphodiester backbone at the 5' and 3' sides of the abasic site to release the base-free deoxyribose and generate a gap (FIG. 36). The abasic sites can be removed using AP lyase, Endo IV endonuclease, FPG glycosylase/AP lyase, Endo VIII glycosylase/AP lyase. In some embodiments, generating the abasic sites and removal of the abasic sites to generate gaps can be achieved using a mixture of uracil DNA glycosylase and DNA glycosylase-lyase endonuclease VIII, for example and without limitation, USER™ (Uracil-Specific Excision Reagent Enzyme from New England Biolabs™) or thermolabile USER™ (also from New England Biolabs™).

In some embodiments, in the methods for generating a plurality of immobilized nucleic acid nanostructures of step (f), the plurality of gap-containing template molecules can be removed using an enzyme, chemical compound and/or heat. After the gap-removal procedure, the plurality of retained forward extension strands are hybridized to the retained immobilized surface primers (FIG. 37). For example, the plurality of gap-containing template molecules can be enzymatically degraded using a 5' to 3' double-stranded DNA exonuclease, including T7 exonuclease (e.g., from New England Biolabs™, catalog #M0263S). When a 5' to 3' double-stranded DNA exonuclease is used for removing gap-containing template molecules, then the plurality of soluble amplification primers in step (f) can comprise at least one phosphorothioate diester bond at their 5' ends which can render the soluble amplification primers resistant to exonuclease degradation. In some embodiments, the plurality of soluble amplification primers in step (e) comprise 2-5 or more consecutive phosphorothioate diester bonds at their 5' ends. In some embodiments, the plurality soluble amplification primers in step (e) comprise at least one ribonucleotide and/or at least one 2'-O-methyl or 2'-O-methoxyethyl (MOE) nucleotide which can render the forward sequencing primers resistant to exonuclease degradation.

In some embodiments, the plurality of gap-containing template molecules can be removed using a chemical reagent that favors nucleic acid denaturation. The denaturation reagent can include any one or any combination of compounds such as formamide, acetonitrile, guanidinium chloride and/or a buffering agent (e.g., Tris-HCl, MES, HEPES, or the like).

In some embodiments, the plurality of gap-containing template molecules can be removed using an elevated temperature (e.g., heat) with or without a nucleic acid denaturation reagent. The gap-containing template molecules can be subjected to a temperature of about 45-50° C., or about 50-60° C., or about 60-70° C., or about 70-80° C., or about 80-90° C., or about 90-95° C., or higher temperatures, or any range therebetween.

In some embodiments, the plurality of gap-containing template molecules can be removed, e.g., using 100% formamide at a temperature of about 65° C. for about 3 minutes, and washing with a reagent comprising about 50 mM NaCl or equivalent ionic strength and having a pH of about 6.5-8.5.

In some embodiments, the methods for generating a plurality of immobilized nucleic acid nanostructures, further comprise step (g): sequencing the plurality of retained forward extension strands (e.g., second strand nanostructures) thereby generating a plurality of extended reverse sequencing primer strands. In some embodiments, the sequencing of step (g) comprises contacting the plurality of retained forward extension strands with a plurality of soluble reverse sequencing primers under a condition suitable to hybridize the reverse sequencing primers to the reverse sequencing primer binding site of the retained forward extension strands, and conducting reverse sequencing reactions to generate a plurality of reverse sequencing products using one or more types of sequencing polymerases, a plurality of nucleotide reagents, and the hybridized reverse sequencing primers (FIG. 37). In some embodiments, the plurality of nucleotide reagents is detectably labeled. In some embodiments, the sequencing of step (g) further comprises detecting and imaging the plurality of reverse sequencing products.

In some embodiments, the sequencing of step (g) further comprises contacting the plurality of plurality of retained forward extension strands with a plurality of compaction oligonucleotides under a condition suitable to hybridize the 5' end of at least one compaction oligonucleotide to a first portion of plurality of retained forward extension strand and to hybridize the second binding region of the same compaction oligonucleotide to a second portion of the same plurality of retained forward extension strand. In some embodiments, the plurality of compaction oligonucleotides of step (g) comprise any of the sequences as described in step (c) above.

In some embodiments, in the sequencing of step (g), the extended reverse sequencing primer strands are hybridized to the retained forward extension strand. The retained forward extension strand is hybridized to the first universal surface primer. The extended reverse sequencing primer strands are not hybridized to the first universal surface primer, or covalently joined to the first universal surface primer. Therefore, the extended reverse sequencing primer strands are not immobilized to the support (e.g., see FIG. 37).

In some embodiments, in the sequencing of step (g), the soluble reverse sequencing primers comprise 3' OH extendible ends. In some embodiments, the soluble reverse sequencing primers comprise a 3' blocking moiety which can be removed to generate a 3' OH extendible end. In some embodiments, the soluble reverse sequencing primers lack a nucleotide having a scissile moiety. The reverse sequencing reactions can generate a plurality of extended reverse sequencing primer strands. In some embodiments, individual retained forward extension strand have multiple copies of the reverse sequencing primer binding sites/sequences, wherein each reverse sequencing primer binding site is capable of hybridizing to a reverse sequencing primer. Individual reverse sequencing primer binding sites in a given retained forward extension strand can be hybridized to a reverse sequencing primer and can undergo a sequencing reaction. Individual retained forward extension strands can undergo two or more reverse sequencing reactions, where each sequencing reaction is initiated from a reverse sequencing primer that is hybridized to a reverse sequencing primer binding site (e.g., see FIG. 37).

In some embodiments, in the sequencing of step (g), the nucleotide reagent comprises a plurality of nucleotides, a plurality of nucleotide analogs, or a plurality of multivalent molecules.

In some embodiments, in the sequencing of step (g), individual nucleotides in the plurality of nucleotides comprises an aromatic base, a five carbon sugar and at least one phosphate group. In some embodiments, the plurality of nucleotides is unlabeled. In some embodiments, at least one nucleotide in the plurality can be labeled with a detectable reporter moiety (e.g., fluorophore). In some embodiments, the sequencing of step (g) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (g), individual nucleotide analogs in the plurality comprise an aromatic base, a five carbon sugar having a 3' chain terminating moiety that inhibits polymerase-catalyzed nucleotide incorporation, and at least one phosphate group. In some embodiments, the plurality of nucleotide analogs is unlabeled. In some embodiments, at least one nucleotide analog in the plurality can be labeled with a detectable reporter moiety (e.g., fluorophore). In some embodiments, the sequencing of step (g) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (g), individual multivalent molecules in the plurality comprise (1) a core; and (2) a plurality of nucleotide arms each comprising (i) a core attachment moiety, (ii) a spacer, (iii) a linker, and (iv) a nucleotide unit, wherein the core is attached to the plurality of nucleotide arms, wherein the spacer is attached to the linker, wherein the linker is attached to the nucleotide unit (e.g., see FIGS. 56-59). In some embodiments, the nucleotide unit comprises an aromatic base, a five carbon sugar and at least one phosphate group, and the linker is attached to the nucleotide unit through the base. In some embodiments, the plurality of multivalent molecules is unlabeled. In some embodiments, at least one multivalent molecule in the plurality is labeled with a detectable reporter moiety (e.g., fluorophore). In some embodiments, the sequencing of step (g) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (g), the method further comprises forming at least one avidity complex, by contacting the plurality of immobilized concatemer template molecules (e.g., second strand nanostructures) with a plurality of soluble reverse sequencing primers, a plurality of sequencing polymerases, and a plurality of multivalent molecules, to form a plurality of binding complexes including at least a first and second binding complex, wherein (i) the first binding complex comprises a first reverse sequencing primer, a first sequencing polymerase, and a first multivalent molecule, bound to a first portion of the immobilized concatemer template molecule (e.g., second strand nanostructure) thereby forming the first binding complex, wherein a first nucleotide unit of the multivalent molecule is bound to the first polymerase, and (ii) the second binding complex comprises a second reverse sequencing primer, a second sequencing polymerase, and the first multivalent molecule, bound to a second portion of the same immobilized concatemer template molecule thereby forming the second binding complex, wherein a second nucleotide unit of the multivalent molecule is bound to the second polymerase, and wherein the first and second binding complexes which include the same multivalent molecule forms an avidity complex. In some embodiments, the multivalent molecule is unlabeled or is labeled with a detectable reporter moiety.

In some embodiments, in any of the primer extension reactions of step (e), the first binding region of the compaction oligonucleotides hybridize to the forward extension strand at a first portion that does not interfere (e.g., little or no overlap) with hybridizing the reverse sequencing primers to the reverse sequencing primer binding sites of the plurality of forward extension strands of step (g).

In some embodiments, in any of the primer extension reactions of step (e), the second binding region of the compaction oligonucleotides hybridize to the forward extension strand at a second portion that does not interfere (e.g., little or no overlap) with hybridizing the reverse sequencing primers to the reverse sequencing primer binding sites of the plurality of forward extension strands of step (g).

In some embodiments, the methods for generating a plurality of immobilized nucleic acid nanostructures further comprises: positioning a cellular biological sample on the immobilized nanostructures after step (b). For example, the cellular biological sample can be placed on the immobilized nucleic acid nanostructures after step (b) and prior to step (c).

In some embodiments, the cellular biological sample comprises a single cell, a plurality of cells, a tissue, an organ, an organism, or a section from any of these cellular biological samples. The cellular biological sample can comprise a sample that is fresh, frozen, fresh-frozen, or archived (e.g., formalin-fixed paraffin-embedded; FFPE). The cellular biological sample can be embedded in a matrix material. The cellular biological sample can be stained, de-stained or non-stained. The cellular biological sample can be permeabilized to permit the nucleic acids within the cellular sample to migrate from the cell(s) to the plurality of immobilized nanostructures.

In some embodiments, in step (g), the condition suitable to hybridize the reverse sequencing primers to the reverse sequencing primer binding sequences of the retained forward extension strands comprises contacting the plurality of soluble reverse sequencing primers and the retained forward extension strands with a high efficiency hybridization buffer. In some embodiments, the high efficiency hybridization buffer comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In an alternative embodiment, the sequencing of step (g) comprises using the immobilized surface primer as a sequencing primer and conducting sequencing reactions to generate a plurality of reverse sequencing strands.

In some embodiments, at least one washing step can be conducted after any of steps (a)-(g). The washing step can be conducted with a wash buffer comprising a pH buffering agent, a metal chelating agent, a salt, and a detergent.

In some embodiments, the pH buffering compound in the wash buffer comprises any one or any combination of two or more of Tris, Tris-HCl, Tricine, Bicine, Bis-Tris propane, HEPES, MES, MOPS, MOPSO, BES, TES, CAPS, TAPS, TAPSO, ACES, PIPES, ethanolamine (i.e., 2-amino methanol; MEA), a citrate compound, a citrate mixture, NaOH and/or KOH. In some embodiments, the pH buffering agent can be present in the wash buffer at a concentration of about 1-100 mM, or about 10-50 mM, or about 10-25 mM. In some embodiments, the pH of the pH buffering agent which is present in any of the reagents described here in can be adjusted to a pH of about 4-9, or a pH of about 5-9, or a pH of about 5-8.

In some embodiments, the metal chelating agent in the wash buffer comprises EDTA (ethylenediaminetetraacetic acid), EGTA (ethylene glycol tetraacetic acid), HEDTA (hydroxyethylethylenediaminetriacetic acid), DPTA (diethylene triamine pentaacetic acid), NTA (N,N-bis(carboxymethyl)glycine), citrate anhydrous, sodium citrate, calcium citrate, ammonium citrate, ammonium bicitrate, citric acid, potassium citrate, or magnesium citrate. In some embodiments, the wash buffer comprises a chelating agent at a concentration of about 0.01-50 mM, or about 0.1-20 mM, or about 0.2-10 mM, or any range therebetween.

In some embodiments, the salt in the wash buffer comprises NaCl, KCl, $NH_2SO_4$ or potassium glutamate. In some embodiments, the detergent comprises an ionic detergent such as SDS (sodium dodecyl sulfate). The wash buffer can include a monovalent salt at a concentration of about 25-500 mM, or about 50-250 mM, or about 100-200 mM, or any range therebetween.

In some embodiments, the detergent in the wash buffer comprises a non-ionic detergent such as Triton X-100, Tween 20, Tween 80 or Nonidet P-40. In some embodiments, the detergent comprises a zwitterionic detergent such as CHAPS (3-[(3-cholamidopropyl)dimethylammonio]-1-propanesulfonate) or N-Dodecyl-N,N-dimethyl-3-amonio-1-propanesulfate (DetX). In some embodiments, the detergent comprises LDS (lithium dodecyl sulfate), sodium taurodeoxycholate, sodium taurocholate, sodium glycocholate, sodium deoxycholate or sodium cholate. In some embodiments, the detergent is included in the wash buffer at a concentration of about 0.01-0.05%, or about 0.05-0.1%, or about 0.1-0.15%, or about 0.15-0.2%, or about 0.2-0.25%, or any range therebetween.

In some embodiments, the methods for generating a plurality of immobilized nucleic acid nanostructures using an in-solution rolling circle amplification reaction, the methods comprise: step (a) conducting in-solution RCA; step (b) distributing the RCA onto a support; step (c) continuing the RCA on the support; and step (d) forward sequencing. In some embodiments, the methods do not include steps (e)-(g). For example, the methods do not include: synthesis of second strand nanostructures (step (e)); generating abasic sites and gaps (step (f)); and reverse sequencing (step (g)).

In some embodiments, the methods for generating a plurality of immobilized nucleic acid nanostructures using an in-solution rolling circle amplification reaction, the methods comprise: step (a) conducting in-solution RCA; step (b) distributing the RCA onto a support; and step (c) continuing the RCA on the support. In some embodiments, the methods do not include steps (d)-(g). For example, the methods do not include: forward sequencing (step (d)); synthesis of second strand nanostructures (step (e)); generating abasic sites and gaps (step (f)); and reverse sequencing (step (g)).

In-Solution Methods
Generating High Density Immobilized Nanostructures Lacking Scissile Moieties The present disclosure provides methods for generating high density nucleic acid nanostructures immobilized on a support, comprising step (a): contacting a plurality of single-stranded circular nucleic acid library molecules to (i) a plurality of soluble first amplification primers, (ii) a plurality of a strand displacing polymerase, and (iii) a plurality of nucleotides which include dATP, dCTP, dGTP, dTTP, under a condition suitable to form a plurality of library-primer duplexes and suitable for conducting an in-solution rolling circle amplification reaction, thereby generating a plurality of single stranded nucleic acid concatemers (FIG. 46). In some embodiments, the soluble first amplification primer comprises a sequence that selectively hybridizes to a universal binding sequence in the circular nucleic acid library molecules, such as for example a universal binding sequence (or a complementary sequence thereof) for the first soluble amplification primer. Alternatively, the soluble first amplification primer comprises a random sequence that binds non-selectively to a sequence in the circular nucleic acid library molecules.

The in-solution rolling circle amplification reaction of step (a) includes a mixture of nucleotides that lack a scissile moiety. Exemplary nucleotides having a scissile moiety include uridine, 8-oxo-7,8-dihydroguanine (e.g., 8oxoG) and deoxyinosine. In some embodiments, the rolling circle amplification reaction generates a plurality of single stranded nucleic acid concatemer template molecules that lack a nucleotide having a scissile moiety.

In some embodiments in step (a), individual single stranded circular nucleic acid library molecules in the plurality comprises a sequence of interest and wherein the individual library molecules further comprise any one or any combination of two or more of (i) a universal binding sequence (or a complementary sequence thereof) for a soluble forward sequencing primer, (ii) a universal binding sequence (or a complementary sequence thereof) for a soluble reverse sequencing primer, (iii) a universal binding sequence (or a complementary sequence thereof) for an immobilized first surface primer, (iv) a universal binding sequence (or a complementary sequence thereof) for an immobilized second surface primer, (v) a universal binding sequence (or a complementary sequence thereof) for a first soluble amplification primer, (vi) a universal binding sequence (or a complementary sequence thereof) for a second soluble amplification primer, (vii) a universal binding sequence (or a complementary sequence thereof) for a soluble compaction oligonucleotide, (viii) at least one sample barcode sequence and/or (ix) a unique molecular index sequence. In some embodiments, the single-stranded circular nucleic acid library molecules comprise covalently closed circular molecules (e.g., FIGS. 18A-B, FIGS. 20A-B).

In some embodiments, the rolling circle amplification reaction of step (a) generates a plurality of single stranded nucleic acid concatemer molecules in solution, comprising a concatemer having at least one nucleotide having a scissile moiety. In some embodiments, individual concatemer template molecules in the plurality comprise two or more copies of a sequence of interest, and wherein the individual immobilized concatemer template molecules further comprise any one or any combination of two or more of: (i) two or more copies of a universal binding sequence for a soluble forward sequencing primer, (ii) two or more copies of a universal binding sequence for a soluble reverse sequencing primer, (iii) two or more copies of a universal binding sequence for an immobilized first surface primer, (iv) two or more copies of a universal binding sequence for an immobilized second surface primer, (v) two or more copies of a universal binding sequence for a first soluble amplification primer, (vi) two or more copies of a universal binding sequence for a second soluble amplification primer, (vii) two or more copies of a universal binding sequence for a soluble compaction oligonucleotide, (viii) two or more copies of a sample barcode sequence and/or (ix) two or more copies of a unique molecular index sequence.

In some embodiments in step (a), the universal binding sequence (or a complementary sequence thereof) for the forward sequencing primer can hybridize to at least a portion of the forward sequencing primer. In some embodiments, the universal binding sequence (or a complementary sequence thereof) for the reverse sequencing primer can hybridize to at least a portion of the reverse sequencing primer. In some embodiments, the universal binding sequence (or a complementary sequence thereof) for the immobilized first surface primer can hybridize to at least a portion of the immobilized first surface primer. In some embodiments, the universal binding sequence (or a complementary sequence thereof) for the immobilized second surface primer can hybridize to at least a portion of the immobilized second surface primer. In some embodiments, the universal binding sequence (or a complementary sequence thereof) for the first soluble amplification primer can hybridize to at least a portion of the first soluble amplification primer. In some embodiments, the universal binding sequence (or a complementary sequence thereof) for the second soluble amplification primer can hybridize to at least a portion of the second soluble amplification primer. In some embodiments, the universal binding sequence (or a complementary sequence thereof) for the soluble compaction oligonucleotide can hybridize to at least a portion of the soluble compaction oligonucleotide.

In some embodiments, the methods for generating high density nucleic acid nanostructures immobilized on a support further comprises step (b): distributing the rolling circle amplification reaction from step (a) onto a support having a plurality of first universal surface primers immobilized thereon, under a condition suitable for hybridizing one or more portions of individual single stranded concatemers to one or more immobilized first universal surface primers (FIG. 47). The concatemers are immobilized to the support by hybridization to the immobilized first universal surface primers. In some embodiments, the support is passivated with at least one hydrophilic polymer layer which includes a plurality of first universal surface primers, wherein each of the first universal surface primers comprises a 3' OH extendible end and lacks a nucleotide having a scissile moiety and wherein the density of the first universal surface primers is about $10^2$-$10^{15}$ per $mm^2$. The first universal surface primers lack a scissile moiety that can be converted into an abasic site in a nucleic acid strand. For example, the first universal surface primers lack uridine, 8-oxo-7,8-dihydroguanine (e.g., 8oxoG) and deoxyinosine. In some embodiments, the support lacks a plurality of second universal surface primers. In some embodiments, the support comprises a plurality of first and second universal surface primers.

In some embodiments, the methods for generating high density nucleic acid nanostructures immobilized on a support further comprises step (c): continuing the rolling circle amplification reaction on the support to generate a plurality of extended concatemer template molecules that are immobilized via hybridization to the immobilized first surface primers (FIGS. 47-48). The on-support RCA reaction can be conducted with a (i) plurality of a strand displacing polymerase, (ii) a plurality of nucleotides which include dATP, dCTP, dGTP, dTTP, and (iii) a plurality of compaction oligonucleotides, under a condition suitable to generate a plurality of extended concatemers lacking a nucleotide with a scissile moiety (FIG. 48).

In some embodiments, individual compaction oligonucleotides comprise a single-stranded linear oligonucleotide having a 5' region that can hybridize to a first portion of an extended concatemer molecule and the compaction oligonucleotide having a 3' region that can hybridize to a second portion of the extended concatemer molecule (FIG. 48). The rolling circle amplification reaction, as shown in FIG. 48, includes a plurality of compaction oligonucleotides. The first binding region of the compaction oligonucleotide hybridizes to a first portion of the immobilized concatemer molecule, and the second binding region of the compaction oligonucleotide hybridizes to a second portion of the concatemer molecule which causes the concatemer molecule to collapse or fold into a nucleic acid nanostructure.

In some embodiments, individual immobilized concatemer molecules collapse or fold into a compact nucleic acid nanostructure (e.g., first strand nanostructure).

In some embodiments, the plurality of extended concatemers remain immobilized to the support upon collapsing or folding into nanostructures, thereby generating a support having a density of about $10^2$-$10^{15}$ per mm$^2$ of nanostructures immobilized to the support.

In some embodiments, individual immobilized nanostructures comprise a plurality of tandem polynucleotide units and each polynucleotide unit has a sequence that is complementary to the sequence of a covalently closed circular nucleic acid library molecule.

The rolling circle amplification reaction of step (c) includes a mixture of nucleotides that lack a scissile moiety. Exemplary nucleotides having a scissile moiety include uridine, 8-oxo-7,8-dihydroguanine (e.g., 8oxoG) and deoxyinosine. In some embodiments, the rolling circle amplification reaction generates a plurality of single stranded nucleic acid concatemer template molecules that lack a nucleotide having a scissile moiety. The plurality of immobilized nucleic acid nanostructures is in fluid communication with each other to permit flowing various reagents in solution including soluble primers, enzymes, nucleotides, divalent cations, buffers and the like, onto the support so that the plurality of immobilized nanostructures react with the solutions in a massively parallel manner.

In some embodiments, the density of the first universal surface primers on the support is about $10^2$-$10^{15}$ per mm$^2$. In some embodiments, the immobilized first universal surface primers comprise single stranded oligonucleotides comprising DNA, RNA or a combination of DNA and RNA. The first universal surface primers comprise a sequence that is wholly complementary or partially complementary along their lengths to at least a portion of a circular nucleic acid library molecule. The first universal surface primers can include a terminal 3' nucleotide having a sugar 3' OH moiety which is extendible for nucleotide polymerization (e.g., polymerase catalyzed polymerization).

In some embodiments, the immobilized first universal surface primers can be immobilized to the support or immobilized to a coating on the support. The immobilized first universal surface primers can be embedded and attached (coupled) to the coating on the support. In some embodiments, the 5' end of the immobilized first universal surface primers are immobilized to a support or immobilized to a coating on the support. Alternatively, an interior portion or the 3' end of the immobilized first universal surface primers can be immobilized to a support or immobilized to a coating on the support. The support comprises a plurality of immobilized first universal surface primers having the same sequence. The immobilized first universal surface primers can be any length, for example 4-50 nucleotides, or 50-100 nucleotides, or 100-150 nucleotides, or longer lengths, or any range therebetween.

In some embodiments, the plurality of immobilized first universal surface primers are located on the coated support at random positions (e.g., non-pre-determined positions). When the immobilized universal surface primers are located on the coated support at random positions, the immobilized nucleic acid nanostructures are also located at random positions. The randomly-located nucleic acid nanostructures can be tightly packed and fill much of the space on the coated support.

In some embodiments, the plurality of immobilized first universal surface primers are located on the coated support at pre-determined positions. For example, the immobilized first universal surface primers are arranged in an organized pattern. When the immobilized universal surface primers are located on the support or the coated support at pre-determined positions, the nucleic acid nanostructures are also located at pre-determined positions.

In some embodiments, the plurality of immobilized first universal surface primers comprise at least one phosphorothioate diester bond at their 5' ends which can render the first universal surface primers resistant to exonuclease degradation. In some embodiments, the plurality of immobilized first universal surface primers comprise 2-5 or more consecutive phosphorothioate diester bonds at their 5' ends. In some embodiments, the plurality of immobilized first universal surface primers comprise at least one ribonucleotide and/or at least one 2'-O-methyl or 2'-O-methoxyethyl (MOE) nucleotide which can render the first universal surface primers resistant to exonuclease degradation.

In some embodiments, the immobilized first universal surface primers comprise at least one locked nucleic acid (LNA) which comprises a methylene bridge bond between a 2' oxygen and 4' carbon of the pentose ring. Immobilized first universal surface primers that include at least one LNA can be resistant to nuclease digestions and can exhibit increased melting temperature when hybridized to the circular nucleic acid library molecules or the nucleic acid concatemer molecules.

In some embodiments, the support further comprises a plurality of a second universal surface primer immobilized thereon (e.g., FIG. 38 but in this embodiment the immobilized concatemer lacks uracil). The second universal surface primers have a sequence that differs from the first universal immobilized surface primer. In some embodiments, the density of the second universal surface primers on the support is about $102$-$10^5$ per mm$^2$. The immobilized second universal surface primers of step (a) comprise single stranded oligonucleotides comprising DNA, RNA or a combination of DNA and RNA. The second universal surface primers comprise a sequence that is wholly complementary or partially complementary along their lengths to at least a portion of an immobilized single stranded concatemer template molecule. The immobilized second universal surface primers can be immobilized to the support or immobilized to a coating on the support. The immobilized second universal surface primers can be embedded and attached (coupled) to the coating on the support. In some embodiments, the 5' end of the second universal surface primers are immobilized to a support or immobilized to a coating on the support. Alternatively, an interior portion or the 3' end of the immobilized second universal surface primers can be immobilized to a support or immobilized to a coating on the support. The support comprises a plurality of immobilized second universal surface primers having the same sequence. The immobilized second universal surface primers can be any length, for example 4-50 nucleotides, or 50-100 nucleotides, or 100-150 nucleotides, or longer lengths, or any range therebetween. In some embodiments, the 3' terminal end of the immobilized second universal surface primers comprise an extendible 3' OH moiety. In some embodiments, the 3' terminal end of the immobilized second universal surface primers comprise a 3' non-extendible moiety. The 3' terminal end of the immobilized second universal surface primers can comprise a moiety that blocks primer extension, such as for example a phosphate group, a dideoxycytidine group, an inverted dT, or an amino group. The immobilized second universal surface primers are not extendible in a primer extension reaction. The immobilized second universal surface primers can lack a nucleotide having a scissile moiety.

In some embodiments, the plurality of immobilized second universal surface primers comprise at least one phosphorothioate diester bond at their 5' ends which can render the second universal surface primers resistant to exonuclease degradation. In some embodiments, the plurality of immobilized second universal surface primers comprise 2-5 or more consecutive phosphorothioate diester bonds at their 5' ends. In some embodiments, the plurality of immobilized second universal surface primers comprise at least one ribonucleotide and/or at least one 2'-O-methyl or 2'-O-methoxyethyl (MOE) nucleotide which can render the second universal surface primers resistant to exonuclease degradation.

In some embodiments, individual immobilized single stranded nucleic acid concatemer template molecule is hybridized to an immobilized first universal surface primer, and at least one portion of the individual concatemer template molecule is hybridized to an immobilized second universal surface primer (e.g., FIG. 38 but in this embodiment the immobilized concatemer lacks uracil). The immobilized second universal surface primers can serve to pin down a portion of the immobilized concatemer template molecules to the support. The immobilized concatemer template molecule has two or more copies of a universal binding sequence for an immobilized second universal surface primer. The portion of the immobilized concatemer template molecule that includes the universal binding sequence for an immobilized second universal surface primer can hybridize to the immobilized second universal surface primer. In some embodiments, the second universal surface primers include a terminal 3' blocking group that renders them non-extendible. In some embodiments, the second universal surface primers have terminal 3' extendible ends.

The immobilized surface primers (e.g., first and second universal surface primers) are in fluid communication with each other to permit flowing various solutions of linear or circular nucleic acid template molecules, soluble primers, enzymes, nucleotides, divalent cations, buffers, reagents, and the like, onto the support so that the plurality of immobilized surface primers (and the primer extension products generated from the immobilized surface primers) react with the solutions in a massively parallel manner.

In some embodiments, in step (c), the first binding region of the compaction oligonucleotides can hybridize to a first portion of the concatemer molecule, where the first portion of the concatemer molecule comprises a universal adaptor sequence according to any one of SEQ ID NOs:157-176, or a complementary sequence thereof (see Table 2)).

In some embodiments, in step (c), the second binding region of the compaction oligonucleotides can hybridize to a second portion of the concatemer molecule, where the second portion of the concatemer molecule comprises a universal adaptor sequence according to any one of SEQ ID NOs:157-176, or a complementary sequence thereof (see Table 2)).

In some embodiments, in step (c), the compaction oligonucleotides comprise a first, second, third, fourth, fifth, sixth, or other binding regions.

In some embodiments, in step (c), any binding region of the compaction oligonucleotide (e.g., first, second, third, fourth, fifth, sixth, or other binding regions) can hybridize to a portion of the concatemer molecule, where the portion of the concatemer molecule comprises a universal adaptor sequence according to any one of SEQ ID NOs:157-176, or a complementary sequence thereof (see Table 2)).

In some embodiments, in step (c), the compaction oligonucleotide comprises two or more binding regions and all of the binding regions have the same sequence. In some embodiments, the compaction oligonucleotide comprises two binding regions having different sequences. In some embodiments, the compaction oligonucleotide comprises three or more binding regions and at least two of the binding regions have different sequences.

In some embodiments, in step (c), the first binding region of the compaction oligonucleotide can have the same sequence as the second binding region.

In some embodiments, in step (c), the first binding region of the compaction oligonucleotide can have a sequence that is different from the second binding region.

In some embodiments, in step (c), the first binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the second, third, fourth, fifth or any subsequent binding region of the compaction oligonucleotide comprises a sequence that is a reverse sequence of the first binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (c), the first binding region of a compaction oligonucleotide comprises a sequence according to any of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (c), the second, third, fourth, fifth or any subsequent binding region of the compaction oligonucleotide comprises a sequence that is a reverse sequence of the first binding region, where the second, third, fourth, fifth or any subsequence binding region comprises any of one of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), first binding region of the compaction oligonucleotide can have a sequence that is a reverse sequence of the second binding region (e.g., the reverse sequence according to any of one of SEQ ID NOs: 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149, 152 or 155; see Table 1).

In some embodiments, in step (c), the second binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the third binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the fourth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the fifth binding region of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the subsequent binding region(s) of a compaction oligonucleotide comprises a sequence according to any of SEQ ID NOs: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151 or 154 (see Table 1).

In some embodiments, in step (c), the compaction oligonucleotides comprise a full-length sequence according to any one of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156 (see Table 1).

In some embodiments, in step (c), the terminal 3' end of any of the compaction oligonucleotides can include at least one additional base comprising one or more 2'-O-methyl RNA bases (e.g., designated mUmUmU) or the terminal 3' end lacks additional 2'-O-methyl RNA bases.

In some embodiments, in step (c), the compaction oligonucleotides comprise one or more modified bases or linkages at their 5' or 3' ends to confer certain functionalities. In some embodiments, the compaction oligonucleotides comprise at least one phosphorothioate linkages at their 5' and/or 3' ends to confer exonuclease resistance. In some embodiments, at least one nucleotide at or near the 3' end comprises a 2' fluoro base which confers exonuclease resistance. In some embodiments, the 3' end of the compaction oligonucleotides comprise at least one 2'-O-methyl RNA base which blocks polymerase-catalyzed extension. For example, the 3' end of the compaction oligonucleotide comprises at least one base comprising 2'-O-methyl RNA base (e.g., designated mUmUmU). In some embodiments, the compaction oligonucleotides comprise a 3' inverted dT at their 3' ends which blocks polymerase-catalyzed extension. In some embodiments, the compaction oligonucleotides comprise 3' phosphorylation which blocks polymerase-catalyzed extension. In some embodiments, the compaction oligonucleotides comprise at least one locked nucleic acid (LNA) which increases the thermal stability of duplexes formed by hybridizing a compaction oligonucleotide to a concatemer molecule.

In some embodiments, in step (c), the compaction oligonucleotides can include at least one region (e.g., hybridization/binding region) having consecutive guanines. For example, the compaction oligonucleotides can include at least one region having 2, 3, 4, 5, 6 or more consecutive guanines. In some embodiments, the compaction oligonucleotides comprise four consecutive guanines which can form a guanine tetrad structure (see FIG. 64). The guanine tetrad structure can be stabilized via Hoogsteen hydrogen bonding. The guanine tetrad structure can be stabilized by a central cation including potassium, sodium, lithium, rubidium, or cesium.

In some embodiments, in step (c), at least one compaction oligonucleotide can form a guanine tetrad (FIG. 64) and hybridize to the universal binding sequences in a concatemer which can cause the concatemer to fold to form an intramolecular G-quadruplex structure (FIG. 65). The concatemers can self-collapse to form compact nanostructures. Formation of the guanine tetrads and G-quadruplexes in the nanostructures may increase the stability of the nanostructures to retain their compact size and shape which can withstand changes in pH, temperature and/or repeated flows of reagents.

In some embodiments, the plurality of compaction oligonucleotides in step (c) comprises a mixture of two or more different populations of compaction oligonucleotides having different sequences. In some embodiments, the plurality of compaction oligonucleotides in step (c) comprise a mixture of 2, 3, 4, 5, 6, 7, 8, 9 or 10 different populations of compaction oligonucleotides wherein the compaction oligonucleotides in the different populations have different sequences. In some embodiments, in the mixture of different compaction oligonucleotides in step (c), any given population of compaction oligonucleotides comprise a sequence according to any one of SEQ ID NOs:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153 or 156.

In some embodiments, in the methods for generating a plurality of immobilized nucleic acid nanostructures of step (c), the nucleic acid nanostructures can include one or more loops, or can have a spherical shape (e.g., nanoball), elongated shape (e.g., nanorod), proto-toroid shape or toroid shape (e.g., nano-toroid). The nucleic acid nanostructure can be a compact nucleic acid structure having a full width half maximum (FWHM) that is smaller compared to a concatemer that is not collapsed/folded into a nanostructure. Inclusion of the plurality of compaction oligonucleotides in the on-support rolling circle amplification reaction can improve the FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, in the methods for generating a plurality of immobilized nucleic acid nanostructures of step (c), individual single stranded covalently closed circular nucleic acid library molecules in the plurality comprise a sequence of interest, and any one or any combination of two or more of (i) a universal binding sequence (or complementary sequence thereof) for a soluble forward sequencing primer, (ii) a universal binding sequence (or complementary sequence thereof) for a soluble reverse sequencing primer, (iii) a universal binding sequence (or complementary sequence thereof) for an immobilized first universal surface primer, (iv) a universal binding sequence (or complementary sequence thereof) for an immobilized second universal surface primer, (v) a universal binding sequence (or complementary sequence thereof) for a first soluble amplification primer, (vi) a universal binding sequence (or complementary sequence thereof) for a second soluble amplification primer, (vii) a universal binding sequence (or complementary sequence thereof) for a soluble compaction oligonucleotide, (viii) at least one sample barcode sequence and/or (ix) a unique molecular index sequence.

In some embodiments, in the methods for generating a plurality of immobilized nucleic acid nanostructures of step (c), the rolling circle amplification reaction generates a plurality of immobilized single stranded nucleic acid concatemer template molecules (e.g., first strand nanostructures) wherein individual concatemer template molecules comprise at least two copies of a polynucleotide unit arranged in tandem. In some embodiments, each polynucleotide unit comprises a sequence-of-interest. In some embodiments, each polynucleotide unit comprises at least one universal adaptor sequence. In some embodiments, each polynucleotide unit comprises a sequence-of-interest and at least one universal adaptor sequence. In some embodiments, individual concatemer molecules comprise 2-100 copies of a polynucleotide unit, or 100-250 copies of a polynucleotide unit, or 250-500 copies of a polynucleotide unit, or 500-750 copies of a polynucleotide unit, or 750-1000 copies of a polynucleotide unit, or more than 1000 copies of a polynucleotide unit, or any range therebetween. In some embodiments, individual concatemer molecules comprise 1000-2000 copies of a polynucleotide unit, or 1000-10,000 copies of a polynucleotide unit, or any range therebetween. In some embodiments, individual concatemers comprise a plurality of tandem polynucleotide units where the sequence of each polynucleotide unit of a given concatemer molecule is complementary to the sequence of a circular library molecule that served as the template library molecule.

In some embodiments, individual immobilized concatemer molecules comprise two or more copies of a sequence of interest, and wherein the immobilized concatemer template molecules further comprise any one or any combination of two or more of: (i) two or more copies of a universal binding sequence (or a complementary sequence thereof) for a soluble forward sequencing primer, (ii) two or more copies of a universal binding sequence (or a complementary sequence thereof) for a soluble reverse sequencing primer, (iii) two or more copies of a universal binding sequence (or a complementary sequence thereof) for an immobilized first universal surface primer, (iv) two or more copies of a universal binding sequence (or a complementary sequence thereof) for an immobilized second universal surface primer, (v) two or more copies of a universal binding sequence (or a complementary sequence thereof) for a first soluble amplification primer, (vi) two or more copies of a universal binding sequence (or a complementary sequence thereof) for a second soluble amplification primer, (vii) two or more copies of a universal binding sequence (or a complementary sequence thereof) for a soluble compaction oligonucleotide, (viii) two or more copies of a sample barcode sequence and/or (ix) two or more copies of a unique molecular index sequence (e.g., FIG. 39).

In some embodiments, in the methods for generating a plurality of immobilized nucleic acid nanostructures of step (c), the rolling circle amplification reaction generates concatemer molecules comprising universal binding sequences that can hybridize/bind to certain primers. In some embodiments, the universal binding sequence (or a complementary sequence thereof) for the forward sequencing primer can hybridize to at least a portion of the forward sequencing primer. In some embodiments, the universal binding sequence (or a complementary sequence thereof) for the reverse sequencing primer can hybridize to at least a portion of the reverse sequencing primer. In some embodiments, the universal binding sequence (or a complementary sequence thereof) for the immobilized first universal surface primer can hybridize to at least a portion of the immobilized first universal surface primer. In some embodiments, the universal binding sequence (or a complementary sequence thereof) for the immobilized second universal surface primer can hybridize to at least a portion of the immobilized second universal surface primer. In some embodiments, the universal binding sequence (or a complementary sequence thereof) for the first soluble amplification primer can hybridize to at least a portion of the first soluble amplification primer. In some embodiments, the universal binding sequence (or a complementary sequence thereof) for the second soluble amplification primer can hybridize to at least a portion of the second soluble amplification primer. In some embodiments, the universal binding sequence (or a complementary sequence thereof) for the soluble compaction oligonucleotide can hybridize to at least a portion of the soluble compaction oligonucleotide.

In some embodiments, in the methods for generating a plurality of immobilized nucleic acid nanostructures of step (c), the plurality of immobilized single stranded nucleic acid concatemer template molecules (e.g., first strand nanostructures) comprise two or more copies of a universal binding sequence (or complementary sequence thereof) for immobilized second sequence surface primers. In some embodiments, individual immobilized single stranded nucleic acid concatemer template molecules are hybridized to an immobilized first universal surface primer, and at least one portion of the individual concatemer template molecule is hybridized to an immobilized second universal surface primer. The immobilized second universal surface primers serve to pin down a portion of the immobilized concatemer template molecules to the support (see FIG. 38 but in this embodiment the immobilized concatemer lacks uracil). In some embodiments, the second universal surface primers include a terminal 3' blocking group that renders them non-extendible.

In some embodiments, in the methods for generating a plurality of immobilized nucleic acid nanostructures of step (c), the method can further comprise removing the single-stranded covalently closed circular nucleic acid library molecules from the concatemer template molecules with at least one washing step which is conducted under a condition suitable to retain the single stranded nucleic acid concatemer template molecules where individual concatemer template molecules are operably joined to an immobilized first universal surface primer.

In some embodiments, the methods for generating a plurality of immobilized nucleic acid nanostructures, further comprise step (d): sequencing the plurality of immobilized concatemer template molecules (e.g., first strand nanostructures) thereby generating a plurality of extended forward sequencing primer strands. The sequencing of step (d) comprises contacting the plurality of immobilized concatemer template molecules with a plurality of soluble forward sequencing primers under a condition suitable to hybridize at least one forward sequencing primer to at least one of the forward sequencing primer binding sites/sequences of the immobilized concatemer template molecules, and conducting forward sequencing reactions to generate a plurality of forward sequencing products using one or more types of sequencing polymerases, a plurality of nucleotide reagents, and the hybridized first forward sequencing primers (FIG. 49). In some embodiments, the plurality of nucleotide reagents is detectably labeled. In some embodiments, the sequencing of step (d) further comprises detecting and imaging the plurality of forward sequencing products.

In some embodiments, in the sequencing of step (d) further comprises contacting the plurality of immobilized concatemer template molecules with a plurality of compaction oligonucleotides under a condition suitable to hybridize the 5' end of at least one compaction oligonucleotide to a first portion of a concatemer molecule and to hybridize the second binding region of the same compaction oligonucleotide to a second portion of the same concatemer molecule.

In some embodiments, in the sequencing of step (d), the soluble forward sequencing primers comprise 3' OH extendible ends. In some embodiments, the soluble forward sequencing primers comprise a 3' blocking moiety which can be removed to generate a 3' OH extendible end. In some embodiments, the soluble forward sequencing primers lack a nucleotide having a scissile moiety. The forward sequencing reactions can generate a plurality of extended forward sequencing primer strands. In some embodiments, individual immobilized concatemer template molecules have multiple copies of the forward sequencing primer binding sites, wherein each forward sequencing primer binding site is capable of hybridizing to a first forward sequencing primer. Individual forward sequencing primer binding sites in a given immobilized concatemer template molecule can be hybridized to a forward sequencing primer and can undergo a sequencing reaction. Individual immobilized concatemer template molecules can undergo two or more sequence reactions, where each sequencing reaction is initiated from a first forward sequencing primer that is hybridized to a forward sequencing primer binding site (e.g., see FIG. 49).

In some embodiments, in the sequencing of step (d), the nucleotide reagent comprises a plurality of nucleotides, a plurality of nucleotide analogs, or a plurality of multivalent molecules.

In some embodiments, in the sequencing of step (d), individual nucleotides in the plurality of nucleotides comprises an aromatic base, a five carbon sugar and at least one phosphate group. In some embodiments, the plurality of nucleotides is unlabeled. In some embodiments, at least one nucleotide in the plurality can be labeled with a detectable reporter moiety (e.g., fluorophore). In some embodiments, the sequencing of step (d) further comprises contacting the plurality of immobilized concatemer template molecules with a catalytic or non-catalytic divalent cation. An exemplary catalytic divalent cation comprises magnesium and/or manganese which promotes polymerase-catalyzed nucleotide incorporation. An exemplary non-catalytic divalent cation comprises strontium, barium and/or calcium which inhibits polymerase-catalyzed nucleotide incorporation.

In some embodiments, in the sequencing of step (d), individual nucleotide analogs in the plurality comprise an aromatic base, a five carbon sugar having a 3' chain terminating moiety that inhibits polymerase-catalyzed nucleotide incorporation, and at least one phosphate group. In some embodiments, the plurality of nucleotide analogs is unlabeled. In some embodiments, at least one nucleotide analog in the plurality can be labeled with a detectable reporter moiety (e.g., fluorophore). In some embodiments, the sequencing of step (d) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (d), individual multivalent molecules in the plurality comprise (1) a core; and (2) a plurality of nucleotide arms each comprising (i) a core attachment moiety, (ii) a spacer, (iii) a linker, and (iv) a nucleotide unit, wherein the core is attached to the plurality of nucleotide arms, wherein the spacer is attached to the linker, wherein the linker is attached to the nucleotide unit (e.g., see FIGS. 56-59). In some embodiments, the nucleotide unit comprises an aromatic base, a five carbon sugar and at least one phosphate group, and the linker is attached to the nucleotide unit through the base. In some embodiments, the plurality of multivalent molecules is unlabeled. In some embodiments, at least one multivalent molecule in the plurality is labeled with a detectable reporter moiety (e.g., fluorophore). In some embodiments, the sequencing of step (d) further comprises contacting the plurality of immobilized concatemer template molecules with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (d), the method further comprises forming at least one avidity complex, by contacting the plurality of immobilized concatemer template molecules (e.g., first strand nanostructures) with a plurality of soluble forward sequencing primers, a plurality of sequencing polymerases, and a plurality of multivalent molecules, to form a plurality of binding complexes including at least a first and second binding complex, wherein (i) the first binding complex comprises a first forward sequencing primer, a first sequencing polymerase, and a first multivalent molecule, bound to a first portion of the immobilized concatemer template molecule (e.g., first strand nanostructure) thereby forming the first binding complex, wherein a first nucleotide unit of the multivalent molecule is bound to the first polymerase, and (ii) the second binding complex comprises a second forward sequencing primer, a second sequencing polymerase, and the first multivalent molecule, bound to a second portion of the same immobilized concatemer template molecule thereby forming the second binding complex, wherein a second nucleotide unit of the multivalent molecule is bound to the second polymerase, and wherein the first and second binding complexes which include the same multivalent molecule forms an avidity complex. In some embodiments, the multivalent molecule is unlabeled or is labeled with a detectable reporter moiety.

In some embodiments, in the rolling circle amplification reaction of step (c), the first binding region of the compaction oligonucleotides hybridize to the concatemer template molecules at a first portion that does not interfere (e.g., little or no overlap) with hybridizing the soluble forward sequencing primers to the forward sequencing primer binding sites of the plurality of concatemer template molecules of step (d).

In some embodiments, in the rolling circle amplification reaction of step (c), the second binding region of the compaction oligonucleotides hybridize to the concatemer template molecules at a second portion that does not interfere (e.g., little or no overlap) with hybridizing the soluble forward sequencing primers to the forward sequencing primer binding sites of the plurality of concatemer template molecules of step (d).

In some embodiments, the methods for generating a plurality of immobilized nucleic acid nanostructures, further comprise step (e): retaining the plurality of immobilized concatemer template molecules (e.g., first strand nanostructures) and replacing the plurality of extended forward sequencing primer strands with a plurality of forward extension strands that are hybridized to the retained immobilized nucleic acid concatemer template molecules. The plurality of extended forward sequencing primer strands can be removed and replaced with a plurality of forward extension strands by conducting a primer extension reaction to synthesize a second strand, a forward extension strand (see FIGS. 50-51). The primer extension reaction can be conducted with a plurality of compaction oligonucleotides to collapse/fold the forward extension strands generate second strand nanostructures. One skilled in the art will recognize that there are several methods for conducting the primer extension reaction, some of which are described below.

In some embodiments, the primer extension reaction of step (e) comprises contacting at least one extended forward sequencing primer strand with (1) a plurality of strand displacing polymerases, (2) a plurality of nucleotides, and (3) a plurality of compaction oligonucleotides, in the absence of soluble amplification primers, under a condition suitable to conduct a strand displacing primer extension reaction using the at least one extended forward sequencing primers strand to initiate the primer extension reaction thereby generating a forward extension strand that is covalently joined to the extended forward sequencing primers strand, wherein the forward extension strand is hybridized to the immobilized concatemer template molecule (e.g., first strand nanostructures) (e.g., FIG. 50). For example, one of the extended forward sequencing primer strands can serve as a primer for the strand displacing polymerase. The strand displacing polymerase can extend the extended forward sequencing primer strand, and displace downstream extended forward sequencing primer strands while synthesizing an extended strand that replaces the downstream extended forward sequencing primer strands. The newly extended strand is covalently joined to an extended forward sequencing primer strand. The immobilized concatemer template molecules are retained. The plurality of nucleotides in the primer extension reaction of step (e) lack a nucleotide having a scissile moiety. The strand displacing primer extension reaction can also generate a plurality of partially displaced forward extension strands that are hybridized to the immobilized concatemer template molecules to form a plurality of immobilized amplicons (FIG. 51). The strand displacing primer extension reaction can also generate a plurality of detached forward extension strands that are not hybridized to the immobilized concatemer template molecules (FIG. 51). The primer extension reaction can include a plurality of compaction oligonucleotides to generate forward extension strands that form nanostructures (e.g., second strand nanostructures). Individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of the forward extension strand and the compaction oligonucleotide having a 3' region that can hybridize to a second portion of the forward extension strand (e.g., the same forward extension strand or a different forward extension strand). A compaction oligonucleotide can hybridize to a forward extension strand and a partially displaced forward extension strand (FIG. 52). A compaction oligonucleotide can hybridize to a partially displaced forward extension strand and a detached forward extension strand thereby immobilizing the detached forward extension strand (FIG. 52). A compaction oligonucleotide can hybridize to a forward extension strand (e.g., which is hybridized to an immobilized concatemer template molecule) and a detached forward extension strand thereby immobilizing the detached forward extension strand (FIG. 52). In some embodiments, the plurality of compaction oligonucleotides of step (e) comprises any of the sequences as described in step (c) above.

Inclusion of compaction oligonucleotides in the primer extension reaction of step (e) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, step (e) comprises: (i) removing the plurality of extended forward sequencing primer strand while retaining the immobilized concatemer template molecules; and (ii) contacting the plurality of retained immobilized concatemer molecules with (1) a plurality of soluble amplification primers, (2) a plurality of nucleotides, (3) a plurality of strand displacing polymerases, and (4) a plurality of compaction oligonucleotides, under a condition suitable to hybridize the plurality of soluble amplification primers to the plurality of retained immobilized concatemer template molecules and suitable for conducting a strand displacing primer extension reaction thereby generating different types of forward extension strands, including a plurality of forward extension strands that are hybridized along at least a portion of their length to the immobilized concatemer template molecules, a plurality of partially displaced forward extension strands that are partially hybridized to the immobilized concatemer template molecules to form a plurality of immobilized amplicons, and a plurality of detached forward extension strands that are not hybridized to the immobilized concatemer template molecules. The soluble amplification primers hybridize with the amplification primer binding sequence in the retained immobilized concatemer molecules. The immobilized concatemer template molecules are thus retained. The plurality of nucleotides in the primer extension reaction of step (e) can lack a nucleotide having a scissile moiety.

The strand displacing primer extension reaction can include a plurality of compaction oligonucleotides that bind to the forward extension strands to form nanostructures (e.g., second strand nanostructures). Upon binding to at least one compaction oligonucleotide, individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of a forward extension strand and the compaction oligonucleotide having a 3' region that can hybridize to a second portion of a forward extension strand (e.g., the same forward extension strand or a different forward extension strand). A compaction oligonucleotide can hybridize to a forward extension strand and a partially displaced forward extension strand. A compaction oligonucleotide can hybridize to a partially displaced forward extension strand and a detached forward extension strand thereby immobilizing the detached forward extension strand. A compaction oligonucleotide can hybridize to a forward extension strand (e.g., which is hybridized to an immobilized concatemer template molecule) and a detached forward extension strand thereby immobilizing the detached forward extension strand.

Inclusion of compaction oligonucleotides in the primer extension reaction of step (e) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, step (e) comprises: (i) removing the plurality of extended forward sequencing primer strand while retaining the immobilized concatemer template molecules; and (ii) contacting the plurality of retained immobilized concatemer molecules with (1) a plurality of soluble forward sequencing primers, (2) a plurality of nucleotides, (3) a plurality of strand displacing polymerases, and (4) a plurality of compaction oligonucleotides, under a condition suitable to hybridize the plurality of soluble forward sequencing primers to the plurality of retained immobilized concatemer template molecules and suitable for conducting a strand displacing primer extension reaction thereby generating different types of forward extension strands, including a plurality of forward extension strands that are hybridized along at least a portion of their length to the immobilized concatemer template molecules, a plurality of partially displaced forward extension strands that are partially hybridized to the immobilized concatemer template molecules to form a plurality of immobilized amplicons, and a plurality of detached forward extension strands that are not hybridized to the immobilized concatemer template molecules. The soluble forward sequencing primers hybridize with the forward sequencing primer binding sequence in the retained immobilized concatemer molecules. The immobilized concatemer template molecules are thus retained. The plurality of nucleotides in the primer extension reaction of step (e) can lack a nucleotide having a scissile moiety.

The strand displacing primer extension reaction can include a plurality of compaction oligonucleotides that bind to the forward extension strands to form nanostructures (e.g., second strand nanostructures). Upon binding to at least one compaction oligonucleotide, individual forward extension strands can collapse into a nanostructure having a more compact size and/or shape compared to a forward extension strand generated from a primer extension reaction conducted without compaction oligonucleotides. In some embodiments, individual compaction oligonucleotides comprise a single-stranded linear oligonucleotide having a 5' region that can hybridize to a first portion of a forward extension strand and the compaction oligonucleotide having a 3' region that can hybridize to a second portion of a forward extension strand (e.g., the same forward extension strand or a different forward extension strand). A compaction oligonucleotide can hybridize to a forward extension strand and a partially displaced forward extension strand. A compaction oligonucleotide can hybridize to a partially displaced forward extension strand and a detached forward extension strand thereby immobilizing the detached forward extension strand. A compaction oligonucleotide can hybridize to a forward extension strand (e.g., which is hybridized to an immobilized concatemer template molecule) and a detached forward extension strand thereby immobilizing the detached forward extension strand.

Inclusion of compaction oligonucleotides in the primer extension reaction of step (e) can improve FWHM (full width half maximum) of a spot image of the nanostructure. The spot image can be represented as a Gaussian spot and the size can be measured as a FWHM. A smaller spot size as indicated by a smaller FWHM typically correlates with an improved image of the spot. In some embodiments, the FWHM of a nanostructure spot can be about 10 μm or smaller.

In some embodiments, in any embodiment of step (e) described above, the plurality of strand displacing polymerases comprises phi29 DNA polymerase, large fragment of Bst DNA polymerase, large fragment of Bsu DNA polymerase (exo-), Bca DNA polymerase (exo-), Klenow fragment of E. coli DNA polymerase, T5 polymerase, M-MuLV reverse transcriptase, HIV viral reverse transcriptase, Deep Vent DNA polymerase and KOD DNA polymerase. The phi29 DNA polymerase can be wild type phi29 DNA polymerase (e.g., MagniPhi from Expedeon™), or variant EquiPhi29 DNA polymerase (e.g., from Thermo Fisher Scientific™), or chimeric QualiPhi DNA polymerase (e.g., from 4basebio™).

In some embodiments, in any embodiment of step (e) described above, the condition suitable to hybridize the plurality of soluble forward sequencing primers to the plurality of retained immobilized single stranded nucleic acid concatemer template molecules, or the condition suitable to hybridize the plurality of soluble amplification primers to the plurality of retained immobilized single stranded nucleic acid concatemer template molecules, comprises hybridizing the retained immobilized concatemer template molecules with the soluble forward sequencing primers in the presence of a primer extension polymerase, a plurality of nucleotides, and a high efficiency hybridization buffer. In some embodiment, the high efficiency hybridization buffer comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In some embodiments, in any embodiment of step (e) described above, the plurality of extended forward sequencing primer strands can be removed from the immobilized concatemer template molecules (e.g., first strand nanostructures) using an enzyme or a chemical reagent. For example, the plurality of extended forward sequencing primer strands can be enzymatically degraded using a 5' to 3' double-stranded DNA exonuclease, including T7 exonuclease (e.g., from New England Biolabs™, catalog #M0263S). In some embodiments, the plurality of extended forward sequencing primer strands can be removed with a temperature that favors nucleic acid denaturation.

In some embodiments, in any embodiment of step (e) described above, a denaturation reagent can be used to remove the plurality of extended forward sequencing primer strands, wherein the denaturation reagent comprises any one or any combination of compounds such as formamide, acetonitrile, guanidinium chloride and/or a buffering agent (e.g., Tris-HCl, MES, HEPES, or the like).

In some embodiments, in any embodiment of step (e) described above, the plurality of extended forward sequencing primer strands can be removed using an elevated temperature (e.g., heat) with or without a nucleic acid denaturation reagent. The plurality of extended forward sequencing primer strands can be subjected to a temperature of about 45-50° C., or about 50-60° C., or about 60-70° C., or about 70-80° C., or about 80-90° C., or about 90-95° C., or higher temperatures, or any range therebetween.

In some embodiments, in any embodiment of step (e) described above, the plurality of extended forward sequencing primer strands can be removed using 100% formamide at a temperature of about 65° C. for about 3 minutes, and washing with a reagent comprising about 50 mM NaCl or equivalent ionic strength and having a pH of about 6.5-8.5.

In some embodiments, in any embodiment of step (e) described above, the primer extension polymerase comprises a high fidelity polymerase. In some embodiments, the primer extension polymerase of step (e) comprises a DNA polymerase capable of catalyzing a primer extension reaction using a uracil-containing template molecule (e.g., a uracil-tolerant polymerase). Exemplary polymerases include, but are not limited to, Q5U Hot Start high-fidelity DNA polymerase (e.g., catalog #M0515S from New England Biolabs™) Taq DNA polymerase, One Taq DNA polymerase (e.g., mixture of Taq and Deep Vent DNA polymerases, catalog #M0480S from New England Biolabs™), LongAmp Taq DNA polymerase (e.g., catalog #M0323S from New England Biolabs™), Epimark Hot Start Taq DNA polymerase (e.g., catalog #M0490S from New England Biolabs), Bst DNA polymerase (e.g., large fragment, catalog #M0275S from New England Biolabs™), Bsu DNA polymerase (e.g., large fragment, catalog #M0330S from New England Biolabs™), Phi29 DNA polymerase (e.g., catalog #M0269S from New England Biolabs™), E. coli DNA polymerase (e.g., catalog #M0209S from New England Biolabs™), Therminator DNA polymerase (e.g., catalog #M0261S from New England Biolabs™), Vent DNA polymerase and Deep Vent DNA polymerase.

In some embodiments, the methods for generating a plurality of immobilized nucleic acid nanostructures, further comprise step (f): sequencing the plurality of immobilized partially displaced forward extension strands thereby generating a first plurality of extended reverse sequencing primer strands. In some embodiments, step (f) further comprises sequencing the plurality of immobilized detached forward extension strands thereby generating a second plurality of extended reverse sequencing primer strands. In some embodiments, individual immobilized partially displaced forward extension strands have two or more extended reverse sequencing primer strands hybridized thereon (FIG. 53). In some embodiments, individual immobilized detached forward extension strands have two or more extended reverse sequencing primer strands hybridized thereon (FIG. 53).

In some embodiments, the sequencing of step (f) comprises contacting the plurality of immobilized partially displaced forward extension strands (e.g., that are hybridized to the immobilized concatemer template molecules), and contacting the plurality of immobilized detached forward extension strands, with a plurality of soluble reverse sequencing primers under a condition suitable to hybridize the reverse sequencing primers to the reverse sequencing primer binding site of the forward extension strands (FIG. 53). The sequencing of step (f) comprises conducting sequencing reactions using the hybridized reverse sequencing primers wherein the reverse sequencing reactions generates a plurality of extended reverse sequencing primer strands (FIG. 53). The plurality of first extended reverse sequencing primer strands is hybridized to an immobilized partially displaced forward extension strand. The plurality of second extended reverse sequencing primer strands is hybridized to an immobilized detached forward extension strand. The first binding region of the compaction oligonucleotide hybridizes to a first portion of the immobilized concatemer molecule, and the second binding region of the compaction oligonucleotide hybridizes to a second portion of the concatemer molecule which causes the concatemer molecule to collapse or fold into a nucleic acid nanostructure.

During the sequencing of step (f), the immobilized partially displaced forward extension strands remain hybridized to the retained immobilized concatemer template molecules. During the sequencing of step (f), the immobilized detached forward extension strands remain hybridized to the immobilized partially displaced forward extension strands.

In some embodiments, the sequencing of step (f) comprises contacting the plurality of hybridized reverse sequencing primers with (1) a plurality of sequencing polymerases, (2) a plurality of nucleotide reagents, and (3) a plurality of compaction oligonucleotides, under a condition suitable for conducting reverse sequencing reactions to generate a plurality of reverse sequencing products (FIG. 53). In some embodiments, the plurality of nucleotide reagents is detectably labeled. In some embodiments, the sequencing of step (f) further comprises detecting and imaging the plurality of reverse sequencing products. In some embodiments, the plurality of compaction oligonucleotides of step (f) comprises any of the sequences as described in step (c) above.

In some embodiments, the sequencing of step (f) comprises contacting the plurality of immobilized forward extension strands with a plurality of compaction oligonucleotides, under a condition suitable to hybridize the 5' end of at least one compaction oligonucleotide to a first portion of a forward extension strand and to hybridize the second binding region of the same compaction oligonucleotide to a second portion of the same forward extension strand. The immobilized forward extension strands can include the immobilized partially displaced forward extension strands and the immobilized detached forward extension strands.

In some embodiments, the sequencing of step (f) further comprises contacting the plurality of immobilized forward extension strands with a plurality of compaction oligonucleotides, under a condition suitable to hybridize the 5' end of at least one compaction oligonucleotide to an immobilized partially displaced forward extension strand and to hybridize the second binding region of the same compaction oligonucleotide to an immobilized detached forward extension strand. The immobilized forward extension strands can include the immobilized partially displaced forward extension strands and the of immobilized detached forward extension strands.

In some embodiments, in the sequencing of step (f), the soluble reverse sequencing primers comprise 3' OH extendible ends. In some embodiments, the soluble reverse sequencing primers comprise a 3' blocking moiety which can be removed to generate a 3' OH extendible end. In some embodiments, the soluble reverse sequencing primers lack a nucleotide having a scissile moiety. The reverse sequencing reactions can generate a plurality of extended reverse sequencing primer strands. In some embodiments, individual immobilized forward extension strands have multiple copies of the reverse sequencing primer binding sites/sequences, wherein each reverse sequencing primer binding site is capable of hybridizing to a reverse sequencing primer. Individual reverse sequencing primer binding sites in a given immobilized forward extension strand can be hybridized to a reverse sequencing primer and can undergo a sequencing reaction. Individual immobilized forward extension strands can undergo two or more reverse sequencing reactions, where each sequencing reaction is initiated from a reverse sequencing primer that is hybridized to a reverse sequencing primer binding site (e.g., see FIG. 53).

In some embodiments, in the sequencing of step (f), the nucleotide reagent comprises a plurality of nucleotides, a plurality of nucleotide analogs, or a plurality of multivalent molecules.

In some embodiments, in the sequencing of step (f), individual nucleotides in the plurality of nucleotides comprises an aromatic base, a five carbon sugar and at least one phosphate group. In some embodiments, the plurality of nucleotides is unlabeled. In some embodiments, at least one nucleotide in the plurality can be labeled with a detectable reporter moiety (e.g., fluorophore). In some embodiments, the sequencing of step (f) further comprises contacting the plurality of immobilized forward extension strands with a catalytic or non-catalytic divalent cation. An exemplary catalytic divalent cation can comprise magnesium and/or manganese which promotes polymerase-catalyzed nucleotide incorporation. An exemplary non-catalytic divalent cation can comprise strontium, barium and/or calcium which inhibits polymerase-catalyzed nucleotide incorporation.

In some embodiments, in the sequencing of step (f), individual nucleotide analogs in the plurality comprise an aromatic base, a five carbon sugar having a 3' chain terminating moiety that inhibits polymerase-catalyzed nucleotide incorporation, and at least one phosphate group. In some embodiments, the plurality of nucleotide analogs is unlabeled. In some embodiments, at least one nucleotide analog in the plurality can be labeled with a detectable reporter moiety (e.g., fluorophore). In some embodiments, the sequencing of step (f) further comprises contacting the plurality of immobilized forward extension strands with a catalytic or non-catalytic divalent cation. An exemplary catalytic divalent cation comprises magnesium and/or manganese which promotes polymerase-catalyzed nucleotide incorporation. An exemplary non-catalytic divalent cation comprises strontium, barium and/or calcium which inhibits polymerase-catalyzed nucleotide incorporation.

In some embodiments, in the sequencing of step (f), individual multivalent molecules in the plurality comprise (1) a core; and (2) a plurality of nucleotide arms each comprising (i) a core attachment moiety, (ii) a spacer, (iii) a linker, and (iv) a nucleotide unit, wherein the core is attached to the plurality of nucleotide arms, wherein the spacer is attached to the linker, wherein the linker is attached to the nucleotide unit (e.g., see FIGS. 56-59). In some embodiments, the nucleotide unit comprises an aromatic base, a five carbon sugar and at least one phosphate group, and the linker is attached to the nucleotide unit through the base. In some embodiments, the plurality of multivalent molecules is unlabeled. In some embodiments, at least one multivalent molecule in the plurality is labeled with a detectable reporter moiety (e.g., fluorophore). In some embodiments, the sequencing of step (f) further comprises contacting the plurality of immobilized forward extension strands with a catalytic or non-catalytic divalent cation. An exemplary catalytic divalent cation comprises magnesium and/or manganese which promotes polymerase-catalyzed nucleotide incorporation. An exemplary non-catalytic divalent cation comprises strontium, barium and/or calcium which inhibits polymerase-catalyzed nucleotide incorporation.

In some embodiments, in the sequencing of step (f), the method further comprises forming at least one avidity complex, by contacting the plurality of immobilized forward extension strands (e.g., second strand nanostructures) with a plurality of soluble reverse sequencing primers, a plurality of sequencing polymerases, and a plurality of multivalent molecules, to form a plurality of binding complexes including at least a first and second binding complex, wherein (i) the first binding complex comprises a first reverse sequencing primer, a first sequencing polymerase, and a first multivalent molecule, bound to a first portion of the immobilized forward extension strand (e.g., second strand nanostructure) thereby forming the first binding complex, wherein a first nucleotide unit of the multivalent molecule is bound to the first polymerase, and (ii) the second binding complex comprises a second reverse sequencing primer, a second sequencing polymerase, and the first multivalent molecule, bound to a second portion of the same immobilized forward extension strand thereby forming the second binding complex, wherein a second nucleotide unit of the multivalent molecule is bound to the second polymerase, and wherein the first and second binding complexes which include the same multivalent molecule forms an avidity complex. In some embodiments, the multivalent molecule is unlabeled or is labeled with a detectable reporter moiety.

In some embodiments, in any of the primer extension reactions of step (e), the second binding region of the compaction oligonucleotides hybridize to any of the immobilized forward extension strands at a second portion that does not interfere (e.g., little or no overlap) with hybridizing the reverse sequencing primers to the reverse sequencing primer binding sites of the plurality of immobilized forward extension strands of step (f).

In some embodiments, in the methods for generating a plurality of immobilized nucleic acid nanostructures, the compaction oligonucleotides of steps (c), (d), (e) and (f), comprise single stranded oligonucleotides comprising DNA, RNA, or a combination of DNA and RNA. The compaction oligonucleotides can be any length, including 20-150 nucleotides, or 30-100 nucleotides, or 40-80 nucleotides in length, or any range therebetween.

In some embodiments, the compaction oligonucleotide comprises a first binding region and a second binding region, and optionally an intervening linker between the first binding and second binding regions. The intervening linker can be any length, for example about 2-20 nucleotides in length. The intervening linker can comprise a homopolymer having consecutive identical bases (e.g., AAA, GGG, CCC, TTT or UUU). The intervening linker can comprise a non-homopolymer sequence.

The first binding region of the compaction oligonucleotides can be wholly complementary or partially complementary along its length to a first portion of a concatemer molecule. The second binding region of the compaction oligonucleotides can be wholly complementary or partially complementary along its length to a second portion of a concatemer molecule. The first binding region of the compaction oligonucleotides can hybridize to a first universal sequence portion of a concatemer molecule having a sequence of any one of SEQ ID NOs:157-176 (see Table 2). The second binding region of the compaction oligonucleotides can hybridize to a second universal sequence portion of a concatemer molecule having a sequence of any one of SEQ ID NOs:157-176 (see Table 2). The first binding and second binding regions of the compaction oligonucleotide can hybridize to the concatemer to pull together distal portions of the concatemer causing compaction of the concatemer to form a nanostructure.

In some embodiments, the methods for generating a plurality of immobilized nucleic acid nanostructures further comprise positioning a cellular biological sample on the immobilized nanostructures after step (b). For example, the cellular biological sample can be placed on the immobilized nucleic acid nanostructures after step (b) and prior to step (c).

In some embodiments, the cellular biological sample comprises a single cell, a plurality of cells, a tissue, an organ, an organism, or a section from any of these cellular biological samples. The cellular biological sample can comprise a sample that is fresh, frozen, fresh-frozen, or archived (e.g., formalin-fixed paraffin-embedded; FFPE). The cellular biological sample can be embedded in a matrix material. The cellular biological sample can be stained, de-stained or non-stained. The cellular biological sample can be permeabilized to permit the nucleic acids within the cellular sample to migrate from the cell(s) to the plurality of immobilized nanostructures.

In some embodiments, in step (f), the condition suitable to hybridize the reverse sequencing primers to the reverse sequencing primer binding sequences of the retained forward extension strands comprises contacting the plurality of soluble reverse sequencing primers and the retained forward extension strands with a high efficiency hybridization buffer. In some embodiments, the high efficiency hybridization buffer comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In an alternative embodiment, the sequencing of step (f) comprises using the immobilized surface primer as a sequencing primer and conducting sequencing reactions to generate a plurality of reverse sequencing strands.

In some embodiments, at least one washing step can be conducted after any of steps (a)-(f). The washing step can be conducted with a wash buffer comprising a pH buffering agent, a metal chelating agent, a salt, and a detergent.

In some embodiments, the pH buffering compound in the wash buffer comprises any one or any combination of two or more of Tris, Tris-HCl, Tricine, Bicine, Bis-Tris propane, HEPES, MES, MOPS, MOPSO, BES, TES, CAPS, TAPS, TAPSO, ACES, PIPES, ethanolamine (a.k.a 2-amino methanol; MEA), a citrate compound, a citrate mixture, NaOH and/or KOH. In some embodiments, the pH buffering agent can be present in the wash buffer at a concentration of about 1-100 mM, or about 10-50 mM, or about 10-25 mM. In some embodiments, the pH of the pH buffering agent which is present in any of the reagents described here in can be adjusted to a pH of about 4-9, or a pH of about 5-9, or a pH of about 5-8.

In some embodiments, the metal chelating agent in the wash buffer comprises EDTA (ethylenediaminetetraacetic acid), EGTA (ethylene glycol tetraacetic acid), HEDTA (hydroxyethylethylenediaminetriacetic acid), DPTA (diethylene triamine pentaacetic acid), NTA (N,N-bis(carboxymethyl)glycine), citrate anhydrous, sodium citrate, calcium citrate, ammonium citrate, ammonium bicitrate, citric acid, potassium citrate, or magnesium citrate. In some embodiments, the wash buffer comprises a chelating agent at a concentration of about 0.01-50 mM, or about 0.1-20 mM, or about 0.2-10 mM, or any range therebetween.

In some embodiments, the salt in the wash buffer comprises NaCl, KCl, $NH_2SO_4$ or potassium glutamate. In some embodiments, the detergent comprises an ionic detergent such as SDS (sodium dodecyl sulfate). The wash buffer can include a monovalent salt at a concentration of about 25-500 mM, or about 50-250 mM, or about 100-200 mM, or any range therebetween.

In some embodiments, the detergent in the wash buffer comprises a non-ionic detergent such as Triton X-100, Tween 20, Tween 80 or Nonidet P-40. In some embodiments, the detergent comprises a zwitterionic detergent such as CHAPS (3-[(3-cholamidopropyl)dimethylammonio]-1-propanesulfonate) or N-Dodecyl-N,N-dimethyl-3-amonio-1-propanesulfate (DetX). In some embodiments, the detergent comprises LDS (lithium dodecyl sulfate), sodium taurodeoxycholate, sodium taurocholate, sodium glycocholate, sodium deoxycholate or sodium cholate. In some embodiments, the detergent is included in the wash buffer at a concentration of about 0.01-0.05%, or about 0.05-0.1%, or about 0.1-0.15%, or about 0.15-0.2%, or about 0.2-0.25%, or any range therebetween.

In some embodiments, the methods for generating a plurality of immobilized nucleic acid nanostructures using an in-solution rolling circle amplification reaction, the methods comprise: step (a) conducting in-solution RCA; step (b) distributing the RCA onto a support; step (c) continuing the RCA on the support; and step (d) forward sequencing. In some embodiments, the methods do not include steps (e)-(f). For example, the methods do not include: synthesis of second strand nanostructures (step (e)); and reverse sequencing (step (f)).

In some embodiments, the methods for generating a plurality of immobilized nucleic acid nanostructures using an in-solution rolling circle amplification reaction, the methods comprise: step (a) conducting in-solution RCA; step (b) distributing the RCA onto a support; and step (c) continuing the RCA on the support. In some embodiments, the methods do not include steps (d)-(f). For example, the methods do not include: forward sequencing (step (d)); synthesis of second strand nanostructures (step (e)); and reverse sequencing (step (f)).

Methods for Sequencing

The present disclosure provides methods for sequencing any of the immobilized nucleic acid nanostructures described herein. Any of the methods described herein for conducting rolling circle amplification reaction with compaction oligonucleotides can be used to generate a plurality of nucleic acid nanostructures immobilized to a support, and the immobilized nanostructures can be subjected to sequencing reactions. In some embodiments, the sequencing reactions employ detectably labeled nucleotide analogs. In some embodiments, the sequencing reactions employ a two-stage sequencing reaction comprising binding detectably labeled multivalent molecules, and incorporating nucleotide analogs. In some embodiments, the sequencing reactions employ non-labeled nucleotide analogs. The terms concatemer molecule, nanostructure and template molecule is used interchangeably.

Figure 16A:
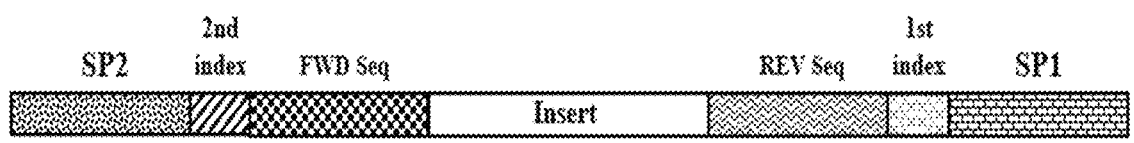
FIG. 16A is a schematic showing an exemplary linear library molecule comprising: a second surface primer binding site (e.g., SP2; surface pinning primer binding site); a second index sequence; a first sequencing primer binding site (e.g., forward sequencing primer binding site); a sequence-of-interest (e.g., insert); a second sequencing primer binding site (e.g., reverse sequencing primer binding site); a first index sequence; and a first surface primer binding site (e.g., SP1; a capture primer binding site). In some embodiments, the linear library molecule shown in FIG. 16A is one polynucleotide unit of a concatemer having two or more tandem copies of the polynucleotide unit, wherein each polynucleotide unit comprises a sequence-of-interest and at least one universal adaptor sequence.
Figure 16B:
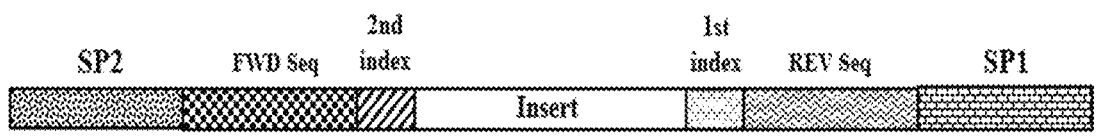
FIG. 16B is a schematic showing an exemplary linear library molecule comprising: a second surface primer binding site (e.g., SP2; surface pinning primer binding site); a first sequencing primer binding site (e.g., forward sequencing primer binding site); a second index sequence; a sequence-of-interest (e.g., insert); a first index sequence; a second sequencing primer binding site (e.g., reverse sequencing primer binding site); and a first surface primer binding site (e.g., SP1; a capture primer binding site). In some embodiments, the linear library molecule shown in FIG. 16B is one polynucleotide unit of a concatemer having two or more tandem copies of the polynucleotide unit, wherein each polynucleotide unit comprises a sequence-of-interest and at least one universal adaptor sequence.

In some embodiments, any of the rolling circle amplification reaction described herein (e.g., RCA conducted on-support or in-solution) can be used to generate immobilized concatemers each containing tandem repeat units of the sequence-of-interest and any adaptor sequences present in the covalently closed circular library molecules. For example, the tandem repeat unit comprises: (i) a first left universal adaptor sequence having a binding sequence for a first surface primer, (ii) a second left universal adaptor sequence having a binding sequence for a first sequencing primer, (iii) a sequence-of-interest, (iv) a second right universal adaptor sequence having a binding sequence for a second sequencing primer, (v) a first right universal adaptor sequence having a binding sequence for a second surface primer, and (vii) a first left index sequence and/or a first right index sequence (e.g., see FIGS. 16A and 16B). In some embodiments, the tandem repeat unit further comprises a first left unique identification sequence and/or a first right unique identification sequence.

Inclusion of one or more compaction oligonucleotides during the RCA reaction can promote folding and/or collapsing the concatemer into a nanostructure having a compact size and/or shape. An increase in the number of tandem repeat units in a given nanostructure increases the number of sites along the nanostructure for hybridizing to multiple sequencing primers (e.g., sequencing primers having a universal sequence) which serve as multiple initiation sites for polymerase-catalyzed sequencing reactions. When the sequencing reaction employs detectably labeled nucleotides and/or detectably labeled multivalent molecules (e.g., having nucleotide units), the signals emitted by the nucleotides or nucleotide units that participate in the parallel sequencing reactions along the nanostructure yields an increased signal intensity for each nanostructure. Multiple portions of a given nanostructure can be simultaneously sequenced. Furthermore, a plurality of binding complexes can form along a particular nanostructure molecule, each binding complex comprising a sequencing polymerase bound to a multivalent molecule wherein the plurality of binding complexes remains stable without dissociation resulting in increased persistence time which increases signal intensity and reduces imaging time.

Methods for Sequencing Using Nucleotide Analogs

The present disclosure provides methods for sequencing any of the immobilized nucleic acid nanostructures described herein, the methods comprising step (a): contacting a sequencing polymerase to (i) a nucleic acid nanostructure and (ii) a nucleic acid sequencing primer, wherein the contacting is conducted under a condition suitable to form a complexed polymerase by binding the sequencing polymerase to the nucleic acid nanostructure which is hybridized to the nucleic acid primer, wherein the nucleic acid nanostructure hybridized to the nucleic acid primer forms the nucleic acid duplex. In some embodiments, the sequencing polymerase comprises a recombinant mutant sequencing polymerase that can bind and incorporate nucleotide analogs. In some embodiments, the sequencing primer comprises a 3' extendible end.

In some embodiments, in the methods for sequencing nucleic acid nanostructures, the sequencing primer comprises a 3' extendible end or a 3' non-extendible end. In some embodiments, the plurality of nucleic acid nanostructures comprises amplified template molecules (e.g., clonally amplified template molecules). Individual nanostructures in the plurality comprise at least two copies of a polynucleotide unit arranged in tandem. In some embodiments, each polynucleotide unit comprises a sequence-of-interest and at least one universal adaptor sequence. In some embodiments, different immobilized nanostructures comprise the same target sequence of interest or different target sequences of interest. In some embodiments, binding individual nanostructures with a plurality of sequencing polymerases and a plurality of sequencing primers generates a plurality of complexed polymerases along the nanostructure. In some embodiments, the plurality of nucleic acid nanostructures is immobilized to $10^2$-$10^{15}$ different sites on a support. In some embodiments, the plurality of nanostructures on the support are immobilized to pre-determined or to random sites on the support. In some embodiments, the plurality of immobilized nanostructures is in fluid communication with each other to permit flowing a solution of reagents (e.g., enzymes including sequencing polymerases, multivalent molecules, nucleotides, and/or divalent cations) onto the support so that the plurality of complexed polymerases on the nanostructures are reacted with the solution of reagents in a massively parallel manner.

In some embodiments, the methods for sequencing further comprise step (b): contacting the sequencing polymerase with a plurality of nucleotide analogs under a condition suitable for binding at least one nucleotide analog to the sequencing polymerase which is bound to the nucleic acid duplex and suitable for polymerase-catalyzed nucleotide incorporation. In some embodiments, the sequencing polymerase is contacted with the plurality of nucleotide analogs in the presence of at least one catalytic cation comprising magnesium and/or manganese. In some embodiments, individual nucleotide analogs comprise a chain terminating moiety at the sugar 2' or 3' position. In some embodiments, the chain terminating moiety is removable from the sugar 2' or 3' position to convert the chain terminating moiety to an OH or H group. In some embodiments, the plurality of nucleotide analogs comprises at least one nucleotide that lacks a chain terminating moiety. In some embodiments, at least one nucleotide analog is labeled with a detectable reporter moiety (e.g., fluorophore).

In some embodiments, the methods for sequencing further comprise step (c): incorporating at least one nucleotide into the 3' end of the extendible primer under a condition suitable for incorporating the at least one nucleotide. In some embodiments, the suitable conditions for nucleotide binding the polymerase and for incorporation the nucleotide can be the same or different. In some embodiments, conditions suitable for incorporating the nucleotide comprise inclusion of at least one catalytic cation comprising magnesium and/or manganese. In some embodiments, the at least one nucleotide binds the sequencing polymerase and incorporates into the 3' end of the extendible primer. In some embodiments, the incorporating the nucleotide into the 3' end of the primer in step (c) comprises a primer extension reaction.

In some embodiments, the methods for sequencing further comprise step (d): removing the chain terminating moiety from the incorporated nucleotide when step (c) is conducted with a plurality of nucleotide analogs having a 2' and/or 3' chain terminating moiety. Removing the chain terminating moiety can convert the chain terminating moiety to an extendible 3'OH group. In some embodiments, step (d) further comprises removing the detectable reporter moiety from the incorporated nucleotide when step (c) is conducted with a plurality of nucleotide analogs that are labeled with a detectable reporter moiety.

In some embodiments, the methods for sequencing further comprise step (e): repeating steps (b), (c) and (d) at least once.

In some embodiments, the plurality of nucleotides comprises a plurality of nucleotides labeled with detectable reporter moiety. The detectable reporter moiety comprises a fluorophore. In some embodiments, the fluorophore is attached to the nucleotide base. In some embodiments, the fluorophore is attached to the nucleotide base with a linker which is cleavable/removable from the base. In some embodiments, at least one of the nucleotides in the plurality is not labeled with a detectable reporter moiety. In some embodiments, a particular detectable reporter moiety (e.g., fluorophore) that is attached to the nucleotide can correspond to the nucleotide base (e.g., dATP, dGTP, dCTP, dTTP or dUTP) to permit detection and identification of the nucleotide base. In some embodiments, the method further comprises detecting the at least one incorporated nucleotide at step (c). In some embodiments, the method further comprises identifying the at least one incorporated nucleotide at step (c). In some embodiments, the sequence of the nucleic acid nanostructure can be determined by detecting and identifying the nucleotide analog that binds the sequencing polymerase, thereby determining the sequence of the nanostructure. In some embodiments, the sequence of the nanostructure can be determined by detecting and identifying the nucleotide analog that incorporates into the 3' end of the sequencing primer, thereby determining the sequence of the nucleic acid nanostructure.

Two-Stage Methods for Nucleic Acid Sequencing

The present disclosure provides a two-stage method for sequencing any of the immobilized nucleic acid nanostructures described herein. In some embodiments, the first stage generally comprises binding multivalent molecules to complexed polymerases to form multivalent-complexed polymerases, and detecting the multivalent-complexed polymerases.

In some embodiments, the first stage comprises step (a): contacting a plurality of a first sequencing polymerase to (i) a plurality of nucleic acid nanostructures and (ii) a plurality of nucleic acid sequencing primers, wherein the contacting is conducted under a condition suitable to bind the plurality of first sequencing polymerases to the plurality of nucleic acid nanostructures and the plurality of nucleic acid primers thereby forming a plurality of first complexed polymerases each comprising a first sequencing polymerase bound to a nucleic acid duplex wherein the nucleic acid duplex comprises a nucleic acid nanostructure hybridized to a nucleic acid primer. In some embodiments, the first polymerase comprises a recombinant mutant sequencing polymerase. In some embodiments, the sequencing primer comprises a 3' extendible end.

In some embodiments, in the methods for sequencing nucleic acid nanostructures, the sequencing primer comprises a 3' extendible end or a 3' non-extendible end. In some embodiments, the plurality of nucleic acid nanostructures comprises amplified template molecules (e.g., clonally amplified template molecules). Individual nanostructures in the plurality comprise at least two copies of a polynucleotide unit arranged in tandem. In some embodiments, each polynucleotide unit comprises a sequence-of-interest and at least one universal adaptor sequence. In some embodiments, different immobilized nanostructures comprise the same target sequence of interest or different target sequences of interest. In some embodiments, binding individual nanostructures with a plurality of sequencing polymerases and a plurality of sequencing primers generates a plurality of complexed polymerases along the nanostructure. In some embodiments, the plurality of nucleic acid nanostructures is immobilized to $10^2$-$10^{15}$ different sites on a support. In some embodiments, the plurality of nanostructures on the support are immobilized to pre-determined or to random sites on the support. In some embodiments, the plurality of immobilized nanostructures is in fluid communication with each other to permit flowing a solution of reagents (e.g., enzymes including sequencing polymerases, multivalent molecules, nucleotides, and/or divalent cations) onto the support so that the plurality of complexed polymerases on the nanostructures are reacted with the solution of reagents in a massively parallel manner.

In some embodiments, the methods for sequencing further comprise step (b): contacting the plurality of first complexed polymerases with a plurality of multivalent molecules to form a plurality of multivalent-complexed polymerases (e.g., binding complexes). In some embodiments, individual multivalent molecules in the plurality of multivalent molecules comprise a core attached to multiple nucleotide arms and each nucleotide arm is attached to a nucleotide (e.g., nucleotide unit) (e.g., FIGS. 55A-C, FIGS. 56-58). In some embodiments, the contacting of step (b) is conducted under a condition suitable for binding complementary nucleotide units of the multivalent molecules to at least two of the plurality of first complexed polymerases thereby forming a plurality of multivalent-complexed polymerases. In some embodiments, the condition is suitable for inhibiting polymerase-catalyzed incorporation of the complementary nucleotide units into the primers of the plurality of multivalent-complexed polymerases. In some embodiments, the plurality of multivalent molecules comprises at least one multivalent molecule having multiple nucleotide arms (e.g., FIGS. 55A-C, FIGS. 56-58) each attached with a nucleotide analog (e.g., nucleotide analog unit), where the nucleotide analog includes a chain terminating moiety at the sugar 2' and/or 3' position. In some embodiments, the plurality of multivalent molecules comprises at least one multivalent molecule comprising multiple nucleotide arms each attached with a nucleotide unit that lacks a chain terminating moiety. In some embodiments, at least one of the multivalent molecules in the plurality of multivalent molecules is labeled with a detectable reporter moiety. In some embodiments, the labeled multivalent molecules comprise a detectable reporter moiety attached to the core, linker and/or nucleotide unit of the multivalent molecules. In some embodiments, the detectable reporter moiety comprises a fluorophore. In some embodiments, the contacting of step (b) is conducted in the presence of at least one non-catalytic cation comprising strontium, barium and/or calcium.

In some embodiments, contacting the plurality of first complexed polymerases with a plurality of multivalent molecules to form a plurality of multivalent-complexed polymerases of step (b) forms a plurality of avidity complexes along a nucleic acid nanostructure, where the plurality of avidity complexes can be detected, and the identity of the bound nucleotide unit can be identified.

In some embodiments, the methods for sequencing further comprise step (c): detecting the plurality of multivalent-complexed polymerases. In some embodiments, the detecting includes detecting the multivalent molecules that are bound to the complexed polymerases, where the complementary nucleotide units of the multivalent molecules are bound to the primers, but incorporation of the complementary nucleotide units is inhibited. In some embodiments, the multivalent molecules are labeled with a detectable reporter moiety to permit detection.

In some embodiments, the methods for sequencing further comprise step (d): identifying the nucleo-base of the complementary nucleotide units that are bound to the plurality of first complexed polymerases, thereby determining the sequence of the nucleic acid nanostructure. In some embodiments, the multivalent molecules are labeled with a detectable reporter moiety that corresponds to the particular nucleotide units attached to the nucleotide arms to permit identification of the complementary nucleotide units (e.g. nucleotide base adenine, guanine, cytosine, thymine or uracil) that are bound to the plurality of first complexed polymerases.

In some embodiments, the methods for sequencing further comprise step (e): dissociating the plurality of multivalent-complexed polymerases and removing the plurality of first sequencing polymerases and their bound multivalent molecules, and retaining the plurality of nucleic acid duplexes.

In some embodiments, the second stage of the two-stage sequencing method generally comprises nucleotide incorporation.

In some embodiments, the methods for sequencing further comprises step (f): contacting the plurality of the retained nucleic acid duplexes of step (e) with a plurality of second sequencing polymerases, wherein the contacting is conducted under a condition suitable for binding the plurality of second sequencing polymerases to the plurality of the retained nucleic acid duplexes, thereby forming a plurality of second complexed polymerases each comprising a second sequencing polymerase bound to a nucleic acid duplex. In some embodiments, the second sequencing polymerase comprises a recombinant mutant sequencing polymerase.

In some embodiments, the plurality of first sequencing polymerases of step (a) has an amino acid sequence that is 100% identical to the amino acid sequence as the plurality of the second sequencing polymerases of step (f). In some embodiments, the plurality of first sequencing polymerases of step (a) has an amino acid sequence that differs from the amino acid sequence of the plurality of the second sequencing polymerases of step (f).

In some embodiments, the methods for sequencing further comprise step (g): contacting the plurality of second complexed polymerases with a plurality of nucleotides, wherein the contacting is conducted under a condition suitable for binding complementary nucleotides from the plurality of nucleotides to at least two of the second complexed polymerases thereby forming a plurality of nucleotide-complexed polymerases. In some embodiments, the contacting of step (g) is conducted under a condition that is suitable for promoting polymerase-catalyzed incorporation of the bound complementary nucleotides into the primers of the nucleotide-complexed polymerases thereby forming a plurality of nucleotide-complexed polymerases. In some embodiments, the incorporating the nucleotide into the 3' end of the primer in step (g) comprises a primer extension reaction. In some embodiments, the contacting of step (g) is conducted in the presence of at least one catalytic cation comprising magnesium and/or manganese. In some embodiments, the plurality of nucleotides comprises canonical nucleotides (e.g., non-analog nucleotides) or nucleotide analogs. In some embodiments, the plurality of nucleotides comprises a 2' and/or 3' chain terminating moiety which is removable or is not removable. In some embodiments, the plurality of nucleotides comprises a plurality of nucleotides labeled with detectable reporter moiety. The detectable reporter moiety comprises a fluorophore. In some embodiments, the fluorophore is attached to the nucleotide base. In some embodiments, the fluorophore is attached to the nucleotide base with a linker which is cleavable/removable from the base or is not removable from the base. In some embodiments, at least one of the nucleotides in the plurality is not labeled with a detectable reporter moiety. In some embodiments, a particular detectable reporter moiety (e.g., fluorophore) that is attached to the nucleotide can correspond to the nucleotide base (e.g., dATP, dGTP, dCTP, dTTP or dUTP) to permit detection and identification of the nucleotide base.

In some embodiments, the methods for sequencing further comprise step (h): detecting the complementary nucleotides which are incorporated into the primers of the nucleotide-complexed polymerases. In some embodiments, the plurality of nucleotides are labeled with a detectable reporter moiety to permit detection. In some embodiments, in the methods for sequencing nucleic acid nanostructures, the detecting of step (h) is omitted.

In some embodiments, the methods for sequencing further comprise step (i): identifying the bases of the complementary nucleotides which are incorporated into the primers of the nucleotide-complexed polymerases. In some embodiments, the identification of the incorporated complementary nucleotides in step (i) can be used to confirm the identity of the complementary nucleotides of the multivalent molecules that are bound to the plurality of first complexed polymerases in step (d). In some embodiments, the identifying of step (i) can be used to determine the sequence of the nucleic acid nanostructures. In some embodiments, in the methods for sequencing nucleic acid nanostructures, the identifying of step (i) is omitted.

In some embodiments, the methods for sequencing further comprise step (j): removing the chain terminating moiety from the incorporated nucleotide when step (g) is conducted by contacting the plurality of second complexed polymerases with a plurality of nucleotides that comprise at least one nucleotide having a 2' and/or 3' chain terminating moiety.

In some embodiments, the methods for sequencing further comprise step (k): repeating steps (a)-(j) at least once. In some embodiments, the sequence of the nucleic acid nanostructures can be determined by detecting and identifying the multivalent molecules that bind the sequencing polymerases but do not incorporate into the 3' end of the primer at steps (c) and (d). In some embodiments, the sequence of the nucleic acid nanostructures can be determined (or confirmed) by detecting and identifying the nucleotide that incorporates into the 3' end of the primer at steps (h) and (i).

In some embodiments, in any of the two-stage methods for sequencing nucleic acid molecules, the binding of the plurality of first complexed polymerases with the plurality of multivalent molecules forms at least one avidity complex, the method comprising the steps: (a) binding a first nucleic acid primer, a first sequencing polymerase, and a first multivalent molecule to a first portion of a nucleic acid nanostructure thereby forming a first binding complex, wherein a first nucleotide unit of the first multivalent molecule binds to the first sequencing polymerase; and (b) binding a second nucleic acid primer, a second sequencing polymerase, and the first multivalent molecule to a second portion of the same nanostructure thereby forming a second binding complex, wherein a second nucleotide unit of the first multivalent molecule binds to the second sequencing polymerase, wherein the first and second binding complexes which include the same multivalent molecule forms an avidity complex. In some embodiments, the first sequencing polymerase comprises any wild type or mutant polymerase described herein. In some embodiments, the second sequencing polymerase comprises any wild type or mutant polymerase described herein. The nucleic acid nanostructure comprises tandem repeat sequences of a sequence of interest and at least one universal sequencing primer binding site. The first and second nucleic acid primers can bind to a sequencing primer binding site along the nucleic acid nanostructure. Exemplary multivalent molecules are shown in FIGS. 55A-C, FIGS. 56-58.

In some embodiments, in any of the two-stage methods for sequencing nucleic acid molecules, wherein the method includes binding the plurality of first complexed polymerases with the plurality of multivalent molecules to form at least one avidity complex, the method comprising the steps: (a) contacting the plurality of sequencing polymerases and the plurality of nucleic acid primers with different portions of a nucleic acid nanostructure to form at least first and second complexed polymerases on the same nanostructure; (b) contacting a plurality of multivalent molecules to the at least first and second complexed polymerases on the same nucleic acid nanostructure, under conditions suitable to bind a single multivalent molecule from the plurality to the first and second complexed polymerases, wherein at least a first nucleotide unit of the single multivalent molecule is bound to the first complexed polymerase which includes a first primer hybridized to a first portion of the nucleic acid nanostructure thereby forming a first binding complex (e.g., first ternary complex), and wherein at least a second nucleotide unit of the single multivalent molecule is bound to the second complexed polymerase which includes a second primer hybridized to a second portion of the nucleic acid nanostructure thereby forming a second binding complex (e.g., second ternary complex), wherein the contacting is conducted under a condition suitable to inhibit polymerase-catalyzed incorporation of the bound first and second nucleotide units in the first and second binding complexes, and wherein the first and second binding complexes which are bound to the same multivalent molecule forms an avidity complex; and (c) detecting the first and second binding complexes on the same nucleic acid nanostructure, and (d) identifying the first nucleotide unit in the first binding complex thereby determining the sequence of the first portion of the nucleic acid nanostructure, and identifying the second nucleotide unit in the second binding complex thereby determining the sequence of the second portion of the nucleic acid nanostructure. In some embodiments, the plurality of sequencing polymerases comprise any wild type or mutant sequencing polymerase described herein. The nucleic acid nanostructure comprises tandem repeat sequences of a sequence of interest and at least one universal sequencing primer binding site. The plurality of nucleic acid primers can bind to a sequencing primer binding site along the nucleic acid nanostructure. Exemplary multivalent molecules are shown in FIGS. 55A-C, FIGS. 56-59.

Sequencing-by-Binding

The present disclosure provides methods for sequencing any of the immobilized nucleic acid nanostructures described herein, wherein the sequencing methods comprise a sequencing-by-binding (SBB) procedure which employs non-labeled chain-terminating nucleotides. In some embodiments, the sequencing-by-binding (SBB) method comprises the steps of (a) sequentially contacting a primed template molecule (e.g., a nucleic acid nanostructure hybridized with at least one sequencing primer) with at least two separate mixtures under ternary complex stabilizing conditions, wherein the at least two separate mixtures each include a polymerase and a nucleotide, whereby the sequentially contacting results in the primed template molecule being contacted, under the ternary complex stabilizing conditions, with nucleotide cognates for first, second and third base type base types in the template molecule; (b) examining the at least two separate mixtures to determine whether a ternary complex formed; and (c) identifying the next correct nucleotide for the primed template molecule, wherein the next correct nucleotide is identified as a cognate of the first, second or third base type if a ternary complex is detected in step (b), and wherein the next correct nucleotide is imputed to be a nucleotide cognate of a fourth base type based on the absence of a ternary complex in step (b); (d) adding a next correct nucleotide to the primer of the primed template molecule after step (b), thereby producing an extended primer; and (e) repeating steps (a) through (d) at least once on the primed template molecule that comprises the extended primer. Exemplary sequencing-by-binding methods are described, for example and without limitation, in U.S. Pat. Nos. 10,246,744 and 10,731,141 (where the contents of both patents are hereby incorporated by reference in their entireties).

Sequencing Polymerases

The present disclosure provides methods for sequencing nucleic acid molecules, where any of the sequencing methods described herein employ at least one type of sequencing polymerase and a plurality of nucleotides, or employ at least one type of sequencing polymerase and a plurality of nucleotides and a plurality of multivalent molecules. In some embodiments, the sequencing polymerase(s) is/are capable of incorporating a complementary nucleotide opposite a nucleotide in a nucleic acid nanostructure. In some embodiments, the sequencing polymerase(s) is/are capable of binding a complementary nucleotide unit of a multivalent molecule opposite a nucleotide in a nucleic acid nanostructure. In some embodiments, the plurality of sequencing polymerases comprises recombinant mutant polymerases.

Examples of suitable polymerases for use in sequencing with nucleotides and/or multivalent molecules include but are not limited to: Klenow DNA polymerase; *Thermus aquaticus* DNA polymerase I (Taq polymerase); KlenTaq polymerase; *Candidatus* altiarchaeales archaeon; *Candidatus* Hadarchaeum Yellowstonense; Hadesarchaea archaeon; Euryarchaeota archaeon; Thermoplasmata archaeon; *Thermococcus* polymerases such as *Thermococcus litoralis*, bacteriophage T7 DNA polymerase; human alpha, delta and epsilon DNA polymerases; bacteriophage polymerases such as T4, RB69 and phi29 bacteriophage DNA polymerases; *Pyrococcus furiosus* DNA polymerase (Pfu polymerase); *Bacillus subtilis* DNA polymerase III; *E. coli* DNA polymerase III alpha and epsilon; 9 degree N polymerase; reverse transcriptases such as HIV type M or O reverse transcriptases; avian myeloblastosis virus reverse transcriptase; Moloney Murine Leukemia Virus (MMLV) reverse transcriptase; or telomerase. Further non-limiting examples of DNA polymerases include those from various *Archaea* genera, such as, Aeropyrum, Archaeglobus, *Desulfurococcus, Pyrobaculum, Pyrococcus, Pyrolobus, Pyrodictium, Staphylothermus, Stetteria, Sulfolobus, Thermococcus,* and *Vulcanisaeta* and the like or variants thereof, including such polymerases as are known in the art such as 9 degrees N, VENT™, DEEP VENT™, THERMINATOR™, Pfu, KOD, Pfx, Tgo and RB69 polymerases.

Nucleotides

The present disclosure provides methods for sequencing nucleic acid molecules, where any of the sequencing methods described herein employ at least one nucleotide. The nucleotides comprise a base, sugar and at least one phosphate group. In some embodiments, at least one nucleotide in the plurality comprises an aromatic base, a five-carbon sugar (e.g., ribose or deoxyribose), and one or more phosphate groups (e.g., 1-10 phosphate groups). The plurality of nucleotides can comprise at least one type of nucleotide selected from a group consisting of dATP, dGTP, dCTP, dTTP and dUTP. The plurality of nucleotides can comprise at a mixture of any combination of two or more types of nucleotides selected from a group consisting of dATP, dGTP, dCTP, dTTP and/or dUTP. In some embodiments, at least one nucleotide in the plurality is not a nucleotide analog. In some embodiments, at least one nucleotide in the plurality comprises a nucleotide analog.

In some embodiments, in any of the methods for sequencing nucleic acid molecules described herein, at least one nucleotide in the plurality of nucleotides comprise a chain of one, two or three phosphorus atoms where the chain is typically attached to the 5' carbon of the sugar moiety via an ester or phosphoramide linkage. In some embodiments, at least one nucleotide in the plurality is an analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordithioate, and O-methylphosphoroamidite groups.

In some embodiments, in any of the methods for sequencing nucleic acid molecules described herein, at least one nucleotide in the plurality of nucleotides comprises a terminator nucleotide analog having a chain terminating moiety (e.g., blocking moiety) at the sugar 2' position, at the sugar 3' position, or at the sugar 2' and 3' position. In some embodiments, the chain terminating moiety can inhibit polymerase-catalyzed incorporation of a subsequent nucleotide unit or free nucleotide in a nascent strand during a primer extension reaction. In some embodiments, the chain terminating moiety is attached to the 3' sugar hydroxyl position where the sugar comprises a ribose or deoxyribose sugar moiety. In some embodiments, the chain terminating moiety is removable/cleavable from the 3' sugar hydroxyl position to generate a nucleotide having a 3'OH sugar group which is extendible with a subsequent nucleotide in a polymerase-catalyzed nucleotide incorporation reaction. In some embodiments, the chain terminating moiety comprises an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the chain terminating moiety is cleavable/removable from the nucleotide, for example by reacting the chain terminating moiety with a chemical agent, pH change, light or heat. In some embodiments, the chain terminating moieties alkyl, alkenyl, alkynyl and allyl are cleavable with tetrakis(triphenylphosphine)palladium(0) ($Pd(PPh_3)_4$) with piperidine, or with 2,3-Dichloro-5,6-dicyano-1,4-benzo-quinone (DDQ). In some embodiments, the chain terminating moieties aryl and benzyl are cleavable with H2 Pd/C. In some embodiments, the chain terminating moieties amine, amide, keto, isocyanate, phosphate, thio, disulfide is cleavable with phosphine or with a thiol group including beta-mercaptoethanol or dithiothritol (DTT). In some embodiments, the chain terminating moiety carbonate is cleavable with potassium carbonate ($K_2CO_3$) in MeOH, with triethylamine in pyridine, or with Zn in acetic acid (AcOH). In some embodiments, the chain terminating moieties urea and silyl are cleavable with tetrabutylammonium fluoride, pyridine-HF, with ammonium fluoride, or with triethylamine trihydrofluoride.

In some embodiments, in any of the methods for sequencing nucleic acid molecules described herein, at least one nucleotide in the plurality of nucleotides comprises a terminator nucleotide analog having a chain terminating moiety (e.g., blocking moiety) at the sugar 2' position, at the sugar 3' position, or at the sugar 2' and 3' position. In some embodiments, the chain terminating moiety comprises an azide, azido or azidomethyl group. In some embodiments, the chain terminating moiety comprises a 3'-O-azido or 3'-O-azidomethyl group. In some embodiments, the chain terminating moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxypropyl)phosphine (THPP). In some embodiments, the cleaving agent comprises 4-dimethylaminopyridine (4-DMAP).

In some embodiments, in any of the methods for sequencing nucleic acid molecules described herein, the nucleotide comprises a chain terminating moiety which is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, in any of the methods for sequencing nucleic acid molecules described herein, the plurality of nucleotides comprises a plurality of nucleotides labeled with detectable reporter moiety. The detectable reporter moiety comprises a fluorophore. In some embodiments, the fluorophore is attached to the nucleotide base. In some embodiments, the fluorophore is attached to the nucleotide base with a linker which is cleavable/removable from the base. In some embodiments, at least one of the nucleotides in the plurality is not labeled with a detectable reporter moiety. In some embodiments, a particular detectable reporter moiety (e.g., fluorophore) that is attached to the nucleotide can correspond to the nucleotide base (e.g., dATP, dGTP, dCTP, dTTP or dUTP) to permit detection and identification of the nucleotide base.

In some embodiments, in any of the methods for sequencing nucleic acid molecules described herein, the cleavable linker on the nucleotide base comprises a cleavable moiety comprising an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the cleavable linker on the base is cleavable/removable from the base by reacting the cleavable moiety with a chemical agent, pH change, light or heat. In some embodiments, the cleavable moieties alkyl, alkenyl, alkynyl and allyl are cleavable with tetrakis(triphenylphosphine)palladium(0) (Pd(PPh$_3$)$_4$) with piperidine, or with 2,3-Dichloro-5,6-dicyano-1,4-benzo-quinone (DDQ). In some embodiments, the cleavable moieties aryl and benzyl are cleavable with H2 Pd/C. In some embodiments, the cleavable moieties amine, amide, keto, isocyanate, phosphate, thio, disulfide is cleavable with phosphine or with a thiol group including beta-mercaptoethanol or dithiothritol (DTT). In some embodiments, the cleavable moiety carbonate is cleavable with potassium carbonate (K$_2$CO$_3$) in MeOH, with triethylamine in pyridine, or with Zn in acetic acid (AcOH). In some embodiments, the cleavable moieties urea and silyl are cleavable with tetrabutylammonium fluoride, pyridine-HF, with ammonium fluoride, or with triethylamine trihydrofluoride.

In some embodiments, in any of the methods for sequencing nucleic acid molecules described herein, the cleavable linker on the nucleotide base comprises cleavable moiety including an azide, azido or azidomethyl group. In some embodiments, the cleavable moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxypropyl)phosphine (THPP). In some embodiments, the cleaving agent comprises 4-dimethylaminopyridine (4-DMAP).

In some embodiments, in any of the methods for sequencing nucleic acid molecules described herein, the chain terminating moiety (e.g., at the sugar 2' and/or sugar 3' position) and the cleavable linker on the nucleotide base have the same or different cleavable moieties. In some embodiments, the chain terminating moiety (e.g., at the sugar 2' and/or sugar 3' position) and the detectable reporter moiety linked to the base are chemically cleavable/removable with the same chemical agent. In some embodiments, the chain terminating moiety (e.g., at the sugar 2' and/or sugar 3' position) and the detectable reporter moiety linked to the base are chemically cleavable/removable with different chemical agents.

Multivalent Molecules

The present disclosure provides methods for sequencing nucleic acid molecules, where any of the sequencing methods described herein employ at least one multivalent molecule. In some embodiments, the multivalent molecule comprises a plurality of nucleotide arms attached to a core and having any configuration including a starburst, helter skelter, or bottle brush configuration (e.g., FIGS. 55A, B and C). The multivalent molecule comprises: (1) a core; and (2) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit. In some embodiments, the nucleotide unit comprises a base, sugar and at least one phosphate group, and the linker is attached to the nucleotide unit through the base. In some embodiments, the linker comprises an aliphatic chain or an oligo ethylene glycol chain where both linker chains having 2-6 subunits. In some embodiments, the linker also includes an aromatic moiety. An exemplary nucleotide arm is shown in FIG. 59. Exemplary multivalent molecules are shown in FIGS. 55A-C, FIGS. 56-58. An exemplary spacer is shown in FIG. 60 (top) and exemplary linkers are shown in FIG. 60 (bottom) and FIG. 61. Exemplary nucleotides attached to a linker are shown in FIGS. 62A-D. An exemplary biotinylated nucleotide arm is shown in FIG. 63.

In some embodiments, a multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, a multivalent molecule comprises a core attached to multiple nucleotide arms, where each arm includes a nucleotide unit. The nucleotide unit comprises an aromatic base, a five-carbon sugar (e.g., ribose or deoxyribose), and one or more phosphate groups (e.g., 1-10 phosphate groups). The plurality of multivalent molecules can comprise one type of multivalent molecule having one type of nucleotide unit selected from a group consisting of dATP, dGTP, dCTP, dTTP and dUTP. The plurality of multivalent molecules can comprise at a mixture of any combination of two or more types of multivalent molecules, where individual multivalent molecules in the mixture comprise nucleotide units selected from a group consisting of dATP, dGTP, dCTP, dTTP and/or dUTP.

In some embodiments, the nucleotide unit comprises a chain of one, two or three phosphorus atoms where the chain is typically attached to the 5' carbon of the sugar moiety via an ester or phosphoramide linkage. In some embodiments, at least one nucleotide unit is a nucleotide analog having a phosphorus chain in which the phosphorus atoms are linked together with intervening O, S, NH, methylene or ethylene. In some embodiments, the phosphorus atoms in the chain include substituted side groups including 0, S or BH$_3$. In some embodiments, the chain includes phosphate groups substituted with analogs including phosphoramidate, phosphorothioate, phosphordithioate, and O-methylphosphoroamidite groups.

In some embodiments, the multivalent molecule comprises a core attached to multiple nucleotide arms, and wherein individual nucleotide arms comprise a nucleotide unit which is a nucleotide analog having a chain terminating moiety (e.g., blocking moiety) at the sugar 2' position, at the sugar 3' position, or at the sugar 2' and 3' position. In some embodiments, the nucleotide unit comprises a chain terminating moiety (e.g., blocking moiety) at the sugar 2' position, at the sugar 3' position, or at the sugar 2' and 3' position. In some embodiments, the chain terminating moiety can inhibit polymerase-catalyzed incorporation of a subsequent nucleotide unit or free nucleotide in a nascent strand during a primer extension reaction. In some embodiments, the chain terminating moiety is attached to the 3' sugar hydroxyl position where the sugar comprises a ribose or deoxyribose sugar moiety. In some embodiments, the chain terminating moiety is removable/cleavable from the 3' sugar hydroxyl position to generate a nucleotide having a 3'OH sugar group which is extendible with a subsequent nucleotide in a polymerase-catalyzed nucleotide incorporation reaction. In some embodiments, the chain terminating moiety comprises an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the chain terminating moiety is cleavable/removable from the nucleotide unit, for example by reacting the chain terminating moiety with a chemical agent, pH change, light or heat. In some embodiments, the chain terminating moieties alkyl, alkenyl, alkynyl and allyl are cleavable with tetrakis(triphenylphosphine)

palladium(0) (Pd(PPh$_3$)$_4$) with piperidine, or with 2,3-Dichloro-5,6-dicyano-1,4-benzo-quinone (DDQ). In some embodiments, the chain terminating moieties aryl and benzyl are cleavable with H2 Pd/C. In some embodiments, the chain terminating moieties amine, amide, keto, isocyanate, phosphate, thio, and disulfide are cleavable with phosphine or with a thiol group including beta-mercaptoethanol or dithiothritol (DTT). In some embodiments, the chain terminating moiety carbonate is cleavable with potassium carbonate (K$_2$CO$_3$) in MeOH, with triethylamine in pyridine, or with Zn in acetic acid (AcOH). In some embodiments, the chain terminating moieties urea and silyl are cleavable with tetrabutylammonium fluoride, pyridine-HF, with ammonium fluoride, or with triethylamine trihydrofluoride.

In some embodiments, the nucleotide unit comprises a chain terminating moiety (e.g., blocking moiety) at the sugar 2' position, at the sugar 3' position, or at the sugar 2' and 3' position. In some embodiments, the chain terminating moiety comprises an azide, azido or azidomethyl group. In some embodiments, the chain terminating moiety comprises a 3'-O-azido or 3'-O-azidomethyl group. In some embodiments, the chain terminating moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxypropyl)phosphine (THPP). In some embodiments, the cleaving agent comprises 4-dimethylaminopyridine (4-DMAP).

In some embodiments, the nucleotide unit comprising a chain terminating moiety which is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, the multivalent molecule comprises a core attached to multiple nucleotide arms, wherein the nucleotide arms comprise a spacer, linker, and nucleotide unit, and wherein the core, linker and/or nucleotide unit is labeled with detectable reporter moiety. In some embodiments, the detectable reporter moiety comprises a fluorophore. In some embodiments, a particular detectable reporter moiety (e.g., fluorophore) that is attached to the multivalent molecule can correspond to the base (e.g., dATP, dGTP, dCTP, dTTP or dUTP) of the nucleotide unit to permit detection and identification of the nucleotide base.

In some embodiments, at least one nucleotide arm of a multivalent molecule has a nucleotide unit that is attached to a detectable reporter moiety. In some embodiments, the detectable reporter moiety is attached to the nucleotide base. In some embodiments, the detectable reporter moiety comprises a fluorophore. In some embodiments, a particular detectable reporter moiety (e.g., fluorophore) that is attached to the multivalent molecule can correspond to the base (e.g., dATP, dGTP, dCTP, dTTP or dUTP) of the nucleotide unit to permit detection and identification of the nucleotide base.

In some embodiments, the core of a multivalent molecule comprises an avidin-like or streptavidin-like moiety and the core attachment moiety comprises biotin. In some embodiments, the core comprises a streptavidin-type or avidin-type moiety which includes an avidin protein, as well as any derivatives, analogs and other non-native forms of avidin that can bind to at least one biotin moiety. Other forms of avidin moieties include native and recombinant avidin and streptavidin as well as derivatized molecules, e.g. non-glycosylated avidin and truncated streptavidins. For example, avidin moiety includes de-glycosylated forms of avidin, bacterial streptavidin produced by *Streptomyces* (e.g., *Streptomyces avidinii*), as well as derivatized forms, for example, N-acyl avidins, e.g., N-acetyl, N-phthalyl and N-succinyl avidin, and the commercially-available products EXTRAVIDIN™, CAPTAVIDIN™, NEUTRAVIDIN™ and NEUTRALITE AVIDIN™.

In some embodiments, any of the methods for sequencing nucleic acid molecules described herein comprises forming a binding complex, where the binding complex comprises a nucleic acid nanostructure hybridized with a primer which forms a duplex, and a polymerase and a nucleotide which are bound to the duplex. In some embodiments, any of the methods for sequencing nucleic acid molecules described herein comprises forming a binding complex, where the binding complex comprises a nucleic acid nanostructure hybridized with a primer which forms a duplex, and a polymerase and a nucleotide unit of a multivalent molecule which are bound to the duplex. In some embodiments, the binding complex has a persistence time of greater than about 0.1, 0.2, 0.3, 0.4, 0.5, 0.6, 0.7, 0.8, 0.9 or 1 second. The binding complex has a persistence time of greater than about 0.1-0.25 seconds, or about 0.25-0.5 seconds, or about 0.5-0.75 seconds, or about 0.75-1 second, or about 1-2 seconds, or about 2-3 seconds, or about 3-4 second, or about 4-5 seconds, and/or wherein the method is or may be carried out at a temperature of at or above 15° C., at or above 20° C., at or above 25° C., at or above 35° C., at or above 37° C., at or above 42° C. at or above 55° C. at or above 60° C., or at or above 72° C., or at or above 80° C., or within a range defined by any of the foregoing. The binding complex (e.g., ternary complex) remains stable until subjected to a condition that causes dissociation of interactions between any of the polymerase, template molecule (e.g., nucleic acid nanostructure), primer and/or the nucleotide unit or the nucleotide. For example, a dissociating condition comprises contacting the binding complex with any one or any combination of a detergent, EDTA and/or water. In some embodiments, the present disclosure provides said method wherein the binding complex is deposited on, attached to, or hybridized to, a surface showing a contrast to noise ratio in the detecting step of greater than 20. In some embodiments, the present disclosure provides said method wherein the contacting is performed under a condition that stabilizes the binding complex when the nucleotide or nucleotide unit is complementary to a next base of the template nucleic acid, and destabilizes the binding complex when the nucleotide or nucleotide unit is not complementary to the next base of the template nucleic acid.

Persistence Time

The persistence time can be measured, for example, by observing the onset and/or duration of a ternary complex (e.g., a binding complex), such as by observing a signal from a labeled component of the ternary complex. For example, a labeled nucleotide or a labeled multivalent molecule may be present in a ternary complex, thus allowing the signal from the label to be detected during the persistence time of the ternary complex.

It has been observed that different ranges of persistence times are achievable with different salts or ions, showing, for example, that ternary complexes formed in the presence of, for example, magnesium or manganese form more quickly than complexes formed with other ions. It has also been observed that ternary complexes formed in the presence of, for example, strontium or barium, form readily and dissociate completely or with substantial completeness upon withdrawal of strontium or barium, or upon washing with a buffer lacking strontium or barium.

The dissociation of ternary complexes can be controlled by changing the buffer conditions. During a sequencing method, an imaging step can be used to detect and/or identify a nucleotide unit bound to a nucleic acid duplex in a ternary complex. After the imaging step, a buffer with increased salt content can be used to dissociate the ternary complexes such that labeled multivalent molecules can be washed out, providing a means by which signals can be attenuated or terminated, such as in the transition between one sequencing cycle and the next. This dissociation may be achieved, in some embodiments, by washing the complexes with a buffer lacking a necessary metal or cofactor. In some embodiments, a wash buffer may comprise one or more reagents for the purpose of maintaining pH control. In some embodiments, a wash buffer may comprise one or more monovalent cations, such as sodium. In some embodiments, a wash buffer lacks or substantially lacks a divalent cation, for example, having no or substantially no strontium, barium, calcium, magnesium, or manganese. In some embodiments, a wash buffer further comprises a chelating agent, such as, for example, EDTA, EGTA, nitrilotriacetic acid, polyhistidine, imidazole, or the like. In some embodiments, a wash buffer may maintain the pH of the environment at the same level as for the ternary complex. In some embodiments, a wash buffer may raise or lower the pH of the environment relative to the level seen for the ternary complex. In some embodiments, the pH may be within a range from 2-4, 2-7, 5-8, 7-9, 7-10, or lower than 2, or higher than 10, or a range defined by any two of the values provided herein.

Addition of a particular ion may affect the binding of the polymerase to a primed nucleic acid nanostructure, the formation of a ternary complex, the dissociation of a ternary complex, or the incorporation of one or more nucleotides into an elongating nucleic acid such as during a polymerase reaction. In some embodiments, relevant anions may comprise chloride, acetate, gluconate, sulfate, phosphate, or the like. In some embodiments, an ion may be included in a binding buffer including one or more acids, bases, or salts, such as $NiCl_2$, $CoCl_2$, $MgCl_2$, $MnCl_2$, $SrCl_2$, $CaCl_2$, $CaSO_4$, $SrCO_3$, $BaCl_2$ or the like. Representative salts, ions, solutions and conditions may be found in Remington: The Science and Practice of Pharmacy, 20th. Edition, Gennaro, A. R., Ed. (2000), which is hereby incorporated by reference in its entirety, and especially with respect to Chapter 17 and related disclosure of salts, ions, salt solutions, and ionic solutions.

The binding between a nucleic acid nanostructure and a multivalent molecule can be conducted in the presence of a sequencing polymerase that has been rendered catalytically inactive. In some embodiments, the sequencing polymerase has been rendered catalytically inactive by mutation. In some embodiments, the sequencing polymerase has been rendered catalytically inactive by chemical modification. In some embodiments, the sequencing polymerase has been rendered catalytically inactive by the absence of a necessary substrate, ion, or cofactor. In some embodiments, the sequencing polymerase has been rendered catalytically inactive by the absence of magnesium or manganese ions.

The binding between a nucleic acid nanostructure and a multivalent molecule can occur in the presence of a sequencing polymerase wherein the binding solution lacks a catalytic ion such as magnesium or manganese. A catalytic ion can promote polymerase-catalyzed incorporation of a nucleotide or nucleotide unit. Alternatively, the binding between a nucleic acid nanostructure and a multivalent molecule can occur in the presence of a sequencing polymerase wherein the binding solution comprises a non-catalytic ion such strontium, barium or calcium. A non-catalytic ion can inhibit polymerase-catalyzed incorporation of a nucleotide or nucleotide unit.

A non-catalytic divalent cation (e.g., strontium or barium) can promote formation of a stable ternary complex having a polymerase bound to a primed nucleic acid nanostructure and a multivalent molecule (e.g., fluorescently labeled multivalent molecule), and inhibit polymerase-catalyzed incorporation of the nucleotide unit, where the stable ternary complex has a persistence time that permits detection and imaging by fluorescence detection or by other methods known in the art. Unbound polymer-nucleotide conjugates may optionally be washed away prior to detection of the ternary binding complex.

A catalytic divalent cation (e.g., magnesium or manganese) can promote formation of a stable ternary complex having a polymerase bound to a primed nucleic acid nanostructure and a free nucleotide (e.g., fluorescently labeled nucleotide), and promote polymerase-catalyzed incorporation of the nucleotide, where the stable ternary complex has a persistence time that permits detection and imaging by fluorescence detection or by other methods known in the art.

Library Molecules

The pairwise sequencing compositions and methods described herein employ nucleic acid library molecules which typically refers to a population of nucleic acid molecules each comprising a sequence of interest (e.g., insert region) covalently joined to at least one adaptor sequence. Individual library molecules in the population can have an insert sequence that is the same or different insert sequence as other library molecules in the population. Individual library molecules in the population can have an adaptor sequence that is the same (e.g., a universal adaptor sequence) or different (e.g., unique identification sequence) adaptor sequence as other library molecules in the population.

The nucleic acid library molecule comprises DNA, RNA, cDNA or chimeric DNA/RNA. The nucleic acid library molecule can be single-stranded or double-stranded, or can include single-stranded or double-stranded portions. The nucleic acid library molecule can be linear, covalently closed circular, dumbbell, hairpin, or other forms.

The insert region of a nucleic acid library molecule comprises a sequence of interest extracted from any source including a biological sample (e.g., fresh or live sample) such as a single cell, a plurality of cells or tissue. The insert region can be isolated from healthy or diseases cells or tissues. The insert region can be obtained from an archived sample such as a fresh frozen paraffin embedded (FFPE) sample, or from needle biopsies, circulating tumor cells, cell free circulating DNA. Cells or tissues are typically treated with a lysis buffer to release their DNA and RNA, and the desired nucleic acid is separated from non-desired macromolecules such as proteins.

The insert region of a nucleic acid library molecule can be isolated in any form, including chromosomal, genomic (e.g., whole genomic), organellar (e.g., mitochondrial, chloroplast or ribosomal), recombinant molecules, cloned or amplified.

The insert region can be prepared using recombinant nucleic acid technology including but not limited to any combination of vector cloning, transgenic host cell preparation, host cell culturing and/or PCR amplification.

The insert region can be prepared using chemical synthesis procedures using native nucleotides with or without nucleotide analogs or modified nucleotide linkages that confer certain properties, including resistance to enzymatic digestion, or increased thermal stability. Examples of nucleotide analogs and modified nucleotide linkages that inhibit nuclease digestion include phosphorothioate, 2'-O-methyl RNA, inverted dT, and 2' 3' dideoxy-dT. Insert regions that include locked nucleic acids (LNA) have increased thermal stability.

The insert region can be isolated from any organism including viruses, fungi, prokaryotes or eukaryotes. The insert region can be isolated from any organism including human, simian, ape, canine, feline, bovine, equine, murine, porcine, caprine, lupine, ranine, piscine, plant, insect or bacteria. The insert region can be isolated from organisms borne in air, water, soil or food.

The insert region can be isolated from any biological fluid, including without limitation, blood, urine, serum, lymph, tumor, saliva, anal secretions, vaginal secretions, amniotic samples, perspiration, semen, environmental samples or culture samples. The insert region can be isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs.

The insert region can be in fragmented or un-fragmented form. Fragmented insert regions can be obtained by mechanical force or enzymatic fragmentation methods. The fragmented insert regions can be generated using procedures that yield a population of fragments having overlapping sequences or non-overlapping sequences.

Mechanical fragmentation typically generates randomly fragmented nucleic acid molecules. Mechanical fragmentation methods include mechanical shearing such as fluid shear, constant shear and pulsatile shear. Mechanical fragmentation methods also include mechanical stress including sonication, nebulization and acoustic cavitation.

Enzymatic fragmentation procedures can be conducted under conditions suitable to generate randomly or non-randomly fragmented nucleic acid molecules. For example, restriction enzyme digestion can be conducted to completion to generate non-randomly fragmented nucleic acid molecule. Alternatively, partial or incomplete restriction enzyme digestion can be conducted to generate randomly-fragmented nucleic acid molecules. Enzymatic fragmentation using restriction enzymes includes any one or any combination of two or more restriction enzymes selected from a group consisting of type I, type II, type IIs, type IIB, type III, or type IV restriction enzymes. Enzymatic fragmentation includes use of any combination of a nicking restriction endonuclease, endonuclease and/or exonuclease.

Fragments of the insert region can be generated with PCR using sequence-specific primers that hybridize to target regions in genomic DNA samples to generate insert regions having known fragment lengths and sequences.

Targeted genome fragmentation methods using CRISPR/Cas9 can be used to generate fragmented insert regions.

Fragments of the insert portion can also be generated using a transposase-based tagmentation method using NEXTERA (from Epicentre).

The insert region can be single stranded or double stranded. The ends of the double stranded insert region can be blunt-ended, or have a 5' overhang or a 3' overhang end, or any combination thereof. One or both ends of the insert region can be subjected to an enzymatic tailing reaction to generate a non-template poly-A tail by employing a terminal transferase reaction. The ends of the insert region can be compatible for joining to at least one adaptor.

The insert region can be joined at one or both ends to at least one adaptor. Covalent linkage between an insert region and adaptor(s) can be achieved with a DNA or RNA ligase. Exemplary DNA ligases that can ligate double stranded DNA molecules include T4 DNA ligase and T7 DNA ligase. An adaptor sequence can be appended to an insert sequence by PCR using a tailed primer having 5' region carrying an adaptor sequence and a 3' region that is complementary to a portion of the insert sequence. An adaptor sequence can be appended to an insert sequence which is flanked one both sides with first and second adaptor sequences by PCR using a tailed primer having 5' region carrying a third adaptor sequence and a 3' region that is complementary to a portion of the first or second adaptor sequence.

Adaptors comprise DNA or RNA or analogs thereof, or chimeric DNA/RNA. Adaptors can include at least one ribonucleoside residue. Adaptors can be single-stranded, double-stranded, or have single-stranded and/or double-stranded portions.

Adaptors can be configured to be linear, stem-looped, hairpin, or Y-shaped forms. Adaptors can be any length, including 4-100 nucleotides or longer.

Adaptors can have blunt ends, overhang ends, or a combination of both. Overhang ends include 5' overhang and 3' overhang ends. The 5' end of a single-stranded adaptor, or one strand of a double-stranded adaptor, can have a 5' phosphate group or lack a 5' phosphate group. Adaptors can include a 5' tail that does not hybridize to a target polynucleotide (e.g., tailed adaptor), or adaptors can be non-tailed.

An adaptor can include a sequence (e.g., a universal adaptor sequence) that is complementary to at least a portion of a primer, such as an amplification primer, a sequencing primer, an immobilized surface capture primer or a soluble primer.

Adaptors can include a random sequence or degenerate sequence. Adaptors can include at least one inosine residue.

Adaptors can be synthesized to include nucleotide analogs or modified nucleotide linkages that confer certain properties, including resistance to enzymatic degradation, or increased thermal stability. Examples of nucleotide analogs and modified nucleotide linkages that inhibit nuclease digestion include phosphorothioate, 2'-O-methyl RNA, inverted dT, or 2' 3' dideoxy-dT. Adaptors that include locked nucleic acids (LNA) have increased thermal stability. Adaptors can include at least one phosphorothioate, phosphorothiolate and/or phosphoramidate linkage.

Adaptors can include at least one restriction enzyme recognition sequence, including any one or any combination of two or more selected from a group consisting of type I, type II, type III, type IV, type IIs or type IIB.

Adaptors can include a sample barcode sequence which is used to distinguish polynucleotides (e.g., insert sequences) from different sample sources in a multiplex assay. Adaptors can include a unique identification sequence (e.g., a molecular tag, unique molecular index, UMI) that is used to uniquely identify an individual nucleic acid molecule (e.g., insert sequence) to which the adaptor is appended in a population of other nucleic acid molecules joined to other distinguishing unique identification sequence adaptors.

In some embodiments, a single stranded nucleic acid library molecule can serve as a template molecule for sequencing analysis. In some embodiments, a complementary strand of the nucleic acid library molecule can be synthesized, and the complementary strand can serve as a template molecule for sequencing analysis. In some embodiments, a single stranded nucleic acid library molecule can be amplified, and the resulting amplicon strands can serve as template molecules for sequencing analysis. In some embodiments, double-stranded library molecules can be denatured or subjected to enzymatic treatment to generate a single stranded library molecule which can be subjected to binding and/or sequencing analysis.

In some embodiments, a single stranded circular library molecule can be hybridized to an amplification primer (e.g., an immobilized surface primer) and subjected to a primer extension reaction to generate a complementary concatemer molecule, where the concatemer molecule serves as a template molecule for sequencing analysis. The sequencing analysis of the concatemer molecule can generate a complementary strand which can in turn serve as a template molecule for sequencing analysis. In some embodiments, a copy of the complementary strand can serve as a template molecule for sequencing analysis.

Circularization of Library Molecules

There are several methods for generating a plurality of circularized library molecule from a plurality of linear library molecules. In general, linear library molecules comprise an insert sequence flanked at both ends with at least one universal adaptor sequence (e.g., see FIGS. 16A and 16B).

In some embodiments, the ends of single-stranded linear library molecules can undergo intramolecular ligation using a single-stranded ligase (e.g., CircLigase from Epicentre™ or Lucigen™).

In some embodiments, circular DNA molecules can be generated using a protelomerase instead of a nucleic acid ligase. Protelomerase enzymes identifies an enzyme recognition sequence within a nucleic acid molecule, cleaves the enzyme recognition sequence to generate an end having a 5' and 3' exposed cleavage ends, rejoins 5' and 3' cleavage ends of a single exposed end at the enzyme recognition site to form a single linear molecule from the cleaved 5' and 3' ends. When this reaction is performed on both ends of a double-stranded nucleic acid molecule having the enzyme recognition sequence at each end, the result is a circular nucleic acid molecule. An adaptor carrying the enzyme recognition sequence can be joined to both ends of the double-stranded DNA molecule via ligation or PCR using tailed PCR primers. A number of enzymes or enzyme combinations are compatible with this reaction, including a protelomerase. One type of protelomerase is TelN protelomerase, such as that from E. coli phage NI.

In some embodiments, a population of double-stranded linear library molecules can be circularized to generate circular library molecules. In some embodiments, the 5' ends of linear library molecules can be phosphorylated for subsequent enzymatic ligation. For example, a population of linear library molecules can be contacted with an enzyme that catalyzes 5' phosphorylation of the ends of the linear molecules, such as for example T4 polynucleotide kinase. In some embodiments, the population of linear library molecules having blunt ends can be contacted with a ligase enzyme for intramolecular ligation, where the ligase enzyme comprises T3 or T4 DNA ligase. In some embodiments, the population of linear library molecules having overhang ends (e.g., sticky ends) can be contacted with a T7 DNA ligase to generate circular molecules. In some embodiments, the linear library molecules can be reacted with the T4 polynucleotide kinase enzyme and the ligase enzyme either sequentially or simultaneously to generate circular molecules. The non-circular molecules can be degraded using at least one exonuclease enzyme, such as for example T7 exonuclease and/or exonuclease I (e.g., thermolabile exonuclease I).

Figure 19:
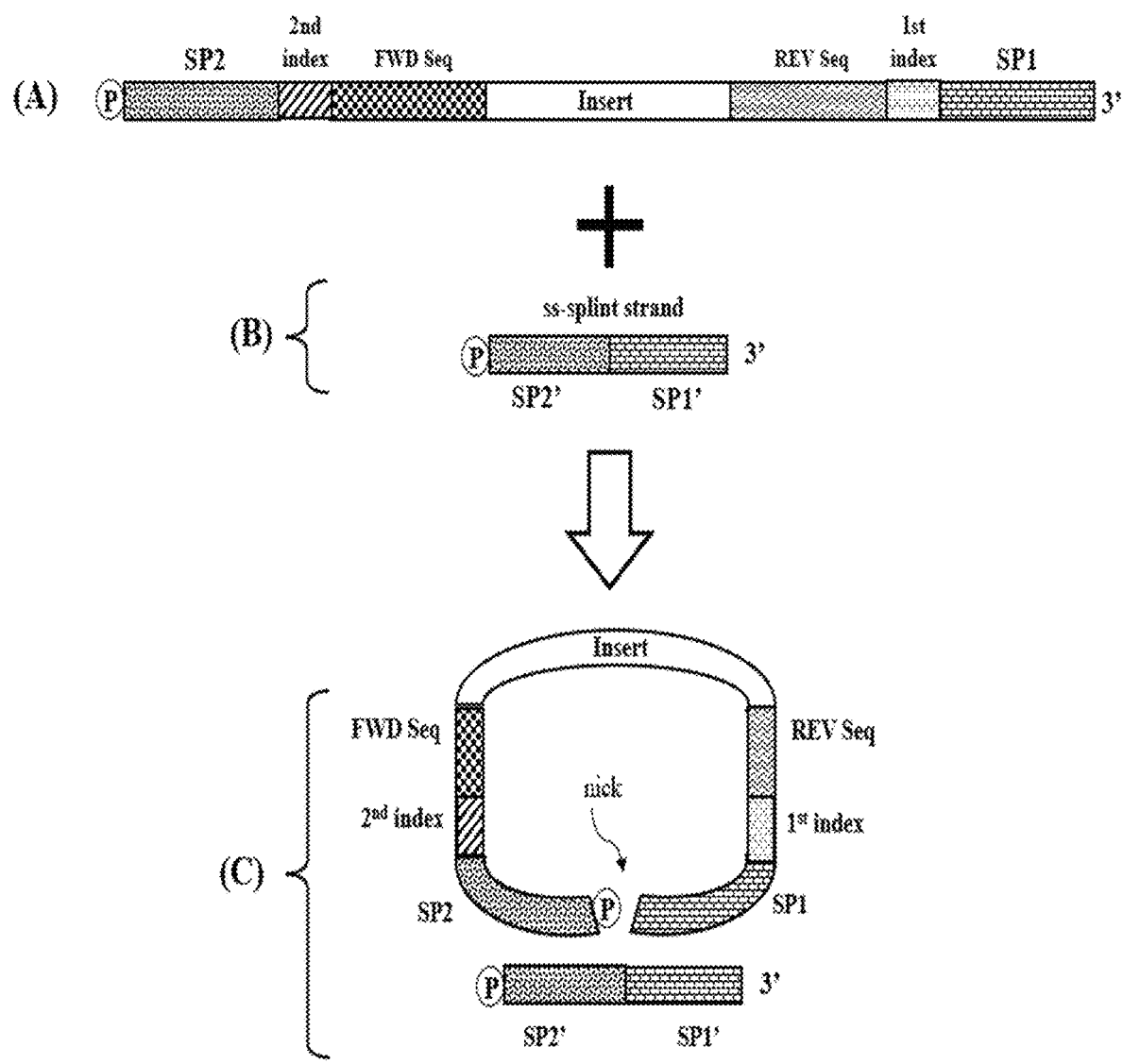
FIG. 19 is a schematic showing an exemplary workflow for circularizing a linear library molecule. The linear library molecule (A) hybridizes with a single-stranded splint molecule (B) thereby circularizing the library molecule to form a library-splint complex (C) with one nick. The library molecule (A) comprises: a second surface primer binding site (e.g., SP2; surface pinning primer binding site); a second index sequence; a first sequencing primer binding site (e.g., forward sequencing primer binding site); a sequence-of-interest (e.g., insert); a second sequencing primer binding site (e.g., reverse sequencing primer binding site); a first index sequence; and a first surface primer binding site (e.g., SP1; a capture primer binding site). The single-stranded splint molecule comprises a first region that hybridizes with a sequence on one end of the linear library molecule, and a second region that hybridizes with a sequence on the other end of the linear library molecule.

In some embodiments, a population of the single stranded linear library molecules can be circularized to generate single stranded circular library molecules using single stranded splint strands. Individual single stranded linear library molecules comprise a sequence of interest (insert sequence) flanked at both ends with at least one universal adaptor sequence. For example, the single stranded linear library molecules comprise the arrangement: 5'-first surface primer binding sequence (SP1); first sequencing primer binding sequence (Seq1); insert sequence (sequence of interest); second sequencing primer binding sequence (Seq2); second surface primer binding sequence (SP2)-3' (e.g., see FIG. 19A). A population of double stranded linear library molecules can be denatured to generate single stranded linear library molecules. The single stranded linear library molecules can be hybridized to single stranded splint strands to generate circular library molecules with a nick (FIGS. 19A, B and C). The single stranded splint strands comprise a first and second region where the first region (SP1') hybridizes with a universal adaptor sequence (SP1) on one end of the linear single stranded library molecule, and the second region (SP2') hybridizes with a universal adaptor sequence (SP2) on the other end of the linear single stranded library molecule (e.g., see FIG. 19B). A single stranded library molecule hybridizes to a single stranded splint strand to generate a library-splint complex having one nick (FIG. 19C). The library-splint complexes can be reacted with T4 polynucleotide kinase and a ligase either sequentially or simultaneously, to (i) phosphorylate the 5' end of the library molecule, the 5' end of the splint strand, and to (ii) close the nick by enzymatic ligation, thereby generating a single stranded covalently closed circular library molecule which is hybridized to the single stranded splint strand (FIGS. 20A, B and C). The ligase comprises T7 DNA ligase, T3 ligase, T4 ligase or Taq ligase. The non-circular molecules and the single stranded splint strands can be degraded using at least one exonuclease enzyme, such as for example T7 exonuclease and/or exonuclease I (e.g., thermolabile exonuclease I).

The non-circular molecules and the splint strands can be degraded using at least one exonuclease enzyme, such as for example T7 exonuclease and/or exonuclease I (e.g., thermolabile exonuclease I). The remaining single stranded circular library molecules can be subjected to a rolling circle amplification reaction, either in-solution or on-support, using the 3' end of the linear first splint strand (FIGS. 20A, B and C). Alternatively, the splint strand can be removed, and the closed circular molecule can be hybridized with a soluble amplification primer which can be used to initiate a rolling circle amplification reaction. In another example, the splint strand can be removed, and the closed circular molecule can be hybridized with an immobilized surface primer on a support and then subjected to a rolling circle amplification reaction.

In some embodiments, a padlock probe workflow can be used to generate single stranded circular molecules from linear library molecules. Typically, in the padlock probe workflow, the arrangement of the sequence of interest (insert sequence) and adaptors in the linear library differs from a standard linear library molecule. In some embodiments, that padlock probe comprises a single-stranded linear oligonucleotide having a 5' portion, an optional internal linker portion, and a 3' portion. The 5' and 3' portions each comprise a portion of a target sequence of interest. The 5' and 3' portions are separately complementary to a target sequence of interest (e.g., a contiguous target sequence of interest), while the linker portion is designed to have little or no complementarity to the target sequence. The 5' and 3' ends of the padlock probe can hybridize to adjacent positions on the target nucleic acid molecule to form an open circularized molecule with a nick between the hybridized 5' and 3' ends. The nick can be ligated to generate a covalently close circular molecule. Alternatively, the 5' and 3' ends of the padlock probe can hybridize to adjacent positions on the target nucleic acid molecule to form an open circularized molecule with a gap between the hybridized 5' and 3' ends. The gap can be subject to a polymerase-mediated filled-in reaction to form a nick, and the nick can be ligated to generate a covalently close circular molecule.

Figure 17:
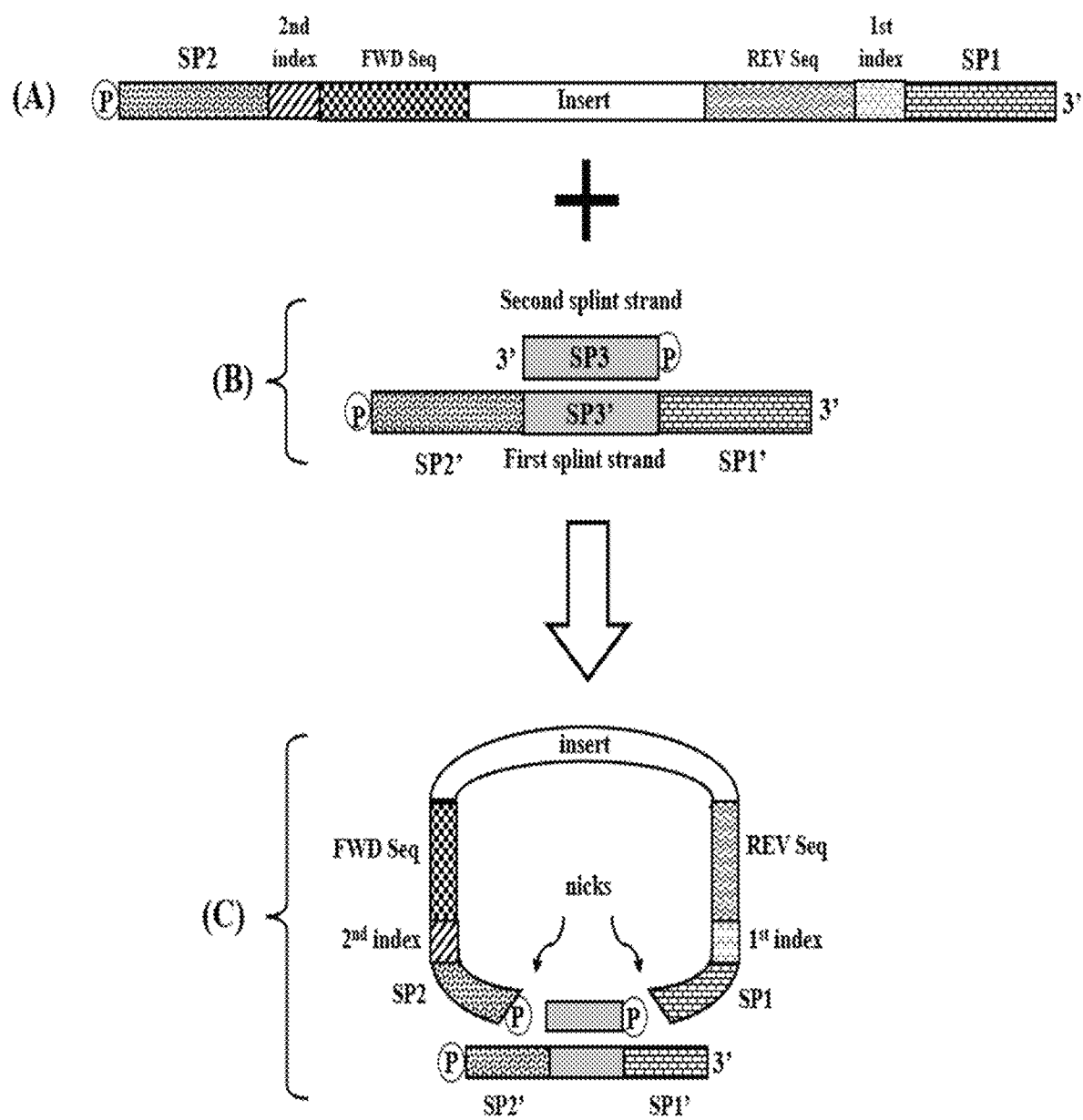
FIG. 17 is a schematic showing an exemplary workflow for circularizing a linear library molecule. The linear library molecule (A) hybridizes with a double-stranded splint molecule (B) thereby circularizing the library molecule to form a library-splint complex (C) with two nicks. The library molecule (A) comprises: a second surface primer binding site (e.g., SP2; surface pinning primer binding site); a second index sequence; a first sequencing primer binding site (e.g., forward sequencing primer binding site); a sequence-of-interest (e.g., insert); a second sequencing primer binding site (e.g., reverse sequencing primer binding site); a first index sequence; and a first surface primer binding site (e.g., SP1; a capture primer binding site). The double-stranded splint molecule comprises a first splint strand (long splint strand) hybridized to a second splint strand (short splint strand). The first splint strand comprises a first region that hybridizes with a sequence on one end of the linear library molecule, and a second region that hybridizes with a sequence on the other end of the linear library molecule. The internal region of the first splint strand hybridizes to the second splint strand.

In some embodiments, a population of the single stranded linear library molecules can be circularized to generate single stranded circular library molecules using double stranded splint molecules (FIGS. 17A, B and C). Individual single stranded linear library molecules comprise a sequence of interest (insert sequence) flanked at both ends with at least one adaptor sequence. For example, the single stranded linear library molecules comprise the arrangement: 5'-first surface primer binding sequence (SP1); first sequencing primer binding sequence (Seq1); insert sequence (sequence of interest); second sequencing primer binding sequence (Seq2); second surface primer binding sequence (SP2)-3' (e.g., see FIG. 17A). A population of double stranded linear library molecules can be denatured to generate single stranded linear library molecules. The single stranded linear library molecules can be hybridized to double stranded splint molecules to generate library-splint complexes comprising circular library molecules with two nicks (e.g., FIGS. 17A, B and C). The double stranded splint molecules comprise double stranded oligonucleotides having a first splint strand (long strand) and a second splint strand (short strand) (e.g., see FIG. 17B). In some embodiments, the first splint strand comprises: (i) a left sequence that hybridizes to a first surface primer binding sequence (SP1'); (ii) an internal portion that hybridizes to the second splint strand; and (iii) a right sequence that hybridizes to a second surface primer binding sequence (SP2') (e.g., see FIG. 17B). The second splint strand comprises at least one sequence that can hybridize to a surface primer. In some embodiments, the second splint strand comprises a sequence (SP3) that can hybridize to a third surface primer binding sequence which differs from the first and second surface primer binding sequences in the library molecules (FIG. 17B). The second splint strand introduces the third surface primer binding sequence into the covalently closed circularized library molecule. In some embodiments, the internal portion of the long splint strand comprises a sequence that can hybridize to the short splint strand. The insert sequence of interest does not hybridize to the short or long splint strands (FIG. 17C).

A single stranded library molecule can hybridize to a double stranded splint molecule to generate a library-splint complex having two nicks (FIGS. 17A, B and C). The first nick is located between the 5' end of the library molecule and the 3' end of the second splint strand. The second nick is located between the 3' end of the library molecule and the 5' end of the second splint strand.

The library-splint complexes can be reacted with T4 polynucleotide kinase and a ligase (e.g., T7 DNA ligase) either sequentially or simultaneously, to (i) phosphorylate the 5' end of the library molecule, the 5' end of the first splint strand, and the 5' end of the second splint strand, and to (ii) close the first and second nicks by enzymatic ligation, thereby generating a single stranded covalently closed circular library molecule which is hybridized to the second splint strand (FIGS. 18A, B and C). The non-circular molecules and the second splint strands can be degraded using at least one exonuclease enzyme, such as for example T7 exonuclease and/or exonuclease I (e.g., thermolabile exonuclease I). The remaining single stranded circular library molecules can be subjected to a rolling circle amplification reaction, either in-solution or on-support, using the 3' end of the linear first splint strand (FIG. 18C). Alternatively, the first splint strand can be removed and the closed circular molecule can be hybridized with a soluble amplification primer which can be used to initiate a rolling circle amplification reaction. In another example, the first splint strand can be removed and the closed circular molecule can be hybridized with an immobilized surface primer on a support and then subjected to a rolling circle amplification reaction.

Supports with Low Non-Specific Binding Coatings

The present disclosure provides compositions and methods for use of a support having a plurality of surface primers immobilized thereon, for preparing any of the immobilized nucleic acid nanostructures described herein. In some embodiments, the support is passivated with a low non-specific binding coating (e.g., FIG. 54). The forward sequencing reaction can be conducted with a plurality of soluble forward sequencing primers and generates a plurality of extended forward sequencing primer strands. The immobilized nanostructure can have two or more extended forward sequencing primer strands hybridized thereon. The surface coatings described herein exhibit very low non-specific binding to reagents typically used for nucleic acid capture, amplification and sequencing workflows, such as dyes, nucleotides, enzymes, and nucleic acid primers. The surface coatings exhibit low background fluorescence signals or high contrast-to-noise (CNR) ratios compared to conventional surface coatings.

In general, the supports comprise a substrate (or support structure), one or more layers of a covalently or non-covalently attached low-binding, chemical modification layers, e.g., silane layers, polymer films, and one or more covalently or non-covalently attached primer sequences that may be used for tethering single-stranded target nucleic acid(s) to the support surface. In some embodiments, the formulation of the surface, e.g., the chemical composition of one or more layers, the coupling chemistry used to cross-link the one or more layers to the support surface and/or to each other, and the total number of layers, may be varied such that non-specific binding of proteins, nucleic acid molecules, and other hybridization and amplification reaction components to the support surface is minimized or reduced relative to a comparable monolayer. Often, the formulation of the surface may be varied such that non-specific hybridization on the support surface is minimized or reduced relative to a comparable monolayer. The formulation of the surface may be varied such that non-specific amplification on the support surface is minimized or reduced relative to a comparable monolayer. The formulation of the surface may be varied such that specific amplification rates and/or yields on the support surface are maximized. Amplification levels suitable for detection are achieved in no more than 2, 3, 4, 5, 6, 7, 8, 9, 10, 15, 20, 25, 30, or more than 30 amplification cycles in some cases disclosed herein.

The substrate or support structure that comprises the one or more chemically-modified layers, e.g., layers of a low non-specific binding polymer, may be independent or integrated into another structure or assembly. For example, in some embodiments, the substrate or support structure may comprise one or more surfaces within an integrated or assembled microfluidic flow cell. The substrate or support structure may comprise one or more surfaces within a microplate format, e.g., the bottom surface of the wells in a microplate. As noted above, in some preferred embodiments, the substrate or support structure comprises the interior surface (such as the lumen surface) of a capillary. In alternate preferred embodiments the substrate or support structure comprises the interior surface (such as the lumen surface) of a capillary etched into a planar chip.

The attachment chemistry used to graft a first chemically-modified layer to a surface will generally be dependent on both the material from which the surface is fabricated and the chemical nature of the layer. In some embodiments, the first layer may be covalently attached to the surface. In some embodiments, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the surface. For example, glass or silicon surfaces may be acid-washed using a Piranha solution (a mixture of sulfuric acid ($H_2SO_4$) and hydrogen peroxide ($H_2O_2$)), base treatment in KOH and NaOH, and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (i.e., comprising a free amino functional group), maleimide-PEG silane, biotin-PEG silane, and the like.

Any of a variety of molecules known to those of skill in the art including, but not limited to, amino acids, peptides, nucleotides, oligonucleotides, other monomers or polymers, or combinations thereof may be used in creating the one or more chemically-modified layers on the surface, where the choice of components used may be varied to alter one or more properties of the surface, e.g., the surface density of functional groups and/or tethered oligonucleotide primers, the hydrophilicity/hydrophobicity of the surface, or the three three-dimensional nature (i.e., "thickness") of the surface. Examples of preferred polymers that may be used to create one or more layers of low non-specific binding material in any of the disclosed surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the surface and/or to cross-link the layers to each other include, but are not limited to, biotin-streptavidin interactions (or variations thereof), his tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

The low non-specific binding surface coating may be applied uniformly across the substrate. Alternately, the surface coating may be patterned, such that the chemical modification layers are confined to one or more discrete regions of the substrate. For example, the surface may be patterned using photolithographic techniques to create an ordered array or random pattern of chemically-modified regions on the surface. Alternately or in combination, the substrate surface may be patterned using, e.g., contact printing and/or ink-jet printing techniques. In some embodiments, an ordered array or random pattern of chemically-modified regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions.

In order to achieve low nonspecific binding surfaces, hydrophilic polymers may be nonspecifically adsorbed or covalently grafted to the surface. Typically, passivation is performed utilizing poly(ethylene glycol) (PEG, also known as polyethylene oxide (PEO) or polyoxyethylene) or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some embodiments, two or more layers of a hydrophilic polymer, e.g., a linear polymer, branched polymer, or multi-branched polymer, may be deposited on the surface. In some embodiments, two or more layers may be covalently coupled to each other or internally cross-linked to improve the stability of the resulting surface. In some embodiments, oligonucleotide primers with different base sequences and base modifications (or other biomolecules, e.g., enzymes or antibodies) may be tethered to the resulting surface layer at various surface densities. In some embodiments, for example, both surface functional group density and oligonucleotide concentration may be varied to target a certain primer density range. Additionally, primer density can be controlled by diluting oligonucleotide with other molecules that carry the same functional group. For example, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure the primer density, fluorescently-labeled primers may be tethered to the surface and a fluorescence reading then compared with that for a dye solution of known concentration.

In order to scale primer surface density and add additional dimensionality to hydrophilic or amphoteric surfaces, surfaces comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some embodiments, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some embodiments, high primer density materials may be constructed in solution and subsequently layered onto the surface in multiple steps.

As noted, the low non-specific binding coatings of the present disclosure exhibit reduced non-specific binding of proteins, nucleic acids, and other components of the hybridization and/or amplification formulation used for solid-phase nucleic acid amplification. The degree of non-specific binding exhibited by a given support surface may be assessed either qualitatively or quantitatively. For example, in some embodiments, exposure of the surface to fluorescent dyes (e.g., cyanine dyes such as Cy3, or Cy5, etc., fluoresceins, coumarins, rhodamines, etc. or other dyes disclosed herein), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some embodiments, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under a condition where fluorescence signal is linearly related (or related in a predictable manner) to the number of fluorophores on the support surface (e.g., under a condition where signal saturation and/or self-quenching of the fluorophore is not an issue) and suitable calibration standards are used. In some embodiments, other techniques known to those of skill in the art, for example, radioisotope labeling and counting methods may be used for quantitative assessment of the degree to which non-specific binding is exhibited by the different support surface formulations of the present disclosure.

Some surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. Some surfaces disclosed herein exhibit a ratio of specific to nonspecific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

As noted, in some embodiments, the degree of non-specific binding exhibited by the disclosed low-binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some embodiments, the label may comprise a fluorescent label. In some embodiments, the label may comprise a radioisotope. In some embodiments, the label may comprise any other detectable label known to one of skill in the art. In some embodiments, the degree of non-specific binding exhibited by a given support surface formulation may thus be assessed in terms of the number of non-specifically bound protein molecules (or other molecules) per unit area. In some embodiments, the low-binding supports of the present disclosure may exhibit non-specific protein binding (or non-specific binding of other specified molecules, (e.g., cyanine dyes such as Cy3, or Cy5, etc., fluoresceins, coumarins, rhodamines, etc. or other dyes disclosed herein)) of less than 0.001 molecule per $\mu m^2$, less than 0.01 molecule per $\mu m^2$, less than 0.1 molecule per $\mu m^2$, less than 0.25 molecule per $\mu m^2$, less than 0.5 molecule per $\mu m^2$, less than 1 molecule per $\mu m^2$, less than 10 molecules per $\mu m^2$, less than 100 molecules per $\mu m^2$, or less than 1,000 molecules per $\mu m^2$. Those of skill in the art will realize that a given support surface of the present disclosure may exhibit non-specific binding falling anywhere within this range, for example, of less than 86 molecules per $\mu m^2$. For example, some modified surfaces disclosed herein exhibit nonspecific protein binding of less than 0.5 molecule/$\mu m^2$ following contact with a 1 $\mu M$ solution of Cy3 labeled streptavidin (GE Amersham™) in phosphate buffered saline (PBS) buffer for 15 minutes, followed by 3 rinses with deionized water. Some modified surfaces disclosed herein exhibit nonspecific binding of Cy3 dye molecules of less than 0.25 molecules per $\mu m^2$. In independent nonspecific binding assays, 1 $\mu M$ labeled Cy3 SA (ThermoFisher™), 1 $\mu M$ Cy5 SA dye (ThermoFisher™), 10 $\mu M$ Aminoallyl-dUTP—ATTO-647N (Jena Biosciences™), 10 $\mu M$ Aminoallyl-dUTP—ATTO-Rho11 (Jena Biosciences™) 10 $\mu M$ Aminoallyl-dUTP—ATTO-Rho11 (Jena Biosciences™), 10 $\mu M$ 7-Propargylamino-7-deaza-dGTP—Cy5 (Jena Biosciences™, and 10 $\mu M$ 7-Propargylamino-7-deaza-dGTP—Cy3 (Jena Biosciences™) were incubated on the low binding substrates at 37° C. for 15 minutes in a 384 well plate format. Each well was rinsed 2-3× with 50 $\mu l$ deionized RNase/DNase Free water and 2-3× with 25 mM ACES buffer pH 7.4. The 384 well plates were imaged on a GE Typhoon instrument using the Cy3, AF555, or Cy5 filter sets (according to dye test performed) as specified by the manufacturer at a PMT gain setting of 800 and resolution of 50-100 $\mu m$. For higher resolution imaging, images were collected on an Olympus IX83 microscope (Olympus Corp., Center Valley, PA) with a total internal reflectance fluorescence (TIRF) objective (100×, 1.5 NA, Olympus), a CCD camera (e.g., an Olympus EM-CCD monochrome camera, Olympus XM-10 monochrome camera, or an Olympus DP80 color and monochrome camera), an illumination source (e.g., an Olympus 100 W Hg lamp, an Olympus 75

W Xe lamp, or an Olympus U-HGLGPS fluorescence light source), and excitation wavelengths of 532 nm or 635 nm. Dichroic mirrors were purchased from Semrock (IDEX Health & Science, LLC, Rochester, New York), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit nonspecific binding of dye molecules of less than 0.25 molecules per $\mu m^2$.

In some embodiments, the surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some embodiments, the surfaces disclosed herein exhibit a ratio of specific to nonspecific fluorescence signals for a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

The low-background surfaces consistent with the disclosure herein may exhibit specific dye attachment (e.g., Cy3 attachment) to non-specific dye adsorption (e.g., Cy3 dye adsorption) ratios of at least 4:1, 5:1, 6:1, 7:1, 8:1, 9:1, 10:1, 15:1, 20:1, 30:1, 40:1, 50:1, or more than 50 specific dye molecules attached per molecule nonspecifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 4:1, 5:1, 6:1, 7:1, 8:1, 9:1, 10:1, 15:1, 20:1, 30:1, 40:1, 50:1, or more than 50:1.

In some embodiments, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some embodiments, a static contact angle may be determined. In some embodiments, an advancing or receding contact angle may be determined. In some embodiments, the water contact angle for the hydrophilic, low-binding support surfaced disclosed herein may range from about 0 degrees to about 30 degrees. In some embodiments, the water contact angle for the hydrophilic, low-binding support surfaced disclosed herein may no more than 50 degrees, 40 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than 40 degrees. Those of skill in the art will realize that a given hydrophilic, low-binding support surface of the present disclosure may exhibit a water contact angle having a value of anywhere within this range.

In some embodiments, the hydrophilic surfaces disclosed herein facilitate reduced wash times for bioassays, often due to reduced nonspecific binding of biomolecules to the low-binding surfaces. In some embodiments, adequate wash steps may be performed in less than 60, 50, 40, 30, 20, 15, 10, or less than 10 seconds. For example, in some embodiments adequate wash steps may be performed in less than 30 seconds.

The low-binding surfaces of the present disclosure exhibit significant improvement in stability or durability to prolonged exposure to solvents and elevated temperatures, or to repeated cycles of solvent exposure or changes in temperature. For example, in some embodiments, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some embodiments, the degree of change in the fluorescence used to assess the quality of the surface may be less than 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents and/or elevated temperatures (or any combination of these percentages as measured over these time periods). In some embodiments, the degree of change in the fluorescence used to assess the quality of the surface may be less than 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes and/or changes in temperature (or any combination of these percentages as measured over this range of cycles).

In some embodiments, the surfaces disclosed herein may exhibit a high ratio of specific signal to nonspecific signal or other background. For example, when used for nucleic acid amplification, some surfaces may exhibit an amplification signal that is at least 4, 5, 6, 7, 8, 9, 10, 15, 20, 30, 40, 50, 75, 100, or greater than 100-fold greater than a signal of an adjacent unpopulated region of the surface. Similarly, some surfaces exhibit an amplification signal that is at least 4, 5, 6, 7, 8, 9, 10, 15, 20, 30, 40, 50, 75, 100, or greater than 100-fold greater than a signal of an adjacent amplified nucleic acid population region of the surface.

In some embodiments, fluorescence images of the disclosed low background surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

One or more types of primer (e.g., capture primers) may be attached or tethered to the support surface. In some embodiments, the one or more types of adapters or primers may comprise spacer sequences, adapter sequences for hybridization to adapter-ligated target library nucleic acid sequences, forward amplification primers, reverse amplification primers, sequencing primers, and/or molecular barcoding sequences, or any combination thereof. In some embodiments, 1 primer or adapter sequence may be tethered to at least one layer of the surface. In some embodiments, at least 2, 3, 4, 5, 6, 7, 8, 9, 10, or more than 10 different primer or adapter sequences may be tethered to at least one layer of the surface.

In some embodiments, the tethered adapter and/or primer sequences may range in length from about 10 nucleotides to about 100 nucleotides. In some embodiments, the tethered adapter and/or primer sequences may be at least 10, at least 20, at least 30, at least 40, at least 50, at least 60, at least 70, at least 80, at least 90, or at least 100 nucleotides in length. In some embodiments, the tethered adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some embodiments the length of the tethered adapter and/or primer sequences may range from about 20 nucleotides to about 80 nucleotides. Those of skill in the art will recognize that the length of the tethered adapter and/or primer sequences may have any value within this range, e.g., about 24 nucleotides.

In some embodiments, the resultant surface density of primers on the low binding support surfaces of the present disclosure may range from about 100 primer molecules per $\mu m^2$ to about 100,000 primer molecules per $\mu m^2$. In some embodiments, the resultant surface density of primers on the low binding support surfaces of the present disclosure may range from about 100,000 primer molecules per $\mu m^2$ to about $10^{15}$ primer molecules per $\mu m^2$. In some embodiments, the surface density of primers may be at least 1,000, at least 10,000, at least 100,000, or at least $10^{15}$ primer molecules per $\mu m^2$. In some embodiments, the surface density of primers may be at most 10,000, at most 100,000, at most 1,000,000, or at most $10^{15}$ primer molecules per $\mu m^2$. Any of the lower and upper values described in this paragraph may be combined to form a range included within the present disclosure, for example, in some embodiments the surface density of primers may range from about 10,000 molecules per $\mu m^2$ to about $10^{15}$ molecules per $\mu m^2$. Those of skill in the art will recognize that the surface density of primer molecules may have any value within this range, e.g., about 455,000 molecules per $\mu m^2$. In some embodiments, the surface density of target library nucleic acid sequences initially hybridized to adapter or primer sequences on the support surface may be less than or equal to that indicated for the surface density of tethered primers. In some embodiments, the surface density of clonally-amplified target library nucleic acid sequences hybridized to adapter or primer sequences on the support surface may span the same range as that indicated for the surface density of tethered primers.

Local densities as listed above do not preclude variation in density across a surface, such that a surface may comprise a region having an oligo density of, for example, 500,000 per $\mu m^2$, while also comprising at least a second region having a substantially different local density.

The low non-specific binding coating comprise one or more layers of a multi-layered surface coating may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some embodiments, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branched.

Linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15,000, at least 20,000, at least 25,000, at least 30,000, at least 35,000, at least 40,000, at least 45,000, or at least 50,000 daltons.

In some embodiments, e.g., wherein at least one layer of a multi-layered surface comprises a branched polymer, the number of covalent bonds between a branched polymer molecule of the layer being deposited and molecules of the previous layer may range from about one covalent linkage per molecule to about 32 covalent linkages per molecule. In some embodiments, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 covalent linkages per molecule.

Any reactive functional groups that remain following the coupling of a material layer to the surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface, may range from 1 to about 10. In some embodiments, the number of layers is at least 1, at least 2, at least 3, at least 4, at least 5, at least 6, at least 7, at least 8, at least 9, or at least 10. In some embodiments, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some embodiments the number of layers may range from about 2 to about 4. In some embodiments, all of the layers may comprise the same material. In some embodiments, each layer may comprise a different material. In some embodiments, the plurality of layers may comprise a plurality of materials. In some embodiments at least one layer may comprise a branched polymer. In some embodiment, all of the layers may comprise a branched polymer.

One or more layers of low non-specific binding material may in some cases be deposited on and/or conjugated to the substrate surface using a polar protic solvent, a polar or polar aprotic solvent, a nonpolar solvent, or any combination thereof. In some embodiments the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some embodiments, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of water or an aqueous buffer solution. In some embodiments, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of an organic solvent. The pH of the solvent mixture used may be less than 6, about 6, 6.5, 7, 7.5, 8, 8.5, 9, or greater than pH 9.

Fluorescence imaging may be performed using any of a variety of fluorophores, fluorescence imaging techniques, and fluorescence imaging instruments known to those of skill in the art. Examples of suitable fluorescence dyes that may be used (e.g., by conjugation to nucleotides, oligonucleotides, or proteins) include, but are not limited to, fluorescein, rhodamine, coumarin, cyanine, and derivatives thereof, including the cyanine derivatives Cyanine dye-3 (Cy3), Cyanine dye-5 (Cy5), Cyanine dye-7 (Cy7), etc. Examples of fluorescence imaging techniques that may be used include, but are not limited to, fluorescence microscopy imaging, fluorescence confocal imaging, two-photon fluorescence, and the like. Examples of fluorescence imaging instruments that may be used include, but are not limited to, fluorescence microscopes equipped with an image sensor or camera, confocal fluorescence microscopes, two-photon fluorescence microscopes, or custom instruments that comprise a suitable selection of light sources, lenses, mirrors, prisms, dichroic reflectors, apertures, and image sensors or cameras, etc. A non-limiting example of a fluorescence microscope equipped for acquiring images of the disclosed low-binding support surfaces and clonally-amplified template molecules (e.g., nucleic acid nanostructures) immobilized thereon is the Olympus IX83 inverted fluorescence microscope equipped with) 20×, 0.75 NA, a 532 nm light source, a bandpass and dichroic mirror filter set optimized for 532 nm long-pass excitation and Cy3 fluorescence emission filter, a Semrock 532 nm dichroic reflector, and a camera (Andor sCMOS, Zyla 4.2) where the excitation light intensity is adjusted to avoid signal saturation. Often, the support surface may be immersed in a buffer (e.g., 25 mM ACES, pH 7.4 buffer) while the image is acquired.

In some instances, the performance of nucleic acid hybridization and/or amplification reactions using the disclosed reaction formulations and low non-specific binding supports may be assessed using fluorescence imaging techniques, where the contrast-to-noise ratio (CNR) of the images provides a key metric in assessing amplification specificity and non-specific binding on the support. CNR is commonly defined as: CNR=(Signal−Background)/Noise. The background term is commonly taken to be the signal measured for the interstitial regions surrounding a particular feature (diffraction limited spot, DLS) in a specified region of interest (ROI). While signal-to-noise ratio (SNR) is often considered to be a benchmark of overall signal quality, it can be shown that improved CNR can provide a significant advantage over SNR as a benchmark for signal quality in applications that require rapid image capture (e.g., sequencing applications for which cycle times must be minimized), as shown in the example below. The surfaces of the instant disclosure are also provided in co-pending International Application Serial No. PCT/US2019/061556, which is hereby incorporated by reference in its entirety.

In most ensemble-based sequencing approaches, the background term is typically measured as the signal associated with 'interstitial' regions. In addition to "interstitial" background ($B_{inter}$), "intrastitial" background ($B_{intra}$) exists within the region occupied by an amplified DNA colony. The combination of these two background signals dictates the achievable CNR, and subsequently directly impacts the optical instrument requirements, architecture costs, reagent costs, run-times, cost/genome, and ultimately the accuracy and data quality for cyclic array-based sequencing applications. The $B_{inter}$ background signal arises from a variety of sources; a few examples include auto-fluorescence from consumable flow cells, non-specific adsorption of detection molecules that yield spurious fluorescence signals that may obscure the signal from the ROI, the presence of non-specific DNA amplification products (e.g., those arising from primer dimers). In typical next generation sequencing (NGS) applications, this background signal in the current field-of-view (FOV) is averaged over time and subtracted. The signal arising from individual DNA colonies (i.e., (S)—$B_{inter}$ in the FOV) yields a discernable feature that can be classified. In some instances, the intrastitial background ($B_{intra}$) can contribute a confounding fluorescence signal that is not specific to the target of interest, but is present in the same ROI, thus making it far more difficult to average and subtract.

The implementation of nucleic acid amplification on the low-binding substrates of the present disclosure may decrease the $B_{inter}$ background signal by reducing non-specific binding, may lead to improvements in specific nucleic acid amplification, and may lead to a decrease in non-specific amplification that can impact the background signal arising from both the interstitial and intrastitial regions. In some instances, the disclosed low-binding support surfaces, optionally used in combination with the disclosed hybridization buffer formulations, may lead to improvements in CNR by a factor of 2, 5, 10, 100, or 1000-fold over those achieved using conventional supports and hybridization, amplification, and/or sequencing protocols. Although described here in the context of using fluorescence imaging as the read-out or detection mode, the same principles apply to the use of the disclosed low non-specific binding supports and nucleic acid hybridization and amplification formulations for other detection modes as well, including both optical and non-optical detection modes.

The disclosed low-binding supports, optionally used in combination with the disclosed hybridization and/or amplification protocols, yield solid-phase reactions that exhibit: (i) negligible non-specific binding of protein and other reaction components (thus minimizing substrate background), (ii) negligible non-specific nucleic acid amplification product, and (iii) provide tunable nucleic acid amplification reactions.

In some embodiments, fluorescence images of the disclosed low background surfaces when used in nucleic acid hybridization or amplification applications to create polonies of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

In some embodiments, a fluorescence image of the surface exhibits a contrast-to-noise ratio (CNR) of at least 20 when a sample nucleic acid molecule or complementary sequences thereof are labeled with a Cyanine dye-3 (Cy3) fluorophore, and when the fluorescence image is acquired using an inverted fluorescence microscope (e.g., Olympus IX83) with a 20×0.75 NA objective, a 532 nm light source, a bandpass and dichroic mirror filter set optimized for 532 nm excitation and Cy3 fluorescence emission, and a camera (e.g., Andor sCMOS, Zyla 4.2) under non-signal saturating conditions while the surface is immersed in a buffer (e.g., 25 mM ACES, pH 7.4 buffer).

Air Bubble Fluidics

The present disclosure provides systems and methods for handling fluidics that can be employed to conduct any of the sequencing methods described herein, including any of the in-solution or on-support rolling circle amplification reactions and/or any of the sequencing reactions. The rolling circle amplification and sequencing workflows that are conducted on a flow cell in a massively parallel manner require numerous reagent changes to conduct different biochemical reactions throughout the workflow. A fluidic dispensing system can be used to deliver the reagents to the flow cell. The fluidic dispensing system needs to handle very small fluid volumes and reduce mixing of different reagents that are sequentially flowed onto the flowcell. In some embodiments, air bubbles can be introduced into the fluidics system to separate different reagents flowing onto the flow cell and reduce mixing.

The system comprises a flow cell fluidically connected to a reagent reservoir and a syringe pump. The flow cell includes an inlet on the upstream side and an outlet on the downstream side. The reagent reservoir is connected to the inlet of the flow cell and the syringe pump is connected to the outlet of the flow cell, in a manner that forms a fluid flow path from the reagent reservoir, through the flow cell, and towards the syringe pump. The system further includes an air bubble injector fluidically connected to the fluid flow path and configured to inject air bubbles between different reagents flowing through the fluid path. Fluidic lines can be used to fluidically connect the reagent reservoir, bubble injector, flow cell and syringe pump.

The system can be used to flow very small volumes of different reagents in the fluid flow path and reduce mixing of the different reagents. For example, a first fluid from the reagent reservoir enters the flow path via a fluidic line that connects the reagent reservoir and the inlet of the flow cell. An air bubble is injected into the flow path behind the first reagent in the fluidic line. A second fluid from the reagent reservoir enters the flow path via the fluidic line that connects the reagent reservoir and the inlet of the flow cell, and the second reagent is behind the air bubble. The air bubble prevents mixing of the first and second reagents in the fluidic line before the reagents reach the flow cell. Subsequent air bubbles and reagents can be flowed through the flow cell. The system further comprises an air bubble aspirator that removes the air bubble between the first and second reagents so that the first and second reagents are flowed sequentially onto the flow cell with no air bubble. The air bubble aspirator is configured to enable introduction of air bubbles between different reagents in the fluidic line before entry onto the flow cell so that air bubbles do not flow onto the flow cell. The syringe pump is configured to pull the first and second fluids and the air bubble along the flow path from the reagent reservoir and towards the outlet of the flow cell. In this manner, different reagents can be flowed sequentially onto the flow cell with no air bubbles.

Reservoirs

The present disclosure provides a system comprising at least one reagent reservoir each reservoir having a plurality of separate compartments, and each compartment holding a reagent for conducting a biochemical or biological reaction. The reservoir(s) contain reagents for conducting nucleic acid amplification and/or nucleic acid sequencing reactions on the flowcell. Each compartment can hold a different reagent in fluid form for conducting a nucleic acid amplification reaction, a nucleic acid sequencing reaction, or washing reagent. For example, a first reservoir compartment can hold a plurality of an amplification polymerase, a plurality of amplification primers, a mixture of four different nucleotide triphosphates or analogs thereof (e.g., dATP, dGTP, dCTP or dTTP) and a nucleotide comprising a scissile moiety. The first reservoir can also include a plurality of compaction oligonucleotides. A second reservoir compartment can hold a plurality of sequencing polymerases, a plurality of soluble sequencing primers, and a mixture of nucleotide triphosphates or analogs thereof (e.g., dATP, dGTP, dCTP or dTTP). The second reservoir can also include a plurality of compaction oligonucleotides. A third reservoir compartment can hold a plurality of sequencing polymerases, a plurality of soluble sequencing primers, and a mixture of multivalent molecules where individual multivalent molecules comprises nucleotide arms having nucleotide units of dATP, dGTP, dCTP or dTTP. The third reservoir can also include a plurality of compaction oligonucleotides. A fourth reservoir compartment can hold a plurality of linear or circular library molecules. A fifth reservoir compartment can hold a wash buffer.

The system includes at least one flow cell having at least one channel. In some embodiments, the flow cell contains 1, 2, 3, 4, or more channels. In some embodiments, the system includes two or more flow cells. Each flow cell can be configured with a plurality of channels arranged in parallel to each other. Each channel has an inlet on the upstream side and an outlet on the downstream side. The flow cell(s) is/are mounted in the fluidics system so that the inlet side of each channel is/are fluidically connected to the reagent reservoir, and the outlet side of each channel is/are fluidically connected to the syringe pump.

The flow cell channels have a surface that can be coated with at least one hydrophilic polymer layer, or at least one functionalized polymer coating. The channel surface can include at least one surface capture primer immobilized on or embedded in the coating. The channel surface can include $10^2$-$10^{15}$ immobilized surface capture primers per mm$^2$. The immobilized surface capture primers on the surface of the channel can be in fluid communication with each other during fluid flow through the channel to permit essentially simultaneously reaction with the reagents in a massively parallel manner. The immobilized surface capture primers can hybridize to linear or circular nucleic acid library molecules each having a sequence of interest. The hybridized linear or circular nucleic molecules can be subjected to an amplification reaction (e.g., a rolling circle amplification reaction) in the channel using the fluidic system to generate a plurality of concatemers. The plurality of concatemers in the channel can be subjected to successive sequencing reactions using the fluidic system.

EXAMPLES

The following examples are meant to be illustrative and can be used to further understand embodiments of the present disclosure and should not be construed as limiting the scope of the present teachings in any way.

Example 1: On-Support Rolling Circle Amplification

On-Support Rolling Circle Amplification:
A support having a low non-specific binding coating with a plurality of one type of surface primers (e.g., first surface primers) immobilized thereon was prepared. The first surface primers included an extendible 3'OH end and lacked any nucleotide having a scissile moiety (e.g., lacked uracil, 8oxoG and deoxyinosine). Optionally, the coating also included a plurality of a second type of surface primers (e.g., second surface primers) which lacked any nucleotide having a scissile moiety and included a non-extendible 3' phosphate group.

The circular library molecules included a sequence of interest (e.g., insert size ranged from 150-400 bases) and a primer binding sequence for each of the following: first surface primer; forward sequencing primer; reverse sequencing primer; and at least one compaction oligonucleotide. The circular library molecules optionally included a primer binding sequence for a second surface primer.

A preparation of a single stranded circular nucleic acid library was distributed onto the support and incubated under a condition suitable for hybridizing the circular library molecules to the first surface primers to form library-primer duplexes. For example, the hybridization was conducted at 70° C. for about 3 minutes, and at 55° C. for 3 minutes, and at 37° C. for 3 minutes, and at room temperature for 3 minutes. The support was washed 3 times with a buffer containing Tris (pH 8), NaCl, EDTA and Tween-20.

A two-stage rolling circle amplification reaction was conducted. In the first stage, the library-primer duplexes were contacted with a strand displacing polymerase (e.g., phi29, amplifying polymerase) in the presence of a binding buffer that lacked magnesium and nucleotides under a condition suitable for the polymerase to bind the library-primer duplexes to form complexed polymerases but inhibit polymerase-catalyzed nucleotide incorporation. For example, the polymerase was incubated with the library-primer duplexes at room temperature for about 15 minutes. The binding buffer was removed. In the second stage, the rolling circle amplification reaction (primer extension) was initiated by adding an extension buffer that included $MgCl_2$ a mixture of nucleotides (e.g., about 1 mM each of dATP, dGTP, dCTP and dTTP) and dUTP (e.g., 1 μM or 10 uM dUTP). The rolling circle amplification reaction contained varying amounts of dUTP (e.g., about 1%, about 2.5%, about 5%, about 10% or about 15%). The amplification reaction also included a plurality of compaction oligonucleotides (e.g., 25-200 nM). The rolling circle reaction was incubated at 45° C. (isothermal condition) for about 60 minutes (or less than 60 minutes) to generate a plurality of immobilized nucleic acid nanostructures. The reaction was cooled to room temperature and washed several times.

Read 1 Sequencing:

A two-stage sequencing reaction was conducted. The first-stage sequencing reaction was conducted by hybridizing a plurality of a soluble forward sequencing primers (e.g., 5' exonuclease-resistant primers) to the immobilized nanostructures to form primer-nanostructure duplexes. A plurality of a first sequencing polymerase was added to the duplexes and incubated under a condition suitable to bind the sequencing polymerase to the duplexes to form complexed polymerases. A mixture of fluorescently labeled multivalent molecules (e.g., about 40-100 nM) was added to the complexed polymerases in the presence of a buffer that included a non-catalytic cation (e.g., strontium or barium) and incubated under conditions suitable to bind complementary nucleotide units of the multivalent molecules to the complexed polymerases without polymerase-catalyzed incorporation of the nucleotide units. The first stage sequencing reaction also included a plurality of compaction oligonucleotides (e.g., 25-200 nM). The complexed polymerases were washed. An image was obtained of the fluorescently labeled multivalent molecules that remained bound to the complexed polymerases. The first sequencing polymerases and multivalent molecules were removed, while retaining the sequencing primers hybridized to the nucleic acid nanostructures (retained duplexes), by washing with a buffer comprising a detergent.

The second-stage sequencing reaction was conducted by contacting the retained duplexes with a plurality of second sequencing polymerases to form complexed polymerases. A mixture of non-labeled nucleotide analogs (e.g., 3'O-methylazido nucleotides) (e.g., about 1-5 uM) was added to the complexed polymerases in the presence of a buffer that included a catalytic cation (e.g., magnesium) and incubated under conditions suitable to bind complementary nucleotides to the complexed polymerases and promote polymerase-catalyzed incorporation of the nucleotides to generate a nascent extended sequencing primer. The second stage sequence reaction also included a plurality of compaction oligonucleotides (e.g., 25-200 nM). The complexed polymerases were washed. The incorporated fluorescently labeled nucleotide analogs were reacted with a cleaving reagent that removes the 3' O-methylazido group and generates an extendible 3'OH group. The second sequencing polymerases were removed, while retaining the nascent extended sequencing primers hybridized to the nucleic acid nanostructures (retained duplexes), by washing with a buffer comprising a detergent. Recurring sequencing reactions were conducted by performing multiple cycles of first-stage and second-stage sequencing reactions to generate extended forward sequencing primer strands.

Replacing the Extended Forward Sequencing Primer Strands:

The extended forward sequencing primer strands were contacted with a plurality of strand displacing polymerases (e.g., Phi29 polymerase) and a mixture of nucleotides in the absence of newly added soluble primers (e.g., no soluble sequencing primers and no soluble amplification primers). Compaction oligonucleotides were included (e.g., 25-200 nM). The mixture of nucleotides included dATP, dGTP, dCTP and dTTP. The reaction was incubated at 45° C. for about 30 minutes to generate a plurality of forward extension strands that are hybridized to the immobilized nucleic acid nanostructures. The support was washed several times with a wash buffer comprising Tris-HCl, NaCl, EDTA and Tween-20.

Generating Abasic Sites and Gaps:

The plurality of forward extension strands were contacted with Thermolabile USER (II) enzyme (0.02 U/uL) (e.g., from New England Biolabs™, catalog #M5508S), and T7 exonuclease (02 U/uL) (e.g., from New England Biolabs™, catalog #M0263S), and 1× CutSmart™ buffer (e.g., from New England Biolabs™, catalog #B7204S), and incubated at 37° C. for about 15 minutes, and then at 25° C. for about 15 minutes to generate a plurality of abasic sites in the immobilized nucleic acid nanostructures and to generate gaps at the abasic sites. The forward extension strands were retained as intact molecules. The support was washed several times with a wash buffer comprising Tris-HCl, NaCl, EDTA and Tween-20 to remove the gap-containing nanostructures.

Read 2 Sequencing:

A two-stage sequencing reaction was conducted as described in 'Read 1 sequencing' described above, except that the first-stage sequencing reaction was conducted by hybridizing a plurality of a soluble reverse sequencing primers (e.g., 5' exonuclease-resistant primers) to the retained forward extension strands to form primer-extension strand duplexes.

Example 2: In-Solution Initiated Rolling Circle Amplification

In-Solution Initiated Rolling Circle Amplification:

A support having a low non-specific binding coating with a plurality of one type of surface primers (e.g., first surface primers) immobilized thereon was prepared. The first surface primers included an extendible 3'OH end and lacked any nucleotide having a scissile moiety (e.g., lacked uracil, 8oxoG and deoxyinosine). Optionally, the coating also included a plurality of a second type of surface primers (e.g., second surface primers) which lacked any nucleotide having a scissile moiety and included a non-extendible 3' phosphate group.

The circular library molecules included a sequence of interest (e.g., insert size ranged from 150-400 bases) and a primer binding sequence for each of the following: first surface primer; forward sequencing primer; reverse sequencing primer; and at least one compaction oligonucleotide (e.g., 25-200 nM). The circular library molecules optionally included a primer binding sequence for a second surface primer.

The circular library molecules (at 1-8 nM) were hybridized with soluble amplification primers (at 2-80 nM)(e.g., about 2-10 equivalents) in a buffer containing 10 mM ACES pH 7.4, 10 uM dNTPs (total), 1 mM strontium acetate, 0.01% Tween-20, (and optionally 50 mM ammonium sulfate). The hybridization mixture was heated to 85° C. and cooled to 40° C. with 5° C. steps, 30 second dwell time at each step, and 0.2° C./second ramp rate between steps, for a total of 10 minutes. The mixture was incubated at a temperature that was about 1-10° C. below the Tm of the primer, for about 10 minutes.

To the hybridization mixture described above, a trapped nucleotide-polymerase mixture was prepared by adding DTT to a final concentration of 1-50 mM, Phi29 polymerase at 2-10 equivalents with respect to the soluble amplification primer, and a 5× trap buffer so that the final concentration of the ACES, dNTPs, strontium acetate and Tween-20 was the same as in the hybridization mixture. The trapped nucleotide-polymerase mixture was incubated at room temperature, or different temperatures up to 35° C., for 15 minutes.

A nucleotide polymerization reaction mixture was prepared by diluting the trapped nucleotide-polymerase mixture (about 40-1000× dilution) with extension buffer so the final concentration included 50 mM ACES pH 74, 100 mM potassium acetate, 10 mM magnesium sulfate, 2 mM dNTPs (including dUTP), 10 mM DTT, 0.01% Tween-20, 50 mM ammonium sulfate, and concentration of the circular library molecules was 5-100 μM. The nucleotide polymerization reaction mixture included a plurality of compaction oligonucleotides (e.g., 25-200 nM).

The nucleotide polymerization reaction mixture was distributed onto a support immobilized with two different types of surface capture primers, and incubated at 30-45° C. for 5 minutes (but time ranges up to 2 hours were also tested) for a rolling circle amplification reaction. The Alternatively, the nucleotide polymerization reaction mixture was incubated at 30-45° C. for 30 minutes and then distributed onto the support, and the rolling circle amplification reaction continued on the surface for 5 minutes or up to 2 hours.

The support was washed with a wash buffer containing 50 mM Tris-HCl pH 8, 750 mM NaCl, 0.1 mM EDTA, and 0.02% Tween-20. The reaction was cooled to room temperature and washed several times.

Read 1 Sequencing:

A two-stage sequencing reaction was conducted as described above in Example 1.

Replacing the Extended Forward Sequencing Primer Strands

The extended forward sequencing primer strands were replaced with forward extension strands as described above in Example 1.

Generating Abasic Sites and Gaps

Abasic sites and gaps were generated in the forward extension strands as described above in Example 1.

Read 2 Sequencing:

A two-stage sequencing reaction was conducted as described above in Example 1.

Example 3: Imaging Immobilized Nanostructures

On-Support Rolling Circle Amplification with Titrating dUTP:

On-support rolling circle amplification was conducted to generate first strand template molecules (e.g., first strand nanostructures) immobilized on a flow cell using a strand displacing polymerase, one type of compaction oligonucleotide (SEQ ID NO:57; 100 nM), and a mixture of nucleotides with titrating concentrations of dUTP or no dUTP as a negative control (e.g., see FIGS. 21 and 39). The on-support rolling circle amplification reaction was conducted as described in Example 1 above.

Sequencing reagents were flowed onto the immobilized first strand nanostructures to form binding complexes on the nanostructures. The sequencing reagents included sequencing primers, sequencing polymerases and a mixture of labeled multivalent molecules (e.g., see FIGS. 56-58). The multivalent molecules were labeled with a fluorophore that corresponds to the particular nucleotide units (e.g., dATP, dGTP, dCTP and dUTP) attached to the nucleotide arms of a given multivalent molecule. As shown in FIG. 66, nanostructures were generated by conducting on-support rolling circle amplification with various compaction oligonucleotides (100 nM) or no compaction oligonucleotides as a negative control (None). The immobilized nanostructures were hybridized with fluorescently-labeled probes, washed, and imaged. The SEQ ID NO of the compaction oligonucleotide is indicated in the upper left corner of each image in FIG. 66. The images show that the shape and size of the resulting immobilized nanostructures are influenced by the type of compaction oligonucleotide tested. Enlarged images are shown in FIGS. 67A-C.

A boxplot showing the number of immobilized nanostructures per field of view is shown in FIG. 68. The nanostructures were generated by conducting on-support rolling circle amplification with titration concentrations of various compaction oligonucleotides or no compaction oligonucleotides as a negative control. The compaction oligonucleotides were tested at 25 nM, 100 nM, 250 nM and 500 nM. Compaction oligonucleotides that were tested included SEQ ID NOS: 57, 126 and 156 (see the sequences in Table 1). The data shows that the compaction oligonucleotides did not inhibit the rolling circle amplification reaction. The number of immobilized nanostructures (spots) was similar for the negative control and the three different compaction oligonucleotides tested in this experiment. The full width half maximum (FWHM) of the immobilized nanostructures described in FIG. 68 is shown in FIG. 69. The data shows that the FWHM of the nanostructures generated with compaction oligonucleotides is smaller compared to the negative control. The data also shows that the immobilized nanostructures generated with compaction oligonucleotides comprising SEQ ID NO:57 have a smaller FWHM compared to the immobilized nanostructures generated with compaction oligonucleotides comprising SEQ ID NO: 126 or 156.

Images of the resulting binding complexes on the immobilized first strand template molecules (e.g., first strand nanostructures) were obtained and are presented in FIG. 71.

Second Strand Synthesis and First Strand Degradation:

The first strand template molecules were used to generate the second strand template molecules. The second strand template molecules were generated by conducting a primer extension reaction on the first strand template molecules using a strand-displacing polymerase, a mixture of nucleotides lacking dUTP, and one type of compaction oligonucleotides (SEQ ID NO:123; 100 nM) (e.g., see FIG. 25). The first strand template molecules were removed by treatment with USER (Uracil-Specific Excision Reagent Enzyme) to generate abasic sites and gaps in the first strand template molecules while retaining the second strand template molecules (e.g., see FIG. 26).

Sequencing reagents were flowed onto the immobilized second template strands to form binding complexes on the second template strands (e.g., second nanostructures). The sequencing reagents included sequencing primers, sequencing polymerases and a mixture of labeled multivalent molecules. The multivalent molecules were labeled with a fluorophore that corresponds to the particular nucleotide units (e.g., dATP, dGTP, dCTP and dUTP) attached to the nucleotide arms of a given multivalent molecule. Images of the resulting binding complexes on the immobilized second strand template molecules (e.g., second strand nanostructures) were obtained and are presented in FIG. 71. Together, the images from FIGS. 71 and 72 demonstrate that pairwise sequencing can be achieved.

Example 4: Imaging Immobilized Nanostructures in the Same FOV

As shown in FIG. 71, first strand nanostructures were generated by conducting on-support rolling circle amplification with compaction oligonucleotides, and a mixture of nucleotides with titrating concentrations of dUTP or no dUTP as a negative control. Sequencing reagents were flowed onto the immobilized nanostructures to form fluorescent binding complexes on the first strand nanostructures. Images of the resulting binding complexes were obtained. FIG. 72 depicts the second strand nanostructures were generated from the first strand nanostructures described in FIG. 71. The second strand nanostructures were generated by conducting a primer extension reaction on the first strand nanostructures using a mixture of nucleotides lacking dUTP, and compaction oligonucleotides. The first strands were removed by enzymatic degradation while retaining the second strand molecules. Sequencing reagents were flowed onto the immobilized second template strands to form fluorescent binding complexes on the second strand nanostructures. Images of the resulting binding complexes were obtained. The procedure for obtaining the fluorescent images is described in Example 3.

In FIG. 73: The top image (R1) shows fluorescent binding complexes on immobilized first strand nanostructures, and the bottom image (R2) shows fluorescent binding complexes on the second strand nanostructures where the second strands were generated from their respective first strands on the same flow cell. When comparing the top and bottom images, it is evident that many of the first and second strand nanostructures are immobilized to the same location on the flow cell and the color of the binding complexes changes. The outlined white boxes in the top and bottom images of FIG. 73 indicate the same field of view. The white arrows indicate the locations of groups of nanostructures that are easily identifiable and comparable in the top and bottom images.

The first strand nanostructures in the top image were generated using the on-support RCA procedure described above in Example 3. For example, on-support RCA was conducted using a strand displacing polymerase, one type of compaction oligonucleotide (SEQ ID NO:57; 100 nM) and a mixture of nucleotides lacking dUTP. Sequencing reagents were flowed onto the immobilized first strand nanostructures to form binding complexes on the nanostructures. The sequencing reagents included sequencing primers, sequencing polymerases and a mixture of labeled multivalent molecules (e.g., see FIGS. 56-58). The multivalent molecules were labeled with a fluorophore that corresponds to the particular nucleotide units (e.g., dATP, dGTP, dCTP and dUTP) attached to the nucleotide arms of a given multivalent molecule. Images of the resulting binding complexes on the immobilized first strand template molecules were obtained.

The first strand nanostructures were used to synthesize second strand nanostructures, and the first strands were subjected to enzymatic degradation, using the procedure described in Example 3 above. The sequencing reagents used to obtain the binding complexes on the second strand nanostructures, and imaging, were conducted as described in Example 3 above.

INCORPORATION BY REFERENCE

All publications and patent applications mentioned in this specification are herein incorporated by reference to the same extent as if each individual publication or patent application was specifically and individually indicated to be incorporated by reference.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What is claimed:

1. A method comprising:
   a) providing a support having a plurality of first universal surface primers immobilized thereon, wherein the density of the first universal surface primers on the support is between about $10^2$-$10^{15}$ per $mm^2$; and
   b) generating a plurality of immobilized single stranded nucleic acid concatemer template molecules, the generating comprising:
      1) hybridizing a plurality of single stranded circular nucleic acid library molecules to the plurality of first universal surface primers; and
      2) conducting an on-support rolling circle amplification reaction, wherein the reaction comprises contacting the plurality of single stranded circular nucleic acid library molecules with (i) a plurality of strand-displacing polymerases, (ii) a plurality of nucleotides, and (iii) a plurality of compaction oligonucleotides, individual compaction oligonucleotides comprising a nucleotide sequence selected from the group consisting of SEQ ID NOs: 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, and 156,
   thereby generating the plurality of immobilized single stranded nucleic acid concatemer template molecules, wherein individual compaction oligonucleotides comprise a single-stranded linear oligonucleotide having a first binding region capable of hybridizing to a first portion of an individual immobilized single stranded nucleic acid concatemer template molecule, and a second binding region capable of hybridizing to a second portion of the individual immobilized single stranded nucleic acid concatemer template molecule, wherein the plurality of immobilized single stranded nucleic acid concatemer template molecules form compact nucleic acid nanostructures, and wherein the plurality of immobilized single stranded nucleic acid concatemer template molecules remains immobilized to the support upon forming the compact nucleic acid nanostructures, thereby generating a density of about $10^2$-$10^{15}$ per $mm^2$ of compact nucleic acid nanostructures immobilized on the support.

2. The method of claim 1, wherein the support is passivated with at least one layer of a hydrophilic polymer coating comprising the plurality of first universal surface primers.

3. The method of claim 1, wherein the plurality of first universal surface primers is located on the support or a hydrophilic polymer coating at random positions or predetermined positions.

4. The method of claim 1, wherein each of the individual first universal surface primers of the plurality lack a scissile moiety that can be converted into abasic sites, and wherein the scissile moiety comprises a uridine, an 8-oxo-7,8-dihydroguanine, or a deoxyinosine.

5. The method of claim 1, wherein:
   a) the plurality of nucleotides for the rolling circle amplification reaction comprises dATP, dCTP, dGTP and dTTP, and wherein the nucleotides lack a scissile moiety that can be converted into an abasic site; or
   b) the plurality of nucleotides for the rolling circle amplification reaction comprises dATP, dCTP, dGTP, dTTP, and comprises nucleotides having a scissile moiety that can be converted into abasic sites,
   wherein the nucleotides having the scissile moiety comprise uridine, 8-oxo-7,8-dihydroguanine, or deoxyinosine.

6. The method of claim 5, wherein individual immobilized single stranded nucleic acid concatemer template molecules include at least two nucleotides each having a scissile moiety distributed at random positions along the individual immobilized single stranded nucleic acid concatemer template molecules.

7. The method of claim 1, wherein the plurality of compaction oligonucleotides in step (b):
   a) comprises a population of compaction oligonucleotides having the same sequence, or
   b) comprises a mixture of two or more different populations of compaction oligonucleotides, each population having different sequences, wherein the compaction oligonucleotides in the different populations have different sequences.

8. The method of claim 1, wherein the compact nucleic acid nanostructures comprise one or more loops, or comprise a spherical shape, elongated shape, proto-toroid shape, or toroid shape, wherein:

a) the spherical shape is a nanoball;
b) the elongated shape is a nanorod, or
c) the toroid shape is a nano-toroid.

9. The method of claim 1, wherein the compact nucleic acid nanostructures comprise a full width half maximum (FWHM) smaller than an immobilized single stranded nucleic acid concatemer template molecule that is not collapsed/folded into a nanostructure.

10. The method of claim 1, further comprising imaging the compact nucleic acid nanostructures immobilized on the support.

11. The method of claim 1, further comprising:
1) A) contacting the plurality of compact nucleic acid nanostructures with labeled oligonucleotides comprising detectable reporter moieties under a condition suitable for hybridizing the labeled oligonucleotides to the compact nucleic acid nanostructures to generate a plurality of labeled nanostructures; and
   b) imaging the plurality of labeled nanostructures, or
2) Contacting the plurality of compact nucleic acid nanostructures with (i) a plurality of soluble sequencing primers, (ii) a plurality of sequencing polymerases, and (iii) a plurality of nucleotide reagents, under a condition suitable for:
   hybridizing the plurality of soluble sequencing primers to individual compact nucleic acid nanostructures to generate a plurality of nucleic acid duplexes along individual compact nucleic acid nanostructures, and binding at least one nucleic acid duplex with a sequencing polymerase and a nucleotide reagent,
   wherein the plurality of nucleotide reagents comprises a plurality of nucleotides, wherein individual nucleotides comprise an aromatic base, a five-carbon sugar, and at least one phosphate group.

12. The method of claim 11, wherein at least one of the nucleotides in the plurality further comprises a detectable reporter moiety, wherein the detectable reporter moiety is a fluorophore.

13. The method of claim 12, further comprising:
a) contacting the plurality of compact nucleic acid nanostructures with a labeled nucleotide; and
b) imaging the plurality of compact nucleic acid nanostructures immobilized on the support.

14. The method of claim 11, wherein the plurality of nucleotide reagents comprises a plurality of nucleotide analogs, wherein individual nucleotide analogs comprise an aromatic base, a five-carbon sugar having a 3' chain terminating moiety that inhibits polymerase-catalyzed nucleotide incorporation, and at least one phosphate group, and
   wherein at least one of the nucleotide analogs in the plurality further comprises a detectable reporter moiety, wherein the detectable reporter moiety is a fluorophore.

15. The method of claim 14, further comprising:
a) contacting the plurality of compact nucleic acid nanostructures with a labeled nucleotide analog; and
b) imaging the plurality of compact nucleic acid nanostructures immobilized on the support.

16. The method of claim 11, wherein the plurality of nucleotide reagents comprises a plurality of multivalent molecules, wherein individual multivalent molecules comprise: (1) a core; and (2) a plurality of nucleotide arms which comprise (i) a core attachment moiety, (ii) a spacer, (iii) a linker, and (iv) a nucleotide unit, wherein the core is attached to the plurality of nucleotide arms, the spacer is attached to the linker, the linker is attached to the nucleotide unit, and the nucleotide unit comprises an aromatic base, a five-carbon sugar, and at least one phosphate group.

17. The method of claim 16, further comprising forming a plurality of binding complexes, comprising the steps:
a) binding a first sequencing primer, a first sequencing polymerase, and a first multivalent molecule to a first portion of an individual compact nucleic acid nanostructure, thereby forming a first binding complex, wherein a first nucleotide unit of the first multivalent molecule binds to the first sequencing polymerase; and
b) binding a second sequencing primer, a second sequencing polymerase, and the first multivalent molecule to a second portion of the same individual compact nucleic acid nanostructure, thereby forming a second binding complex, wherein a second nucleotide unit of the first multivalent molecule binds to the second sequencing polymerase, wherein the first and second binding complexes including the same multivalent molecule form an avidity complex, wherein at least one of the multivalent molecules in the plurality further comprises at least one detectable reporter moiety, wherein the at least one detectable reporter moiety comprises at least one fluorophore.

18. The method of claim 17, further comprising:
a) contacting the plurality of compact nucleic acid nanostructures with a labeled multivalent molecule; and
b) imaging the plurality of compact nucleic acid nanostructures immobilized on the support.

19. The method of claim 1, further comprising: contacting the plurality of compact nucleic acid nanostructures with a cellular biological sample, wherein the cellular biological sample comprises a single cell, a section of a single cell, a plurality of cells, a section of a plurality of cells, a tissue, a section of a tissue, an organ, a section of an organ, an organism, or a section of an organism.

20. The method of claim 1, wherein the plurality of compact nucleic acid nanostructures is in fluid communication with each other to permit flowing a solution of reagents onto the support whereby the plurality of compact nucleic acid nanostructures on the support reacts with the solution of reagents in a massively parallel manner.

* * * * *

UNITED STATES PATENT AND TRADEMARK OFFICE
CERTIFICATE OF CORRECTION

PATENT NO. : 12,421,545 B2  
APPLICATION NO. : 18/450302  
DATED : September 23, 2025  
INVENTOR(S) : Arslan et al.

Page 1 of 1

It is certified that error appears in the above-identified patent and that said Letters Patent is hereby corrected as shown below:

In the Claims

In Column 231, in Claim 11, Line 14, delete "A)" and insert -- a) --, therefor.

In Column 231, in Claim 11, Line 21, delete "Contacting" and insert -- contacting --, therefor.

Signed and Sealed this  
Ninth Day of December, 2025

John A. Squires  
*Director of the United States Patent and Trademark Office*

SEQUENCE LISTING

```
Sequence total quantity: 176
SEQ ID NO: 1                moltype = DNA  length = 21
FEATURE                     Location/Qualifiers
source                      1..21
                            mol_type = other DNA
                            organism = synthetic construct
SEQUENCE: 1
acacgtctga actccagtca c                                              21

SEQ ID NO: 2                moltype = DNA  length = 21
FEATURE                     Location/Qualifiers
source                      1..21
                            mol_type = other DNA
                            organism = synthetic construct
SEQUENCE: 2
cactgacctc aagtctgcac a                                              21

SEQ ID NO: 3                moltype = DNA  length = 45
FEATURE                     Location/Qualifiers
source                      1..45
                            mol_type = other DNA
                            organism = synthetic construct
SEQUENCE: 3
acacgtctga actccagtca caaaacacgt ctgaactcca gtcac                    45

SEQ ID NO: 4                moltype = DNA  length = 25
FEATURE                     Location/Qualifiers
source                      1..25
                            mol_type = other DNA
                            organism = synthetic construct
SEQUENCE: 4
gagcacacgt ctgaactcca gtcac                                          25

SEQ ID NO: 5                moltype = DNA  length = 25
FEATURE                     Location/Qualifiers
source                      1..25
                            mol_type = other DNA
                            organism = synthetic construct
SEQUENCE: 5
cactgacctc aagtctgcac acgag                                          25

SEQ ID NO: 6                moltype = DNA  length = 53
FEATURE                     Location/Qualifiers
source                      1..53
                            mol_type = other DNA
                            organism = synthetic construct
SEQUENCE: 6
gagcacacgt ctgaactcca gtcacaaaga gcacacgtct gaactccagt cac           53

SEQ ID NO: 7                moltype = DNA  length = 31
FEATURE                     Location/Qualifiers
source                      1..31
                            mol_type = other DNA
                            organism = synthetic construct
SEQUENCE: 7
ctgaactcca gtcacaaaaa aaccctgaaa g                                   31

SEQ ID NO: 8                moltype = DNA  length = 31
FEATURE                     Location/Qualifiers
source                      1..31
                            mol_type = other DNA
                            organism = synthetic construct
SEQUENCE: 8
gaaagtccca aaaaacact gacctcaagt c                                    31

SEQ ID NO: 9                moltype = DNA  length = 68
FEATURE                     Location/Qualifiers
source                      1..68
                            mol_type = other DNA
                            organism = synthetic construct
SEQUENCE: 9
ctgaactcca gtcacaaaaa aaccctgaaa gaaactgaac tccagtcaca aaaaaccct     60
gaaagtac                                                             68

SEQ ID NO: 10               moltype = DNA  length = 33
FEATURE                     Location/Qualifiers
```

```
source                  1..33
                        mol_type = other DNA
                        organism = synthetic construct
SEQUENCE: 10
ctgaactcca gtcacaaaaa aaaccctga aag                                         33

SEQ ID NO: 11           moltype = DNA   length = 33
FEATURE                 Location/Qualifiers
source                  1..33
                        mol_type = other DNA
                        organism = synthetic construct
SEQUENCE: 11
gaaagtccca aaaaaaaaca ctgacctcaa gtc                                        33

SEQ ID NO: 12           moltype = DNA   length = 72
FEATURE                 Location/Qualifiers
source                  1..72
                        mol_type = other DNA
                        organism = synthetic construct
SEQUENCE: 12
ctgaactcca gtcacaaaaa aaaccctga aagaaactga actccagtca caaaaaaaa            60
ccctgaaagt ac                                                              72

SEQ ID NO: 13           moltype = DNA   length = 32
FEATURE                 Location/Qualifiers
source                  1..32
                        mol_type = other DNA
                        organism = synthetic construct
SEQUENCE: 13
ctgaactcca gtcacaaaaa aatctcgtat gc                                        32

SEQ ID NO: 14           moltype = DNA   length = 32
FEATURE                 Location/Qualifiers
source                  1..32
                        mol_type = other DNA
                        organism = synthetic construct
SEQUENCE: 14
cgtatgctct aaaaaaacac tgacctcaag tc                                        32

SEQ ID NO: 15           moltype = DNA   length = 70
FEATURE                 Location/Qualifiers
source                  1..70
                        mol_type = other DNA
                        organism = synthetic construct
SEQUENCE: 15
ctgaactcca gtcacaaaaa aatctcgtat gcaaactgaa ctccagtcac aaaaaatct          60
cgtatgccgt                                                                 70

SEQ ID NO: 16           moltype = DNA   length = 25
FEATURE                 Location/Qualifiers
source                  1..25
                        mol_type = other DNA
                        organism = synthetic construct
SEQUENCE: 16
cttctgcttg aatgatacgg cgacc                                                25

SEQ ID NO: 17           moltype = DNA   length = 25
FEATURE                 Location/Qualifiers
source                  1..25
                        mol_type = other DNA
                        organism = synthetic construct
SEQUENCE: 17
ccagcggcat agtaagttcg tcttc                                                25

SEQ ID NO: 18           moltype = DNA   length = 53
FEATURE                 Location/Qualifiers
source                  1..53
                        mol_type = other DNA
                        organism = synthetic construct
SEQUENCE: 18
cttctgcttg aatgatacgg cgaccaaact tctgcttgaa tgatacggcg acc                 53

SEQ ID NO: 19           moltype = DNA   length = 25
FEATURE                 Location/Qualifiers
source                  1..25
                        mol_type = other DNA
                        organism = synthetic construct
SEQUENCE: 19
gcattacatg cataatagtg tgacg                                                25
```

```
SEQ ID NO: 20          moltype = DNA   length = 25
FEATURE                Location/Qualifiers
source                 1..25
                       mol_type = other DNA
                       organism = synthetic construct
SEQUENCE: 20
gcagtgtgat aatacgtaca ttacg                                              25

SEQ ID NO: 21          moltype = DNA   length = 53
FEATURE                Location/Qualifiers
source                 1..53
                       mol_type = other DNA
                       organism = synthetic construct
SEQUENCE: 21
gcattacatg cataatagtg tgacgaaagc attacatgca taatagtgtg acg               53

SEQ ID NO: 22          moltype = DNA   length = 21
FEATURE                Location/Qualifiers
source                 1..21
                       mol_type = other DNA
                       organism = synthetic construct
SEQUENCE: 22
cataatagtg tgacgtaata g                                                  21

SEQ ID NO: 23          moltype = DNA   length = 21
FEATURE                Location/Qualifiers
source                 1..21
                       mol_type = other DNA
                       organism = synthetic construct
SEQUENCE: 23
gataatgcag tgtgataata c                                                  21

SEQ ID NO: 24          moltype = DNA   length = 45
FEATURE                Location/Qualifiers
source                 1..45
                       mol_type = other DNA
                       organism = synthetic construct
SEQUENCE: 24
cataatagtg tgacgtaata gaaacataat agtgtgacgt aatag                        45

SEQ ID NO: 25          moltype = DNA   length = 24
FEATURE                Location/Qualifiers
source                 1..24
                       mol_type = other DNA
                       organism = synthetic construct
SEQUENCE: 25
cgtaatagac atacactctt tccc                                               24

SEQ ID NO: 26          moltype = DNA   length = 24
FEATURE                Location/Qualifiers
source                 1..24
                       mol_type = other DNA
                       organism = synthetic construct
SEQUENCE: 26
ccctttctca catacagata atgc                                               24

SEQ ID NO: 27          moltype = DNA   length = 51
FEATURE                Location/Qualifiers
source                 1..51
                       mol_type = other DNA
                       organism = synthetic construct
SEQUENCE: 27
cgtaatagac atacactctt tcccaaacgt aatagacata cactctttcc c                 51

SEQ ID NO: 28          moltype = DNA   length = 20
FEATURE                Location/Qualifiers
source                 1..20
                       mol_type = other DNA
                       organism = synthetic construct
SEQUENCE: 28
aatgatacgg cgaccaccga                                                    20

SEQ ID NO: 29          moltype = DNA   length = 20
FEATURE                Location/Qualifiers
source                 1..20
                       mol_type = other DNA
                       organism = synthetic construct
```

```
SEQUENCE: 29
agccaccagc ggcatagtaa                                              20

SEQ ID NO: 30          moltype = DNA   length = 43
FEATURE                Location/Qualifiers
source                 1..43
                       mol_type = other DNA
                       organism = synthetic construct
SEQUENCE: 30
aatgatacgg cgaccaccga aaaaatgata cggcgaccac cga                    43

SEQ ID NO: 31          moltype = DNA   length = 35
FEATURE                Location/Qualifiers
source                 1..35
                       mol_type = other DNA
                       organism = synthetic construct
SEQUENCE: 31
tgtagggaaa gagtgtagtc gtcgcagcct cacct                             35

SEQ ID NO: 32          moltype = DNA   length = 35
FEATURE                Location/Qualifiers
source                 1..35
                       mol_type = other DNA
                       organism = synthetic construct
SEQUENCE: 32
tccactccga cgctgctgat gtgagaaagg gatgt                             35

SEQ ID NO: 33          moltype = DNA   length = 73
FEATURE                Location/Qualifiers
source                 1..73
                       mol_type = other DNA
                       organism = synthetic construct
SEQUENCE: 33
tgtagggaaa gagtgtagtc gtcgcagcct cacctaaatg tagggaaaga gtgtagtcgt  60
cgcagcctca cct                                                     73

SEQ ID NO: 34          moltype = DNA   length = 35
FEATURE                Location/Qualifiers
source                 1..35
                       mol_type = other DNA
                       organism = synthetic construct
SEQUENCE: 34
aggtgaggct gcgacgacta cactctttcc ctaca                             35

SEQ ID NO: 35          moltype = DNA   length = 35
FEATURE                Location/Qualifiers
source                 1..35
                       mol_type = other DNA
                       organism = synthetic construct
SEQUENCE: 35
acatcccttt ctcacatcag cagcgtcgga gtgga                             35

SEQ ID NO: 36          moltype = DNA   length = 73
FEATURE                Location/Qualifiers
source                 1..73
                       mol_type = other DNA
                       organism = synthetic construct
SEQUENCE: 36
aggtgaggct gcgacgacta cactctttcc ctacaaaaag gtgaggctgc gacgactaca  60
ctctttccct aca                                                     73

SEQ ID NO: 37          moltype = DNA   length = 23
FEATURE                Location/Qualifiers
source                 1..23
                       mol_type = other DNA
                       organism = synthetic construct
SEQUENCE: 37
gatgaggtga ggctgcgacg act                                          23

SEQ ID NO: 38          moltype = DNA   length = 23
FEATURE                Location/Qualifiers
source                 1..23
                       mol_type = other DNA
                       organism = synthetic construct
SEQUENCE: 38
tcagcagcgt cggagtggag tag                                          23

SEQ ID NO: 39          moltype = DNA   length = 49
FEATURE                Location/Qualifiers
```

```
source                    1..49
                          mol_type = other DNA
                          organism = synthetic construct
SEQUENCE: 39
gatgaggtga ggctgcgacg actaaagatg aggtgaggct gcgacgact              49

SEQ ID NO: 40             moltype = DNA  length = 25
FEATURE                   Location/Qualifiers
source                    1..25
                          mol_type = other DNA
                          organism = synthetic construct
SEQUENCE: 40
tgacgtaata gacatctttc cctac                                        25

SEQ ID NO: 41             moltype = DNA  length = 25
FEATURE                   Location/Qualifiers
source                    1..25
                          mol_type = other DNA
                          organism = synthetic construct
SEQUENCE: 41
catcccttc tacagataat gcagt                                         25

SEQ ID NO: 42             moltype = DNA  length = 53
FEATURE                   Location/Qualifiers
source                    1..53
                          mol_type = other DNA
                          organism = synthetic construct
SEQUENCE: 42
tgacgtaata gacatctttc cctacaaatg acgtaataga catctttccc tac         53

SEQ ID NO: 43             moltype = DNA  length = 25
FEATURE                   Location/Qualifiers
source                    1..25
                          mol_type = other DNA
                          organism = synthetic construct
SEQUENCE: 43
gtagggaaag atgtctatta cgtca                                        25

SEQ ID NO: 44             moltype = DNA  length = 25
FEATURE                   Location/Qualifiers
source                    1..25
                          mol_type = other DNA
                          organism = synthetic construct
SEQUENCE: 44
actgcattat ctgtagaaag ggatg                                        25

SEQ ID NO: 45             moltype = DNA  length = 53
FEATURE                   Location/Qualifiers
source                    1..53
                          mol_type = other DNA
                          organism = synthetic construct
SEQUENCE: 45
gtagggaaag atgtctatta cgtcaaaagt agggaaagat gtctattacg tca         53

SEQ ID NO: 46             moltype = DNA  length = 18
FEATURE                   Location/Qualifiers
source                    1..18
                          mol_type = other DNA
                          organism = synthetic construct
SEQUENCE: 46
agggaaagat gtctatta                                                18

SEQ ID NO: 47             moltype = DNA  length = 18
FEATURE                   Location/Qualifiers
source                    1..18
                          mol_type = other DNA
                          organism = synthetic construct
SEQUENCE: 47
attatctgta gaaaggga                                                18

SEQ ID NO: 48             moltype = DNA  length = 39
FEATURE                   Location/Qualifiers
source                    1..39
                          mol_type = other DNA
                          organism = synthetic construct
SEQUENCE: 48
agggaaagat gtctattaaa aagggaaaga tgtctatta                         39

SEQ ID NO: 49             moltype = DNA  length = 30
```

```
FEATURE              Location/Qualifiers
source               1..30
                     mol_type = other DNA
                     organism = synthetic construct
SEQUENCE: 49
ttacatggat gaggtgaggc tgcgacgact                                30

SEQ ID NO: 50        moltype = DNA  length = 30
FEATURE              Location/Qualifiers
source               1..30
                     mol_type = other DNA
                     organism = synthetic construct
SEQUENCE: 50
tcagcagcgt cggagtggag taggtacatt                                30

SEQ ID NO: 51        moltype = DNA  length = 63
FEATURE              Location/Qualifiers
source               1..63
                     mol_type = other DNA
                     organism = synthetic construct
SEQUENCE: 51
ttacatggat gaggtgaggc tgcgacgact aaattacatg gatgaggtga ggctgcgacg   60
act                                                                63

SEQ ID NO: 52        moltype = DNA  length = 18
FEATURE              Location/Qualifiers
source               1..18
                     mol_type = other DNA
                     organism = synthetic construct
SEQUENCE: 52
cacactatta tgcgagct                                             18

SEQ ID NO: 53        moltype = DNA  length = 18
FEATURE              Location/Qualifiers
source               1..18
                     mol_type = other DNA
                     organism = synthetic construct
SEQUENCE: 53
tcgagcgtat tatcacac                                             18

SEQ ID NO: 54        moltype = DNA  length = 39
FEATURE              Location/Qualifiers
source               1..39
                     mol_type = other DNA
                     organism = synthetic construct
SEQUENCE: 54
cacactatta tgcgagctaa acacactatt atgcgagct                      39

SEQ ID NO: 55        moltype = DNA  length = 25
FEATURE              Location/Qualifiers
source               1..25
                     mol_type = other DNA
                     organism = synthetic construct
SEQUENCE: 55
catgtaatgc acgtactttc agggt                                     25

SEQ ID NO: 56        moltype = DNA  length = 25
FEATURE              Location/Qualifiers
source               1..25
                     mol_type = other DNA
                     organism = synthetic construct
SEQUENCE: 56
tgggactttc atgcacgtaa tgtac                                     25

SEQ ID NO: 57        moltype = DNA  length = 53
FEATURE              Location/Qualifiers
source               1..53
                     mol_type = other DNA
                     organism = synthetic construct
SEQUENCE: 57
catgtaatgc acgtactttc agggtaaaca tgtaatgcac gtactttcag ggt       53

SEQ ID NO: 58        moltype = DNA  length = 30
FEATURE              Location/Qualifiers
source               1..30
                     mol_type = other DNA
                     organism = synthetic construct
SEQUENCE: 58
tcatccatgt aatgcacgta ctttcagggt                                30
```

```
SEQ ID NO: 59           moltype = DNA  length = 30
FEATURE                 Location/Qualifiers
source                  1..30
                        mol_type = other DNA
                        organism = synthetic construct
SEQUENCE: 59
tgggactttc atgcacgtaa tgtacctact                                          30

SEQ ID NO: 60           moltype = DNA  length = 63
FEATURE                 Location/Qualifiers
source                  1..63
                        mol_type = other DNA
                        organism = synthetic construct
SEQUENCE: 60
tcatccatgt aatgcacgta ctttcagggt aaatcatcca tgtaatgcac gtactttcag         60
ggt                                                                       63

SEQ ID NO: 61           moltype = DNA  length = 22
FEATURE                 Location/Qualifiers
source                  1..22
                        mol_type = other DNA
                        organism = synthetic construct
SEQUENCE: 61
tgtagggaaa gagtgtagtc gt                                                  22

SEQ ID NO: 62           moltype = DNA  length = 22
FEATURE                 Location/Qualifiers
source                  1..22
                        mol_type = other DNA
                        organism = synthetic construct
SEQUENCE: 62
tgctgatgtg agaaagggat gt                                                  22

SEQ ID NO: 63           moltype = DNA  length = 47
FEATURE                 Location/Qualifiers
source                  1..47
                        mol_type = other DNA
                        organism = synthetic construct
SEQUENCE: 63
tgtagggaaa gagtgtagtc gtaaatgtag ggaaagagtg tagtcgt                       47

SEQ ID NO: 64           moltype = DNA  length = 22
FEATURE                 Location/Qualifiers
source                  1..22
                        mol_type = other DNA
                        organism = synthetic construct
SEQUENCE: 64
acgactacac tctttcccta ca                                                  22

SEQ ID NO: 65           moltype = DNA  length = 22
FEATURE                 Location/Qualifiers
source                  1..22
                        mol_type = other DNA
                        organism = synthetic construct
SEQUENCE: 65
acatcccttt ctcacatcag ca                                                  22

SEQ ID NO: 66           moltype = DNA  length = 47
FEATURE                 Location/Qualifiers
source                  1..47
                        mol_type = other DNA
                        organism = synthetic construct
SEQUENCE: 66
acgactacac tctttcccta caaaaacgac tacactcttt ccctaca                       47

SEQ ID NO: 67           moltype = DNA  length = 15
FEATURE                 Location/Qualifiers
source                  1..15
                        mol_type = other DNA
                        organism = synthetic construct
SEQUENCE: 67
tccagtcacc gagct                                                          15

SEQ ID NO: 68           moltype = DNA  length = 15
FEATURE                 Location/Qualifiers
source                  1..15
                        mol_type = other DNA
                        organism = synthetic construct
```

| | | |
|---|---|---|
| SEQUENCE: 68 | | |
| tcgagccact gacct | | 15 |
| | | |
| SEQ ID NO: 69 | moltype = DNA   length = 33 | |
| FEATURE | Location/Qualifiers | |
| source | 1..33 | |
| | mol_type = other DNA | |
| | organism = synthetic construct | |
| SEQUENCE: 69 | | |
| tccagtcacc gagctaaatc cagtcaccga gct | | 33 |
| | | |
| SEQ ID NO: 70 | moltype = DNA   length = 20 | |
| FEATURE | Location/Qualifiers | |
| source | 1..20 | |
| | mol_type = other DNA | |
| | organism = synthetic construct | |
| SEQUENCE: 70 | | |
| aatgatacgg cgaccaccga | | 20 |
| | | |
| SEQ ID NO: 71 | moltype = DNA   length = 20 | |
| FEATURE | Location/Qualifiers | |
| source | 1..20 | |
| | mol_type = other DNA | |
| | organism = synthetic construct | |
| SEQUENCE: 71 | | |
| agccaccagc ggcatagtaa | | 20 |
| | | |
| SEQ ID NO: 72 | moltype = DNA   length = 43 | |
| FEATURE | Location/Qualifiers | |
| source | 1..43 | |
| | mol_type = other DNA | |
| | organism = synthetic construct | |
| SEQUENCE: 72 | | |
| aatgatacgg cgaccaccga aaaaatgata cggcgaccac cga | | 43 |
| | | |
| SEQ ID NO: 73 | moltype = DNA   length = 32 | |
| FEATURE | Location/Qualifiers | |
| source | 1..32 | |
| | mol_type = other DNA | |
| | organism = synthetic construct | |
| modified_base | 16..23 | |
| | mod_base = i | |
| SEQUENCE: 73 | | |
| gtagggaaag agtgtnnnnn nnngtgtaga tc | | 32 |
| | | |
| SEQ ID NO: 74 | moltype = DNA   length = 32 | |
| FEATURE | Location/Qualifiers | |
| source | 1..32 | |
| | mol_type = other DNA | |
| | organism = synthetic construct | |
| modified_base | 9..17 | |
| | mod_base = i | |
| SEQUENCE: 74 | | |
| ctagatgtgn nnnnnnntgt gagaaaggga tg | | 32 |
| | | |
| SEQ ID NO: 75 | moltype = DNA   length = 67 | |
| FEATURE | Location/Qualifiers | |
| source | 1..67 | |
| | mol_type = other DNA | |
| | organism = synthetic construct | |
| modified_base | 16..23 | |
| | mod_base = i | |
| modified_base | 51..58 | |
| | mod_base = i | |
| SEQUENCE: 75 | | |
| gtagggaaag agtgtnnnnn nnngtgtaga tcaaagtagg gaaagagtgt nnnnnnnngt | | 60 |
| gtagatc | | 67 |
| | | |
| SEQ ID NO: 76 | moltype = DNA   length = 29 | |
| FEATURE | Location/Qualifiers | |
| source | 1..29 | |
| | mol_type = other DNA | |
| | organism = synthetic construct | |
| SEQUENCE: 76 | | |
| aatgatacgg cgaccaccga gatctacac | | 29 |
| | | |
| SEQ ID NO: 77 | moltype = DNA   length = 29 | |
| FEATURE | Location/Qualifiers | |

```
source                  1..29
                        mol_type = other DNA
                        organism = synthetic construct
SEQUENCE: 77
cacatctaga gccaccagcg gcatagtaa                                29

SEQ ID NO: 78           moltype = DNA   length = 61
FEATURE                 Location/Qualifiers
source                  1..61
                        mol_type = other DNA
                        organism = synthetic construct
SEQUENCE: 78
aatgatacgg cgaccaccga gatctacaca aaaatgatac ggcgaccacc gagatctaca  60
c                                                                 61

SEQ ID NO: 79           moltype = DNA   length = 24
FEATURE                 Location/Qualifiers
source                  1..24
                        mol_type = other DNA
                        organism = synthetic construct
SEQUENCE: 79
gagcgtcgtg tagggaaaga gtgt                                      24

SEQ ID NO: 80           moltype = DNA   length = 24
FEATURE                 Location/Qualifiers
source                  1..24
                        mol_type = other DNA
                        organism = synthetic construct
SEQUENCE: 80
tgtgagaaag ggatgtgctg cgag                                      24

SEQ ID NO: 81           moltype = DNA   length = 51
FEATURE                 Location/Qualifiers
source                  1..51
                        mol_type = other DNA
                        organism = synthetic construct
SEQUENCE: 81
gagcgtcgtg tagggaaaga gtgtaaagag cgtcgtgtag ggaaagagtg t         51

SEQ ID NO: 82           moltype = DNA   length = 25
FEATURE                 Location/Qualifiers
source                  1..25
                        mol_type = other DNA
                        organism = synthetic construct
SEQUENCE: 82
cttctgcttg aatgatacgg cgacc                                     25

SEQ ID NO: 83           moltype = DNA   length = 25
FEATURE                 Location/Qualifiers
source                  1..25
                        mol_type = other DNA
                        organism = synthetic construct
SEQUENCE: 83
ccagcggcat agtaagttcg tcttc                                     25

SEQ ID NO: 84           moltype = DNA   length = 53
FEATURE                 Location/Qualifiers
source                  1..53
                        mol_type = other DNA
                        organism = synthetic construct
SEQUENCE: 84
cttctgcttg aatgatacgg cgaccaaact tctgcttgaa tgatacggcg acc        53

SEQ ID NO: 85           moltype = DNA   length = 24
FEATURE                 Location/Qualifiers
source                  1..24
                        mol_type = other DNA
                        organism = synthetic construct
SEQUENCE: 85
caagcagaag acggcatacg agat                                      24

SEQ ID NO: 86           moltype = DNA   length = 24
FEATURE                 Location/Qualifiers
source                  1..24
                        mol_type = other DNA
                        organism = synthetic construct
SEQUENCE: 86
tagagcatac ggcagaagac gaac                                      24
```

-continued

```
SEQ ID NO: 87              moltype = DNA   length = 51
FEATURE                    Location/Qualifiers
source                     1..51
                           mol_type = other DNA
                           organism = synthetic construct
SEQUENCE: 87
caagcagaag acggcatacg agataaacaa gcagaagacg gcatacgaga t          51

SEQ ID NO: 88              moltype = DNA   length = 24
FEATURE                    Location/Qualifiers
source                     1..24
                           mol_type = other DNA
                           organism = synthetic construct
SEQUENCE: 88
acactctttc cctacacgac gctc                                         24

SEQ ID NO: 89              moltype = DNA   length = 24
FEATURE                    Location/Qualifiers
source                     1..24
                           mol_type = other DNA
                           organism = synthetic construct
SEQUENCE: 89
ctcgcagcac atccctttct caca                                         24

SEQ ID NO: 90              moltype = DNA   length = 51
FEATURE                    Location/Qualifiers
source                     1..51
                           mol_type = other DNA
                           organism = synthetic construct
SEQUENCE: 90
acactctttc cctacacgac gctcaaaaca ctctttccct acacgacgct c            51

SEQ ID NO: 91              moltype = DNA   length = 25
FEATURE                    Location/Qualifiers
source                     1..25
                           mol_type = other DNA
                           organism = synthetic construct
SEQUENCE: 91
gtgactggag ttcagacgtg tgctc                                        25

SEQ ID NO: 92              moltype = DNA   length = 25
FEATURE                    Location/Qualifiers
source                     1..25
                           mol_type = other DNA
                           organism = synthetic construct
SEQUENCE: 92
ctcgtgtgca gacttgaggt cagtg                                        25

SEQ ID NO: 93              moltype = DNA   length = 53
FEATURE                    Location/Qualifiers
source                     1..53
                           mol_type = other DNA
                           organism = synthetic construct
SEQUENCE: 93
gtgactggag ttcagacgtg tgctcaaagt gactggagtt cagacgtgtg ctc         53

SEQ ID NO: 94              moltype = DNA   length = 25
FEATURE                    Location/Qualifiers
source                     1..25
                           mol_type = other DNA
                           organism = synthetic construct
SEQUENCE: 94
gagcacacgt ctgaactcca gtcac                                        25

SEQ ID NO: 95              moltype = DNA   length = 25
FEATURE                    Location/Qualifiers
source                     1..25
                           mol_type = other DNA
                           organism = synthetic construct
SEQUENCE: 95
cactgacctc aagtctgcac acgag                                        25

SEQ ID NO: 96              moltype = DNA   length = 53
FEATURE                    Location/Qualifiers
source                     1..53
                           mol_type = other DNA
                           organism = synthetic construct
SEQUENCE: 96
gagcacacgt ctgaactcca gtcacaaaga gcacacgtct gaactccagt cac         53
```

| SEQ ID NO: 97 | moltype = DNA length = 32 |
| --- | --- |
| FEATURE | Location/Qualifiers |
| source | 1..32 |
| | mol_type = other DNA |
| | organism = synthetic construct |
| modified_base | 16..23 |
| | mod_base = i |
| SEQUENCE: 97 | |
| ctgaactcca gtcacnnnnn nnatctcgt at | 32 |

| SEQ ID NO: 98 | moltype = DNA length = 32 |
| --- | --- |
| FEATURE | Location/Qualifiers |
| source | 1..32 |
| | mol_type = other DNA |
| | organism = synthetic construct |
| modified_base | 9..17 |
| | mod_base = i |
| SEQUENCE: 98 | |
| tatgctctan nnnnnnncac tgacctcaag tc | 32 |

| SEQ ID NO: 99 | moltype = DNA length = 67 |
| --- | --- |
| FEATURE | Location/Qualifiers |
| source | 1..67 |
| | mol_type = other DNA |
| | organism = synthetic construct |
| modified_base | 16..23 |
| | mod_base = i |
| modified_base | 51..58 |
| | mod_base = i |
| SEQUENCE: 99 | |
| ctgaactcca gtcacnnnnn nnatctcgt ataaactgaa ctccagtcac nnnnnnnat | 60 |
| ctcgtat | 67 |

| SEQ ID NO: 100 | moltype = DNA length = 17 |
| --- | --- |
| FEATURE | Location/Qualifiers |
| source | 1..17 |
| | mol_type = other DNA |
| | organism = synthetic construct |
| SEQUENCE: 100 | |
| gagctcgacc ctgaaag | 17 |

| SEQ ID NO: 101 | moltype = DNA length = 17 |
| --- | --- |
| FEATURE | Location/Qualifiers |
| source | 1..17 |
| | mol_type = other DNA |
| | organism = synthetic construct |
| SEQUENCE: 101 | |
| gaaagtccca gctcgag | 17 |

| SEQ ID NO: 102 | moltype = DNA length = 37 |
| --- | --- |
| FEATURE | Location/Qualifiers |
| source | 1..37 |
| | mol_type = other DNA |
| | organism = synthetic construct |
| SEQUENCE: 102 | |
| gagctcgacc ctgaaagaaa gagctcgacc ctgaaag | 37 |

| SEQ ID NO: 103 | moltype = DNA length = 17 |
| --- | --- |
| FEATURE | Location/Qualifiers |
| source | 1..17 |
| | mol_type = other DNA |
| | organism = synthetic construct |
| SEQUENCE: 103 | |
| cgtgcattac atgcgag | 17 |

| SEQ ID NO: 104 | moltype = DNA length = 17 |
| --- | --- |
| FEATURE | Location/Qualifiers |
| source | 1..17 |
| | mol_type = other DNA |
| | organism = synthetic construct |
| SEQUENCE: 104 | |
| gagcgtacat tacgtgc | 17 |

| SEQ ID NO: 105 | moltype = DNA length = 37 |
| --- | --- |
| FEATURE | Location/Qualifiers |
| source | 1..37 |
| | mol_type = other DNA |
| | organism = synthetic construct |

```
SEQUENCE: 105
cgtgcattac atgcgagaaa cgtgcattac atgcgag                            37

SEQ ID NO: 106         moltype = DNA  length = 21
FEATURE                Location/Qualifiers
source                 1..21
                       mol_type = other DNA
                       organism = synthetic construct
SEQUENCE: 106
gcaggctacc gcttgtcaac t                                             21

SEQ ID NO: 107         moltype = DNA  length = 21
FEATURE                Location/Qualifiers
source                 1..21
                       mol_type = other DNA
                       organism = synthetic construct
SEQUENCE: 107
tcaactgttc gccatcggac g                                             21

SEQ ID NO: 108         moltype = DNA  length = 45
FEATURE                Location/Qualifiers
source                 1..45
                       mol_type = other DNA
                       organism = synthetic construct
SEQUENCE: 108
gcaggctacc gcttgtcaac taaagcaggc taccgcttgt caact                   45

SEQ ID NO: 109         moltype = DNA  length = 21
FEATURE                Location/Qualifiers
source                 1..21
                       mol_type = other DNA
                       organism = synthetic construct
SEQUENCE: 109
agttgacaag cggtagcctg c                                             21

SEQ ID NO: 110         moltype = DNA  length = 21
FEATURE                Location/Qualifiers
source                 1..21
                       mol_type = other DNA
                       organism = synthetic construct
SEQUENCE: 110
cgtccgatgg cgaacagttg a                                             21

SEQ ID NO: 111         moltype = DNA  length = 45
FEATURE                Location/Qualifiers
source                 1..45
                       mol_type = other DNA
                       organism = synthetic construct
SEQUENCE: 111
agttgacaag cggtagcctg caaaagttga caagcggtag cctgc                   45

SEQ ID NO: 112         moltype = DNA  length = 26
FEATURE                Location/Qualifiers
source                 1..26
                       mol_type = other DNA
                       organism = synthetic construct
SEQUENCE: 112
ggtgtgcagg ctaccgcttg tcaact                                        26

SEQ ID NO: 113         moltype = DNA  length = 26
FEATURE                Location/Qualifiers
source                 1..26
                       mol_type = other DNA
                       organism = synthetic construct
SEQUENCE: 113
tcaactgttc gccatcggac gtgtgg                                        26

SEQ ID NO: 114         moltype = DNA  length = 55
FEATURE                Location/Qualifiers
source                 1..55
                       mol_type = other DNA
                       organism = synthetic construct
SEQUENCE: 114
ggtgtgcagg ctaccgcttg tcaactaaag gtgtgcaggc taccgcttgt caact         55

SEQ ID NO: 115         moltype = DNA  length = 26
FEATURE                Location/Qualifiers
```

```
source                  1..26
                        mol_type = other DNA
                        organism = synthetic construct
SEQUENCE: 115
agttgacaag cggtagcctg cacacc                                              26

SEQ ID NO: 116          moltype = DNA   length = 26
FEATURE                 Location/Qualifiers
source                  1..26
                        mol_type = other DNA
                        organism = synthetic construct
SEQUENCE: 116
ccacacgtcc gatggcgaac agttga                                              26

SEQ ID NO: 117          moltype = DNA   length = 55
FEATURE                 Location/Qualifiers
source                  1..55
                        mol_type = other DNA
                        organism = synthetic construct
SEQUENCE: 117
agttgacaag cggtagcctg cacaccaaaa gttgacaagc ggtagcctgc acacc              55

SEQ ID NO: 118          moltype = DNA   length = 23
FEATURE                 Location/Qualifiers
source                  1..23
                        mol_type = other DNA
                        organism = synthetic construct
SEQUENCE: 118
agtcgtcgca gcctcacctg atc                                                 23

SEQ ID NO: 119          moltype = DNA   length = 23
FEATURE                 Location/Qualifiers
source                  1..23
                        mol_type = other DNA
                        organism = synthetic construct
SEQUENCE: 119
ctagtccact ccgacgctgc tga                                                 23

SEQ ID NO: 120          moltype = DNA   length = 49
FEATURE                 Location/Qualifiers
source                  1..49
                        mol_type = other DNA
                        organism = synthetic construct
SEQUENCE: 120
agtcgtcgca gcctcacctg atcaaaagtc gtcgcagcct cacctgatc                     49

SEQ ID NO: 121          moltype = DNA   length = 23
FEATURE                 Location/Qualifiers
source                  1..23
                        mol_type = other DNA
                        organism = synthetic construct
SEQUENCE: 121
gatcaggtga ggctgcgacg act                                                 23

SEQ ID NO: 122          moltype = DNA   length = 23
FEATURE                 Location/Qualifiers
source                  1..23
                        mol_type = other DNA
                        organism = synthetic construct
SEQUENCE: 122
tcagcagcgt cggagtggac tag                                                 23

SEQ ID NO: 123          moltype = DNA   length = 49
FEATURE                 Location/Qualifiers
source                  1..49
                        mol_type = other DNA
                        organism = synthetic construct
SEQUENCE: 123
gatcaggtga ggctgcgacg actaaagatc aggtgaggct gcgacgact                     49

SEQ ID NO: 124          moltype = DNA   length = 23
FEATURE                 Location/Qualifiers
source                  1..23
                        mol_type = other DNA
                        organism = synthetic construct
SEQUENCE: 124
ggaaggtgtg caggctaccg ctt                                                 23

SEQ ID NO: 125          moltype = DNA   length = 23
```

```
FEATURE                 Location/Qualifiers
source                  1..23
                        mol_type = other DNA
                        organism = synthetic construct
SEQUENCE: 125
ttcgccatcg gacgtgtgga agg                                           23

SEQ ID NO: 126          moltype = DNA  length = 49
FEATURE                 Location/Qualifiers
source                  1..49
                        mol_type = other DNA
                        organism = synthetic construct
SEQUENCE: 126
ggaaggtgtg caggctaccg cttaaaggaa ggtgtgcagg ctaccgctt               49

SEQ ID NO: 127          moltype = DNA  length = 20
FEATURE                 Location/Qualifiers
source                  1..20
                        mol_type = other DNA
                        organism = synthetic construct
SEQUENCE: 127
tggtgagcca atccagcacg                                               20

SEQ ID NO: 128          moltype = DNA  length = 20
FEATURE                 Location/Qualifiers
source                  1..20
                        mol_type = other DNA
                        organism = synthetic construct
SEQUENCE: 128
gcacgaccta accgagtggt                                               20

SEQ ID NO: 129          moltype = DNA  length = 43
FEATURE                 Location/Qualifiers
source                  1..43
                        mol_type = other DNA
                        organism = synthetic construct
SEQUENCE: 129
tggtgagcca atccagcacg aaatggtgag ccaatccagc acg                     43

SEQ ID NO: 130          moltype = DNA  length = 22
FEATURE                 Location/Qualifiers
source                  1..22
                        mol_type = other DNA
                        organism = synthetic construct
SEQUENCE: 130
atgtcggaag gtgtgcaggc ta                                            22

SEQ ID NO: 131          moltype = DNA  length = 22
FEATURE                 Location/Qualifiers
source                  1..22
                        mol_type = other DNA
                        organism = synthetic construct
SEQUENCE: 131
atcggacgtg tggaaggctg ta                                            22

SEQ ID NO: 132          moltype = DNA  length = 47
FEATURE                 Location/Qualifiers
source                  1..47
                        mol_type = other DNA
                        organism = synthetic construct
SEQUENCE: 132
atgtcggaag gtgtgcaggc taaaaatgtc ggaaggtgtg caggcta                 47

SEQ ID NO: 133          moltype = DNA  length = 24
FEATURE                 Location/Qualifiers
source                  1..24
                        mol_type = other DNA
                        organism = synthetic construct
SEQUENCE: 133
tgtctggtga gccaatccag cacg                                          24

SEQ ID NO: 134          moltype = DNA  length = 24
FEATURE                 Location/Qualifiers
source                  1..24
                        mol_type = other DNA
                        organism = synthetic construct
SEQUENCE: 134
gcacgaccta accgagtggt ctgt                                          24
```

```
SEQ ID NO: 135          moltype = DNA   length = 51
FEATURE                 Location/Qualifiers
source                  1..51
                        mol_type = other DNA
                        organism = synthetic construct
SEQUENCE: 135
tgtctggtga gccaatccag cacgaaatgt ctggtgagcc aatccagcac g            51

SEQ ID NO: 136          moltype = DNA   length = 25
FEATURE                 Location/Qualifiers
source                  1..25
                        mol_type = other DNA
                        organism = synthetic construct
SEQUENCE: 136
ttgagtcgtc gcagcctcac ctgat                                         25

SEQ ID NO: 137          moltype = DNA   length = 25
FEATURE                 Location/Qualifiers
source                  1..25
                        mol_type = other DNA
                        organism = synthetic construct
SEQUENCE: 137
tagtccactc cgacgctgct gagtt                                         25

SEQ ID NO: 138          moltype = DNA   length = 53
FEATURE                 Location/Qualifiers
source                  1..53
                        mol_type = other DNA
                        organism = synthetic construct
SEQUENCE: 138
ttgagtcgtc gcagcctcac ctgataaatt gagtcgtcgc agcctcacct gat          53

SEQ ID NO: 139          moltype = DNA   length = 24
FEATURE                 Location/Qualifiers
source                  1..24
                        mol_type = other DNA
                        organism = synthetic construct
SEQUENCE: 139
tcttctgctt gagtcgtcgc agcc                                          24

SEQ ID NO: 140          moltype = DNA   length = 24
FEATURE                 Location/Qualifiers
source                  1..24
                        mol_type = other DNA
                        organism = synthetic construct
SEQUENCE: 140
ccgacgctgc tgagttcgtc ttct                                          24

SEQ ID NO: 141          moltype = DNA   length = 51
FEATURE                 Location/Qualifiers
source                  1..51
                        mol_type = other DNA
                        organism = synthetic construct
SEQUENCE: 141
tcttctgctt gagtcgtcgc agccaaatct tctgcttgag tcgtcgcagc c            51

SEQ ID NO: 142          moltype = DNA   length = 24
FEATURE                 Location/Qualifiers
source                  1..24
                        mol_type = other DNA
                        organism = synthetic construct
SEQUENCE: 142
atctcgtatg ccgtcttctg cttg                                          24

SEQ ID NO: 143          moltype = DNA   length = 24
FEATURE                 Location/Qualifiers
source                  1..24
                        mol_type = other DNA
                        organism = synthetic construct
SEQUENCE: 143
gttcgtcttc tgccgtatgc tcta                                          24

SEQ ID NO: 144          moltype = DNA   length = 51
FEATURE                 Location/Qualifiers
source                  1..51
                        mol_type = other DNA
                        organism = synthetic construct
SEQUENCE: 144
atctcgtatg ccgtcttctg cttgaaaatc tcgtatgccg tcttctgctt g            51
```

```
SEQ ID NO: 145        moltype = DNA   length = 26
FEATURE               Location/Qualifiers
source                1..26
                      mol_type = other DNA
                      organism = synthetic construct
SEQUENCE: 145
cctgatccat gtaatgcacg tacttt                                          26

SEQ ID NO: 146        moltype = DNA   length = 26
FEATURE               Location/Qualifiers
source                1..26
                      mol_type = other DNA
                      organism = synthetic construct
SEQUENCE: 146
tttcatgcac gtaatgtacc tagtcc                                          26

SEQ ID NO: 147        moltype = DNA   length = 55
FEATURE               Location/Qualifiers
source                1..55
                      mol_type = other DNA
                      organism = synthetic construct
SEQUENCE: 147
cctgatccat gtaatgcacg tactttaaac ctgatccatg taatgcacgt acttt          55

SEQ ID NO: 148        moltype = DNA   length = 25
FEATURE               Location/Qualifiers
source                1..25
                      mol_type = other DNA
                      organism = synthetic construct
SEQUENCE: 148
cacgtacttt cagggtaatg atacg                                           25

SEQ ID NO: 149        moltype = DNA   length = 25
FEATURE               Location/Qualifiers
source                1..25
                      mol_type = other DNA
                      organism = synthetic construct
SEQUENCE: 149
gcatagtaat gggactttca tgcac                                           25

SEQ ID NO: 150        moltype = DNA   length = 53
FEATURE               Location/Qualifiers
source                1..53
                      mol_type = other DNA
                      organism = synthetic construct
SEQUENCE: 150
cacgtacttt cagggtaatg atacgaaaca cgtactttca gggtaatgat acg            53

SEQ ID NO: 151        moltype = DNA   length = 25
FEATURE               Location/Qualifiers
source                1..25
                      mol_type = other DNA
                      organism = synthetic construct
SEQUENCE: 151
aatgatacgc acgtactttc agggt                                           25

SEQ ID NO: 152        moltype = DNA   length = 25
FEATURE               Location/Qualifiers
source                1..25
                      mol_type = other DNA
                      organism = synthetic construct
SEQUENCE: 152
tgggactttc atgcacgcat agtaa                                           25

SEQ ID NO: 153        moltype = DNA   length = 53
FEATURE               Location/Qualifiers
source                1..53
                      mol_type = other DNA
                      organism = synthetic construct
SEQUENCE: 153
aatgatacgc acgtactttc agggtaaaaa tgatacgcac gtactttcag ggt            53

SEQ ID NO: 154        moltype = DNA   length = 24
FEATURE               Location/Qualifiers
source                1..24
                      mol_type = other DNA
                      organism = synthetic construct
```

```
SEQUENCE: 154
gtagggaaag atgtctatta cgtc                                              24

SEQ ID NO: 155          moltype = DNA   length = 24
FEATURE                 Location/Qualifiers
source                  1..24
                        mol_type = other DNA
                        organism = synthetic construct
SEQUENCE: 155
ctgcattatc tgtagaaagg gatg                                              24

SEQ ID NO: 156          moltype = DNA   length = 52
FEATURE                 Location/Qualifiers
source                  1..52
                        mol_type = other DNA
                        organism = synthetic construct
SEQUENCE: 156
gtagggaaag atgtctatta cgtcaaaagt agggaaagat gtctattacg tc               52

SEQ ID NO: 157          moltype = DNA   length = 24
FEATURE                 Location/Qualifiers
source                  1..24
                        mol_type = other DNA
                        organism = synthetic construct
SEQUENCE: 157
aatgatacgg cgaccaccga gatc                                              24

SEQ ID NO: 158          moltype = DNA   length = 24
FEATURE                 Location/Qualifiers
source                  1..24
                        mol_type = other DNA
                        organism = synthetic construct
SEQUENCE: 158
gatctcggtg gtcgccgtat catt                                              24

SEQ ID NO: 159          moltype = DNA   length = 24
FEATURE                 Location/Qualifiers
source                  1..24
                        mol_type = other DNA
                        organism = synthetic construct
SEQUENCE: 159
atctcgtatg ccgtcttctg cttg                                              24

SEQ ID NO: 160          moltype = DNA   length = 24
FEATURE                 Location/Qualifiers
source                  1..24
                        mol_type = other DNA
                        organism = synthetic construct
SEQUENCE: 160
caagcagaag acggcatacg agat                                              24

SEQ ID NO: 161          moltype = DNA   length = 33
FEATURE                 Location/Qualifiers
source                  1..33
                        mol_type = other DNA
                        organism = synthetic construct
SEQUENCE: 161
acactctttc cctacacgac gctcttccga tct                                    33

SEQ ID NO: 162          moltype = DNA   length = 33
FEATURE                 Location/Qualifiers
source                  1..33
                        mol_type = other DNA
                        organism = synthetic construct
SEQUENCE: 162
agatcggaag agcgtcgtgt agggaaagag tgt                                    33

SEQ ID NO: 163          moltype = DNA   length = 34
FEATURE                 Location/Qualifiers
source                  1..34
                        mol_type = other DNA
                        organism = synthetic construct
SEQUENCE: 163
agatcggaag agcacacgtc tgaactccag tcac                                   34

SEQ ID NO: 164          moltype = DNA   length = 34
FEATURE                 Location/Qualifiers
```

```
source                  1..34
                        mol_type = other DNA
                        organism = synthetic construct
SEQUENCE: 164
gtgactggag ttcagacgtg tgctcttccg atct                                34

SEQ ID NO: 165          moltype = DNA   length = 33
FEATURE                 Location/Qualifiers
source                  1..33
                        mol_type = other DNA
                        organism = synthetic construct
SEQUENCE: 165
tcgtcggcag cgtcagatgt gtataagaga cag                                 33

SEQ ID NO: 166          moltype = DNA   length = 33
FEATURE                 Location/Qualifiers
source                  1..33
                        mol_type = other DNA
                        organism = synthetic construct
SEQUENCE: 166
ctgtctctta tacacatctg acgctgccga cga                                 33

SEQ ID NO: 167          moltype = DNA   length = 34
FEATURE                 Location/Qualifiers
source                  1..34
                        mol_type = other DNA
                        organism = synthetic construct
SEQUENCE: 167
ctgtctctta tacacatctc cgagcccacg agac                                34

SEQ ID NO: 168          moltype = DNA   length = 34
FEATURE                 Location/Qualifiers
source                  1..34
                        mol_type = other DNA
                        organism = synthetic construct
SEQUENCE: 168
gtctcgtggg ctcggagatg tgtataagag acag                                34

SEQ ID NO: 169          moltype = DNA   length = 23
FEATURE                 Location/Qualifiers
source                  1..23
                        mol_type = other DNA
                        organism = synthetic construct
SEQUENCE: 169
agtcgtcgca gcctcacctg atc                                            23

SEQ ID NO: 170          moltype = DNA   length = 23
FEATURE                 Location/Qualifiers
source                  1..23
                        mol_type = other DNA
                        organism = synthetic construct
SEQUENCE: 170
gatcaggtga ggctgcgacg act                                            23

SEQ ID NO: 171          moltype = DNA   length = 25
FEATURE                 Location/Qualifiers
source                  1..25
                        mol_type = other DNA
                        organism = synthetic construct
SEQUENCE: 171
catgtaatgc acgtactttc agggt                                          25

SEQ ID NO: 172          moltype = DNA   length = 25
FEATURE                 Location/Qualifiers
source                  1..25
                        mol_type = other DNA
                        organism = synthetic construct
SEQUENCE: 172
accctgaaag tacgtgcatt acatg                                          25

SEQ ID NO: 173          moltype = DNA   length = 35
FEATURE                 Location/Qualifiers
source                  1..35
                        mol_type = other DNA
                        organism = synthetic construct
SEQUENCE: 173
cgtgctggat tggctcacca gacaccttcc gacat                               35

SEQ ID NO: 174          moltype = DNA   length = 35
```

```
FEATURE             Location/Qualifiers
source              1..35
                    mol_type = other DNA
                    organism = synthetic construct
SEQUENCE: 174
atgtcggaag gtgtctggtg agccaatcca gcacg                              35

SEQ ID NO: 175      moltype = DNA  length = 35
FEATURE             Location/Qualifiers
source              1..35
                    mol_type = other DNA
                    organism = synthetic construct
SEQUENCE: 175
atgtcggaag gtgtgcaggc taccgcttgt caact                              35

SEQ ID NO: 176      moltype = DNA  length = 35
FEATURE             Location/Qualifiers
source              1..35
                    mol_type = other DNA
                    organism = synthetic construct
SEQUENCE: 176
agttgacaag cggtagcctg cacaccttcc gacat                              35
```